US008741933B2

(12) United States Patent
Hadida Ruah et al.

(10) Patent No.: US 8,741,933 B2
(45) Date of Patent: *Jun. 3, 2014

(54) MODULATORS OF ATP-BINDING CASSETTE TRANSPORTERS

(71) Applicant: Vertex Pharmaceuticals Incorporated, Cambridge, MA (US)

(72) Inventors: Sara S. Hadida Ruah, La Jolla, CA (US); Matthew Hamilton, Hackettstown, NJ (US); Mark Miller, San Diego, CA (US); Peter D. J. Grootenhuis, San Diego, CA (US); Brian Bear, Carlsbad, CA (US); Jason McCartney, Cardiff by the Sea, CA (US); Jinglan Zhou, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/871,356

(22) Filed: Apr. 26, 2013

(65) Prior Publication Data

US 2013/0237568 A1    Sep. 12, 2013

Related U.S. Application Data

(60) Division of application No. 12/114,935, filed on May 5, 2008, which is a continuation of application No. PCT/US2006/043289, filed on Nov. 8, 2006.

(60) Provisional application No. 60/802,458, filed on May 22, 2006, provisional application No. 60/754,086, filed on Dec. 27, 2005, provisional application No. 60/734,506, filed on Nov. 8, 2005.

(51) Int. Cl.
*A61K 31/443*    (2006.01)

(52) U.S. Cl.
USPC .................................. 514/338; 546/293.7

(58) Field of Classification Search
USPC ........................................ 514/338; 546/293.7
See application file for complete search history.

(56) References Cited

U.S. PATENT DOCUMENTS

| | | | |
|---|---|---|---|
| 6,426,331 B1 | 7/2002 | McKinney et al. |
| 6,479,483 B2 | 11/2002 | Bos et al. |
| 6,770,637 B2 | 8/2004 | Godel et al. |
| 7,297,700 B2 | 11/2007 | Kelly et al. |
| 7,407,976 B2 | 8/2008 | Miller et al. |
| 7,495,103 B2 | 2/2009 | Hadida-Ruah et al. |
| 7,553,855 B2 | 6/2009 | Young et al. |
| 7,598,412 B2 | 10/2009 | Hadida Ruah et al. |
| 7,645,789 B2 | 1/2010 | Hadida-Ruah et al. |
| 7,659,268 B2 | 2/2010 | Hadida-Ruah et al. |
| 7,671,221 B2 | 3/2010 | Hadida-Ruah et al. |
| 7,691,902 B2 | 4/2010 | Hadida-Ruah et al. |
| 7,741,321 B2 | 6/2010 | Hadida-Ruah et al. |
| 7,754,739 B2 | 7/2010 | Hadida-Ruah et al. |
| 7,776,905 B2 | 8/2010 | Hadida-Ruah et al. |
| 7,846,951 B2 | 12/2010 | Miller et al. |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Ruah et al. |
| 7,999,113 B2 | 8/2011 | Hadida-Ruah et al. |
| 8,012,999 B2 | 9/2011 | Hadida Ruah et al. |
| 8,039,491 B2 | 10/2011 | Hadida Ruah et al. |
| 8,076,357 B2 | 12/2011 | Young et al. |
| 8,101,767 B2 | 1/2012 | Ruah et al. |
| 8,124,781 B2 | 2/2012 | Siesel et al. |
| 8,163,772 B2 | 4/2012 | DeMattei et al. |
| 8,188,283 B2 | 5/2012 | Binch et al. |
| 8,227,615 B2 | 7/2012 | Hadida Ruah et al. |
| 8,232,302 B2 | 7/2012 | Miller et al. |
| 8,242,149 B2 | 8/2012 | Ruah et al. |
| 8,299,099 B2 | 10/2012 | Ruah et al. |
| 8,314,239 B2 | 11/2012 | Binch et al. |
| 8,314,256 B2 | 11/2012 | Ruah et al. |
| 8,318,733 B2 | 11/2012 | Hadida Ruah et al. |
| 8,324,207 B2 | 12/2012 | Hadida-Ruah et al. |
| 8,324,242 B2 | 12/2012 | Ruah et al. |
| 8,344,147 B2 | 1/2013 | Ambhaikar et al. |
| 8,354,427 B2 | 1/2013 | VanGoor et al. |
| 8,362,253 B2 | 1/2013 | DeMattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Ruah et al. |
| 2003/0125315 A1 | 7/2003 | Mjalli et al. |
| 2005/0059687 A1 | 3/2005 | Makings |
| 2005/0070718 A1 | 3/2005 | Lubisch et al. |
| 2005/0113423 A1 | 5/2005 | VanGoor |
| 2006/0052358 A1 | 3/2006 | Ruah et al. |
| 2007/0105833 A1 | 5/2007 | Ruah et al. |
| 2008/0071095 A1 | 3/2008 | Hadida Ruah et al. |
| 2008/0306062 A1 | 12/2008 | Hadida Ruah et al. |
| 2009/0105272 A1 | 4/2009 | Grootenhuis et al. |
| 2009/0143381 A1 | 6/2009 | Hadida Ruah et al. |
| 2009/0170905 A1 | 7/2009 | Keshavarz-Shokri et al. |
| 2009/0176839 A1 | 7/2009 | Keshavarz-Shokri et al. |

(Continued)

FOREIGN PATENT DOCUMENTS

EP    0081756    5/1985
EP    591830 A1    4/1994

(Continued)

*Primary Examiner* — Celia Chang
(74) *Attorney, Agent, or Firm* — Michael J. DiVerdi

(57)    ABSTRACT

Compounds of the present invention, and pharmaceutically acceptable compositions thereof, are useful as modulators of ATP-Binding Cassette ("ABC") transporters or fragments thereof, including Cystic Fibrosis Transmembrane Conductance Regulator ("CFTR"). The present invention also relates to methods of treating ABC transporter mediated diseases using compounds of the present invention.

4 Claims, No Drawings

(56) References Cited

U.S. PATENT DOCUMENTS

| | | |
|---|---|---|
| 2009/0246820 A1 | 10/2009 | Singh et al. |
| 2009/0253736 A1 | 10/2009 | Hadida Ruah et al. |
| 2010/0036130 A1 | 2/2010 | Siesel et al. |
| 2010/0074949 A1 | 3/2010 | Rowe et al. |
| 2010/0087490 A1 | 4/2010 | Young et al. |
| 2010/0113508 A1 | 5/2010 | Binch et al. |
| 2010/0125090 A1 | 5/2010 | Hadida Ruah et al. |
| 2010/0130547 A1 | 5/2010 | Zhang et al. |
| 2010/0144798 A1 | 6/2010 | VanGoor et al. |
| 2010/0249113 A1 | 9/2010 | Hadida Ruah et al. |
| 2010/0249180 A1 | 9/2010 | Gallardo-Godoy |
| 2010/0256184 A1 | 10/2010 | Rowe et al. |
| 2010/0267768 A1 | 10/2010 | DeMattei et al. |
| 2010/0331344 A1 | 12/2010 | Hadida Ruah et al. |
| 2011/0008259 A1 | 1/2011 | Binch et al. |
| 2011/0060024 A1 | 3/2011 | Hadida Ruah et al. |
| 2011/0064811 A1 | 3/2011 | Hurter et al. |
| 2011/0071206 A1 | 3/2011 | Ruah et al. |
| 2011/0098311 A1 | 4/2011 | Van Goor et al. |
| 2011/0177999 A1 | 7/2011 | Singh et al. |
| 2011/0230519 A1 | 9/2011 | Arekar et al. |
| 2011/0251253 A1 | 10/2011 | Keshavarz-Shokri et al. |
| 2011/0256220 A1 | 10/2011 | Verwijs et al. |
| 2011/0257223 A1 | 10/2011 | Goor et al. |
| 2011/0263654 A1 | 10/2011 | Keshavarz-Shokri et al. |
| 2011/0288122 A1 | 11/2011 | Van Goor et al. |
| 2011/0306637 A1 | 12/2011 | Hadida-Ruah et al. |
| 2012/0004216 A1 | 1/2012 | Hadida Ruah et al. |
| 2012/0010257 A1 | 1/2012 | Hadida Ruah et al. |
| 2012/0015999 A1 | 1/2012 | Alargova et al. |
| 2012/0035179 A1 | 2/2012 | Hadida Ruah et al. |
| 2012/0046330 A1 | 2/2012 | Alargova et al. |
| 2012/0064157 A1 | 3/2012 | Dokou et al. |
| 2012/0071504 A1 | 3/2012 | Yang et al. |
| 2012/0122921 A1 | 5/2012 | DeMattei et al. |
| 2012/0122922 A1 | 5/2012 | Young et al. |
| 2012/0184583 A1 | 7/2012 | Van Goor et al. |
| 2012/0190856 A1 | 7/2012 | Siesel et al. |
| 2012/0203006 A1 | 8/2012 | Siesel et al. |
| 2012/0208841 A1 | 8/2012 | Binch et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2012/0259129 A1 | 10/2012 | Ambhaikar |
| 2012/0270869 A1 | 10/2012 | Hadida Ruah et al. |
| 2012/0277268 A1 | 11/2012 | Keshavarz-Shokri et al. |
| 2012/0309758 A1 | 12/2012 | Sheth et al. |
| 2012/0322798 A1 | 12/2012 | Hadida Ruah et al. |
| 2013/0011923 A1 | 1/2013 | Ruah et al. |
| 2013/0012536 A1 | 1/2013 | Hadida Ruah et al. |
| 2013/0018071 A1 | 1/2013 | Arekar et al. |
| 2013/0023538 A1 | 1/2013 | Hadida Ruah et al. |
| 2013/0035327 A1 | 2/2013 | Hadida-Ruah et al. |
| 2013/0040986 A1 | 2/2013 | Binch et al. |
| 2013/0072522 A1 | 3/2013 | DeMattei et al. |
| 2013/0072687 A1 | 3/2013 | Ambhaikar et al. |
| 2013/0079367 A1 | 3/2013 | Arekar et al. |
| 2013/0085158 A1 | 4/2013 | Keshavarz-Shokri et al. |
| 2013/0090354 A1 | 4/2013 | Van Goor et al. |
| 2014/0023706 A1 | 1/2014 | Verwijs et al. |
| 2014/0024672 A1 | 1/2014 | Hadida-Ruah et al. |
| 2014/0051724 A1 | 2/2014 | Hadida-Ruah et al. |
| 2014/0057906 A1 | 2/2014 | Hadida Ruah et al. |

FOREIGN PATENT DOCUMENTS

| | | |
|---|---|---|
| JP | 2003155285 A2 | 5/2003 |
| WO | 95/06046 A1 | 3/1995 |
| WO | 96/19444 A1 | 6/1996 |
| WO | 97/36876 A1 | 10/1997 |
| WO | 98/07420 A1 | 2/1998 |
| WO | 98/28980 A1 | 7/1998 |
| WO | 98/47868 A1 | 10/1998 |
| WO | 99/41405 A1 | 8/1999 |
| WO | 99/64394 A1 | 12/1999 |
| WO | 00/16798 A1 | 3/2000 |
| WO | 00/50398 A1 | 8/2000 |
| WO | 00/50401 A1 | 8/2000 |
| WO | 01/54690 A1 | 8/2001 |
| WO | 01/56989 A2 | 8/2001 |
| WO | 01/81317 A1 | 11/2001 |
| WO | 01/83517 A1 | 11/2001 |
| WO | 01/92235 A1 | 12/2001 |
| WO | 02/16324 A1 | 2/2002 |
| WO | 02/30875 A1 | 4/2002 |
| WO | 02/34739 A1 | 5/2002 |
| WO | 02/38107 A2 | 5/2002 |
| WO | 02/079134 A1 | 10/2002 |
| WO | 02/085458 A2 | 10/2002 |
| WO | 03/006016 A2 | 1/2003 |
| WO | 03/007888 A2 | 1/2003 |
| WO | 03/007945 A1 | 5/2003 |
| WO | 03/042191 A1 | 5/2003 |
| WO | 03/055482 A1 | 7/2003 |
| WO | 03/084997 A1 | 10/2003 |
| WO | 03/105788 A2 | 12/2003 |
| WO | 2004/035571 A1 | 4/2004 |
| WO | 2004/041163 A2 | 5/2004 |
| WO | 2004/063179 A1 | 7/2004 |
| WO | 2004/099168 A2 | 11/2004 |
| WO | 2005/000300 A1 | 1/2005 |
| WO | 2005/030755 A1 | 4/2005 |
| WO | 2005/044797 A1 | 5/2005 |
| WO | 2005/075435 A1 | 8/2005 |
| WO | 2006/014012 A2 | 2/2006 |
| WO | 2006/040520 A1 | 4/2006 |
| WO | 2006/080884 A1 | 8/2006 |
| WO | 2006/129199 A1 | 12/2006 |
| WO | 2006130403 A1 | 12/2006 |
| WO | 2007/028654 A1 | 3/2007 |
| WO | 2007/039420 A1 | 4/2007 |
| WO | 2007045462 A1 | 4/2007 |
| WO | 2007056341 A1 | 5/2007 |

MODULATORS OF ATP-BINDING CASSETTE TRANSPORTERS

CROSS-REFERENCE TO RELATED APPLICATIONS

The present application is a divisional patent application of and claims priority to U.S. patent application Ser. No. 12/114,935, filed May 5, 2008, which is a continuing application of and claims priority to International Application Serial No. PCT/US06/043289, filed Nov. 8, 2006, which claims the benefit, under 35 U.S.C. §119, of U.S. provisional patent application Ser. Nos. 60/734,506, filed on Nov. 8, 2005; 60/754,086, filed on Dec. 27, 2005; and 60/802,458, filed on May 22, 2006, the entire contents of each of above applications is incorporated herein by reference.

TECHNICAL FIELD OF THE INVENTION

The present invention relates to modulators of ATP-Binding Cassette ("ABC") transporters or fragments thereof, including Cystic Fibrosis Transmembrane Conductance Regulator ("CFTR"), compositions thereof, and methods therewith. The present invention also relates to methods of treating ABC transporter mediated diseases using such modulators.

BACKGROUND OF THE INVENTION

ABC transporters are a family of membrane transporter proteins that regulate the transport of a wide variety of pharmacological agents, potentially toxic drugs, and xenobiotics, as well as anions. ABC transporters are homologous membrane proteins that bind and use cellular adenosine triphosphate (ATP) for their specific activities. Some of these transporters were discovered as multi-drug resistance proteins (like the MDR1-P glycoprotein, or the multi-drug resistance protein, MRP1), defending malignant cancer cells against chemotherapeutic agents. To date, 48 ABC Transporters have been identified and grouped into 7 families based on their sequence identity and function.

ABC transporters regulate a variety of important physiological roles within the body and provide defense against harmful environmental compounds. Because of this, they represent important potential drug targets for the treatment of diseases associated with defects in the transporter, prevention of drug transport out of the target cell, and intervention in other diseases in which modulation of ABC transporter activity may be beneficial.

One member of the ABC transporter family commonly associated with disease is the cAMP/ATP-mediated anion channel, CFTR. CFTR is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in Cystic Fibrosis ("CF"), the most common fatal genetic disease in humans. Cystic Fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the Na$^+$—K$^+$-ATPase pump and Cl$^-$ channels expressed on the basolateral surface of the cell. Secondary active transport of chloride from the luminal side leads to the accumulation of intracellular chloride, which can then passively leave the cell via Cl$^-$ channels, resulting in a vectorial transport. Arrangement of Na$^+$/2Cl$^-$/K$^+$ co-transporter, Na$^+$—K$^+$-ATPase pump and the basolateral membrane K$^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to Cystic Fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome.

COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as Cystic Fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. The diseases associated with the first class of ER malfunction are Cystic fibrosis (due to misfolded ΔF508-CFTR as discussed above), Hereditary emphysema (due to a1-antitrypsin; non Piz variants), Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses (due to Lysosomal processing enzymes), Sandhof/Tay-Sachs (due to β-Hexosaminidase), Crigler-Najjar type II (due to UDP-glucuronyl-sialyc-transferase), Polyendocrinopathy/Hyperinsulemia, Diabetes mellitus (due to Insulin receptor), Laron dwarfism (due to Growth hormone receptor), Myleoperoxidase deficiency, Primary hypoparathyroidism (due to Preproparathyroid hormone), Melanoma (due to Tyrosinase). The diseases associated with the latter class of ER malfunction are Glycanosis CDG type 1, Hereditary emphysema (due to α1-Antitrypsin (PiZ variant), Congenital hyperthyroidism, Osteogenesis imperfecta (due to Type I, II, IV procollagen), Hereditary hypofibrinogenemia (due to Fibrinogen), ACT deficiency (due to α1-Antichymotrypsin), Diabetes insipidus (DI), Neurophyseal DI (due to Vasopvessin hormone/V2-receptor), Neprogenic DI (due to Aquaporin II), Charcot-Marie Tooth syndrome (due to Peripheral myelin protein 22), Perlizaeus-Merzbacher disease, neurodegenerative diseases such as Alzheimer's disease (due to βAPP and presenilins), Parkinson's disease, Amyotrophic lateral sclerosis, Progressive supranuclear plasy, Pick's disease, several polyglutamine neurological disorders a such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease (due to lysosomal α-galactosidase A) and Straussler-Scheinker syndrome (due to Prp processing defect).

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). 16 million travelers to developing countries from industrialized nations every year develop diarrhea, with the severity and number of cases of diarrhea varying depending on the country and area of travel.

Diarrhea in barn animals and pets such as cows, pigs, and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrhea causing bacteria is enterotoxogenic *E-coli* (ETEC) having the K99 pilus antigen. Common viral causes of diarrhea include rotavirus and coronavirus. Other infectious agents include cryptosporidium, *giardia lamblia*, and *salmonella*, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

Accordingly, there is a need for modulators of an ABC transporter activity, and compositions thereof, that can be used to modulate the activity of the ABC transporter in the cell membrane of a mammal.

There is a need for methods of treating ABC transporter mediated diseases using such modulators of ABC transporter activity.

There is a need for methods of modulating an ABC transporter activity in an ex vivo cell membrane of a mammal.

There is a need for modulators of CFTR activity that can be used to modulate the activity of CFTR in the cell membrane of a mammal.

There is a need for methods of treating CFTR-mediated diseases using such modulators of CFTR activity.

There is a need for methods of modulating CFTR activity in an ex vivo cell membrane of a mammal.

SUMMARY OF THE INVENTION

It has now been found that compounds of this invention, and pharmaceutically acceptable compositions thereof, are useful as modulators of ABC transporter activity. These compounds have the general formula (I):

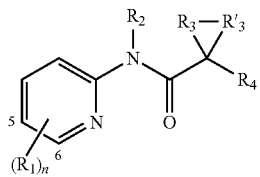

or a pharmaceutically acceptable salt thereof, wherein $R_1$, $R_2$, $R_3$, $R'_3$, $R_4$, and n are described herein.

These compounds and pharmaceutically acceptable compositions are useful for treating or lessening the severity of a variety of diseases, disorders, or conditions, including, but not limited to, cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes Mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes Insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders a such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease, Fabry disease, Straussler-Scheinker syndrome, COPD, dry-eye disease, and Sjogren's disease.

DETAILED DESCRIPTION OF THE INVENTION

Definitions

As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cft/, for CFTR mutations).

The term "modulating" as used herein means increasing or decreasing, e.g. activity, by a measurable amount. Compounds that modulate ABC Transporter activity, such as CFTR activity, by increasing the activity of the ABC Transporter, e.g., a CFTR anion channel, are called agonists. Compounds that modulate ABC Transporter activity, such as CFTR activity, by decreasing the activity of the ABC Transporter, e.g., CFTR anion channel, are called antagonists. An agonist interacts with an ABC Transporter, such as CFTR anion channel, to increase the ability of the receptor to transduce an intracellular signal in response to endogenous ligand binding. An antagonist interacts with an ABC Transporter, such as CFTR, and competes with the endogenous ligand(s) or substrate(s) for binding site(s) on the receptor to decrease the ability of the receptor to transduce an intracellular signal in response to endogenous ligand binding.

The phrase "treating or reducing the severity of an ABC Transporter mediated disease" refers both to treatments for diseases that are directly caused by ABC Transporter and/or CFTR activities and alleviation of symptoms of diseases not directly caused by ABC Transporter and/or CFTR anion channel activities. Examples of diseases whose symptoms may be affected by ABC Transporter and/or CFTR activity include, but are not limited to, Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders a such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B. and March, J., John Wiley & Sons, New York: 2001, the entire contents of which are hereby incorporated by reference.

For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

As used herein the term "aliphatic' encompasses the terms alkyl, alkenyl, alkynyl, each of which being optionally substituted as set forth below.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino], amino [e.g., aliphaticamino, cycloaliphaticamino, or heterocycloaliphaticamino], sulfonyl [e.g., aliphaticsulfonyl], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, hydroxyalkyl, aralkyl, (alkoxyaryl)alkyl, (sulfonylamino)alkyl (such as (alkylsulfonylamino)alkyl), aminoalkyl, amidoalkyl, (cycloaliphatic)alkyl, cyanoalkyl, or haloalkyl.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo, cycloaliphatic, heterocycloaliphatic, aryl, heteroaryl, alkoxy, aroyl, heteroaroyl, acyl [e.g., (cycloaliphatic)carbonyl, or (heterocycloaliphatic)carbonyl], nitro, cyano, acyl [e.g., aliphaticcarbonyl, cycloaliphaticcarbonyl, arylcarbonyl, heterocycloaliphaticcarbonyl or heteroarylcarbonyl], amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, or aliphaticsulfonylamino], sulfonyl [e.g., alkylsulfonyl, cycloaliphaticsulfonyl, or arylsulfonyl], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphaticsulfonyl, aliphaticaminosulfonyl, or cycloaliphaticsulfonyl], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino" These terms when used alone or in connection with another group refers to an amido group such as $N(R^X R^Y)$—C(O)— or $R^Y C(O)$—$N(R^X)$— when used terminally and —C(O)—$N(R^X)$— or —$N(R^X)$—C(O)— when used internally, wherein $R^X$ and $R^Y$ are defined below. Examples of amido groups include alkylamido (such as alkylcarbonylamino or alkylcarbonylamino), (heterocycloaliphatic)amido, (heteroaralkyl)amido, (heteroaryl) amido, (heterocycloalkyl)alkylamido, arylamido, aralkylamido, (cycloalkyl)alkylamido, or cycloalkylamido.

As used herein, an "amino" group refers to —$NR^X R^Y$ wherein each of $R^X$ and $R^Y$ is independently hydrogen, alkyl, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic) carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic) carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—. R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic ring systems include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl or cycloaliphaticsulfinyl]; sulfanyl [e.g., aliphaticsulfanyl]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p, m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, azacycloalkyl, or ((aminocarbonyl)cycloalkyl)cycloalkyl. A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl. A cycloalkyl or cycloalkenyl group can be optionally substituted with one or more substituents such as aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkylsulfonyl and arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

As used herein, "cyclic moiety" includes cycloaliphatic, heterocycloaliphatic, aryl, or heteroaryl, each of which has been defined previously.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicyclic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo [3.3.1.0$^{3,7}$]nonyl. A monocyclic heterocycloalkyl group can be fused with a phenyl moiety such as tetrahydroisoquinoline. A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicycloheteroaliphatics are numbered according to standard chemical nomenclature.

A heterocycloalkyl or heterocycloalkenyl group can be optionally substituted with one or more substituents such as aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pyranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl) amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; [((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaraliphatic" (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" includes cycloalkyl, heterocycloalkyl, cycloalkenyl, heterocycloalkenyl, aryl, or heteroaryl, each of which has been defined previously.

As used herein, an "acyl" group refers to a formyl group or $R^X$—C(O)— (such as -alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—$NR^XR^Y$ or —$NR^X$—OO—O—$R^Z$ wherein $R^X$ and $R^Y$ have been defined above and $R^Z$ can be aliphatic, aryl, araliphatic, heterocycloaliphatic, heteroaryl, or heteroaraliphatic.

As used herein, a "carboxy" group refers to —COOH, —COOR$^X$, —OC(O)H, —OC(O)$R^X$ when used as a terminal group; or —OC(O)— or —C(O)O— when used as an internal group.

As used herein, a "haloaliphatic" group refers to an aliphatic group substituted with 1, 2, or 3 halogen. For instance, the term haloalkyl includes the group —$CF_3$.

As used herein, a "mercapto" group refers to —SH.

As used herein, a "sulfo" group refers to —$SO_3H$ or —$SO_3R^X$ when used terminally or —$S(O)_3$— when used internally.

As used herein, a "sulfamide" group refers to the structure —$NR^X$—$S(O)_2$—$NR^YR^Z$ when used terminally and —$NR^X$—$S(O)_2$—$NR^Y$— when used internally, wherein $R^X$, $R^Y$, and $R^Z$ have been defined above.

As used herein, a "sulfamoyl" group refers to the structure —$S(O)_2$—$NR^XR^Y$ or —$NR^X$—$S(O)_2$—$R^Z$ when used terminally; or —$S(O)_2$—$NR^X$— or —$NR^X$—$S(O)_2$— when used internally, wherein $R^X$, $R^Y$, and $R^Z$ are defined above.

As used herein a "sulfanyl" group refers to —S—$R^X$ when used terminally and —S— when used internally, wherein $R^X$ has been defined above. Examples of sulfanyls include alkylsulfanyl.

As used herein a "sulfinyl" group refers to —S(O)—$R^X$ when used terminally and —S(O)— when used internally, wherein $R^X$ has been defined above.

As used herein, a "sulfonyl" group refers to —$S(O)_2$—$R^X$ when used terminally and —$S(O)_2$— when used internally, wherein $R^X$ has been defined above.

As used herein, a "sulfoxy" group refers to —O—SO—$R^X$ or —SO—O—$R^X$, when used terminally and —O—S(O)— or —S(O)—O— when used internally, where $R^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, an "aminoalkyl" refers to the structure $(R^XR^Y)$N-alkyl-.

As used herein, a "cyanoalkyl" refers to the structure (NC)-alkyl-.

As used herein, a "urea" group refers to the structure —$NR^X$—CO—$NR^YR^Z$ and a "thiourea" group refers to the structure —$NR^X$—CS—$NR^YR^Z$ when used terminally and —$NR^x$—CO—$NR^Y$— or —$NR^X$—CS—$NR^Y$— when used internally, wherein $R^X$, $R^Y$, and $R^Z$ have been defined above.

As used herein, a "guanidino" group refers to the structure —N=C(N($R^X R^Y$))N($R^XR^Y$) wherein $R^X$ and $R^Y$ have been defined above.

As used herein, the term "amidino" group refers to the structure —C=(NR$^X$)N($R^XR^Y$) wherein $R^X$ and $R^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^XO(O)$C-alkyl is an example of a carboxy group used terminally. A group is internal when the group is present in the middle of a substituent to at the end of the substituent bound to the rest of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, the term "amidino" group refers to the structure —C=(NR$^X$)N($R^XR^Y$) wherein $R^X$ and e have been defined above.

As used herein, "cyclic group" includes mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aliphatic chain" refers to a branched or straight aliphatic group (e.g., alkyl groups, alkenyl groups, or alkynyl groups). A straight aliphatic chain has the structure —$[CH_2]_v$—, where v is 1-6. A branched aliphatic chain is a straight aliphatic chain that is substituted with one or more aliphatic groups. A branched aliphatic chain has the structure —$[CHQ]_v$— where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_2$, $R_3$, and $R_4$, and other variables contained therein formulae I encompass specific groups, such as alkyl and aryl. Unless otherwise noted, each of the specific groups for the variables $R_1$, $R_2$, $R_3$, and $R_4$, and other variables contained therein can be optionally substituted with one or more substituents described herein. Each substituent of a specific group is further optionally substituted with one to three of halo, cyano, oxoalkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxoalkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "up to", as used herein, refers to zero or any integer number that is equal or less than the number following the phrase. For example, "up to 3" means any one of 0, 1, 2, and 3.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.,* 50: 219 (1966). Body surface area may be approximately determined from height and weight of the patient. See, e.g., Scientific Tables, Geigy Pharmaceuticals, Ardsley, N.Y. , 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Compounds

Compounds of the present invention are useful modulators of ABC transporters and are useful in the treatment of ABC transport mediated diseases.

A. Generic Compounds

The present invention includes a compound of formula (I),

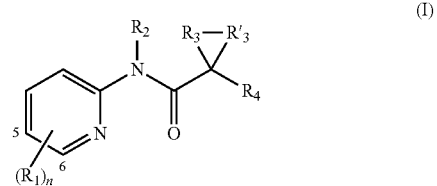

or a pharmaceutically acceptable salt thereof, wherein:

Each $R_1$ is an optionally substituted $C_{1-6}$ aliphatic, an optionally substituted aryl, an optionally substituted heteroaryl, an optionally substituted $C_{3-10}$ cycloaliphatic, an optionally substituted 3 to 10 membered heterocycloaliphatic, carboxy [e.g., hydroxycarbonyl or alkoxycarbonyl], amido [e.g., aminocarbonyl], amino, halo, or hydroxy;

provided that at least one $R_1$ is an optionally substituted cycloaliphatic, an optionally substituted heterocycloaliphatic, an optionally substituted aryl, or an optionally substituted heteroaryl attached to the 5- or 6-position of the pyridyl ring;

Each $R_2$ is hydrogen, an optionally substituted $C_{1-6}$ aliphatic, an optionally substituted $C_{3-6}$ cycloaliphatic, an optionally substituted phenyl, or an optionally substituted heteroaryl;

Each $R_3$ and $R'_3$ together with the carbon atom to which they are attached form an optionally substituted $C_{3-7}$ cycloaliphatic or an optionally substituted heterocycloaliphatic;

Each $R_4$ is an optionally substituted aryl or an optionally substituted heteroaryl; and Each n is 1, 2, 3 or 4.

In another aspect, the present invention includes compounds of formula (I'):

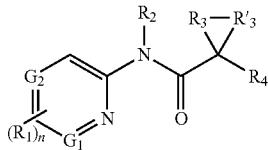

or a pharmaceutically acceptable salt thereof,
wherein:
one of $G_1$ and $G_2$ is a nitrogen, and the other is a carbon; and $R_1$, $R_2$, $R_3$, $R'_3$, $R_4$, and n are defined above.

Specific Embodiments

A. Substituent $R_1$

Each $R_1$ is independently an optionally substituted $C_{1-6}$ aliphatic, an optionally substituted aryl, an optionally substituted heteroaryl, an optionally substituted $C_{3-10}$ membered cycloaliphatic, an optionally substituted 3 to 10 membered heterocycloaliphatic, carboxy [e.g., hydroxycarbonyl or alkoxycarbonyl], amido [e.g., aminocarbonyl], amino, halo, or hydroxy.

In some embodiments, one $R_1$ is an optionally substituted $C_{1-6}$ aliphatic. In several examples, one $R_1$ is an optionally substituted $C_{1-6}$ alkyl, an optionally substituted $C_{2-6}$ alkenyl, or an optionally substituted $C_{2-6}$ alkynyl. In several examples, one $R_1$ is $C_{1-6}$ alkyl, $C_{2-6}$ alkenyl, or $C_{2-6}$ alkynyl.

In several embodiments, one $R_1$ is an aryl or heteroaryl with 1, 2, or 3 substituents. In several examples, one $R_1$ is a monocyclic aryl or heteroaryl. In several embodiments, $R_1$ is an aryl or heteroaryl with 1, 2, or 3 substituents. In several examples, $R_1$ is a monocyclic aryl or heteroaryl.

In several embodiments, at least one $R_1$ is an optionally substituted aryl or an optionally substituted heteroaryl and $R_1$ is bonded to the core structure at the 6 position on the pyridine ring.

In several embodiments, at least one $R_1$ is an optionally substituted aryl or an optionally substituted heteroaryl and $R_1$ is bonded to the core structure at the 5 position on the pyridine ring.

In several embodiments, one $R_1$ is phenyl with up to 3 substituents. In several embodiments, $R_1$ is phenyl with up to 3 substituents.

In several embodiments, one $R_1$ is a heteroaryl ring with up to 3 substituents. In certain embodiments, one $R_1$ is a monocyclic heteroaryl ring with up to 3 substituents. In other embodiments, one $R_1$ is a bicyclic heteroaryl ring with up to 3 substituents. In several embodiments, $R_1$ is a heteroaryl ring with up to 3 substituents. In certain embodiments, $R_1$ is a monocyclic heteroaryl ring with up to 3 substituents. In other embodiments, $R_1$ is a bicyclic heteroaryl ring with up to 3 substituents.

In several embodiments, one $R_1$ is carboxy [e.g., hydroxycarbonyl or alkoxycarbonyl]. Or, one $R_1$ is amido [e.g., aminocarbonyl]. Or, one $R_1$ is amino. Or, is halo. Or, is cyano. Or, hydroxyl.

In some embodiments, $R_1$ is hydrogen, methyl, ethyl, i-propyl, t-butyl, cyclopropyl, cyclobutyl, cyclopentyl, cyclohexyl, allyl, F, Cl, methoxy, ethoxy, i-propoxy, t-butoxy, $CF_3$, $OCF_3$, CN, hydroxyl, or amino. In several examples, $R_1$ is hydrogen, methyl, methoxy, F, $CF_3$ or $OCF_3$. In several examples, $R_1$ can be hydrogen. Or, $R_1$ can be methyl. Or, $R_1$ can be $CF_3$. Or, $R_1$ can be methoxy.

In several embodiments, $R_1$ is substituted with no more than three substituents selected from halo, oxo, or optionally substituted aliphatic, cycloaliphatic, heterocycloaliphatic, amino [e.g., (aliphatic)amino], amido [e.g., aminocarbonyl, ((aliphatic)amino)carbonyl, and ((aliphatic)$_2$-amino)carbonyl], carboxy [e.g., alkoxycarbonyl and hydroxycarbonyl], sulfamoyl [e.g., aminosulfonyl, ((aliphatic)$_2$amino)sulfonyl, ((cycloaliphatic)aliphatic)aminosulfonyl, and ((cycloaliphatic)amino)sulfonyl], cyano, alkoxy, aryl, heteroaryl [e.g., monocyclic heteroaryl and bicycloheteroaryl], sulfonyl [e.g., aliphaticsulfonyl or (heterocycloaliphatic)sulfonyl], sulfinyl [e.g., aliphaticsulfinyl], aroyl, heteroaroyl, or heterocycloaliphaticcarbonyl.

In several embodiments, $R_1$ is substituted with halo. Examples of $R_1$ substituents include F, Cl, and Br. In several examples, $R_1$ is substituted with F.

In several embodiments, $R_1$ is substituted with an optionally substituted aliphatic. Examples of $R_1$ substituents include optionally substituted alkoxyaliphatic, heterocycloaliphatic, aminoalkyl, hydroxyalkyl, (heterocycloalkyl)aliphatic, alkylsulfonylaliphatic, alkylsulfonylaminoaliphatic, alkylcarbonylaminoaliphatic, alkylaminoaliphatic, or alkylcarbonylaliphatic.

In several embodiments, $R_1$ is substituted with an optionally substituted amino Examples of $R_1$ substituents include aliphaticcarbonylamino, aliphaticamino, arylamino, or aliphaticsulfonylamino.

In several embodiments, $R_1$ is substituted with a sulfonyl. Examples of $R_1$ substituents include heterocycloaliphaticsulfonyl, aliphatic sulfonyl, aliphaticaminosulfonyl, aminosulfonyl, aliphaticcarbonylaminosulfonyl, alkoxyalkylheterocycloalkylsulfonyl, alkylheterocycloalkylsulfonyl, alkylaminosulfonyl, cycloalkylaminosulfonyl, (heterocycloalkyl)alkylaminosulfonyl, and heterocycloalkylsulfonyl.

In several embodiments, $R_1$ is substituted with carboxy. Examples of $R_1$ substituents include alkoxycarbonyl and hydroxycarbonyl.

In several embodiments $R_1$ is substituted with amido. Examples of $R_1$ substituents include alkylaminocarbonyl, aminocarbonyl, ((aliphatic)$_2$amino)carbonyl, and [((aliphatic)aminoaliphatic)amino]carbonyl.

In several embodiments, $R_1$ is substituted with carbonyl. Examples of $R_1$ substituents include arylcarbonyl, cycloaliphaticcarbonyl, heterocycloaliphaticcarbonyl, and heteroarylcarbonyl.

In some embodiments, $R_1$ is hydrogen. In some embodiments, $R_1$ is $-Z^A R_5$, wherein each $Z^A$ is independently a bond or an optionally substituted branched or straight $C_{1-6}$ aliphatic chain wherein up to two carbon units of $Z^A$ are optionally and independently replaced by $-CO-$, $-CS-$, $-CONR^A-$, $-CONR^A NR^A-$, $-CO_2-$, $-OCO-$, $-NR^A CO_2-$, $-O-$, $-NR^A CONR^A-$, $-OCONR^A-$, $-NR^A NR^A-$, $-NR^A CO-$, $-S-$, $-SO-$, $-SO_2-$, $-NR^A-$, $-SO_2 NR^A-$, $-NR^A SO_2-$, or $-NR^A SO_2 NR^A-$. Each $R_5$ is independently $R^A$, halo, $-OH$, $-NH_2$, $-NO_2$, $-CN$, $-CF_3$, or $-OCF_3$. Each $R^A$ is independently a $C_{1-8}$ aliphatic group, a cycloaliphatic, a heterocycloaliphatic, an aryl, or a heteroaryl, each of which is optionally substituted with 1, 2, or 3 of $R^D$. Each $R^D$ is $-Z^D R_9$, wherein each $Z^D$ is independently a bond or an optionally substituted branched or straight $C_{1-6}$ aliphatic chain wherein up to two carbon units of $Z^D$ are optionally and independently replaced by $-CO-$, $-CS-$, $-CONR^E-$, $-CONR^E NR^E-$, $-CO_2-$, $-OCO-$, $-NR^E CO_2-$, $-O-$, $-NR^E CONR^E-$, $-OCONR^E-$, $-NR^E NR^E-$, —NR$^E$CO—, —S—, —SO—, —SO$_2$—, —NR$^E$—, —SO$_2$NR$^E$—, —NR$^E$SO$_2$—, or —NR$^E$SO$_2$NR$^E$—. Each R$_9$ is independently R$^E$, halo, —OH, —NH$_2$, —NO$_2$, —CN, —CF$_3$, or —OCF$_3$. Each R$^E$ is independently hydrogen, an optionally substituted C$_{1-8}$ aliphatic group, an optionally substituted cycloaliphatic, an optionally substituted heterocycloaliphatic, an optionally substituted aryl, or an optionally substituted heteroaryl.

In some embodiments, each R$^D$ is independently —Z$^D$R$_9$; wherein each Z$^D$ can independently be a bond or an optionally substituted branched or straight C$_{1-6}$ aliphatic chain wherein up to two carbon units of Z$^D$ are optionally and independently replaced by —O—, —NHC(O)—, —C(O)NR$^E$—, —SO$_2$—, —NHSO$_2$—, —NHC(O)—, —NR$^E$SO$_2$—, —SO$_2$NH—, —SO$_2$NR$^E$—, —NH—, or —C(O)O—. In some embodiments, one carbon unit of Z$^D$ is replaced by —O—. Or, by —NHC(O)—. Or, by —C(O)NR$^E$—. Or, by —SO$_2$—. Or, by —NHSO$_2$—. Or, by —NHC(O)—. Or, by —SO—. Or, by —NR$^E$SO$_2$—. Or, by —SO$_2$NH—. Or, by —SO$_2$NR$^E$—. Or, by —NH—. Or, by —C(O)O—.

In some embodiments, R$_9$ is hydrogen. In some embodiments, R$_9$ is independently an optionally substituted aliphatic. In some embodiments, R$_9$ is an optionally substituted cycloaliphatic. Or, is an optionally substituted heterocycloaliphatic. Or, is an optionally substituted aryl. Or, is an optionally substituted heteroaryl. Or, halo.

In some embodiments, one R$_1$ is aryl or heteroaryl, each optionally substituted with 1, 2, or 3 of R$^D$, wherein R$^D$ is defined above.

In several embodiments, one R$_1$ is carboxy [e.g., hydroxycarbonyl or alkoxycarbonyl]. Or, one R$_1$ is amido [e.g., aminocarbonyl]. Or, one R$_1$ is amino Or, is halo. Or, is cyano. Or, hydroxyl.

In some embodiments, one R$_1$ that is attached to 5- or 6-position of the pyridyl ring is aryl or heteroaryl, each optionally substituted with 1, 2, or 3 of R$^D$, wherein R$^D$ is defined above. In some embodiments, the one R$_1$ attached to the 5- or 6-position of the pyridyl ring is phenyl optionally substituted with 1, 2, or 3 of R$^D$, wherein R$^D$ is defined above. In some embodiments, the one R$_1$ attached to the 5- or 6-position of the pyridyl ring is heteroaryl optionally substituted with 1, 2, or 3 of R$^D$. In several embodiments, the one R$_1$ attached to the 5- or 6-position of the pyridyl ring is 5 or 6 membered heteroaryl having 1, 2, or 3 heteroatom independently selected from the group consisting of oxygen, nitrogen and sulfur. In other embodiments, the 5 or 6 membered heteroaryl is substituted with 1 R$^D$.

In some embodiments, one R$_1$ attached to the 5- or 6-position of the pyridyl ring is a phenyl substituted with 1 R$^D$. In some embodiments, one R$_1$ attached to the 5- or 6-position of the pyridyl ring is a phenyl substituted with 2 R$^D$. In some embodiments, one R$_1$ attached to the 5- or 6-position of the pyridyl ring is a phenyl substituted with 3 R$^D$.

In several embodiments, R$_1$ is:

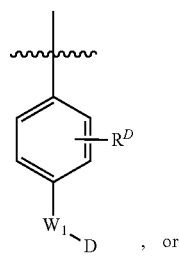

(Z-1)

, or

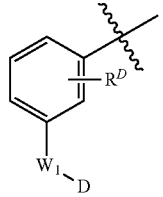

(Z-2)

wherein

W$_1$ is —C(O)—, —SO$_2$—, or —CH$_2$—;

D is H, hydroxyl, or an optionally substituted group selected from aliphatic, cycloaliphatic, alkoxy, and amino; and R$^D$ is defined above.

In several embodiments, W$_1$ is —C(O)—. Or, W$_1$ is —SO$_2$—. Or, W$_1$ is —CH$_2$—.

In several embodiments, D is OH. Or, D is an optionally substituted C$_{1-6}$ aliphatic or an optionally substituted C$_3$-C$_8$ cycloaliphatic. Or, D is an optionally substituted alkoxy. Or, D is an optionally substituted amino

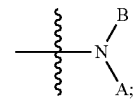

In several examples, D is wherein each of A and B is independently H, an optionally substituted C$_{1-6}$ aliphatic, an optionally substituted C$_3$-C$_8$ cycloaliphatic, or A and B, taken together, form an optionally substituted 3-7 membered heterocycloaliphatic ring.

In several embodiments, A is H and B is an optionally substituted C$_{1-6}$ aliphatic. In several embodiments, B is substituted with 1, 2, or 3 substituents. Or, both, A and B, are H. Exemplary substituents include oxo, alkyl, hydroxy, hydroxyalkyl, alkoxy, alkoxyalkyl, dialkyamino, or an optionally substituted group selected from cycloaliphatic, heterocycloaliphatic, aryl, and heteroaryl.

In several embodiments, A is H and B is an optionally substituted C$_{1-6}$ aliphatic. Or, both, A and B, are H. Exemplary substituents include oxo, alkyl, hydroxy, hydroxyalkyl, alkoxy, alkoxyalkyl, and an optionally substituted heterocycloaliphatic.

In several embodiments, B is C$_{1-6}$ alkyl, optionally substituted with oxo, alkyl, hydroxy, hydroxyalkyl, alkoxy, alkoxyalkyl, or an optionally substituted group selected from cycloaliphatic, heterocycloaliphatic, aryl, and heteroaryl. In several embodiments, B is substituted with oxo, C$_{1-6}$ alkyl, hydroxy, hydroxy-(C$_{1-6}$)alkyl, (C$_{1-6}$)alkoxy, (C$_{1-6}$)alkoxy (C$_{1-6}$)alkyl, C$_{3-8}$ cycloaliphatic, 3-8 membered heterocycloaliphatic, phenyl, and 5-10 membered heteroaryl. In one example, B is C$_{1-6}$ alkyl substituted with optionally substituted phenyl.

In several embodiments, A and B, taken together, form an optionally substituted 3-7 membered heterocycloaliphatic ring. In several examples, the heterocycloaliphatic ring is optionally substituted with 1, 2, or 3 substituents. Exemplary such rings include optionally substituted pyrrolidinyl, piperidinyl, morpholinyl, and piperazinyl. Exemplary substituents on such rings include halo, oxo, alkyl, hydroxy, hydroxyalkyl, alkoxy, alkoxyalkyl, acyl (e.g., alkylcarbonyl), amino, amido, and carboxy. In some embodiments, the substituent is halo, oxo, alkyl, hydroxy, hydroxyalkyl, alkoxy, alkoxyalkyl, amino, amido, or carboxy.

In several embodiments, $R^D$ is hydrogen, halo, or an optionally substituted group selected from aliphatic, cycloaliphatic, amino, hydroxy, alkoxy, carboxy, amido, carbonyl, cyano, aryl, or heteroaryl. In several examples, $R^D$ is hydrogen, halo, an optionally substituted $C_{1-6}$ aliphatic, or an optionally substituted alkoxy. In several examples, $R^D$ is hydrogen, F, Cl, an optionally substituted $C_{1-6}$ alkyl, or an optionally substituted —O($C_{1-6}$ alkyl). Examples of $R^D$ include hydrogen, F, Cl, methyl, ethyl, i-propyl, t-butyl, —OMe, —OEt, 1-propoxy, t-butoxy, $CF_3$, or —$OCF_3$. In some examples, $R^D$ is hydrogen, F, methyl, methoxy, $CF_3$, or —$OCF_3$. $R^D$ can be hydrogen. $R^D$ can be F. $R^D$ can be methyl. $R^D$ can be methoxy.

In several embodiments, $R_1$ is:

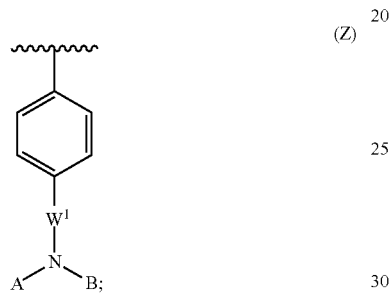

wherein:
$W_1$ is —C(O)—, —$SO_2$—, or —$CH_2$—;
Each of A and B is independently H, an optionally substituted $C_{1-6}$ aliphatic, an optionally substituted $C_3$-$C_8$ cycloaliphatic; or
A and B, taken together, form an optionally substituted 3-7 membered heterocycloaliphatic ring.

In some embodiments, one $R_1$ that is attached to the 5- or 6-position of the pyridyl ring is cycloaliphatic or heterocycloaliphatic, each optionally substituted with 1, 2, or 3 of $R^D$; wherein $R^D$ is —$Z^DR_9$; wherein each $Z^D$ is independently a bond or an optionally substituted branched or straight $C_{1-6}$ aliphatic chain wherein up to two carbon units of $Z^D$ are optionally and independently replaced by —CO—, —CS—, —$CONR^E$—, —$CONR^ENR^E$—, —$CO_2$—, —OCO—, $NR^ECO_2$—, —O—, —$NR^ECONR^E$—, —$OCONR^E$—, —$NR^ENR^E$—, —$NR^ECO$—, —S—, —SO—, —$SO_2$—, —$NR^E$—, —$SO_2NR^E$—, —$NR^ESO_2$—, or —$NR^ESO_2NR^E$—; each $R_9$ is independently $R^E$, halo, —OH, —$NH_2$, —$NO_2$, —CN, —$CF_3$, or —$OCF_3$; and each $R^E$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

In several examples, one $R_1$ that is attached to the 5- or 6-position of the pyridyl ring is an optionally substituted $C_3$-$C_8$ cycloaliphatic.

In some embodiments, one $R_1$ that is attached to the 5- or 6-position of the pyridyl ring is an optionally substituted $C_3$-$C_8$ cycloalkyl or an optionally substituted $C_3$-$C_8$ cycloalkenyl.

In several embodiments, one $R_1$ that is attached to the 5- or 6-position of the pyridyl ring is $C_3$-$C_8$ cycloalkyl or $C_3$-$C_8$ cycloalkenyl. Examples of cycloalkyl and cycloalkenyl include cyclopropyl, cyclobutyl, cyclopentyl, cyclohexyl, cycloheptyl, cyclopentenyl, cyclohexenyl, and cycloheptenyl.

In some embodiments, R1 is:

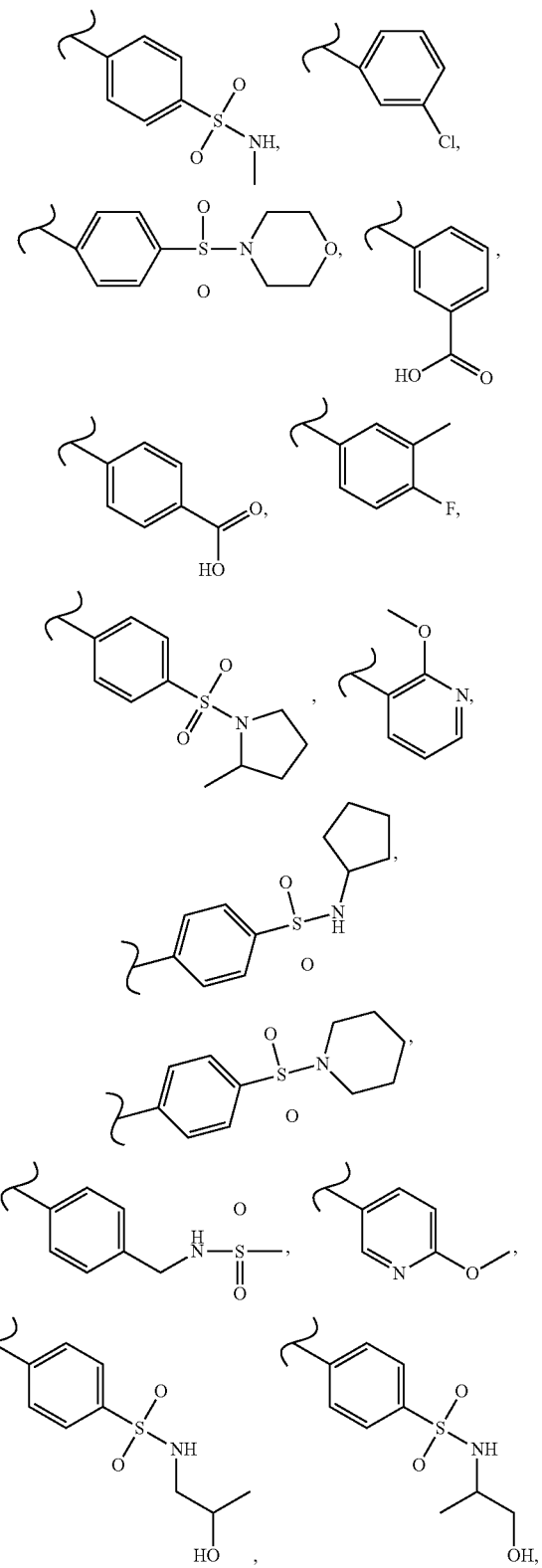

23
-continued
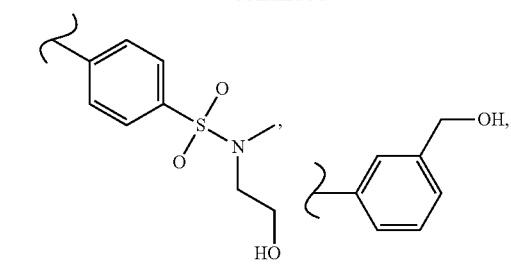
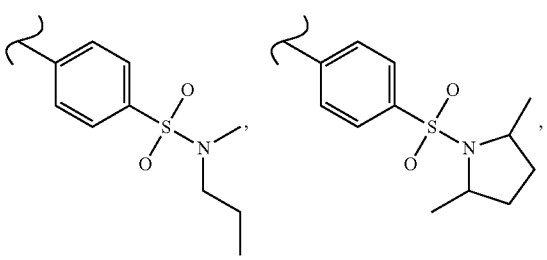
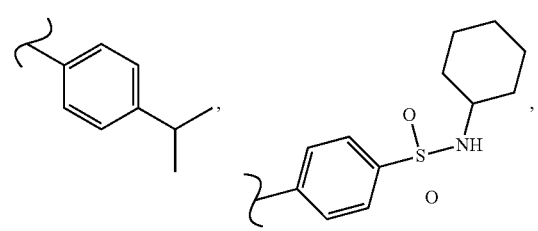
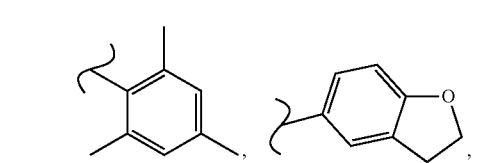
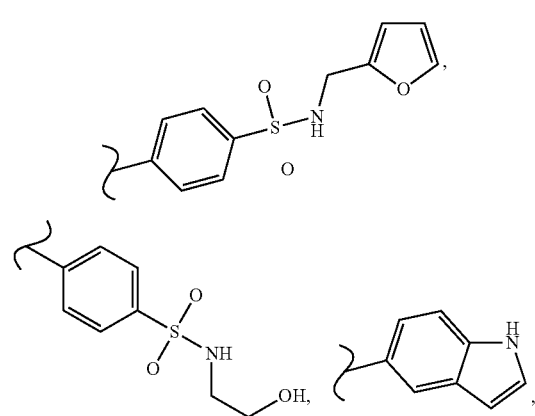
24
-continued
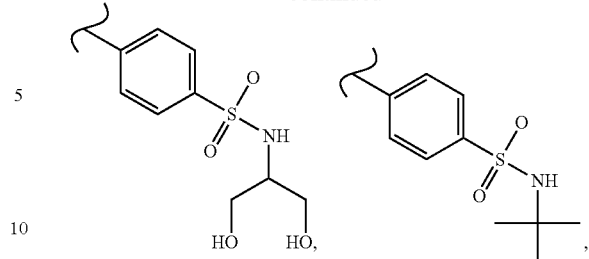
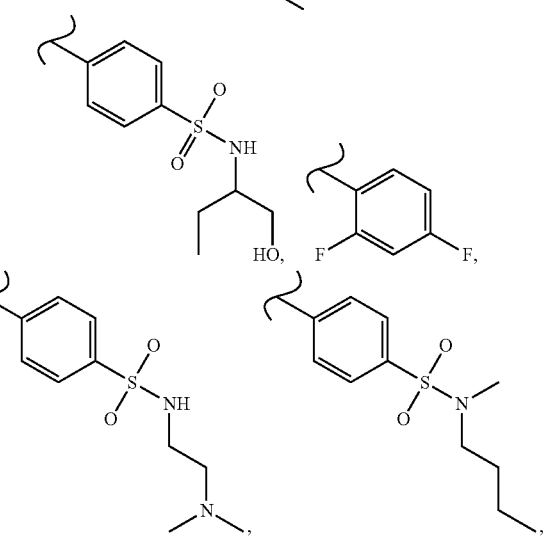
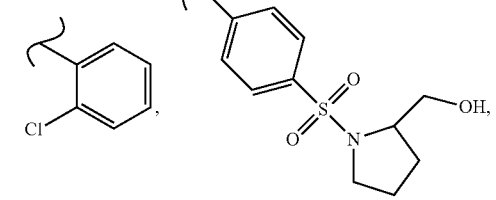
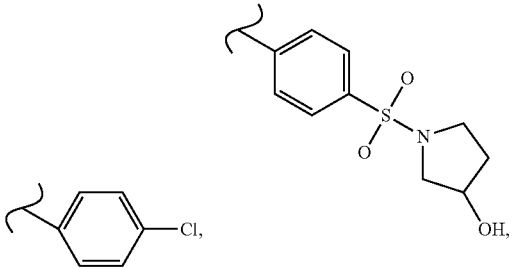

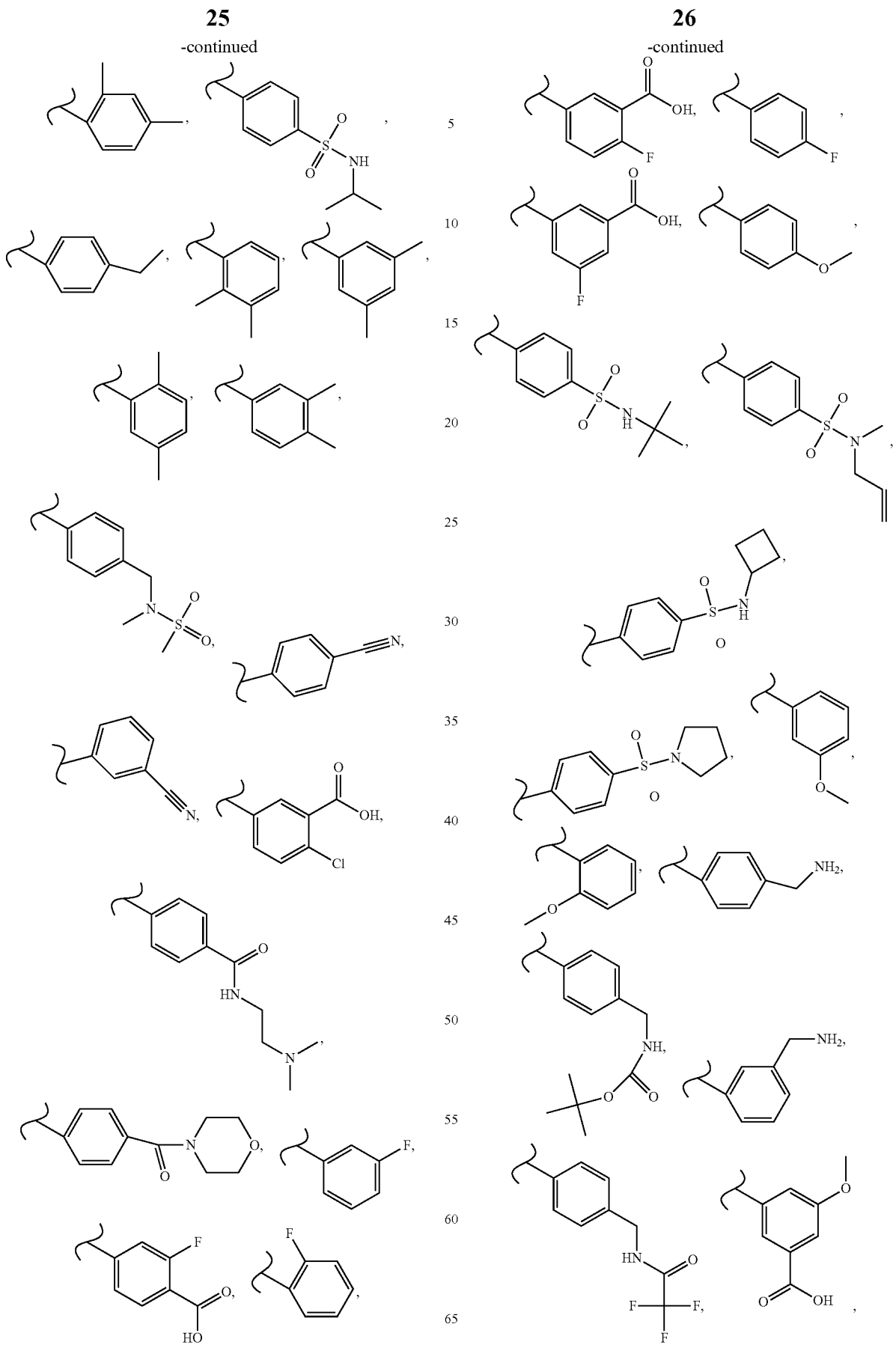

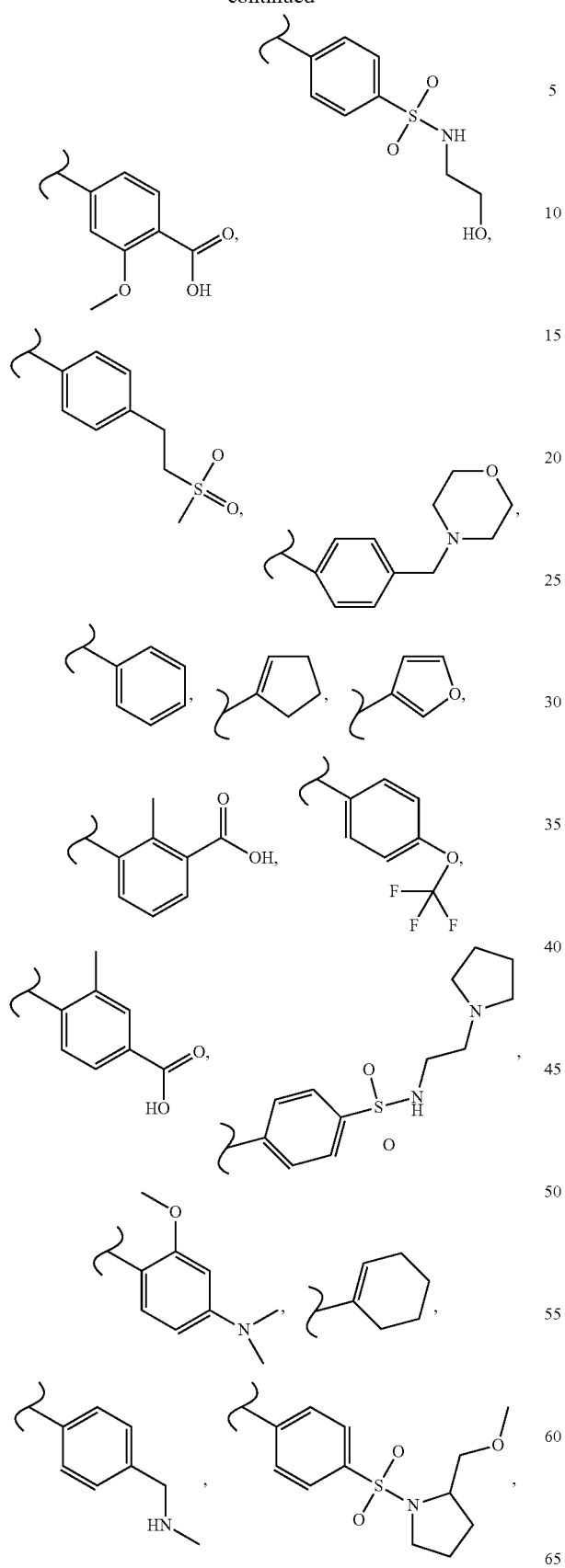
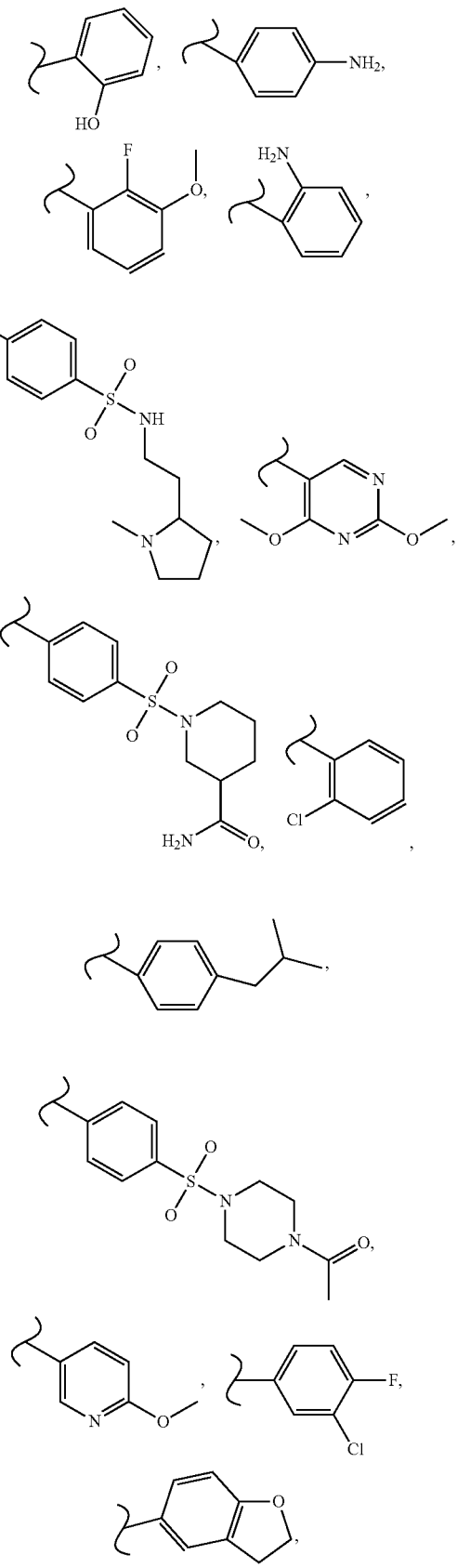

-continued
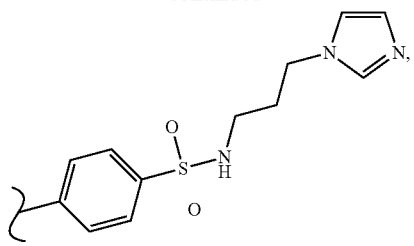
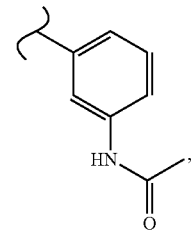
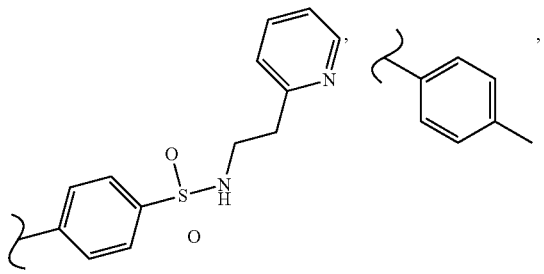
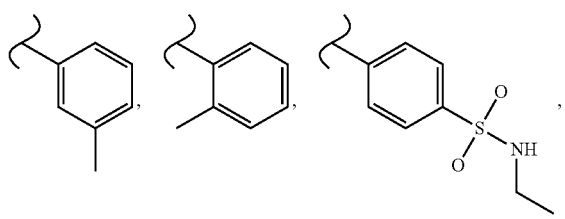
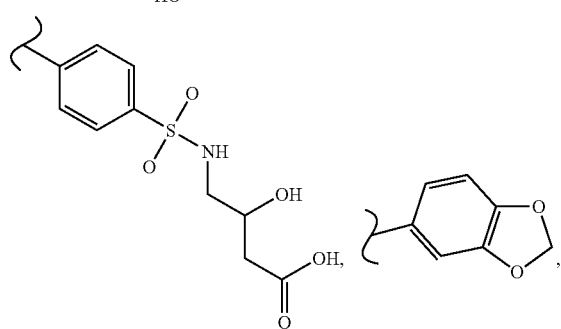
-continued
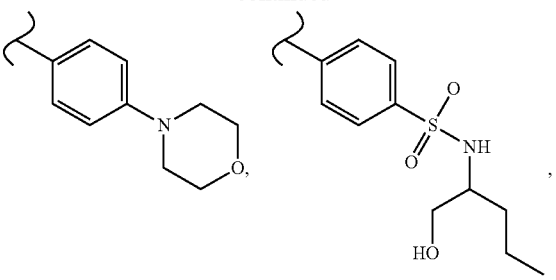
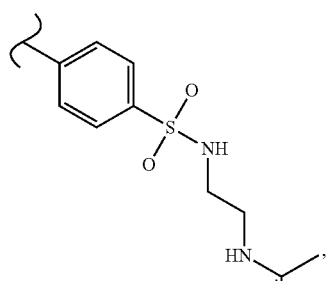 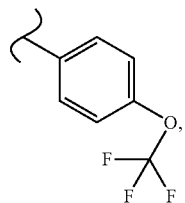
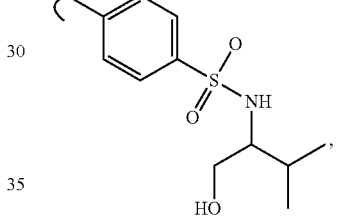 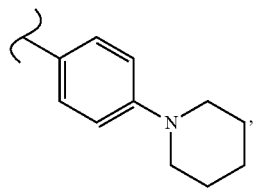
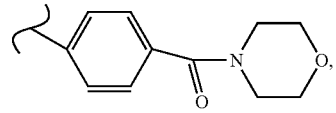
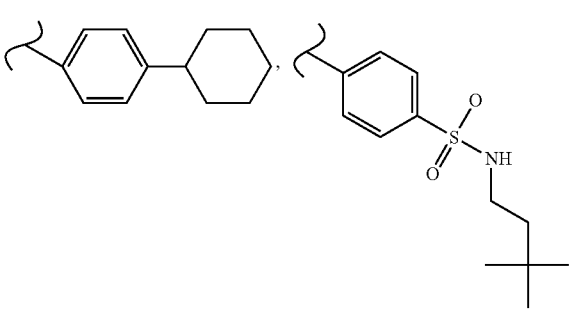
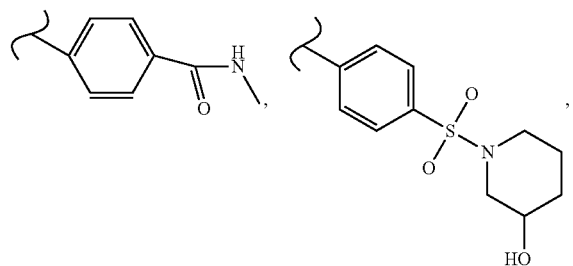

-continued
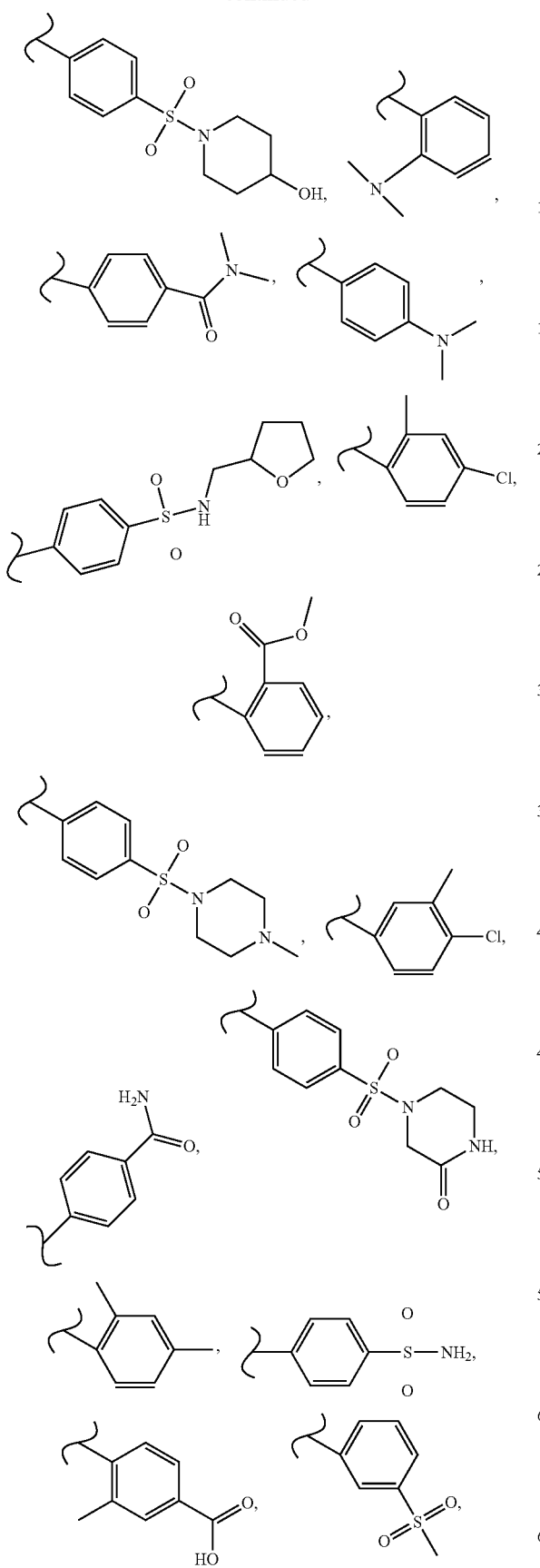
-continued
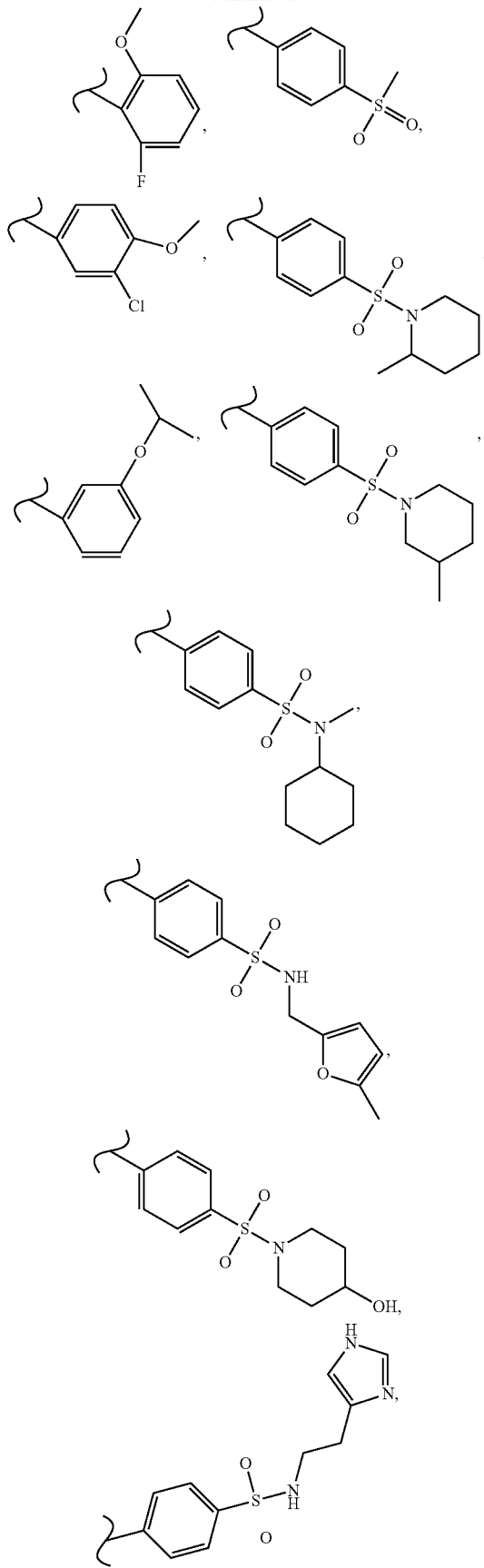

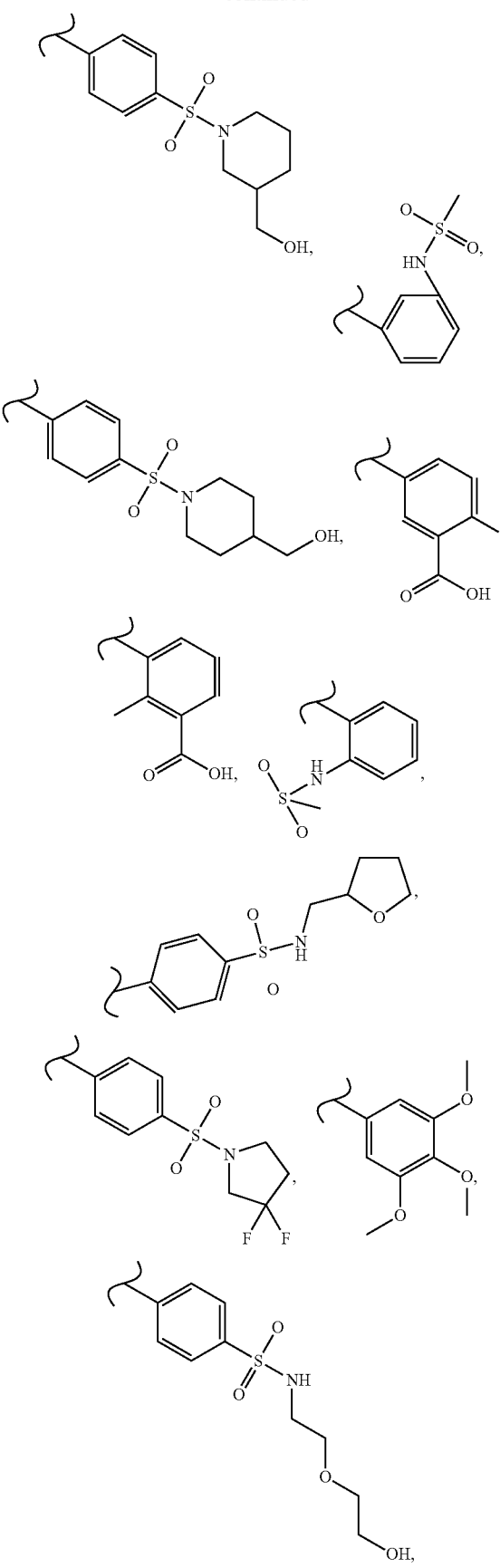
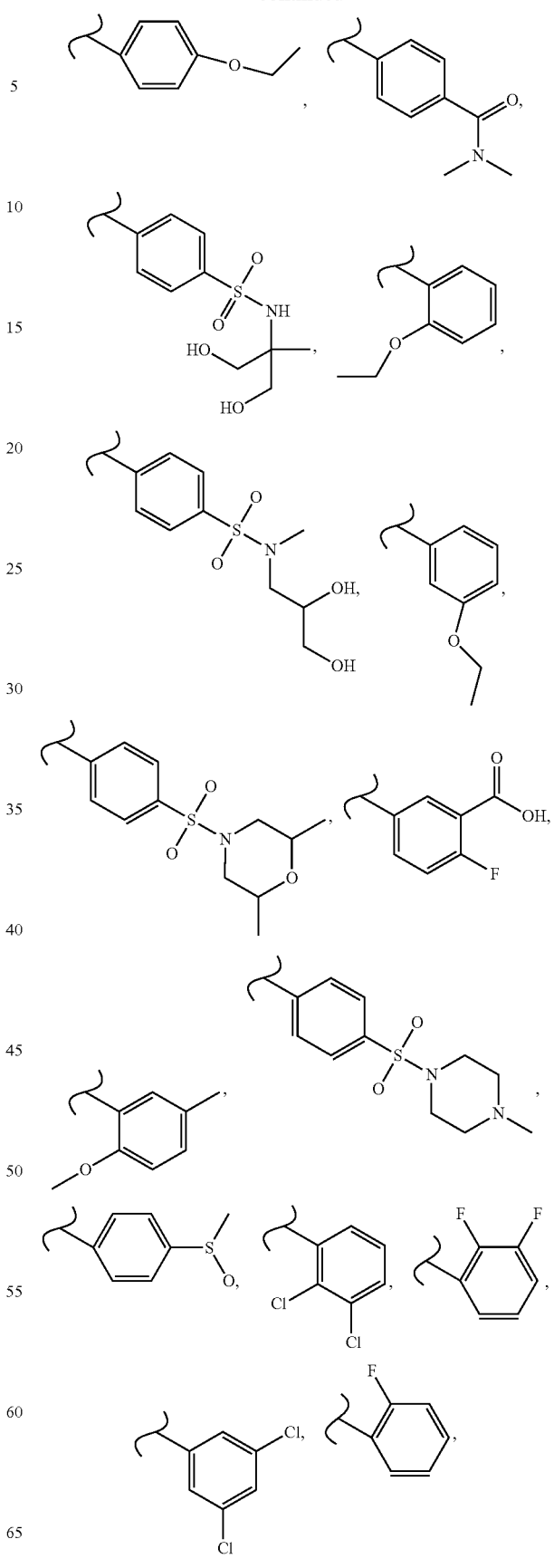

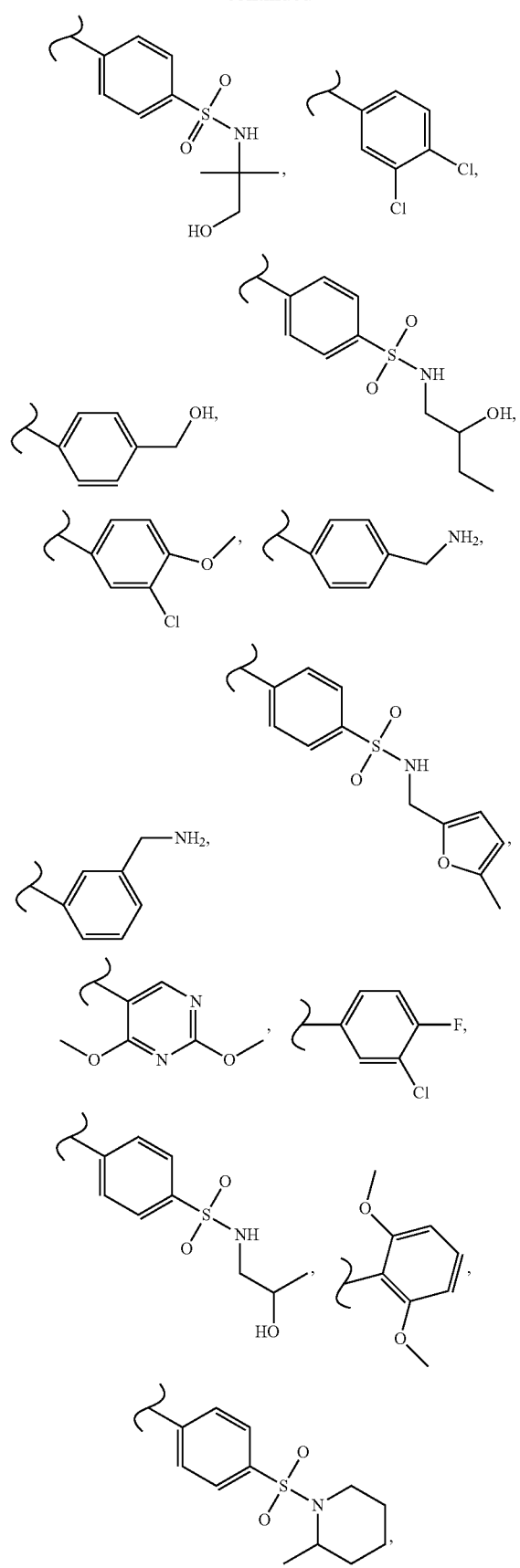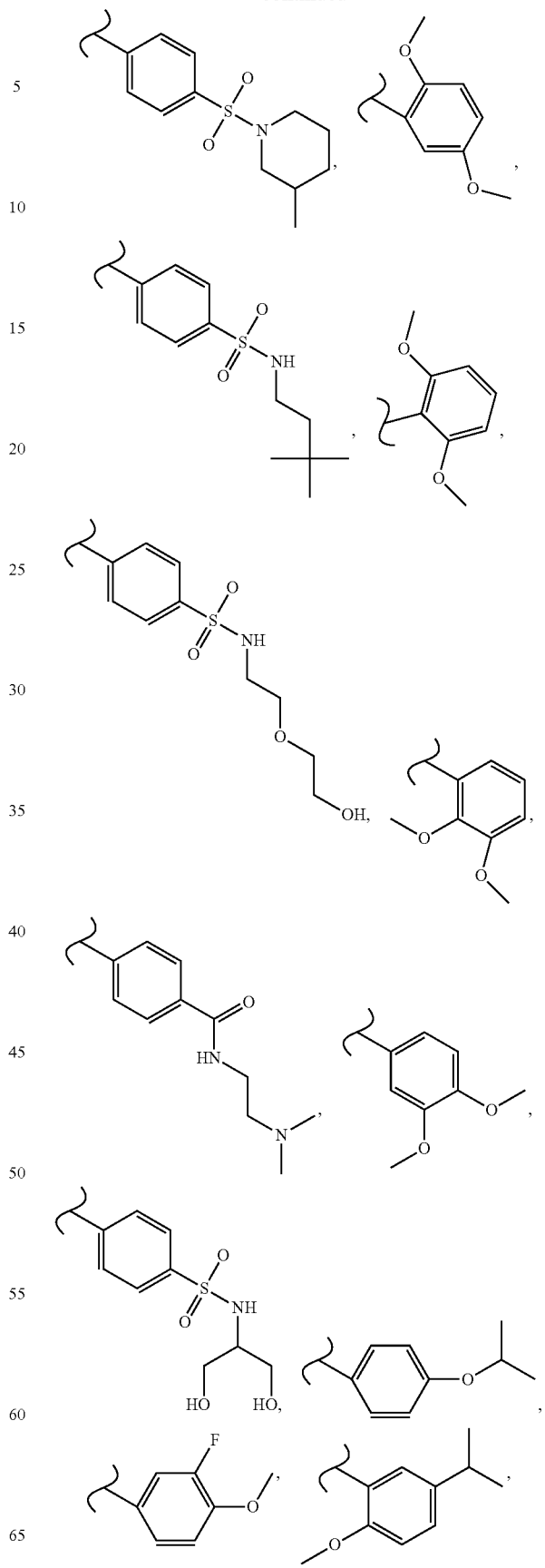

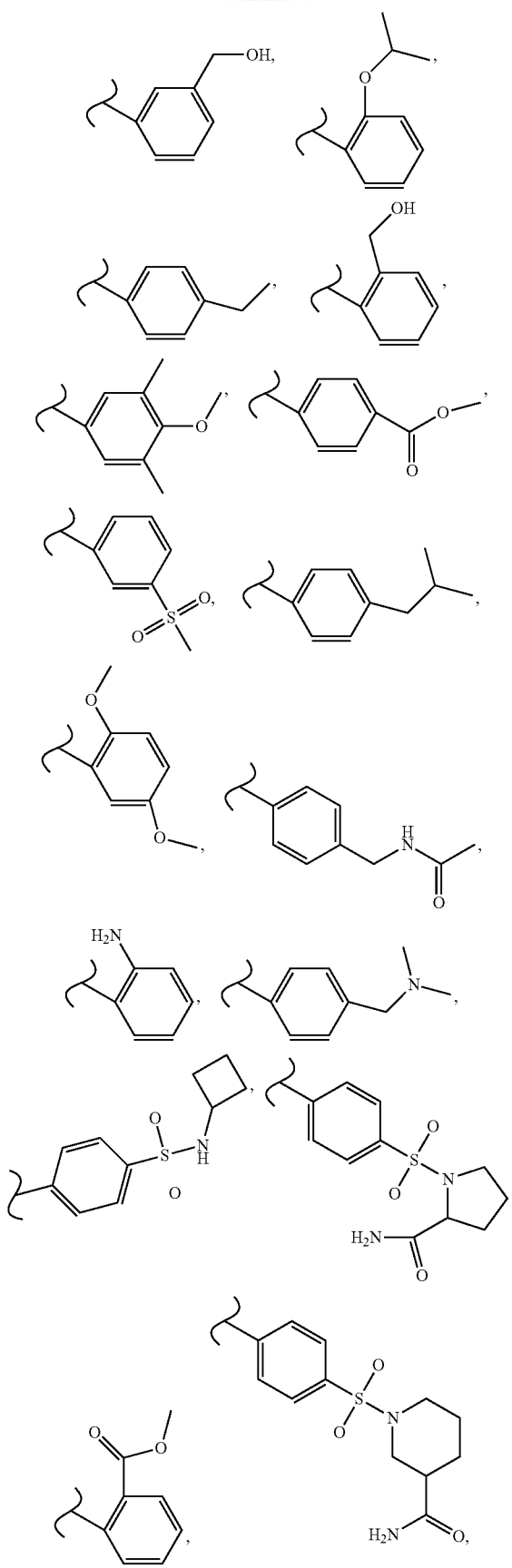
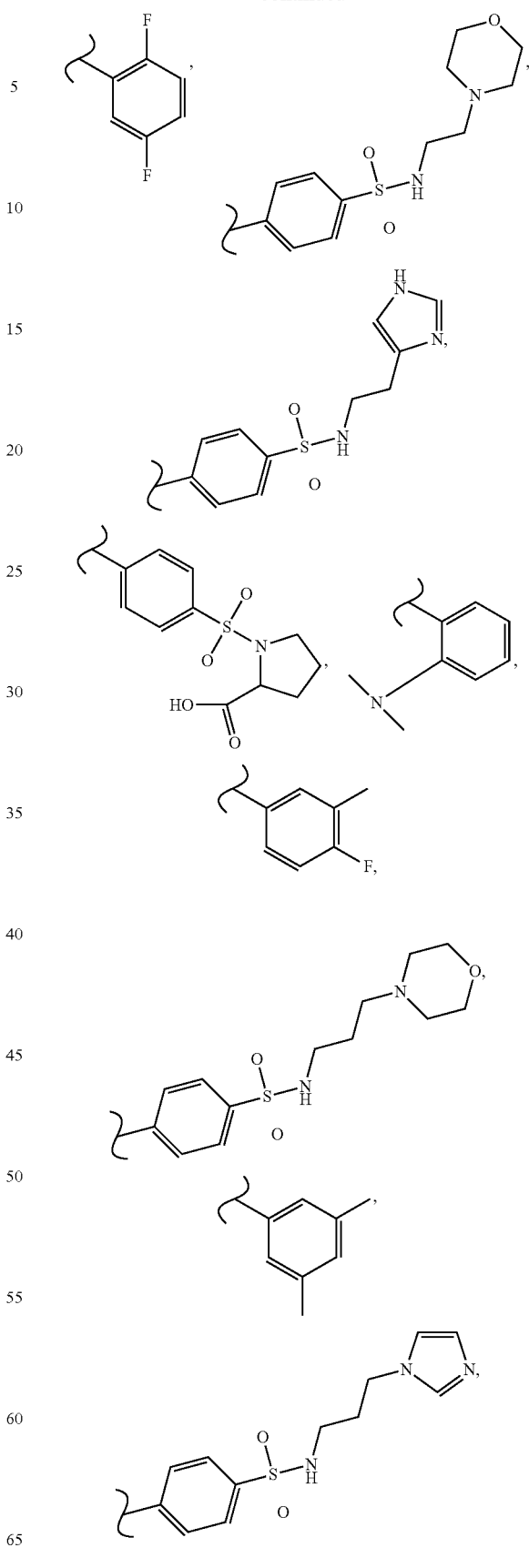

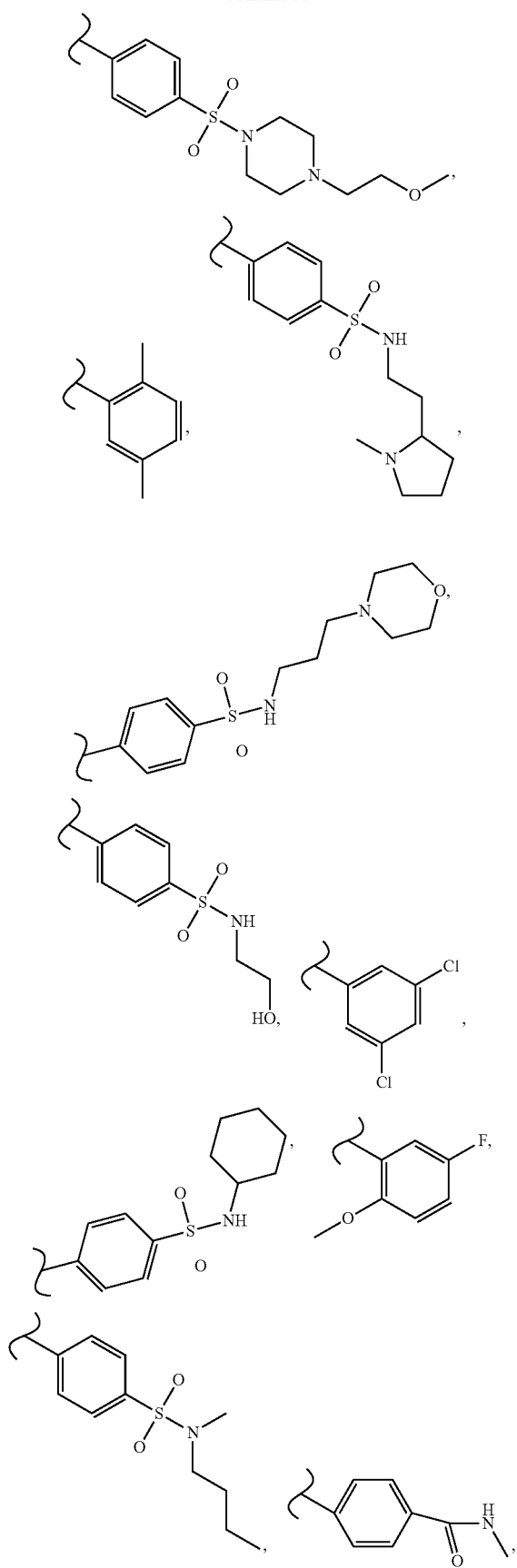
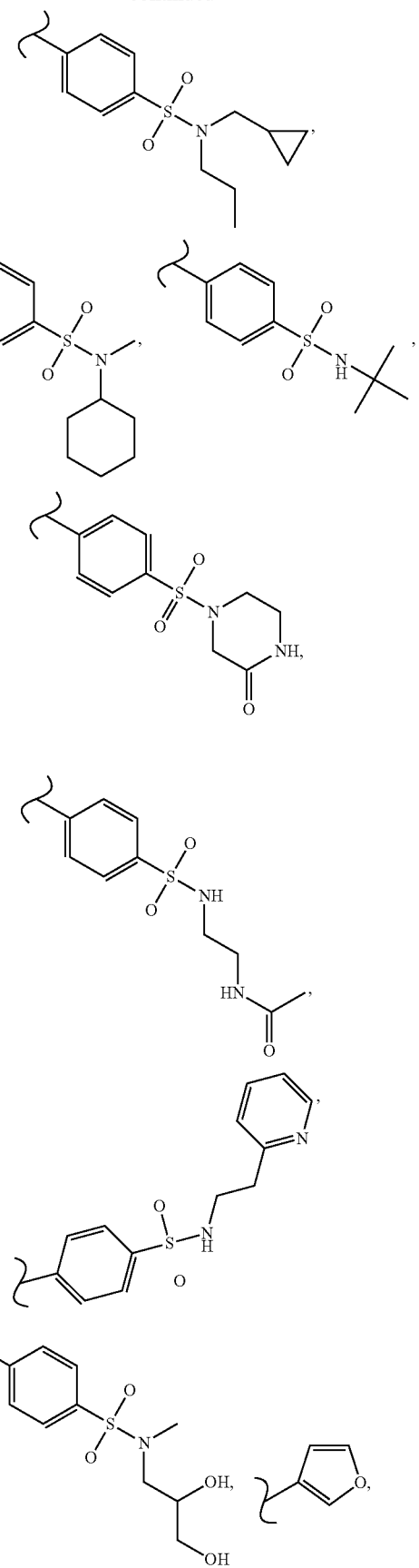

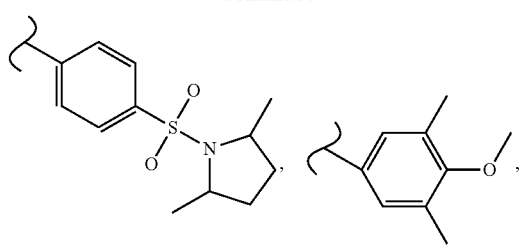
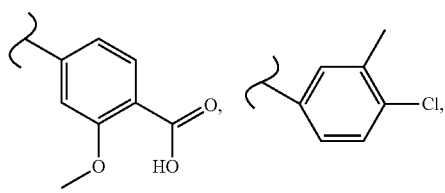
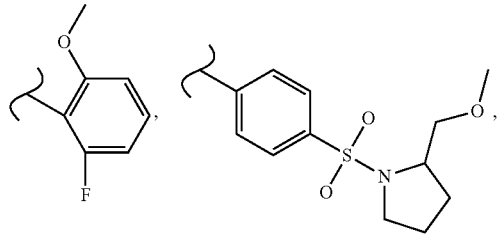
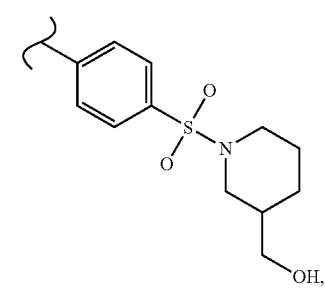
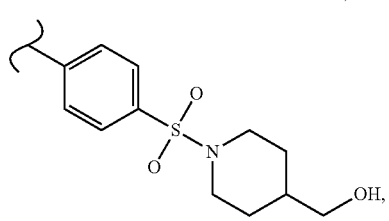
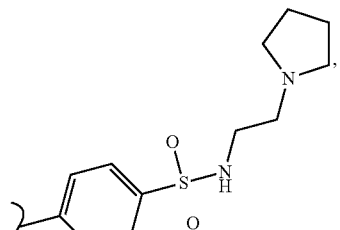
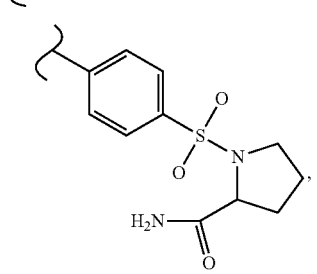
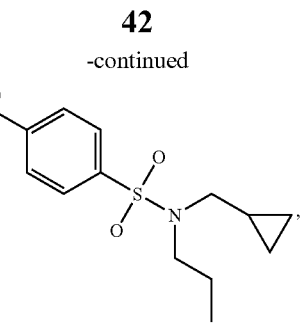
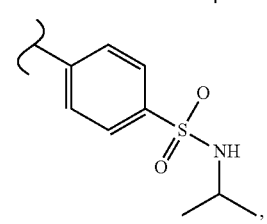
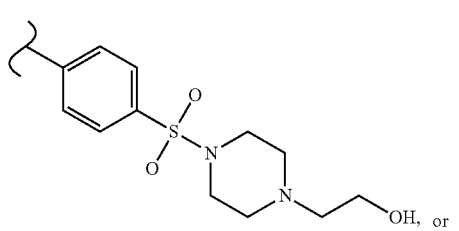
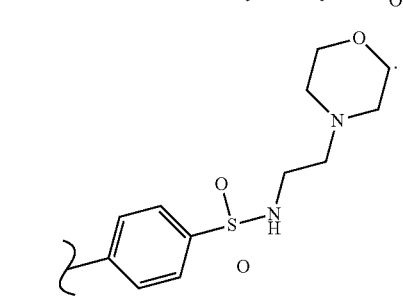
In several examples, $R_1$ is one selected from:
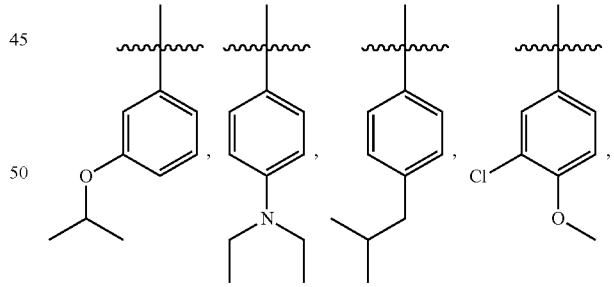
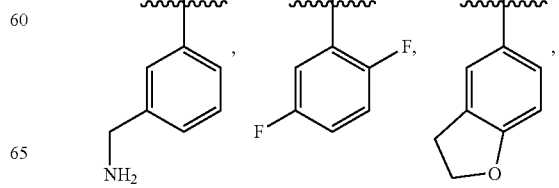

-continued
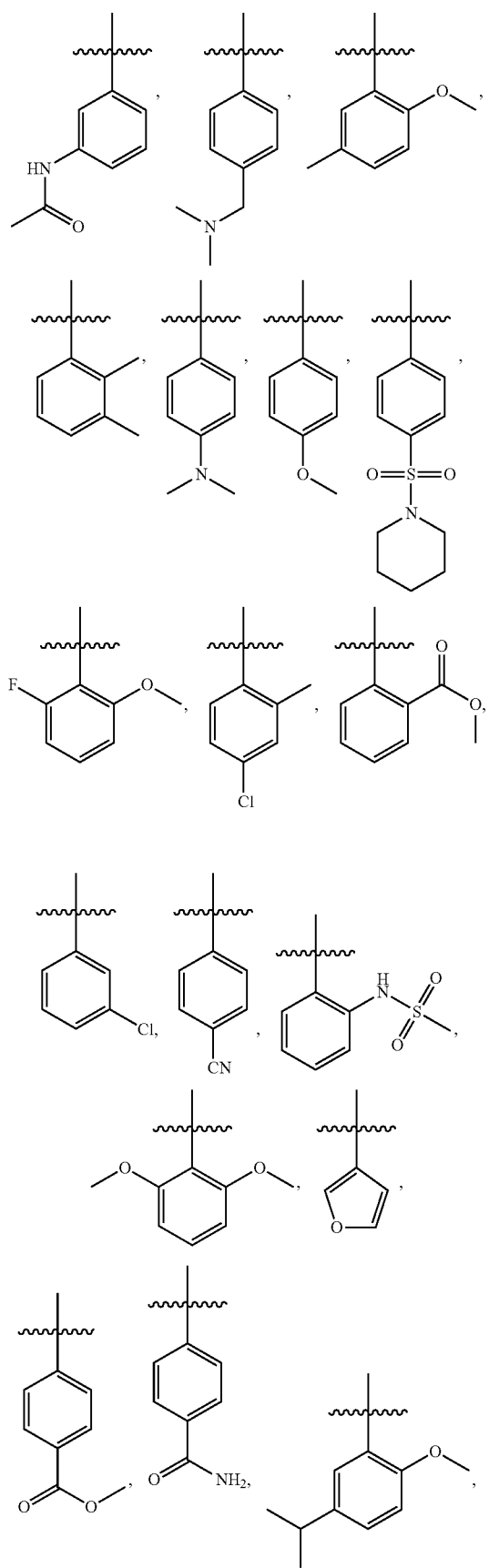
-continued
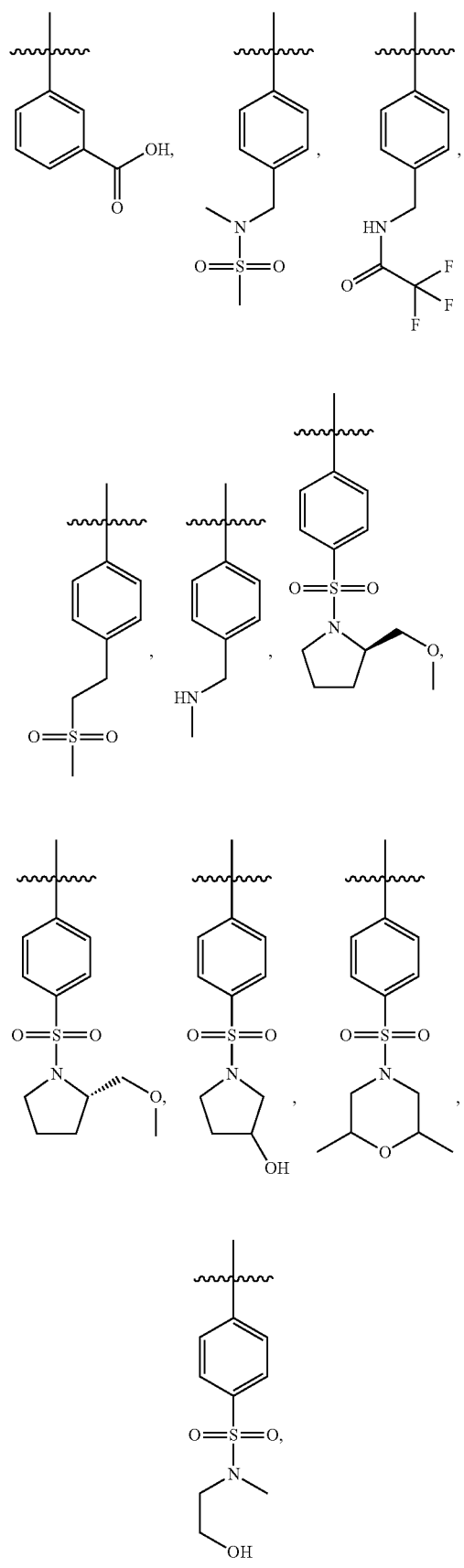

-continued
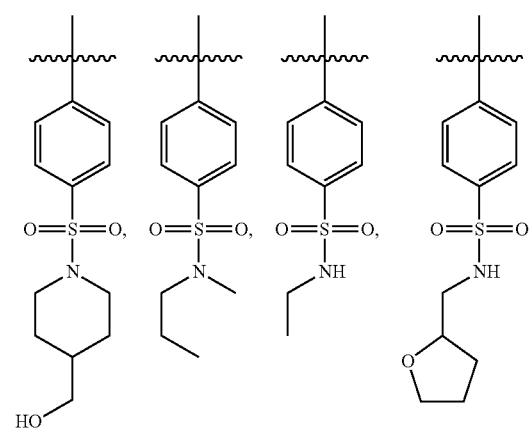
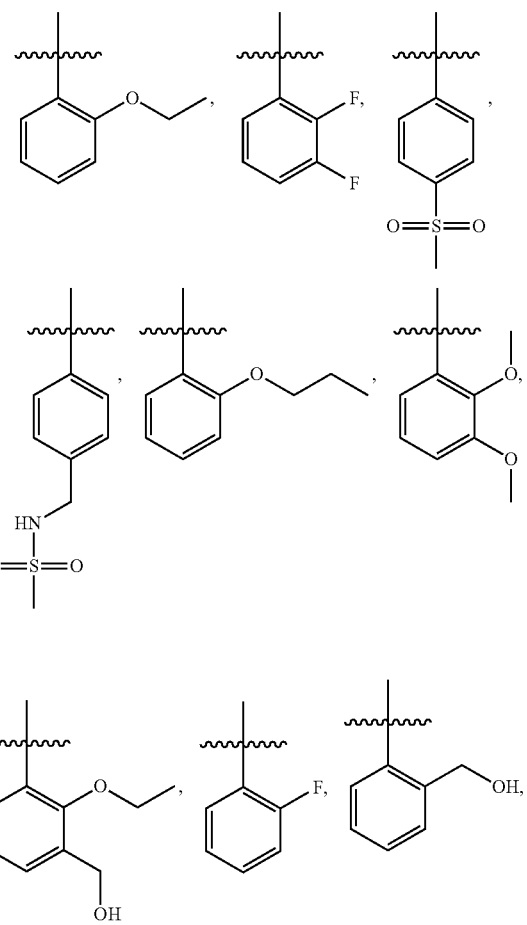
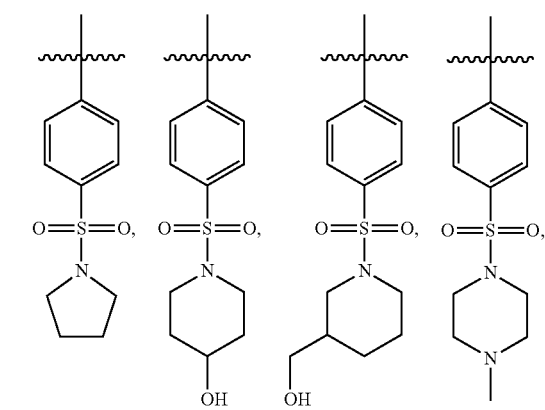
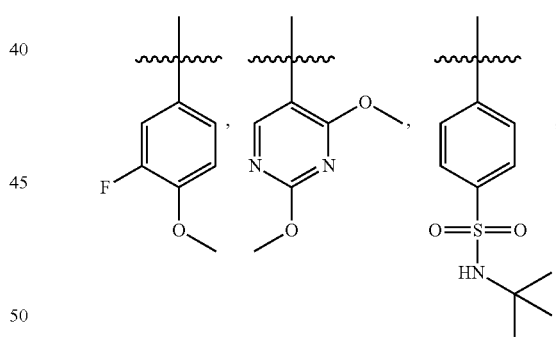
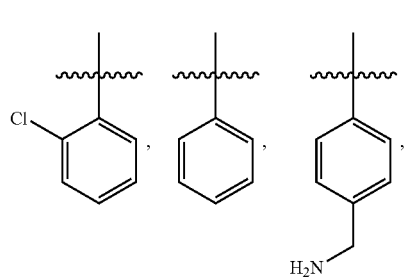
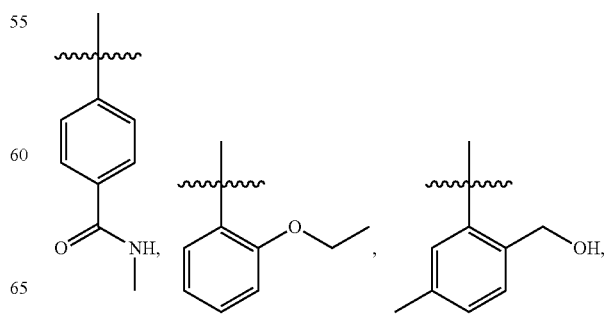

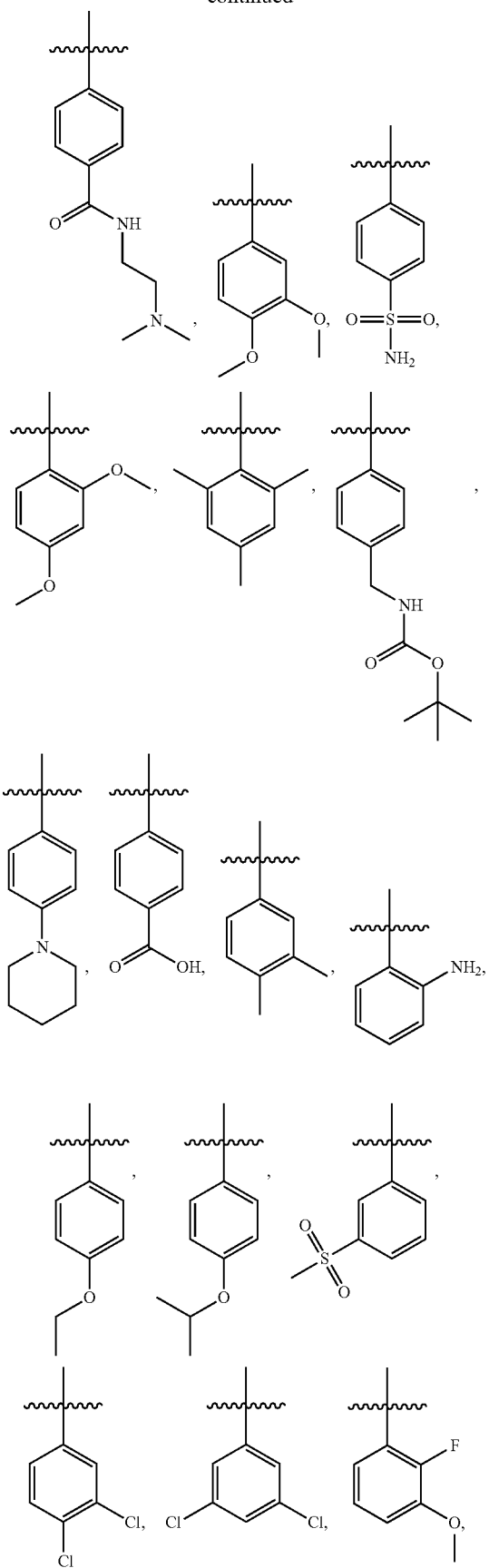
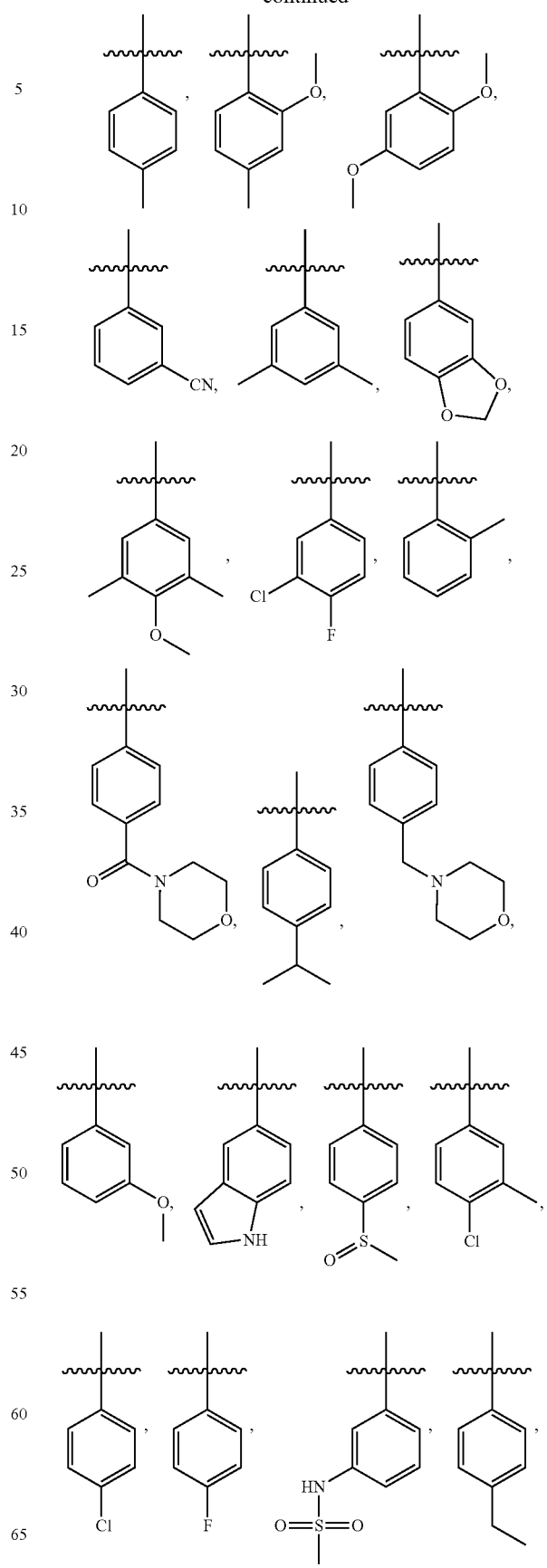

-continued
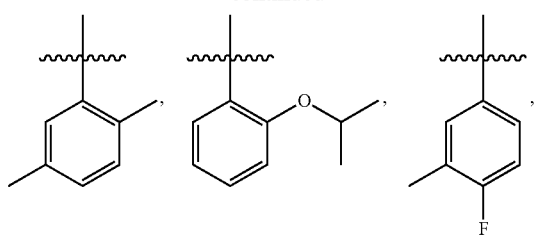
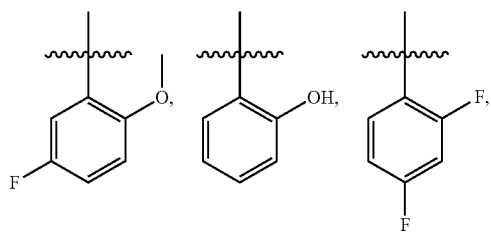
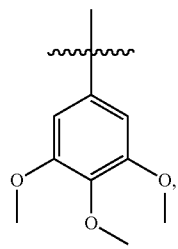
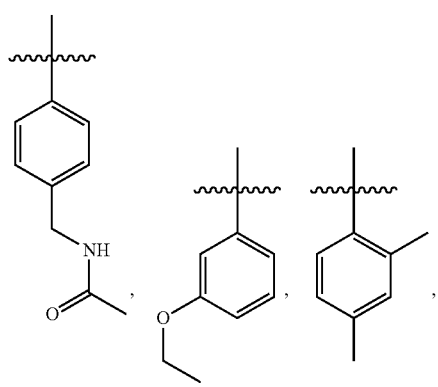
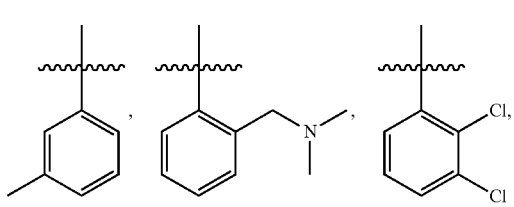
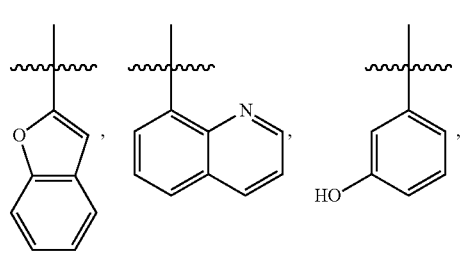
-continued
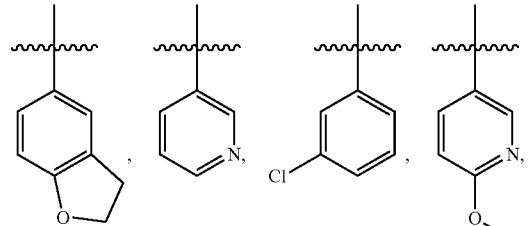
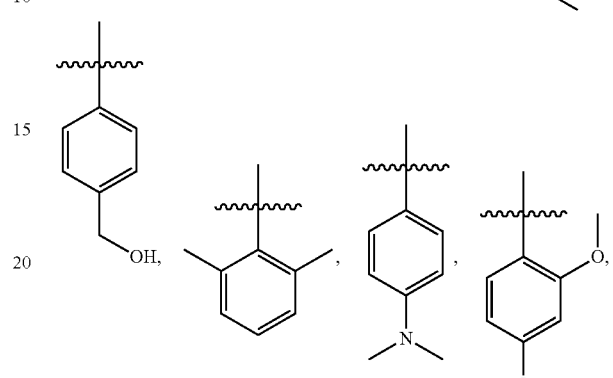
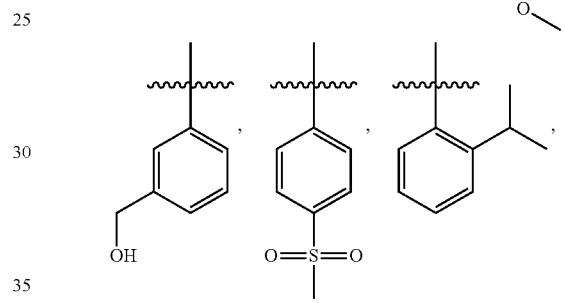
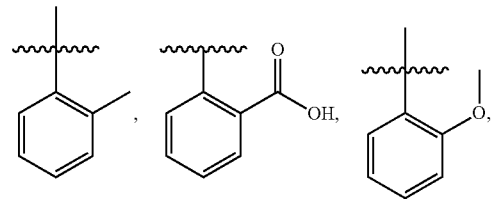
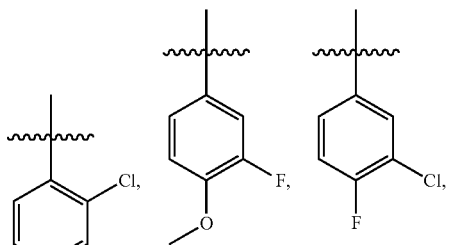
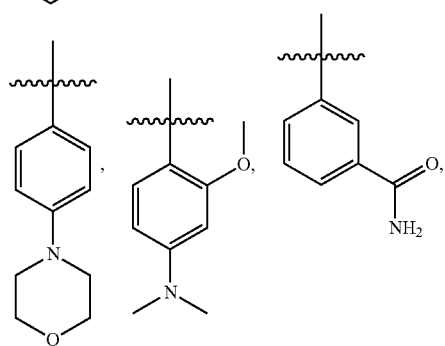

51
-continued
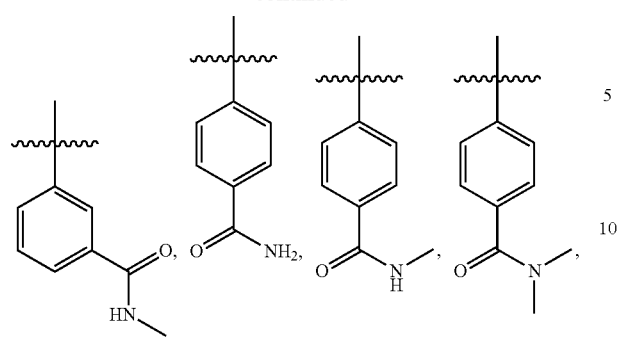
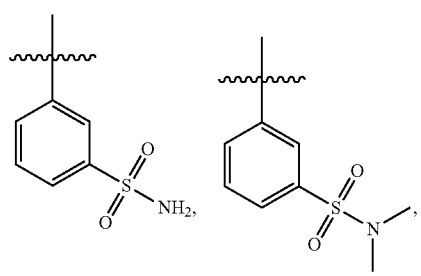
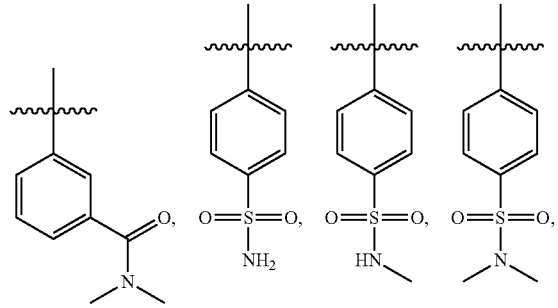
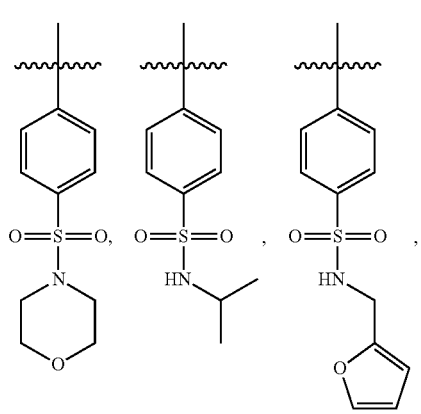
52
-continued
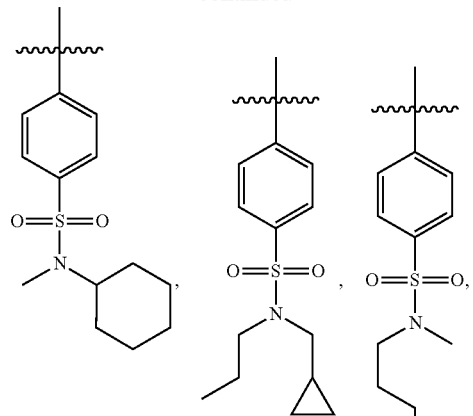
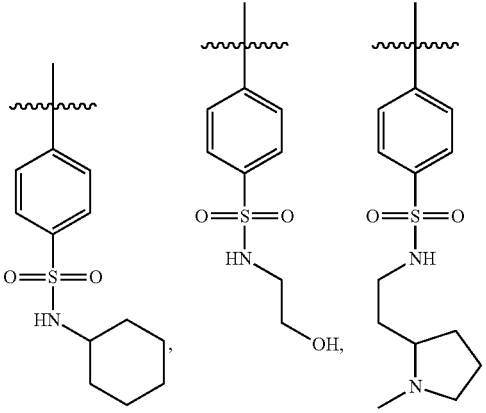
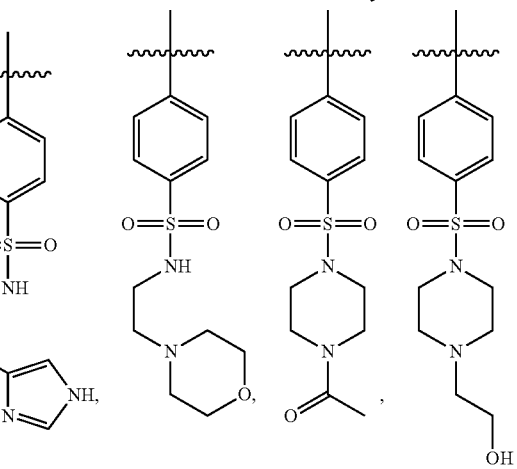
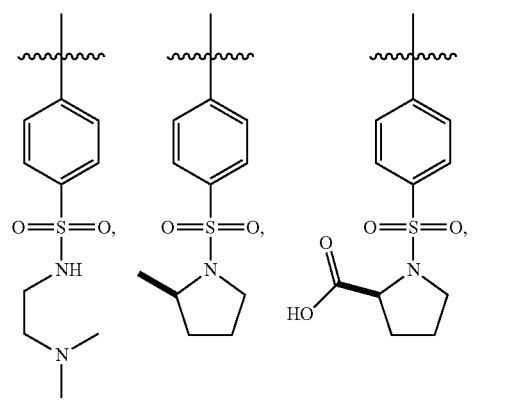

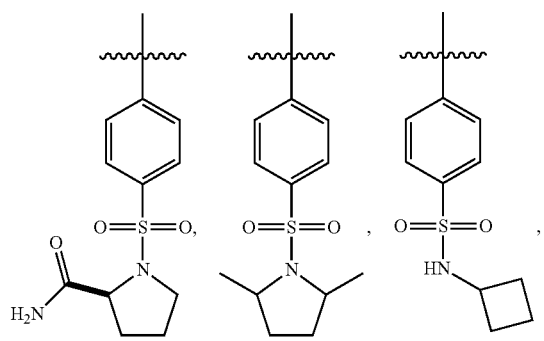

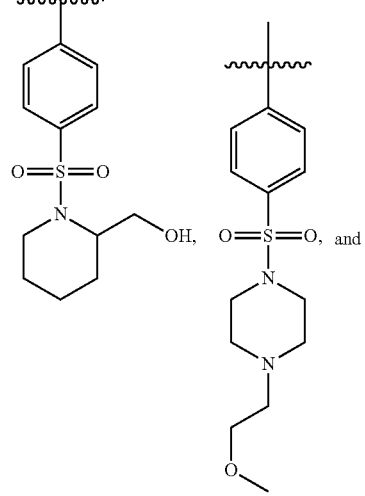

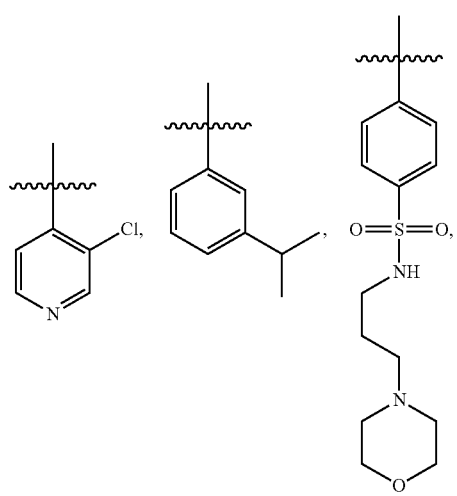

B. Substituent $R_2$

Each $R_2$ can be hydrogen. Each $R_2$ can be an optionally substituted group selected from $C_{1-6}$ aliphatic, $C_{3-6}$ cycloaliphatic, phenyl, and heteroaryl.

In several embodiments, $R_2$ is a $C_{1-6}$ aliphatic optionally substituted with 1, 2, or 3 halo, $C_{1-2}$ aliphatic, or alkoxy. In several examples, $R_2$ can be substituted methyl, ethyl, propyl, or butyl. In several examples, $R_2$ can be methyl, ethyl, propyl, or butyl.

In several embodiments, $R_2$ is hydrogen.

C. Substituents $R_3$ and $R'_3$

Each $R_3$ and $R'_3$ together with the carbon atom to which they are attached form a $C_{3-7}$ cycloaliphatic or a heterocycloaliphatic, each of which is optionally substituted with 1, 2, or 3 substituents.

In several embodiments, $R_3$ and $R'_3$ together with the carbon atom to which they are attached form a $C_{3-7}$ cycloaliphatic or a $C_{3-7}$ heterocycloaliphatic, each of which is optionally substituted with 1, 2, or 3 of $-Z^B R_7$, wherein each $Z^B$ is independently a bond, or an optionally substituted branched or straight $C_{1-4}$ aliphatic chain wherein up to two carbon units of $Z^B$ are optionally and independently replaced by $-CO-$, $-CS-$, $-CONR^B-$, $-CONR^B NR^B-$, $-CO_2-$, $-OCO-$, $-NR^B CO_2-$, $-O-$, $-NR^B CONR^B-$, $-OCONR^B-$, $-NR^B NR^B-$, $-NR^B CO-$, $-S-$, $-SO-$, $-SO_2 NR^B-$, $-NR^B SO_2-$, or $-NR^B SO_2 NR^B-$; each $R_7$ is independently $R^B$, halo, $-OH$, —NH$_2$, —NO$_2$, —CN, —CF$_3$, or —OCF$_3$; and each R$^B$ is independently hydrogen, an optionally substituted C$_{1-8}$ aliphatic group, an optionally substituted cycloaliphatic, an optionally substituted heterocycloaliphatic, an optionally substituted aryl, or an optionally substituted heteroaryl.

In several embodiments, R$_3$ and R'$_3$ together with the carbon atom to which they are attached form a 3, 4, 5, or 6 membered cycloaliphatic that is optionally substituted with 1, 2, or 3 substituents. In several examples, R$_3$, R'$_3$, and the carbon atom to which they are attached form an optionally substituted cyclopropyl group. In several alternative examples, R$_3$, R'$_3$, and the carbon atom to which they are attached form an optionally substituted cyclobutyl group. In several other examples, R$_3$, R'$_3$, and the carbon atom to which they are attached form an optionally substituted cyclopentyl group. In other examples, R$_3$, R'$_3$, and the carbon atom to which they are attached form an optionally substituted cyclohexyl group. In more examples, R$_3$ and R'$_3$ together with the carbon atom to which they are attached form an unsubstituted cyclopropyl.

In several embodiments, R$_3$ and R'$_3$ together with the carbon atom to which they are attached form a 5, 6, or 7 membered optionally substituted heterocycloaliphatic. In other examples, R$_3$, R'$_3$, and the carbon atom to which they are attached form an optionally substituted tetrahydropyranyl group.

In some embodiments, R$_3$ and R'$_3$ together with the carbon atom to which they are attached form an unsubstituted C$_{3-7}$ cycloaliphatic or an unsubstituted heterocycloaliphatic. In several examples, R$_3$ and R'$_3$ together with the carbon atom to which they are attached form an unsubstituted cyclopropyl, an unsubstituted cyclopentyl, or an unsubstituted cyclohexyl.

D. Substituent R$_4$

Each R$_4$ is independently an optionally substituted aryl or an optionally substituted heteroaryl.

In several embodiments, R$_4$ is an aryl having 6 to 10 members (e.g., 7 to 10 members) optionally substituted with 1, 2, or 3 substituents. Examples of R$_4$ include optionally substituted benzene, naphthalene, or indene. Or, examples of R$_4$ can be optionally substituted phenyl, optionally substituted naphthyl, or optionally substituted indenyl.

In several embodiments, R$_4$ is an optionally substituted heteroaryl. Examples of R$_4$ include monocyclic and bicyclic heteroaryl, such a benzofused ring system in which the phenyl is fused with one or two 4-8 membered heterocycloaliphatic groups.

In some embodiments, R$_4$ is an aryl or heteroaryl, each optionally substituted with 1, 2, or 3 of —Z$^C$R$_8$. In some embodiments, R$_4$ is an aryl optionally substituted with 1, 2, or 3 of —Z$^C$R$_8$. In some embodiments, R$_4$ is phenyl optionally substituted with 1, 2, or 3 of —Z$^C$R$_8$. Or, R$_4$ is a heteroaryl optionally substituted with 1, 2, or 3 of —Z$^C$R$_8$. Each Z$^C$ is independently a bond or an optionally substituted branched or straight C$_{1-6}$ aliphatic chain wherein up to two carbon units of Z$^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —SO—, —SO$_2$—, —NR$^S$—, —SO$_2$NR$^C$—, —NR$^C$SO$_2$—, or —NR$^C$SO$_2$NR$^C$—. Each R$_8$ is independently R$^C$, halo, —OH, —NH$_2$, —NO$_2$, —CN, —CF$_3$, or —OCF$_3$. Each R$^C$ is independently hydrogen, an optionally substituted C$_{1-8}$ aliphatic group, an optionally substituted cycloaliphatic, an optionally substituted heterocycloaliphatic, an optionally substituted aryl, or an optionally substituted heteroaryl.

In some embodiments, two occurrences of —Z$^C$R$_8$, taken together with carbons to which they are attached, form a 4-8 membered saturated, partially saturated, or aromatic ring with up to 3 ring atoms independently selected from the group consisting of O, NH, NR$^C$, and S; wherein R$^C$ is defined herein.

In several embodiments, R$_4$ is one selected from

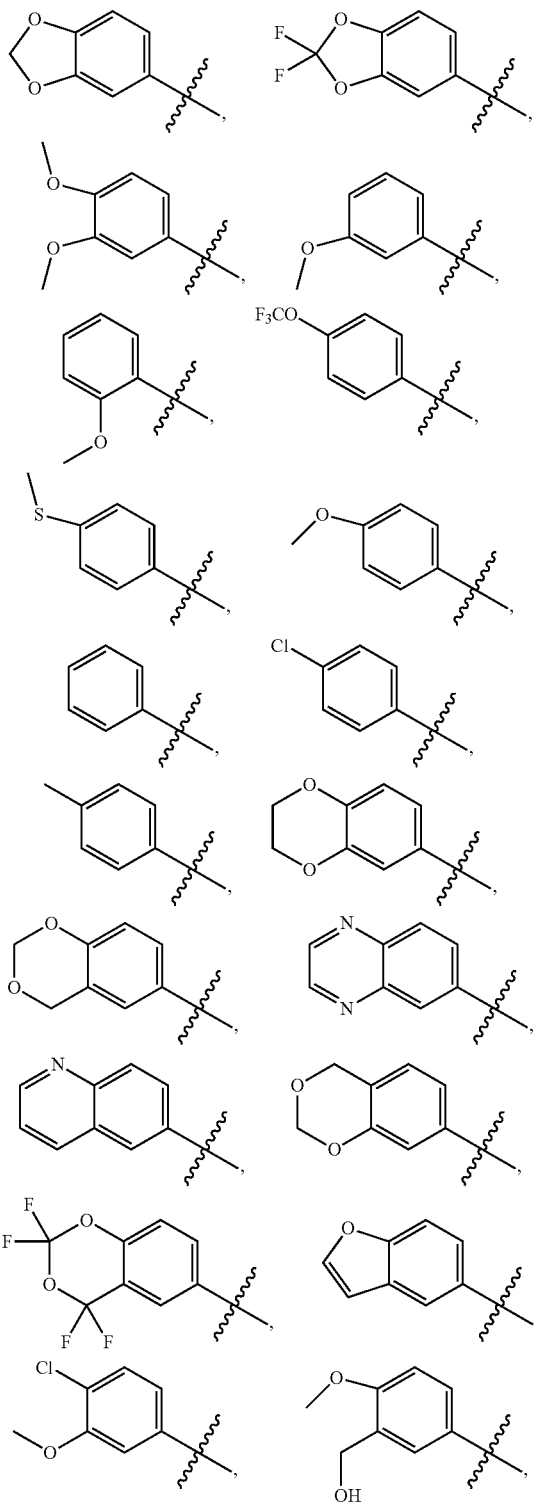

-continued

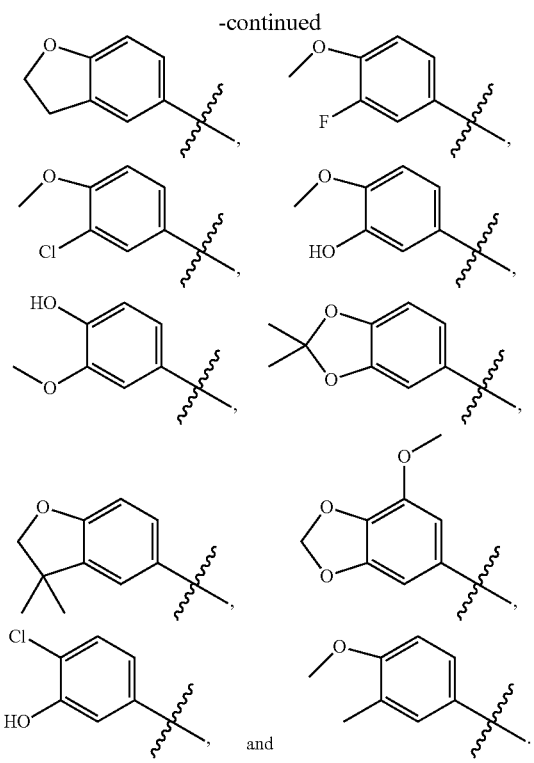

E. Exemplary Compound Families

In several embodiments, $R_1$ is an optionally substituted cyclic group that is attached to the core structure at the 5 or 6 position of the pyridine ring.

In several examples, $R_1$ is an optionally substituted aryl that is attached to the 5 position of the pyridine ring. In other examples, $R_1$ is an optionally substituted aryl that is attached to the 6 position of the pyridine ring.

In more examples, $R_1$ is an optionally substituted heteroaryl that is attached to the 5 position of the pyridine ring. In still other examples, $R_1$ is an optionally substituted heteroaryl that is attached to the 6 position of the pyridine ring.

In other embodiments, $R_1$ is an optionally substituted cycloaliphatic or an optionally substituted heterocycloaliphatic that is attached to the pyridine ring at the 5 or 6 position.

Accordingly, another aspect of the present invention provides compounds of formula (II):

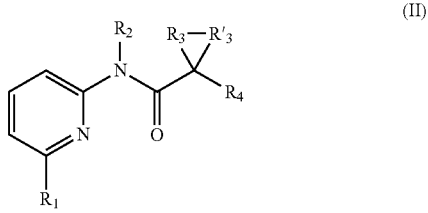

(II)

or a pharmaceutically acceptable salt thereof, wherein $R_1$, $R_2$, $R_3$, $R'_3$, and $R_4$ are defined in formula I.

In some embodiments, each $R_1$ is aryl or heteroaryl optionally substituted with 1, 2, or 3 of $R^D$, wherein $R^D$ is $-Z^D R_9$, wherein each $Z^D$ is independently a bond or an optionally substituted branched or straight $C_{1-6}$ aliphatic chain wherein up to two carbon units of $Z^D$ are optionally and independently replaced by $-CO-$, $-CS-$, $-CONR^E-$, $-CONR^ENR^E-$, $-CO_2-$, $-OCO-$, $-NR^ECO_2-$, $-O-$, $-NR^ECONR^E-$, $-OCONR^E-$, $-NR^ENR^E-$, $-NR^ECO-$, $-S-$, $-SO-$, $-SO_2-$, $-NR^E-$, $-SO_2NR^E-$, $-NR^ESO_2-$, or $-NR^ESO_2NR^E-$; each $R_9$ is independently $R^E$, halo, $-OH$, $-NH_2$, $-NO_2$, $-CN$, $-CF_3$, or $-OCF_3$; each $R^E$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

In some embodiment, each $R_1$ is cycloaliphatic or heterocycloaliphatic optionally substituted with 1, 2, or 3 of $R^D$; wherein $R^D$ is defined above.

Another aspect of the present invention provides compounds of formula (III):

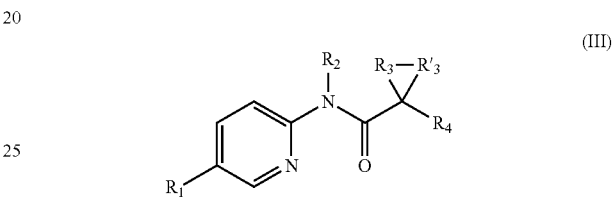

(III)

or a pharmaceutically acceptable salt thereof, wherein $R_1$, $R_2$, $R_3$, $R'_3$, and $R_4$ are defined in formula I.

In some embodiments, each $R_1$ is aryl or heteroaryl optionally substituted with 1, 2, or 3 of $R^D$, wherein $R^D$ is $-Z^D R_9$, wherein each $Z^D$ is independently a bond or an optionally substituted branched or straight $C_{1-6}$ aliphatic chain wherein up to two carbon units of $Z^D$ are optionally and independently replaced by $-CO-$, $-CS-$, $-CONR^E-$, $-CONR^ENR^E-$, $-CO_2-$, $-OCO-$, $-NR^ECO_2-$, $-O-$, $-NR^ECONR^E-$, $-OCONR^E-$, $-NR^ENR^E-$, $-NR^ECO-$, $-S-$, $-SO-$, $-SO_2-$, $-NR^E-$, $-SO_2NR^E-$, $-NR^ESO_2-$, or $-NR^ESO_2NR^E-$; each $R_9$ is independently $R^E$, halo, $-OH$, $-NH_2$, $-NO_2$, $-CN$, $-CF_3$, or $-OCF_3$; each $R^E$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

In some embodiments, each $R_1$ is cycloaliphatic or heterocycloaliphatic optionally substituted with 1, 2, or 3 of $R^D$; wherein $R^D$ is defined above.

In another aspect, the present invention includes compounds of formula (IV):

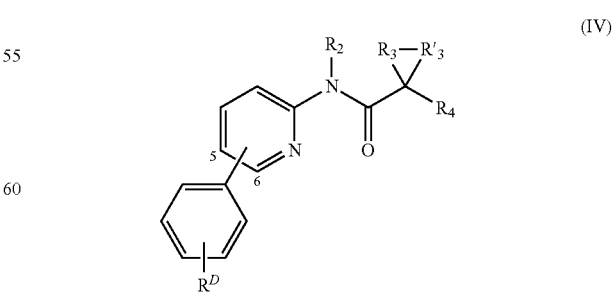

(IV)

or a pharmaceutically acceptable salt thereof, wherein $R_2$, $R_3$, $R'_3$, and $R_4$ are defined in formula I.

$R^D$ is —$Z^D R_9$; wherein each $Z^D$ is independently a bond or an optionally substituted branched or straight $C_{1-6}$ aliphatic chain wherein up to two carbon units of $Z^D$ are optionally and independently replaced by —CO—, —CS—, —CONR$^E$—, —CONR$^E$NR$^E$—, —CO$_2$—, —OCO—, —NR$^E$CO$_2$—, —O—, —NR$^E$CONR$^E$—, —OCONR$^E$—, —NR$^E$NR$^E$—, —NR$^E$CO—, —S—, —SO—, —SO$_2$—, —NR$^E$—, —SO$_2$NR$^E$—, —NR$^E$SO$_2$—, or —NR$^E$SO$_2$NR$^E$—.

$R_9$ is independently $R^E$, halo, —OH, —NH$_2$, —NO$_2$, —CN, —CF$_3$, or —OCF$_3$.

Each $R^E$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

In several embodiments, $Z^D$ is independently a bond or is an optionally substituted branched or straight $C_{1-6}$ aliphatic chain wherein one carbon unit of $Z^D$ is optionally replaced by —SO$_2$—, —CONR$^E$—, —NR$^E$SO$_2$—, or —SO$_2$NR$^E$—. For example, $Z^D$ is an optionally substituted branched or straight $C_{1-6}$ aliphatic chain wherein one carbon unit of $Z^D$ is optionally replaced by —SO$_2$—. In other examples, $R_9$ is an optionally substituted heteroaryl or an optionally substituted heterocycloaliphatic. In additional examples, $R_9$ is an optionally substituted heterocycloaliphatic having 1-2 nitrogen atoms, and $R_9$ attaches directly to —SO$_2$— via a ring nitrogen.

In another aspect, the present invention includes compounds of formula V-A or formula V-B:

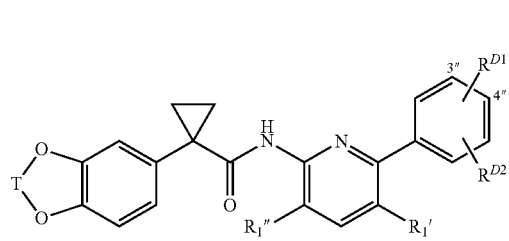

V-A

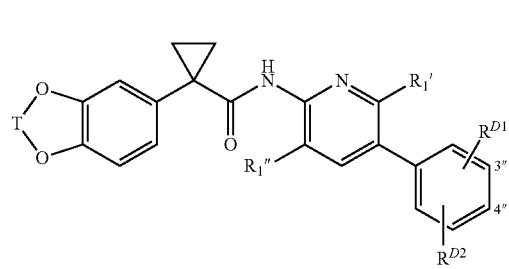

V-B or a pharmaceutically acceptable salt thereof, wherein:

T is an optionally substituted $C_{1-2}$ aliphatic chain, wherein each of the carbon units is optionally and independently replaced by —CO—, —CS—, —COCO—, —SO$_2$—, —B(OH)—, or —B(O($C_{1-6}$ alkyl))—;

Each of $R_1'$ and $R_1''$ is independently a bond or an optionally substituted $C_{1-6}$ aliphatic, an optionally substituted aryl, an optionally substituted heteroaryl, an optionally substituted 3 to 10 membered cycloaliphatic, an optionally substituted 3 to 10 membered heterocycloaliphatic, carboxy, amido, amino, halo, or hydroxy;

$R^{D1}$ is attached to carbon 3" or 4";

each $R^{D1}$ and $R^{D2}$ is —$Z^D R_9$, wherein each $Z^D$ is independently a bond or an optionally substituted branched or straight $C_{1-6}$ aliphatic chain wherein up to two carbon units of $Z^D$ are optionally and independently replaced by —CO—, —CS—, —CONR$^E$—, —CONR$^E$NR$^E$—, —CO$_2$—, —OCO—, —NR$^E$CO$_2$—, —O—, —NR$^E$CONR$^E$—, —OCONR$^E$—, —NR$^E$NR$^E$—, —NR$^E$CO—, —S—, —SO—, —SO$_2$—, —NR$^E$—, —SO$_2$NR$^E$—, —NR$^E$SO$_2$—, or —NR$^E$SO$_2$NR$^E$—;

$R_9$ is independently $R^E$, halo, —OH, —NH$_2$, —NO$_2$, —CN, —CF$_3$, or —OCF$_3$;

or $R^{D1}$ and $R^{D2}$, taken together with atoms to which they are attached, form a 3-8 membered saturated, partially unsaturated, or aromatic ring with up to 3 ring members independently selected from the group consisting of O, NH, NR$^E$, and S; and each $R^E$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

In some embodiments, T is an optionally substituted —CH$_2$—. In some other embodiments, T is an optionally substituted —CH$_2$CH$_2$—.

In some embodiments, T is optionally substituted by —$Z^E R_{10}$; wherein each $Z^E$ is independently a bond or an optionally substituted branched or straight $C_{1-6}$ aliphatic chain wherein up to two carbon units of $Z^E$ are optionally and independently replaced by —CO—, —CS—, —CONR$^F$—, —CONR$^F$NR$^F$—, —CO$_2$—, —OCO—, —NR$^F$CO$_2$—, —O—, —NR$^F$CONR$^F$—, —OCONR$^F$—, —NR$^F$NR$^F$—, —NR$^F$CO—, —S—, —SO—, —SO$_2$—, —NR$^F$—, —SO$_2$NR$^F$—, —NR$^F$SO$_2$—, or —NR$^F$SO$_2$NR$^F$—; $R_{10}$ is independently $R^E$, halo, —OH, —NH$_2$, —NO$_2$, —CN, —CF$_3$, or —OCF$_3$; each $R^E$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl. In one example, $Z^E$ is —O—.

In some embodiments, $R_{10}$ can be an optionally substituted $C_{1-6}$ alkyl, an optionally substituted $C_{2-6}$ alkenyl, an optionally substituted $C_{3-7}$ cycloaliphatic, or an optionally substituted $C_{6-10}$ aryl. In one embodiment, $R_{10}$ is methyl, ethyl, i-propyl, or t-butyl.

In some embodiments, up to two carbon units of T are optionally substituted by —CO—, —CS—, —B(OH)—, or —B(O($C_{1-6}$ alkyl))—.

In some embodiments, T is selected from the group consisting of —CH$_2$—, —CH$_2$CH$_2$—, —CF$_2$—, —C(CH$_3$)$_2$—, —C(O)—,

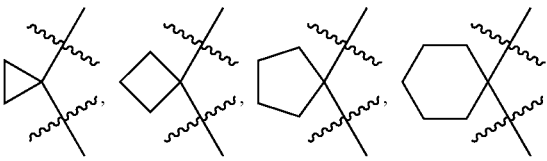

—C(Phenyl)$_2$—, —B(OH)—, and —CH(OEt)—. In some embodiments, T is —CH$_2$—, —CF$_2$—, —C(CH$_3$)$_2$—,

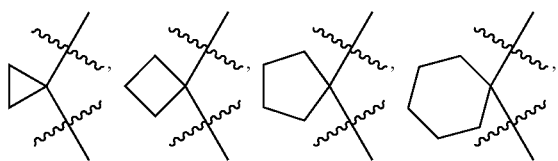

or —C(Phenyl)$_2$—. In other embodiments, T is —CH$_2$H$_2$—, —C(O)—, —B(OH)—, and —CH(OEt)-. In several embodiments, T is —CH$_2$—, —CF$_2$—, —C(CH$_3$)$_2$—,

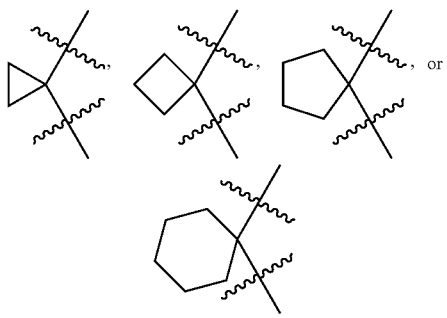

More preferably, T is —CH$_2$—, —CF$_2$—, or —C(CH$_3$)$_2$—. In several embodiments, T is —CH$_2$—. Or, T is —CF$_2$—. Or, T is —C(CH$_3$)$_2$—.

In some embodiments, each of $R_1'$ and $R_1''$ is hydrogen. In some embodiments, each of $R_1'$ and $R_1''$ is independently —$Z^A R_5$, wherein each $Z^A$ is independently a bond or an optionally substituted branched or straight C$_{1-6}$ aliphatic chain wherein up to two carbon units of $Z^A$ are optionally and independently replaced by —CO—, —CS—, —CONR$^A$—, —CONR$^A$NR$^A$—, —CO$_2$—, —OCO—, —NR$^A$CO$_2$—, —O—, —NR$^A$CONR$^A$—, —OCONR$^A$—, —NR$^A$NR$^A$—, —NR$^A$CO—, —S—, —SO—, —SO$_2$—, —NR$^A$—, —SO$_2$NR$^A$—, —NR$^A$SO$_2$—, or —NR$^A$SO$_2$NR$^A$—. Each R$_5$ is independently R$^A$, halo, —OH, —NH$_2$, —NO$_2$, —CN, —CF$_3$, or —OCF$_3$. Each R$^A$ is independently an optionally substituted group selected from C$_{1-8}$ aliphatic group, a cycloaliphatic, a heterocycloaliphatic, an aryl, and a heteroaryl.

In some embodiments, $R_1'$ is selected from the group consisting of H, C$_{1-6}$ aliphatic, halo, CF$_3$, CHF$_2$, —O(C$_{1-6}$ aliphatic), C3-C5 cycloalkyl, or C4-C6 heterocycloalkyl containing one oxygen atom. In some embodiments, $R_1'$ is selected from the group consisting of H, methyl, ethyl, i-propyl, t-butyl, F. C$_1$, CF$_3$, CHF$_2$, —OCH$_3$, —OCH$_2$CH$_3$, —O-(i-propyl), or —O-(t-butyl). More preferably, $R_1'$ is H. Or, $R_1'$ is methyl. Or, ethyl. Or, CF$_3$.

In some embodiments, $R_1''$ is selected from the group consisting of H, C$_{1-6}$ aliphatic, halo, CF$_3$, CHF$_2$, and —O(C$_{1-6}$ aliphatic). In some embodiments, $R_1''$ is selected from the group consisting of H, methyl, ethyl, i-propyl, t-butyl, F. C$_1$, CF$_3$, CHF$_2$, —OCH$_3$, —OCH$_2$CH$_3$, —O-(i-propyl), or —O-(t-butyl). More preferably, $R_1''$ is H. Or, $R_1''$ is methyl. Or, ethyl. Or, CF$_3$.

In some embodiments, $R^{D1}$ is attached to carbon 3" or 4", and is —$Z^D R_9$, wherein each $Z^D$ is independently a bond or an optionally substituted branched or straight C$_{1-6}$ aliphatic chain wherein up to two carbon units of $Z^D$ are optionally and independently replaced by —CO—, —CS—, —CONR$^E$—, —CONR$^E$NR$^E$—, —CO$_2$—, —OCO—, —NR$^E$CO$_2$—, —O—, —NR$^E$CONR$^E$—, —OCONR$^E$—, —NR$^E$NR$^E$—, —NR$^E$CO—, —S—, —SO—, —SO$_2$—, —NR$^E$—, —SO$_2$NR$^E$—, —NR$^E$SO$_2$—, or —NR$^E$SO$_2$NR$^E$—. In yet some embodiments, $Z^D$ is independently a bond or an optionally substituted branched or straight C$_{1-6}$ aliphatic chain wherein one carbon unit of $Z^D$ is optionally replaced by —CO—, —SO—, —SO$_2$—, —COO—, —OCO—, —CONR$^E$—, —NR$^E$CO—, NR$^E$CO$_2$—, —O—, —NR$^E$SO$_2$—, or —SO$_2$NR$^E$—. In some embodiments, one carbon unit of $Z^D$ is optionally replaced by —CO—. Or, by —SO—. Or, by —SO$_2$—. Or, by —COO—. Or, by —OCO—. Or, by —CONR$^E$—. Or, by —NR$^E$CO—. Or, by —NR$^E$CO$_2$—. Or, by —O—. Or, by —NR$^E$SO$_2$—. Or, by —SO$_2$NR$^E$—.

In several embodiments, R$_9$ is hydrogen, halo, —OH, —NH$_2$, —CN, —CF$_3$, —OCF$_3$, or an optionally substituted group selected from the group consisting of C$_{1-6}$ aliphatic, C$_{3-8}$ cycloaliphatic, 3-8 membered heterocycloaliphatic, C$_{6-10}$ aryl, and 5-10 membered heteroaryl. In several examples, R$_9$ is hydrogen, F, Cl, —OH, —CN, —CF$_3$, or —OCF$_3$. In some embodiments, $R^9$ is C$_{1-6}$ aliphatic, C$_{3-8}$ cycloaliphatic, 3-8 membered heterocycloaliphatic, C$_{6-10}$ aryl, and 5-10 membered heteroaryl, each of which is optionally substituted by 1 or 2 substituents independently selected from the group consisting of R$^E$, oxo, halo, —OH, —NR$^E$R$^E$, —OR$^E$, —COOR$^E$, and —CONR$^E$R$^E$. In several examples, R$_9$ is optionally substituted by 1 or 2 substituents independently selected from the group consisting of oxo, F, Cl, methyl, ethyl, i-propyl, t-butyl, —CH$_2$OH, —CH$_2$CH$_2$OH, —C(O)OH, —C(O)NH$_2$, —CH$_2$O(C$_{1-6}$ alkyl), —CH$_2$CH$_2$O (C$_{1-6}$ alkyl), and —C(O)(C$_{1-6}$ alkyl).

In one embodiment, R$_9$ is hydrogen. In some embodiments, R$_9$ is selected from the group consisting of C$_{1-6}$ straight or branched alkyl or C$_{2-6}$ straight or branched alkenyl; wherein said alkyl or alkenyl is optionally substituted by 1 or 2 substituents independently selected from the group consisting of R$^E$, oxo, halo, —OH, —NR$^E$R$^E$, —OR$^E$, —COOR$^E$, and —CONR$^E$R$^E$.

In other embodiments, R$_9$ is C$_{3-8}$ cycloaliphatic optionally substituted by 1 or 2 substituents independently selected from the group consisting of R$^E$, oxo, halo, —OH, —NR$^E$R$^E$, —OR$^E$, —COOR$^E$, and —CONR$^E$R$^E$. Examples of cycloaliphatic include but are not limited to cyclopropyl, cyclobutyl, cyclopentyl, cyclohexyl, and cycloheptyl.

In yet other embodiments, R$_9$ is a 3-8 membered heterocyclic with 1 or 2 heteroatoms independently selected from the group consisting of O, NH, NR$^E$, and S; wherein said heterocyclic is optionally substituted by 1 or 2 substituents independently selected from the group R$^E$, oxo, halo, —OH, —NR$^E$R$^E$, —OR$^E$, COOR$^E$, and —CONR$^E$R$^E$. Example of 3-8 membered heterocyclic include but are not limited to

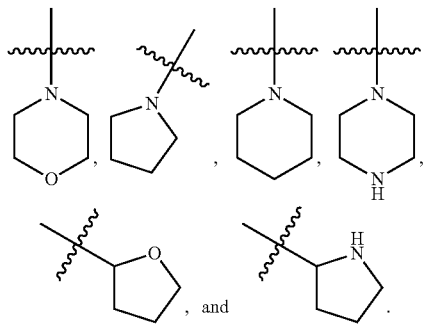

In yet some other embodiments, R₉ is an optionally substituted 5-8 membered heteroaryl with one or two ring atom independently selected from the group consisting of O, S, and NR$^E$. Examples of 5-8 membered heteroaryl include but are not limited to

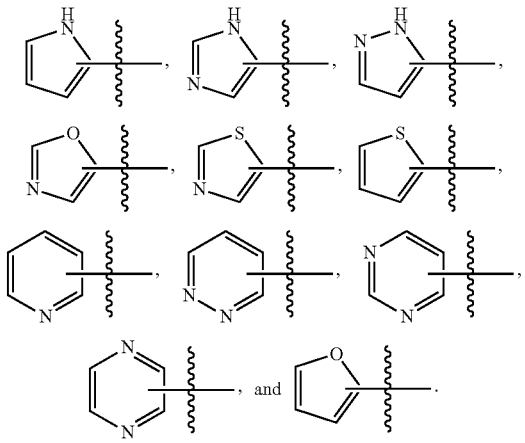

In some embodiments, R$^{D1}$ and R$^{D2}$, taken together with carbons to which they are attached, form an optionally substituted 4-8 membered saturated, partially unsaturated, or aromatic ring with 0-2 ring atoms independently selected from the group consisting of O, NH, NR$^E$, and S. Examples of R$^{D1}$ and R$^{D2}$, taken together with phenyl containing carbon atoms 3" and 4", include but are not limited to

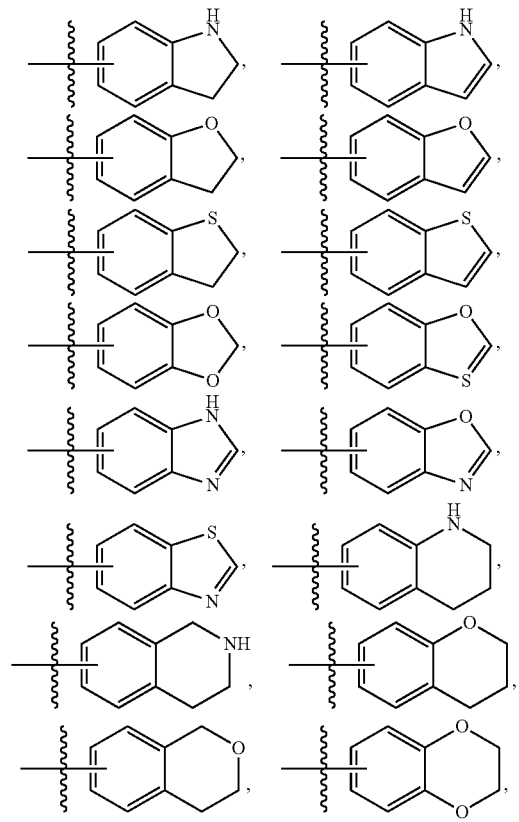

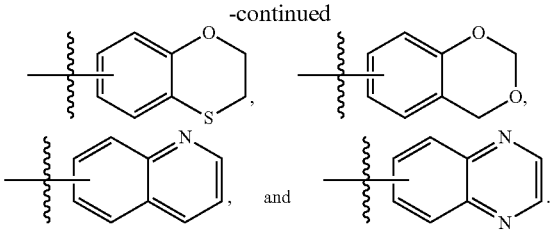

In some embodiments, R$^{D2}$ is selected from the group consisting of H, R$^E$, halo, —OH, —(CH$_2$)$_r$NR$^E$R$^E$, —(CH$_2$)$_r$OR$^E$, —SO$_2$—R$^E$, —NR$^E$—SO$_2$—R$^E$, —SO$_2$NR$^E$R$^E$, —C(O)R$^E$, —C(O)OR$^E$, —OC(O)OR$^E$, —NR$^E$C(O)OR$^E$, and —C(O)NR$^E$R$^E$; wherein r is 0, 1, or 2. In other embodiments, R$^{D2}$ is selected from the group consisting of H, C$_{1-6}$ aliphatic, halo, —CN, —NH$_2$, —NH(C$_{1-6}$ aliphatic), —N(C$_{1-6}$ aliphatic)$_2$, —CH$_2$—N(C$_{1-6}$ aliphatic)$_2$, —CH$_2$—NH(C$_{1-6}$ aliphatic), —CH$_2$NH$_2$, —OH, —O(C$_{1-6}$ aliphatic), —CH$_2$OH, —CH$_2$—O(C$_{1-6}$ aliphatic), —SO$_2$(C$_{1-6}$ aliphatic), —N(C$_{1-6}$ aliphatic)-SO$_2$(C$_{1-6}$ aliphatic), —NH—SO$_2$(C$_{1-6}$ aliphatic), —SO$_2$NH$_2$, —SO$_2$NH(C$_{1-6}$ aliphatic), —SO$_2$N(C$_{1-6}$ aliphatic)$_2$, —C(O)(C$_{1-6}$ aliphatic), —C(O)O(C$_{1-6}$ aliphatic), —C(O)OH, —OC(O)O(C$_{1-6}$ aliphatic), —NHC(O)(C$_{1-6}$ aliphatic), —NHC(O)O(C$_{1-6}$ aliphatic), —N(C$_{1-6}$ aliphatic)C(O)O(C$_{1-6}$ aliphatic), —C(O)NH$_2$, and —C(O)N(C$_{1-6}$ aliphatic)$_2$. In several examples, R$^{D2}$ is selected from the group consisting of H, C$_{1-6}$ aliphatic, halo, —CN, —NH$_2$, —CH$_2$NH$_2$, —OH, —O(C$_{1-6}$ aliphatic), —CH$_2$OH, —SO$_2$(C$_{1-6}$ aliphatic), —NH—SO$_2$(C$_{1-6}$ aliphatic), —C(O)O(C$_{1-6}$ aliphatic), —C(O)OH, —NHC(O)(C$_{1-6}$ aliphatic), —C(O)NH$_2$, —C(O)NH(C$_{1-6}$ aliphatic), and —C(O)N(C$_{1-6}$ aliphatic)$_2$. For examples, R$^{D2}$ is selected from the group consisting of H, methyl, ethyl, n-propyl, i-propyl, t-butyl, F, Cl, CN, —NH$_2$, —CH$_2$NH$_2$, —OH, —OCH$_3$, —O-ethyl, —O-(i-propyl), —O-(n-propyl), —CH$_2$OH, —SO$_2$CH$_3$, —NH—SO$_2$CH$_3$, —C(O)OCH$_3$, —C(O)OCH$_2$CH$_3$, —C(O)OH, —NHC(O)CH$_3$, —C(O)NH$_2$, and —C(O)N(CH$_3$)$_2$. In one embodiment, R$^{D2}$ is hydrogen. In another embodiment, R$^{D2}$ is methyl. Or, R$^{D2}$ is ethyl. Or, R$^{D2}$ is F. Or, R$^{D2}$ is Cl. Or, —OCH$_3$.

In one embodiment, the present invention provides compounds of formula VI-A-i or formula VI-A-ii:

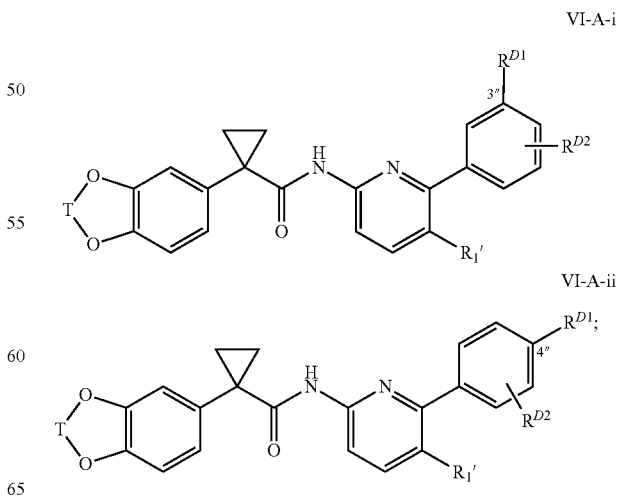

wherein T, R$^{D1}$, R$^{D2}$, and R$_1$' are as defined above.

In one embodiment, T is —CH$_2$—, —CF$_2$—, or —C(CH$_3$)$_2$—.

In one embodiment, R$_1$' is selected from the group consisting of H, C$_{1-6}$ aliphatic, halo, CF$_3$, CHF$_2$, —O(C$_{1-6}$ aliphatic), C3-C5 cycloalkyl, or C4-C6 heterocycloalkyl containing one oxygen atom. Exemplary embodiments include H, methyl, ethyl, i-propyl, t-butyl, F. C$_1$, CF$_3$, CHF$_2$, —OCH$_3$, —OCH$_2$CH$_3$, —O-(i-propyl), —O-(t-butyl), cyclopropyl, or oxetanyl. More preferably, R$_1$' is H. Or, R$_1$' is methyl. Or, ethyl. Or, CF$_3$. Or, oxetanyl.

In one embodiment, R$^{D1}$ is Z$^D$R$_9$, wherein Z$^D$ is selected from CONH, NHCO, SO$_2$NH, SO$_2$N(C$_{1-6}$ alkyl), NHSO$_2$, CH$_2$NHSO$_2$, CH$_2$N(CH$_3$)SO$_2$, CH$_2$NHCO, COO, SO$_2$, or CO. In one embodiment, R$^{D1}$ is Z$^D$R$_9$, wherein Z$^D$ is selected from CONH, SO$_2$NH, SO$_2$N(C$_{1-6}$ alkyl), CH$_2$NHSO$_2$, CH$_2$N(CH$_3$)SO$_2$, CH$_2$NHCO, COO, SO$_2$, or CO.

In one embodiment, Z$^D$ is COO and R$_9$ is H. In one embodiment, Z$^D$ is COO and R$_9$ is an optionally substituted straight or branched C$_{1-6}$ aliphatic. In one embodiment, Z$^D$ is COO and R$_9$ is an optionally substituted straight or branched C$_{1-6}$ alkyl. In one embodiment, Z$^D$ is COO and R$_9$ is C$_{1-6}$ alkyl. In one embodiment, Z$^D$ is COO and R$_9$ is methyl.

In one embodiment, Z$^D$ is CONH and R$_9$ is H. In one embodiment, Z$^D$ is CONH and R$_9$ is an optionally substituted straight or branched C$_{1-6}$ aliphatic. In one embodiment, Z$^D$ is CONH and R$_9$ is straight or branched C$_{1-6}$ alkyl. In one embodiment, Z$^D$ is CONH and R$_9$ is methyl. In one embodiment, Z$^D$ is CONH and R$_9$ is an optionally substituted straight or branched C$_{1-6}$ alkyl. In one embodiment, In one embodiment, Z$^D$ is CONH and R$_9$ is 2-(dimethylamino)-ethyl.

In some embodiments, Z$^D$ is CH$_2$NHCO and R$_9$ is an optionally substituted straight or branched C$_{1-6}$ aliphatic or an optionally substituted alkoxy. In some embodiments, Z$^D$ is CH$_2$NHCO and R$_9$ is straight or branched C$_{1-6}$ alkyl optionally substituted with halo, oxo, hydroxyl, or an optionally substituted group selected from aliphatic, cyclic, aryl, heteroaryl, alkoxy, amino, carboxyl, or carbonyl. In one embodiment, Z$^D$ is CH$_2$NHCO and R$_9$ is methyl. In one embodiment, Z$^D$ is CH$_2$NHCO and R$_9$ is CF$_3$. In one embodiment, Z$^D$ is CH$_2$NHCO and R$_9$ is t-butoxy.

In one embodiment, Z$^D$ is SO$_2$NH and R$_9$ is H. In some embodiments, Z$^D$ is SO$_2$NH and R$_9$ is an optionally substituted straight or branched C$_{1-6}$ aliphatic. In some embodiments, Z$^D$ is SO$_2$NH and R$_9$ is straight or branched C$_{1-6}$ alkyl optionally substituted with halo, oxo, hydroxyl, or an optionally substituted group selected from C$_{1-6}$ aliphatic, 3-8 membered cyclic, C$_{6-10}$ aryl, 5-8 membered heteroaryl, alkoxy, amino, amido, carboxyl, or carbonyl. In one embodiment, Z$^D$ is SO$_2$NH and R$_9$ is methyl. In one embodiment, Z$^D$ is SO$_2$NH and R$_9$ is ethyl. In one embodiment, Z$^D$ is SO$_2$NH and R$_9$ is i-propyl. In one embodiment, Z$^D$ is SO$_2$NH and R$_9$ is t-butyl. In one embodiment, Z$^D$ is SO$_2$NH and R$_9$ is 3,3-dimethylbutyl. In one embodiment, Z$^D$ is SO$_2$NH and R$_9$ is CH$_2$CH$_2$OH. In one embodiment, Z$^D$ is SO$_2$NH and R$_9$ is CH(CH$_3$)CH$_2$OH. In one embodiment, Z$^D$ is SO$_2$NH and R$_9$ is CH$_2$CH(CH$_3$)OH. In one embodiment, Z$^D$ is SO$_2$NH and R$_9$ is CH(CH$_2$OH)$_2$. In one embodiment, Z$^D$ is SO$_2$NH and R$_9$ is CH$_2$CH(OH)CH$_2$OH. In one embodiment, Z$^D$ is SO$_2$NH and R$_9$ is CH$_2$CH(OH)CH$_2$CH$_3$. In one embodiment, Z$^D$ is SO$_2$NH and R$_9$ is C(CH$_3$)$_2$CH$_2$OH. In one embodiment, Z$^D$ is SO$_2$NH and R$_9$ is CH(CH$_2$CH$_3$)CH$_2$OH. In one embodiment, Z$^D$ is SO$_2$NH and R$_9$ is CH$_2$CH$_2$OCH$_2$CH$_2$OH. In one embodiment, Z$^D$ is SO$_2$NH and R$_9$ is C(CH$_3$)(CH$_2$OH)$_2$. In one embodiment, Z$^D$ is SO$_2$NH and R$_9$ is CH$_2$CH(OH)CH$_2$C(O)OH. In one embodiment, Z$^D$ is SO$_2$NH and R$_9$ is CH$_2$CH$_2$N(CH$_3$)$_2$. In one embodiment, Z$^D$ is SO$_2$NH and R$_9$ is CH$_2$CH$_2$NHC(O)CH$_3$. In one embodiment, Z$^D$ is SO$_2$NH and R$_9$ is CH(CH(CH$_3$)$_2$)CH$_2$OH. In one embodiment, Z$^D$ is SO$_2$NH and R$_9$ is CH(CH$_2$CH$_2$CH$_3$)CH$_2$OH. In one embodiment, Z$^D$ is SO$_2$NH and R$_9$ is 1-tetrahydrofuryl-methyl. In one embodiment, Z$^D$ is SO$_2$NH and R$_9$ is furylmethyl. In one embodiment, Z$^D$ is SO$_2$NH and R$_9$ is (5-methylfuryl)-methyl. In one embodiment, Z$^D$ is SO$_2$NH and R$_9$ is 2-pyrrolidinyl-ethyl. In one embodiment, Z$^D$ is SO$_2$NH and R$_9$ is 2-(1-methylpyrrolidinyl)-ethyl. In one embodiment, Z$^D$ is SO$_2$NH and R$_9$ is 2-(4-morpholinyl)-ethyl. In one embodiment, Z$^D$ is SO$_2$NH and R$_9$ is 3-(4-morpholinyl)-propyl. In one embodiment, Z$^D$ is SO$_2$NH and R$_9$ is C(CH$_2$CH$_3$)(CH$_2$OH)$_2$. In one embodiment, Z$^D$ is SO$_2$NH and R$_9$ is 2-(1H-imidazol-4-yl) ethyl. In one embodiment, Z$^D$ is SO$_2$NH and R$_9$ is 3-(1H-imidazol-1-yl)-propyl. In one embodiment, Z$^D$ is SO$_2$NH and R$_9$ is 2-(2-pyridinyl)-ethyl.

In some embodiment, Z$^D$ is SO$_2$NH and R$_9$ is an optionally substituted C$_{1-6}$ cycloaliphatic. In several examples, Z$^D$ is SO$_2$NH and R$_9$ is an optionally substituted C$_{1-6}$ cycloalkyl. In several examples, Z$^D$ is SO$_2$NH and R$_9$ is C$_{1-6}$ cycloalkyl. In one embodiment, Z$^D$ is SO$_2$NH and R$_9$ is cyclobutyl. In one embodiment, Z$^D$ is SO$_2$NH and R$_9$ is cyclopentyl. In one embodiment, Z$^D$ is SO$_2$NH and R$_9$ is cyclohexyl.

In some embodiments, Z$^D$ is SO$_2$N(C$_{1-6}$ alkyl) and R$_9$ is an optionally substituted straight or branched C$_{1-6}$ aliphatic or an optionally substituted cycloaliphatic. In some embodiments, Z$^D$ is SO$_2$N(C$_{1-6}$ alkyl) and R$_9$ is an optionally substituted straight or branched C$_{1-6}$ aliphatic. In some embodiments, Z$^D$ is SO$_2$N(C$_{1-6}$ alkyl) and R$_9$ is an optionally substituted straight or branched C$_{1-6}$ alkyl or an optionally substituted straight or branched C$_{1-6}$ alkenyl. In one embodiments, Z$^D$ is SO$_2$N(CH$_3$) and R$_9$ is methyl. In one embodiments, Z$^D$ is SO$_2$N(CH$_3$) and R$_9$ is n-propyl. In one embodiments, Z$^D$ is SO$_2$N(CH$_3$) and R$_9$ is n-butyl. In one embodiments, Z$^D$ is SO$_2$N(CH$_3$) and R$_9$ is cyclohexyl. In one embodiments, Z$^D$ is SO$_2$N(CH$_3$) and R$_9$ is allyl. In one embodiments, Z$^D$ is SO$_2$N(CH$_3$) and R$_9$ is CH$_2$CH$_2$OH. In one embodiments, Z$^D$ is SO$_2$N(CH$_3$) and R$_9$ is CH$_2$CH(OH)CH$_2$OH. In one embodiments, Z$^D$ is SO$_2$N(CH$_2$CH$_2$CH$_3$) and R$_9$ is cyclopropylmethyl.

In one embodiment, Z$^D$ is CH$_2$NHSO$_2$ and R$_9$ is methyl. In one embodiment, Z$^D$ is CH$_2$N(CH$_3$)SO$_2$ and R$_9$ is methyl.

In some embodiments, Z$^D$ is SO$_2$ and R$_9$ is an optionally substituted C$_{1-6}$ straight or branched aliphatic or an optionally substituted 3-8 membered heterocyclic, having 1, 2, or 3 ring members selected from the group consisting of nitrogen, oxygen, sulfur, SO, or SO$_2$. In some embodiments, Z$^D$ is SO$_2$ and R$_9$ is straight or branched C$_{1-6}$ alkyl or 3-8 membered heterocycloaliphatic each of which is optionally substituted with 1, 2, or 3 of oxo, halo, hydroxyl, or an optionally substituted group selected from C$_{1-6}$ aliphatic, carbonyl, amino, and carboxy. In one embodiment, Z$^D$ is SO$_2$ and R$_9$ is methyl. In some embodiments, Z$^D$ is SO$_2$ and examples of R$_9$ include

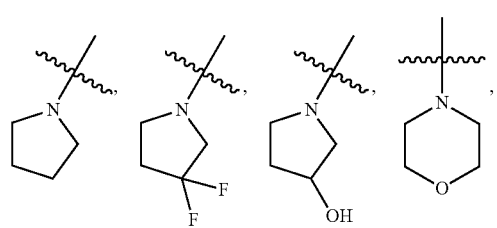

-continued

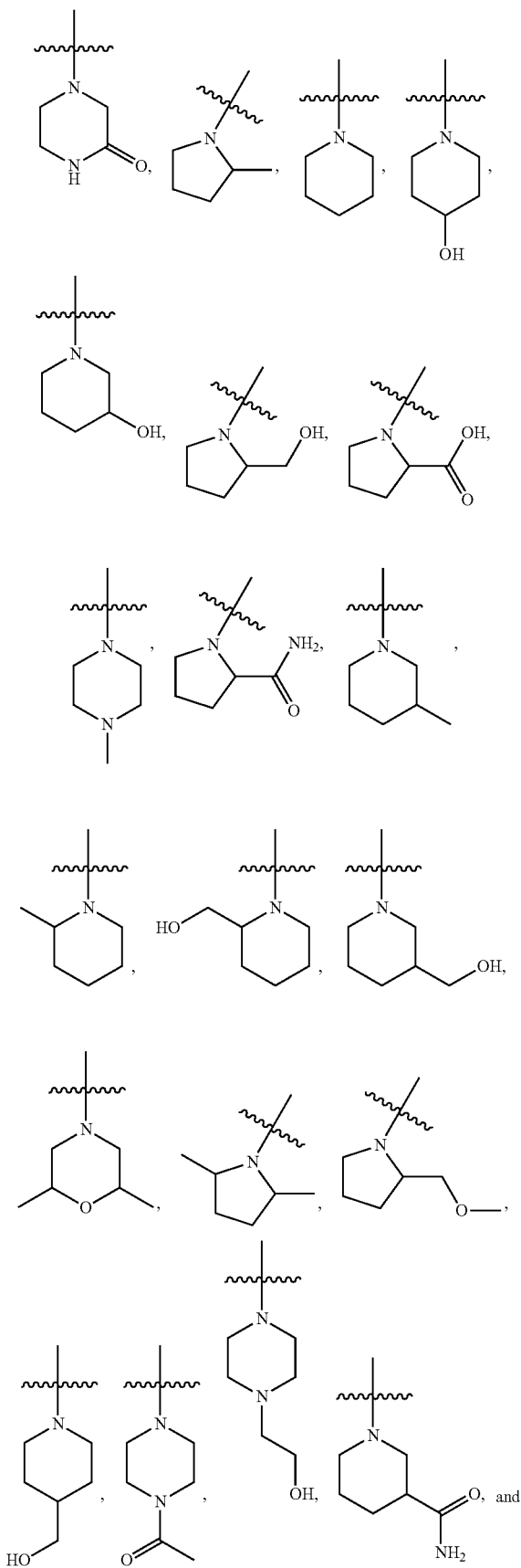

-continued

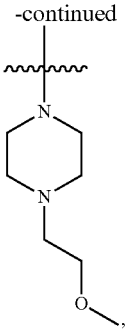

In some embodiments, $R^{D2}$ is H, hydroxyl, halo, $C_{1-6}$ alkyl, $C_{1-6}$ alkoxy, $C_{3-6}$ cycloalkyl, or $NH_2$. In several examples, $R^{D2}$ is H, halo, $C_{1-4}$ alkyl, or $C_{1-4}$ alkoxy. Examples of $R^{D2}$ include H, F, Cl, methyl, ethyl, and methoxy.

In some embodiments, the present invention provides compounds of formula (I'-A) or formula (I'-B):

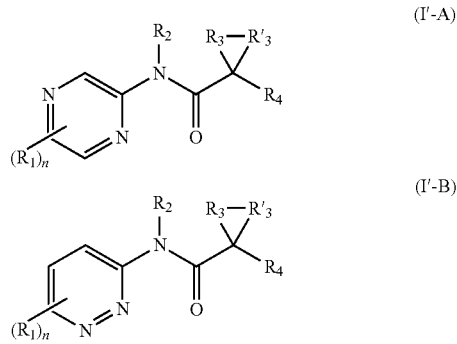

or a pharmaceutically acceptable salt thereof,
wherein $R_1$, $R_2$, $R_3$, $R'_3$, $R_4$, and n are defined above.

In some embodiments, $R_1$ is an optionally substituted aryl. In several examples, $R_1$ is phenyl optionally substituted with 1, 2, or 3 of halo, OH, —O($C_{1-6}$ aliphatic), amino, $C_{1-6}$ aliphatic, $C_{3-7}$ cycloaliphatic, 3-8 membered heterocycloaliphatic, $C_{6-10}$ aryl, or 5-8 membered heteroaryl. In some embodiments, $R_1$ is phenyl optionally substituted with alkoxy, halo, or amino. In one embodiment, $R_1$ is phenyl. In one embodiment, $R_1$ is phenyl substituted with Cl, methoxy, ethoxy, or dimethylamino.

In some embodiments, $R_2$ is hydrogen. In some embodiments, $R_2$ is optionally substituted $C_{1-6}$ aliphatic.

In some embodiments, $R_3$, $R'_3$, and the carbon atom to which they are attached form an optionally substituted $C_{3-8}$ cycloaliphatic or an optionally substituted 3-8 membered heterocycloaliphatic. In some embodiments, $R_3$, $R'_3$, and the carbon atom to which they are attached form an optionally substituted $C_{3-8}$ cycloalkyl. In one example, $R_3$, $R'_3$, and the carbon atom to which they are attached is cyclopropyl, cyclobutyl, cyclopentyl, cyclohexyl or cycloheptyl, each of which is optionally substituted. In one example, $R_3$, $R'_3$, and the carbon atom to which they are attached is cyclopropyl, cyclobutyl, cyclopentyl, cyclohexyl or cycloheptyl. In several examples, $R_3$, $R'_3$, and the carbon atom to which they are attached is cyclopropyl.

In some embodiments, $R_4$ is an optionally substituted aryl or an optionally substituted heteroaryl. In some embodiments, $R_4$ is an optionally substituted phenyl. In several embodiments, $R_4$ is phenyl fused to a 3, 4, 5, or 6 membered heterocyclic having 1, 2, or 3 ring membered selected from oxygen, sulfur and nitrogen. In several embodiments, $R_4$ is

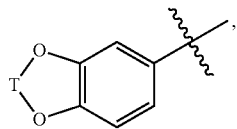

wherein T is defined above. In several examples, T is —$CH_2$—.

Alternative embodiments of $R_1$, $R_2$, $R_3$, $R'_3$, $R_4$, and n in formula (I'-A) or formula (I'-B) are as defined for formula (I), formula (I'), and embodiments thereof.

Exemplary compounds of the present invention include, but are not limited to, those illustrated in Table 1 below.

TABLE 1

Examples of compounds of the present invention

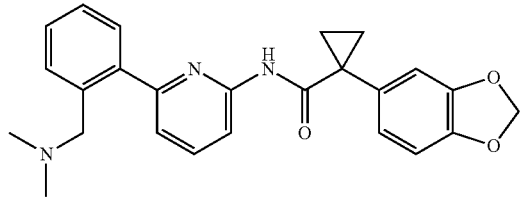 [SMILES: CN(C)Cc1ccccc1-c1cccc(NC(=O)C2(c3ccc4c(c3)OCO4)CC2)n1]

1

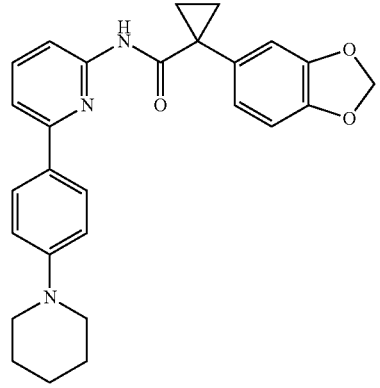 [SMILES: O=C(Nc1cccc(-c2ccc(N3CCCCC3)cc2)n1)C1(c2ccc3c(c2)OCO3)CC1]

2

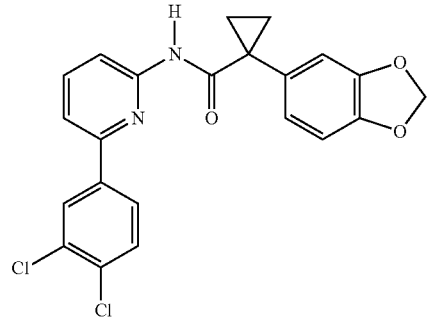

3

TABLE 1-continued
Examples of compounds of the present invention
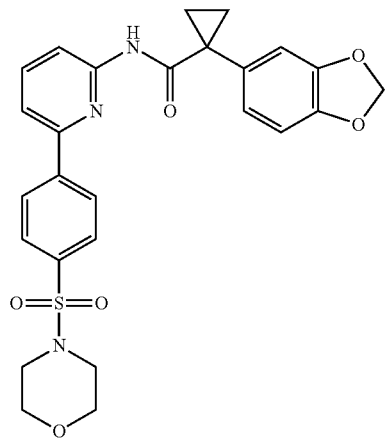 [SMILES: O=C(Nc1cccc(-c2ccc(S(=O)(=O)N3CCOCC3)cc2)n1)C1(c2ccc3c(c2)OCO3)CC1]
4
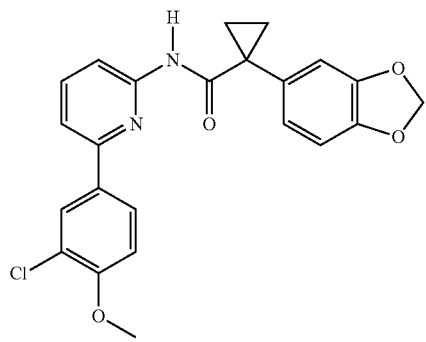 [SMILES: COc1ccc(-c2cccc(NC(=O)C3(c4ccc5c(c4)OCO5)CC3)n2)cc1Cl]
5
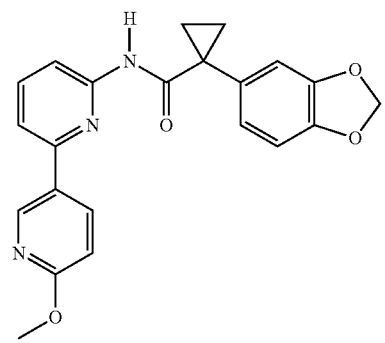 [SMILES: COc1ccc(-c2cccc(NC(=O)C3(c4ccc5c(c4)OCO5)CC3)n2)cn1]
6
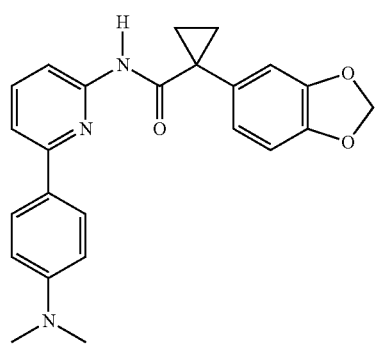 [SMILES: CN(C)c1ccc(-c2cccc(NC(=O)C3(c4ccc5c(c4)OCO5)CC3)n2)cc1]
7

TABLE 1-continued
Examples of compounds of the present invention
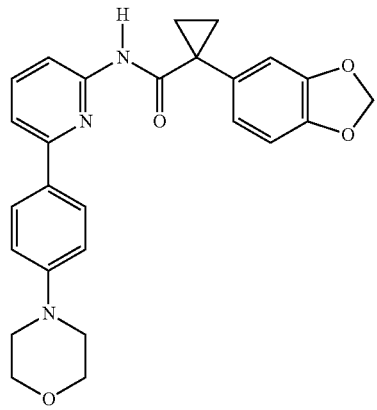 [SMILES: O=C(Nc1cccc(-c2ccc(N3CCOCC3)cc2)n1)C1(c2ccc3c(c2)OCO3)CC1]
8
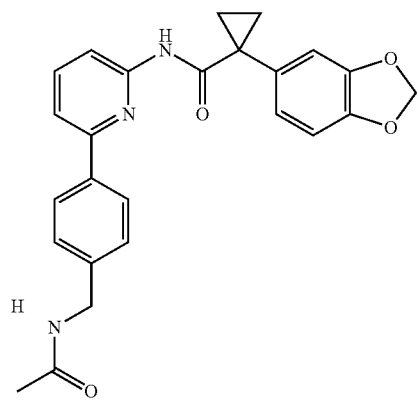
9
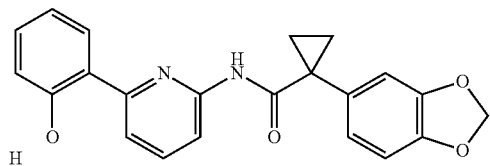
10
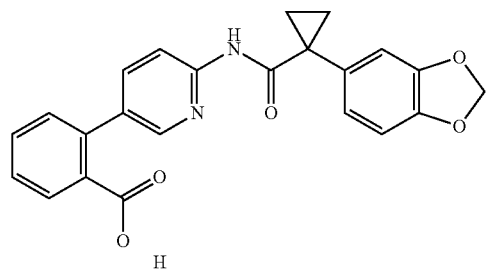
11
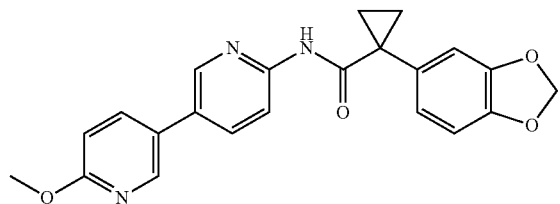 [SMILES: COc1ccc(-c2ccc(NC(=O)C3(c4ccc5c(c4)OCO5)CC3)nc2)cn1]
12

TABLE 1-continued
Examples of compounds of the present invention
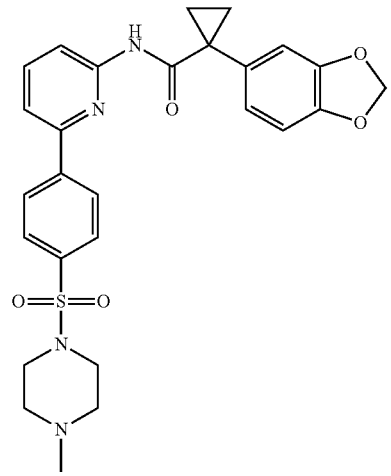 [SMILES: CN1CCN(S(=O)(=O)c2ccc(-c3cccc(NC(=O)C4(c5ccc6c(c5)OCO6)CC4)n3)cc2)CC1]
13
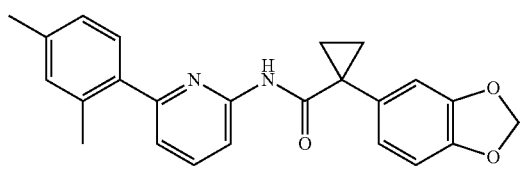 [SMILES: Cc1ccc(-c2cccc(NC(=O)C3(c4ccc5c(c4)OCO5)CC3)n2)c(C)c1]
14
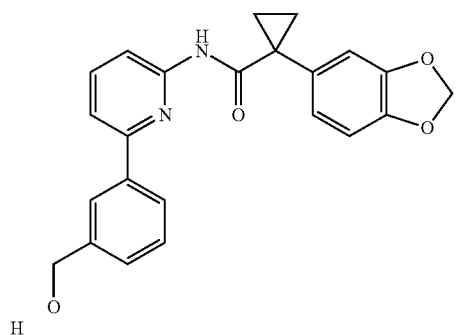
15
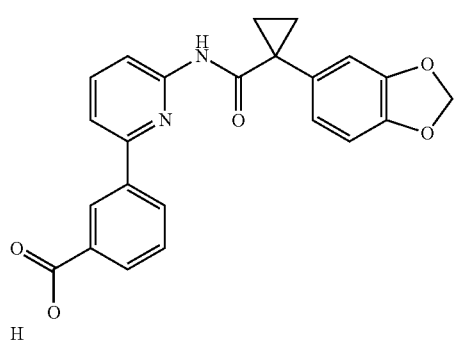
16

TABLE 1-continued
Examples of compounds of the present invention
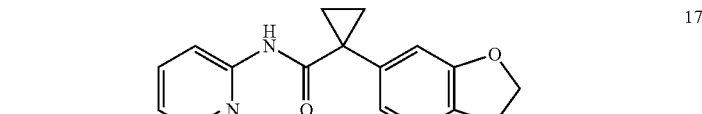
17
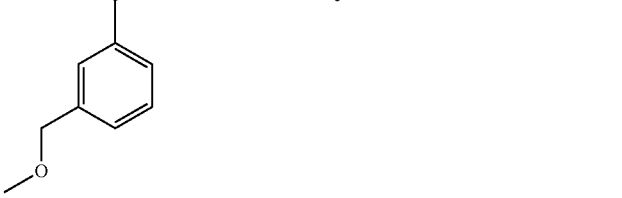
18
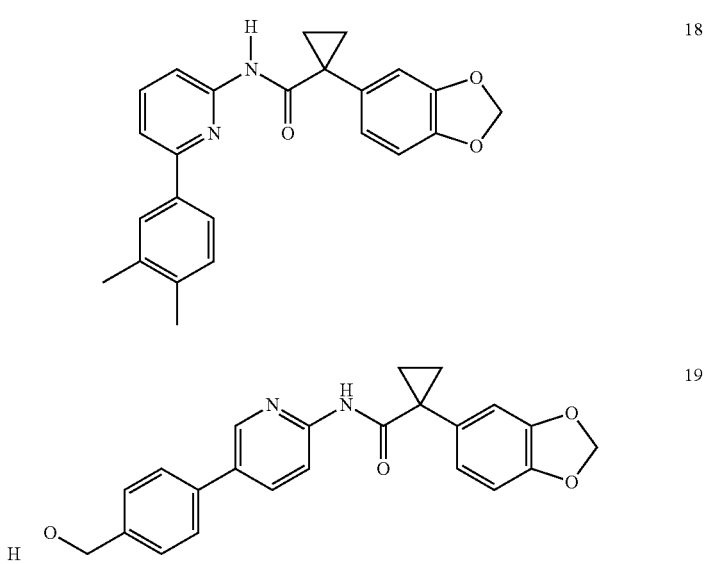
19
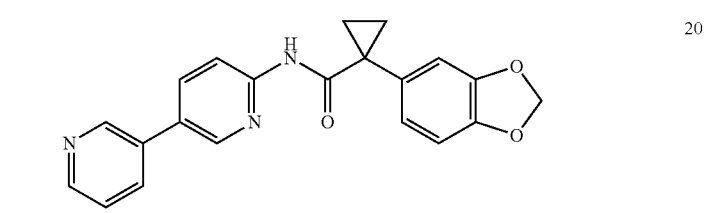
20
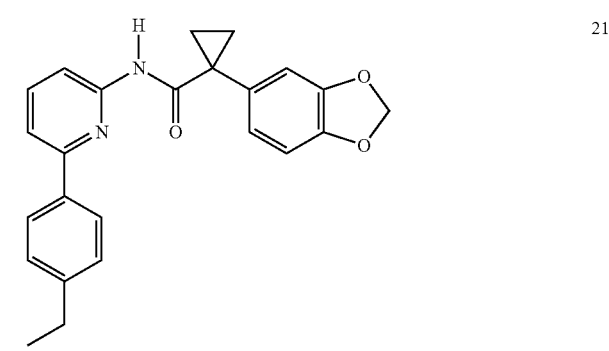
21

TABLE 1-continued
Examples of compounds of the present invention
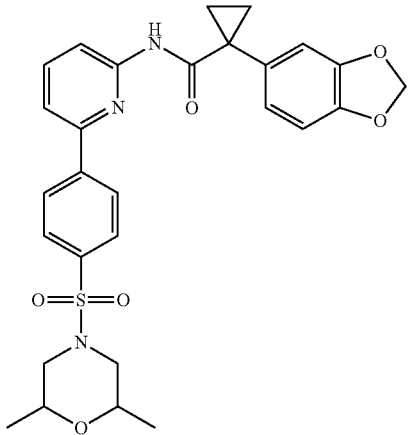 [SMILES: CC1CN(S(=O)(=O)c2ccc(-c3cccc(NC(=O)C4(c5ccc6c(c5)OCO6)CC4)n3)cc2)CC(C)O1]
22
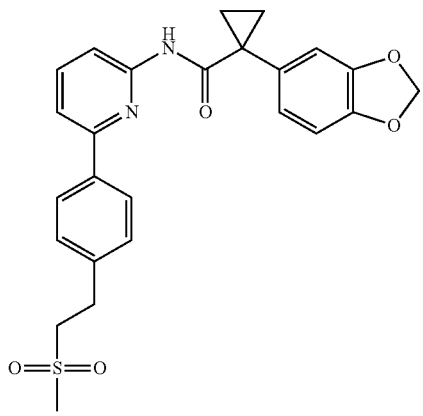 [SMILES: CS(=O)(=O)CCc1ccc(-c2cccc(NC(=O)C3(c4ccc5c(c4)OCO5)CC3)n2)cc1]
23
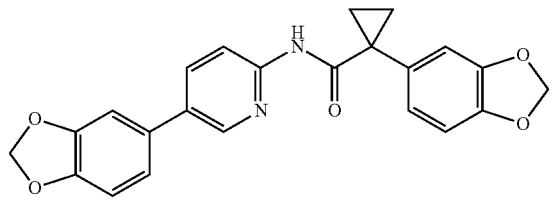 [SMILES: O=C(Nc1ccc(-c2ccc3c(c2)OCO3)cn1)C1(c2ccc3c(c2)OCO3)CC1]
24
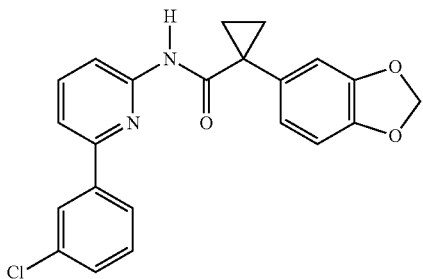 [SMILES: O=C(Nc1cccc(-c2cccc(Cl)c2)n1)C1(c2ccc3c(c2)OCO3)CC1]
25

TABLE 1-continued
Examples of compounds of the present invention
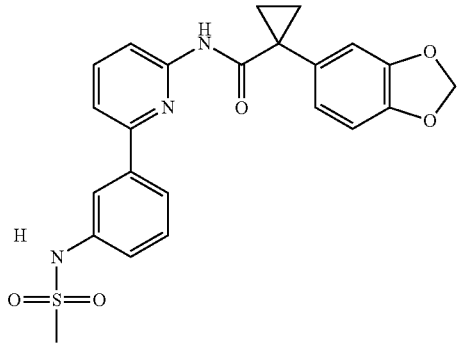
26
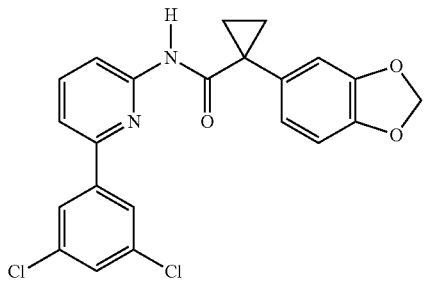 [SMILES: O=C(Nc1cccc(-c2cc(Cl)cc(Cl)c2)n1)C1(c2ccc3c(c2)OCO3)CC1]
27
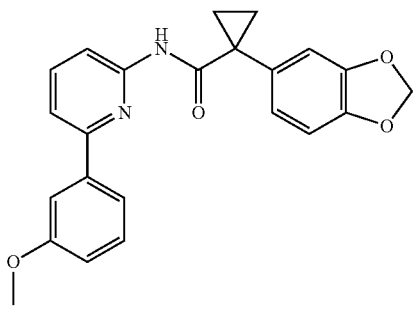 [SMILES: COc1cccc(-c2cccc(NC(=O)C3(c4ccc5c(c4)OCO5)CC3)n2)c1]
28
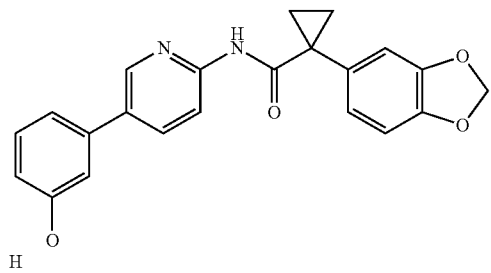
29

TABLE 1-continued
Examples of compounds of the present invention
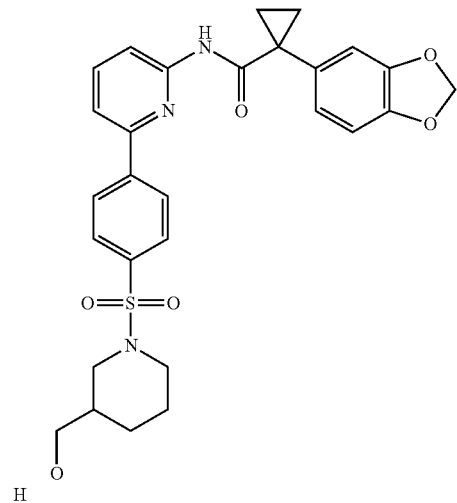
30
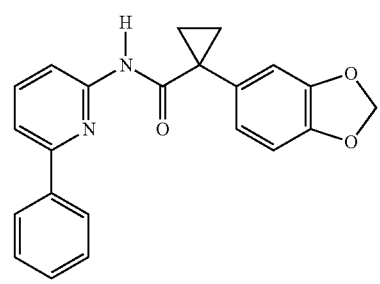 [SMILES: O=C(Nc1cccc(-c2ccccc2)n1)C1(c2ccc3c(c2)OCO3)CC1]
31
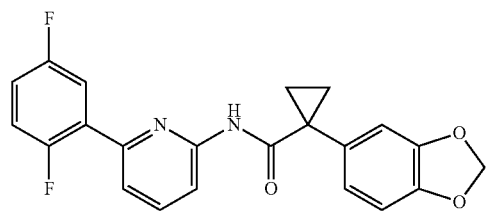 [SMILES: O=C(Nc1cccc(-c2cc(F)ccc2F)n1)C1(c2ccc3c(c2)OCO3)CC1]
32
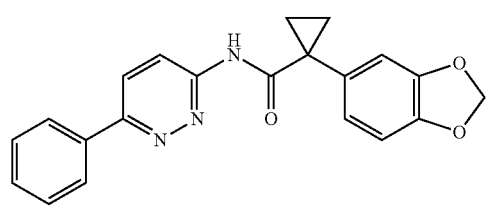 [SMILES: O=C(Nc1ccc(-c2ccccc2)nn1)C1(c2ccc3c(c2)OCO3)CC1]
33

TABLE 1-continued
Examples of compounds of the present invention
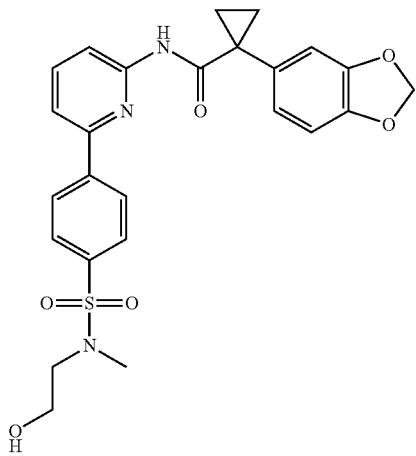 [SMILES: CN(CCO)S(=O)(=O)c1ccc(-c2cccc(NC(=O)C3(c4ccc5c(c4)OCO5)CC3)n2)cc1]
34
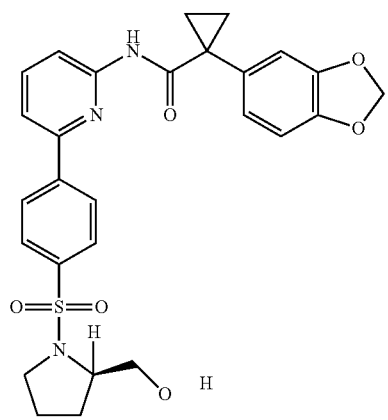
35
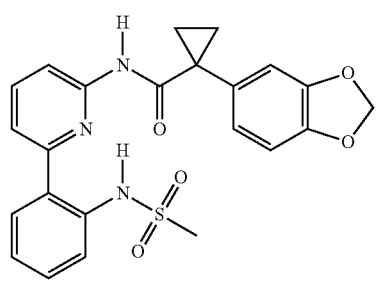 [SMILES: CS(=O)(=O)Nc1ccccc1-c1cccc(NC(=O)C2(c3ccc4c(c3)OCO4)CC2)n1]
36
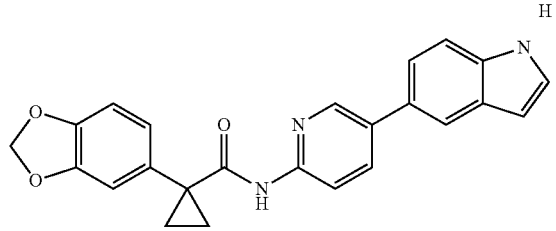
37

TABLE 1-continued
Examples of compounds of the present invention
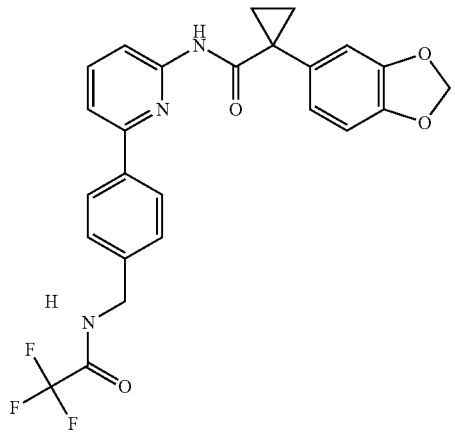 38
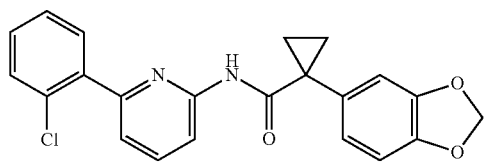 [SMILES: O=C(Nc1cccc(-c2ccccc2Cl)n1)C1(c2ccc3c(c2)OCO3)CC1] 39
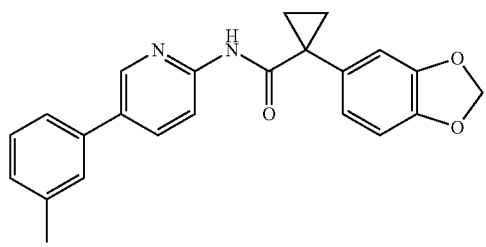 [SMILES: Cc1cccc(-c2ccc(NC(=O)C3(c4ccc5c(c4)OCO5)CC3)nc2)c1] 40
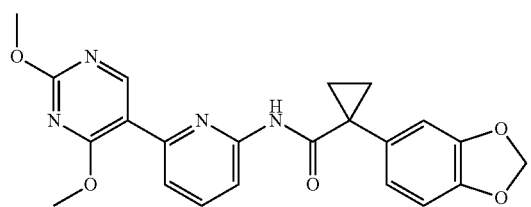 [SMILES: COc1ncc(-c2cccc(NC(=O)C3(c4ccc5c(c4)OCO5)CC3)n2)c(OC)n1] 41
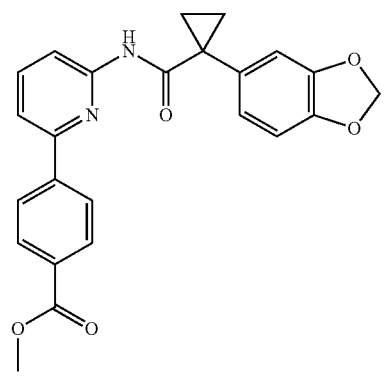 [SMILES: COC(=O)c1ccc(-c2cccc(NC(=O)C3(c4ccc5c(c4)OCO5)CC3)n2)cc1] 42

TABLE 1-continued
Examples of compounds of the present invention
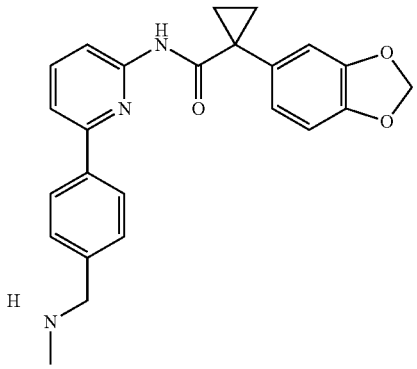 43
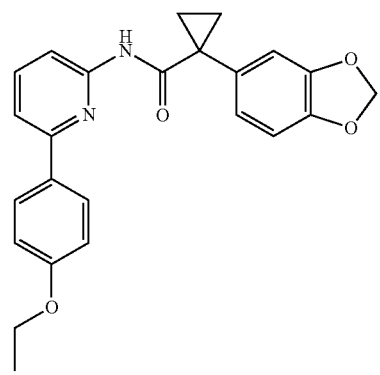 [SMILES: CCOc1ccc(-c2cccc(NC(=O)C3(c4ccc5c(c4)OCO5)CC3)n2)cc1] 44
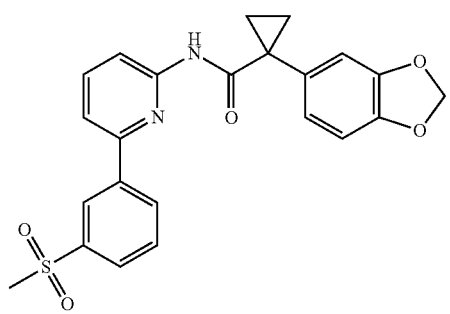 [SMILES: CS(=O)(=O)c1cccc(-c2cccc(NC(=O)C3(c4ccc5c(c4)OCO5)CC3)n2)c1] 45
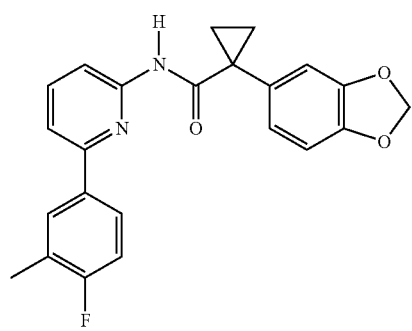 [SMILES: Cc1cc(-c2cccc(NC(=O)C3(c4ccc5c(c4)OCO5)CC3)n2)ccc1F] 46

TABLE 1-continued
Examples of compounds of the present invention
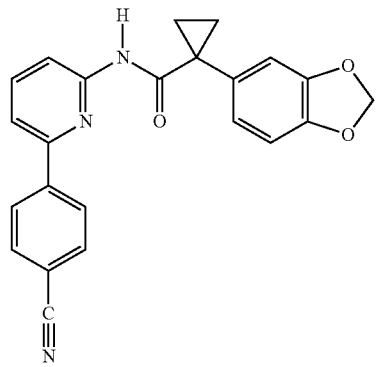 [SMILES: N#Cc1ccc(-c2cccc(NC(=O)C3(c4ccc5c(c4)OCO5)CC3)n2)cc1] 47
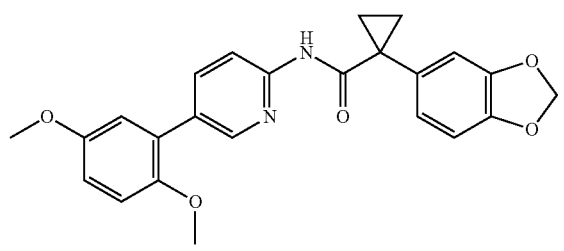 [SMILES: COc1ccc(OC)c(-c2ccc(NC(=O)C3(c4ccc5c(c4)OCO5)CC3)nc2)c1] 48
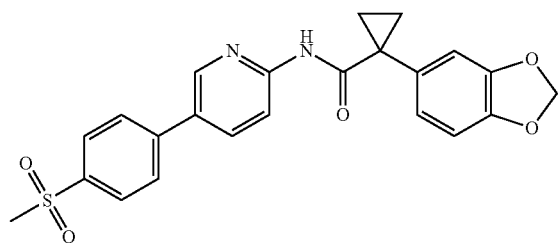 [SMILES: CS(=O)(=O)c1ccc(-c2ccc(NC(=O)C3(c4ccc5c(c4)OCO5)CC3)nc2)cc1] 49
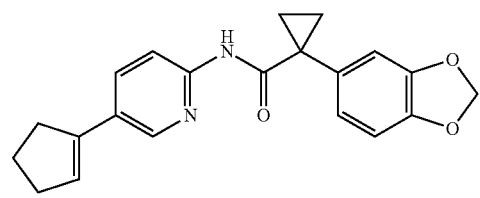 [SMILES: O=C(Nc1ccc(C2=CCCC2)cn1)C1(c2ccc3c(c2)OCO3)CC1] 50
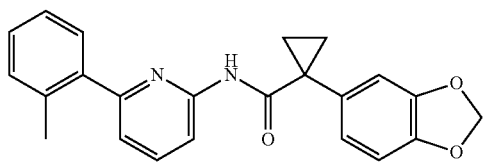 [SMILES: Cc1ccccc1-c1cccc(NC(=O)C2(c3ccc4c(c3)OCO4)CC2)n1] 51
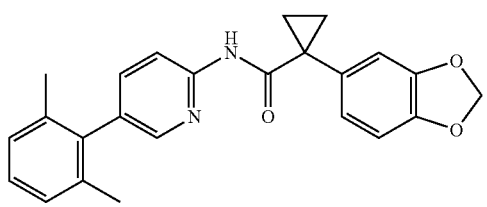 [SMILES: Cc1cccc(C)c1-c1ccc(NC(=O)C2(c3ccc4c(c3)OCO4)CC2)nc1] 52

TABLE 1-continued
Examples of compounds of the present invention
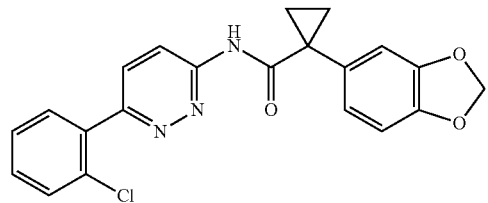 [SMILES: O=C(Nc1ccc(-c2ccccc2Cl)nn1)C1(c2ccc3c(c2)OCO3)CC1] 53
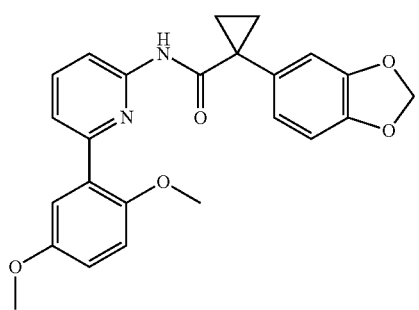 [SMILES: COc1ccc(OC)c(-c2cccc(NC(=O)C3(c4ccc5c(c4)OCO5)CC3)n2)c1] 54
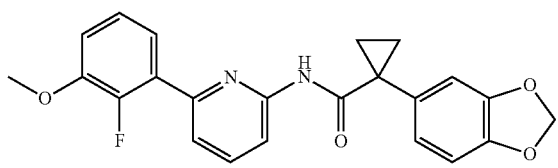 [SMILES: COc1cccc(-c2cccc(NC(=O)C3(c4ccc5c(c4)OCO5)CC3)n2)c1F] 55
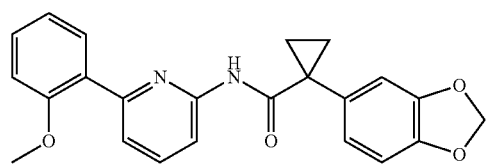 [SMILES: COc1ccccc1-c1cccc(NC(=O)C2(c3ccc4c(c3)OCO4)CC2)n1] 56
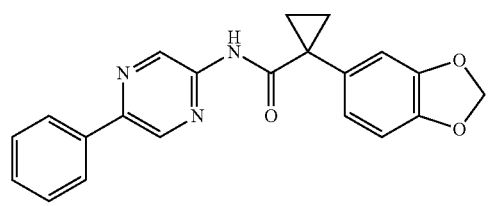 [SMILES: O=C(Nc1cnc(-c2ccccc2)cn1)C1(c2ccc3c(c2)OCO3)CC1] 57
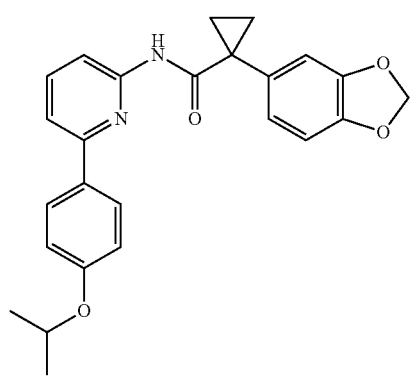 58

TABLE 1-continued
Examples of compounds of the present invention
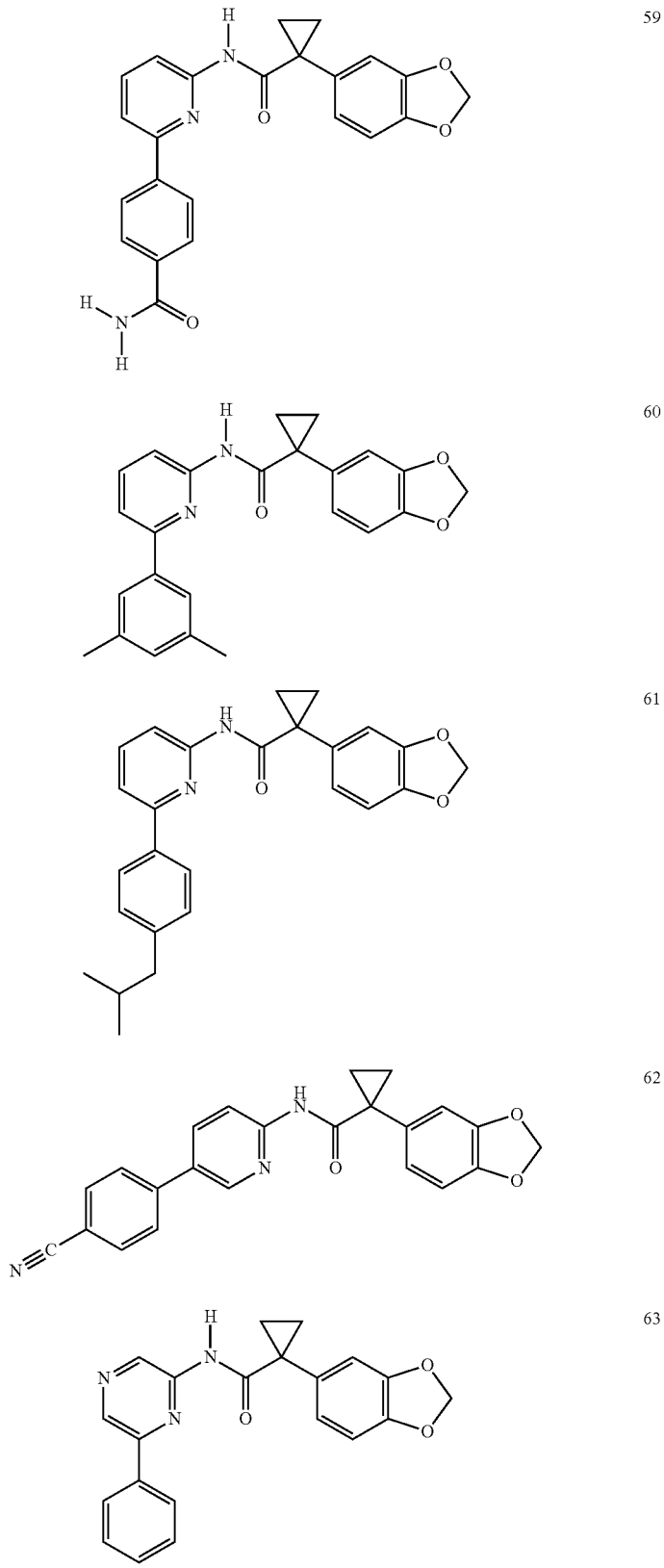

TABLE 1-continued
Examples of compounds of the present invention
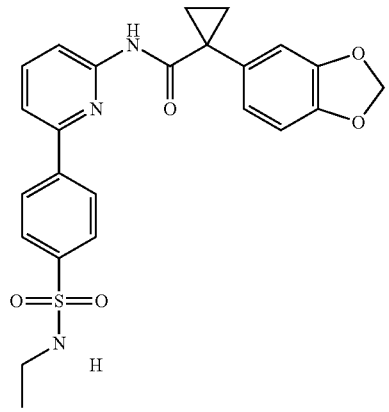
64
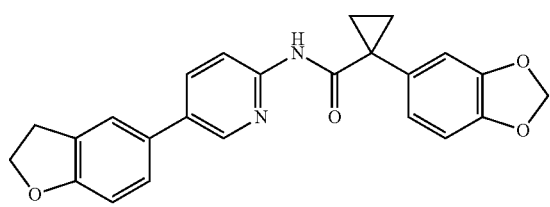
65
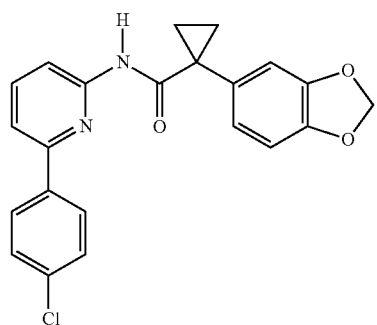 [SMILES: O=C(Nc1cccc(-c2ccc(Cl)cc2)n1)C1(c2ccc3c(c2)OCO3)CC1]
66
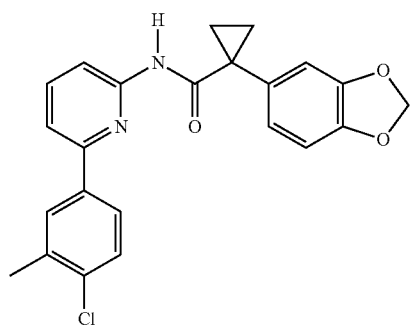
67
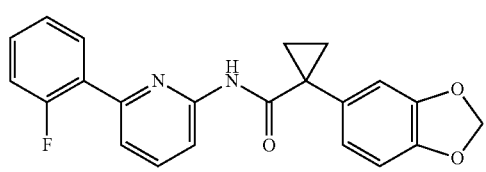 [SMILES: O=C(Nc1cccc(-c2ccccc2F)n1)C1(c2ccc3c(c2)OCO3)CC1]
68

TABLE 1-continued
Examples of compounds of the present invention
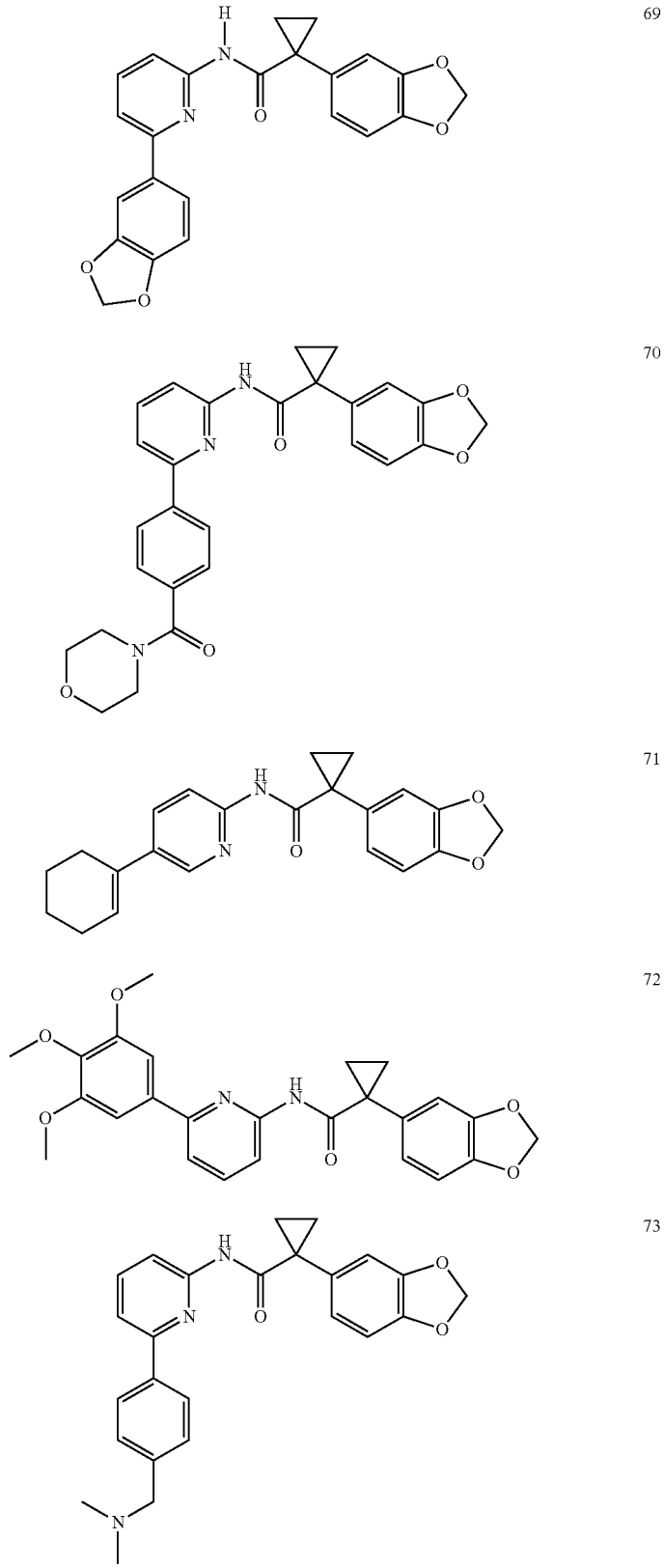

TABLE 1-continued
Examples of compounds of the present invention
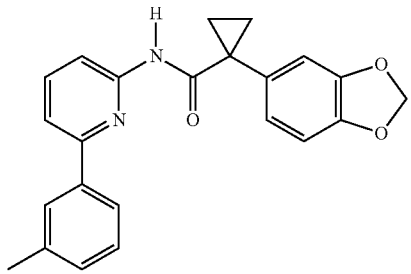 [SMILES: Cc1cccc(-c2cccc(NC(=O)C3(c4ccc5c(c4)OCO5)CC3)n2)c1]
74
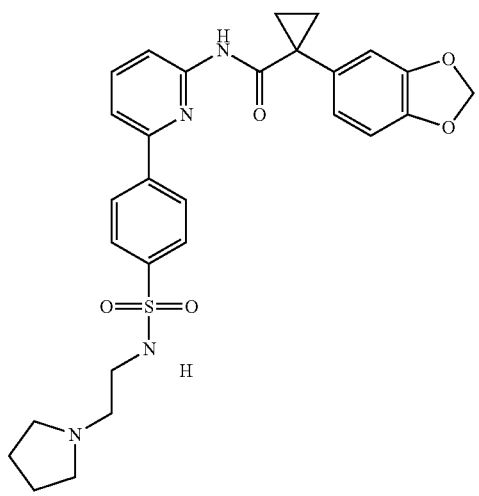
75
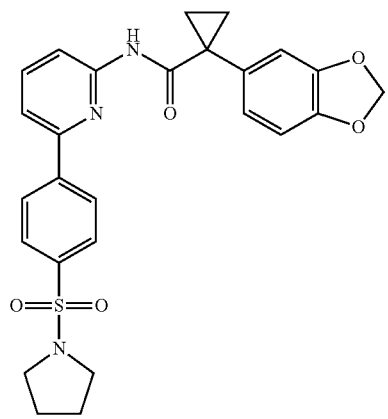 [SMILES: O=C(Nc1cccc(-c2ccc(S(=O)(=O)N3CCCC3)cc2)n1)C1(c2ccc3c(c2)OCO3)CC1]
76
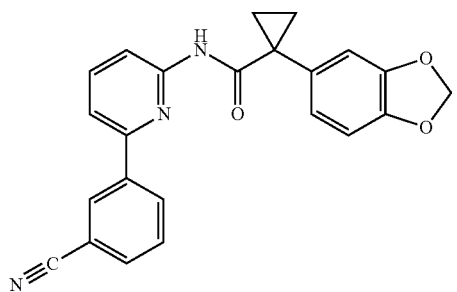 [SMILES: N#Cc1cccc(-c2cccc(NC(=O)C3(c4ccc5c(c4)OCO5)CC3)n2)c1]
77

103
104
TABLE 1-continued
Examples of compounds of the present invention
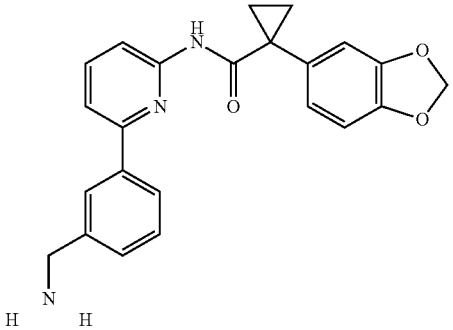
78
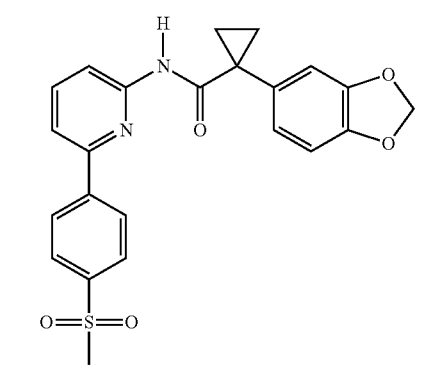 [SMILES: CS(=O)(=O)c1ccc(-c2cccc(NC(=O)C3(c4ccc5c(c4)OCO5)CC3)n2)cc1]
79
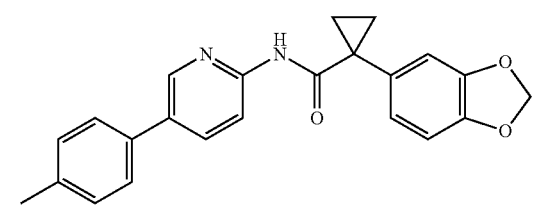 [SMILES: Cc1ccc(-c2ccc(NC(=O)C3(c4ccc5c(c4)OCO5)CC3)nc2)cc1]
80
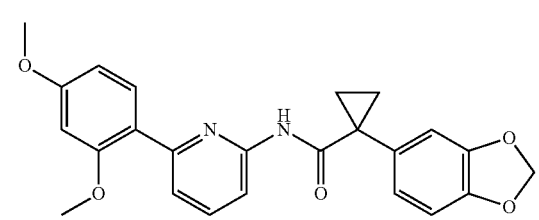 [SMILES: COc1ccc(-c2cccc(NC(=O)C3(c4ccc5c(c4)OCO5)CC3)n2)c(OC)c1]
81
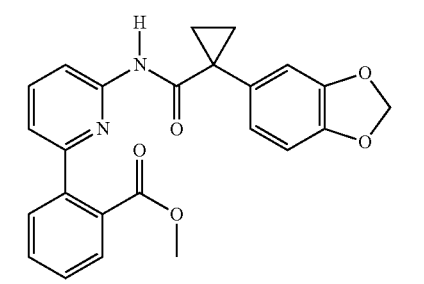
82
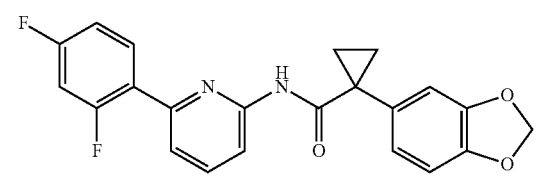 [SMILES: O=C(Nc1cccc(-c2ccc(F)cc2F)n1)C1(c2ccc3c(c2)OCO3)CC1]
83

TABLE 1-continued
Examples of compounds of the present invention
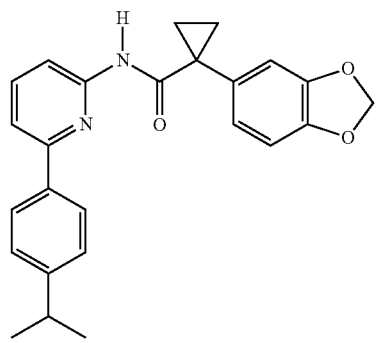 [SMILES: CC(C)c1ccc(-c2cccc(NC(=O)C3(c4ccc5c(c4)OCO5)CC3)n2)cc1]
84
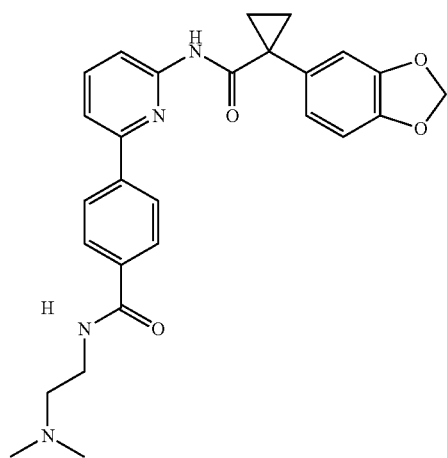
85
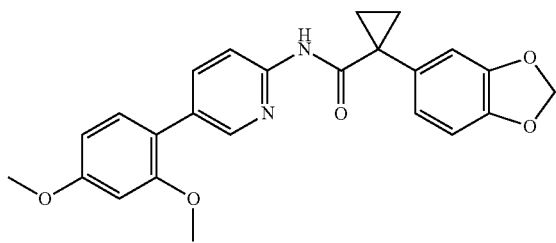 [SMILES: COc1ccc(-c2ccc(NC(=O)C3(c4ccc5c(c4)OCO5)CC3)nc2)c(OC)c1]
86
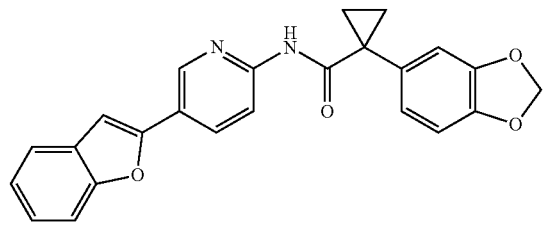 [SMILES: O=C(Nc1ccc(-c2cc3ccccc3o2)cn1)C1(c2ccc3c(c2)OCO3)CC1]
87
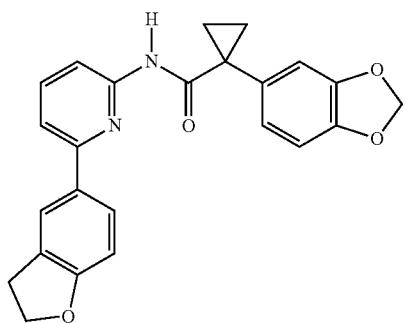 [SMILES: O=C(Nc1cccc(-c2ccc3c(c2)CCO3)n1)C1(c2ccc3c(c2)OCO3)CC1]
88

TABLE 1-continued
Examples of compounds of the present invention
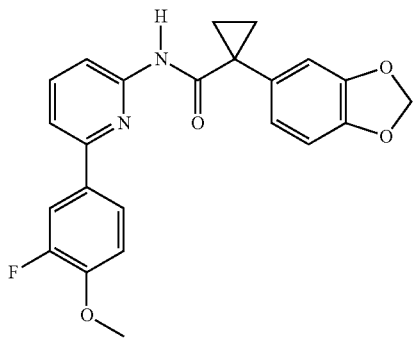 [SMILES: COc1ccc(-c2cccc(NC(=O)C3(c4ccc5c(c4)OCO5)CC3)n2)cc1F]
89
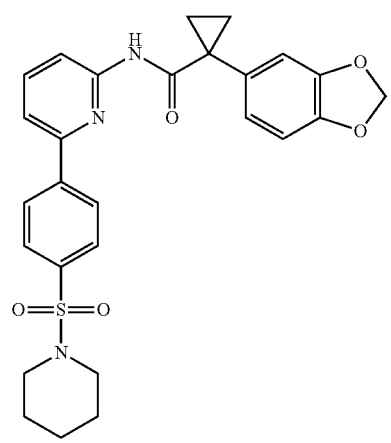 [SMILES: O=C(Nc1cccc(-c2ccc(S(=O)(=O)N3CCCCC3)cc2)n1)C1(c2ccc3c(c2)OCO3)CC1]
90
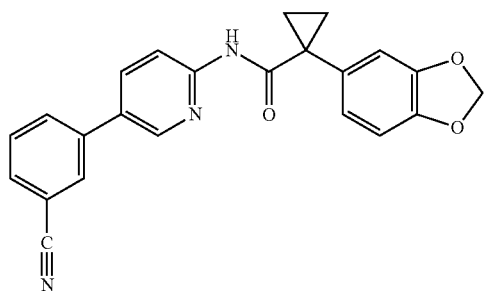 [SMILES: N#Cc1cccc(-c2ccc(NC(=O)C3(c4ccc5c(c4)OCO5)CC3)nc2)c1]
91
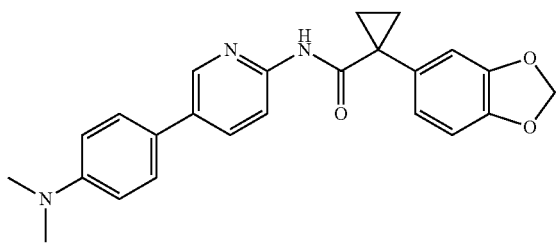
92
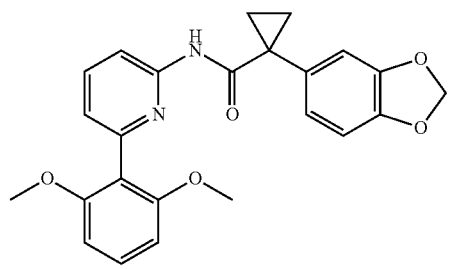 [SMILES: COc1cccc(OC)c1-c1cccc(NC(=O)C2(c3ccc4c(c3)OCO4)CC2)n1]
93

TABLE 1-continued
Examples of compounds of the present invention
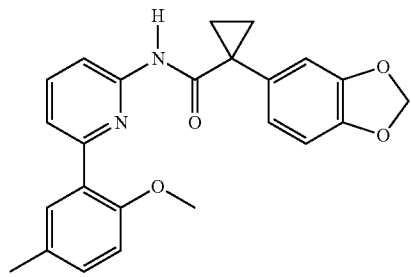 [SMILES: COc1ccc(C)cc1-c1cccc(NC(=O)C2(c3ccc4c(c3)OCO4)CC2)n1]
94
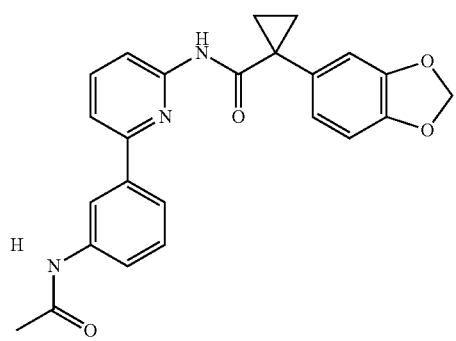
95
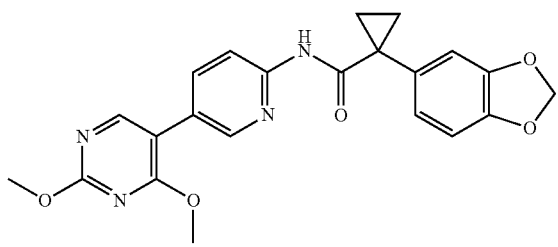 [SMILES: COc1ncc(-c2ccc(NC(=O)C3(c4ccc5c(c4)OCO5)CC3)nc2)c(OC)n1]
96
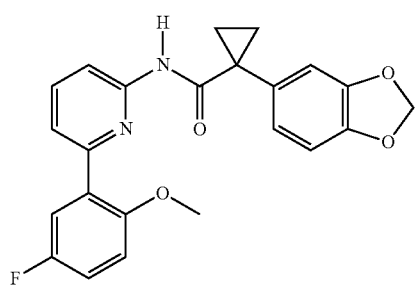 [SMILES: COc1ccc(F)cc1-c1cccc(NC(=O)C2(c3ccc4c(c3)OCO4)CC2)n1]
97
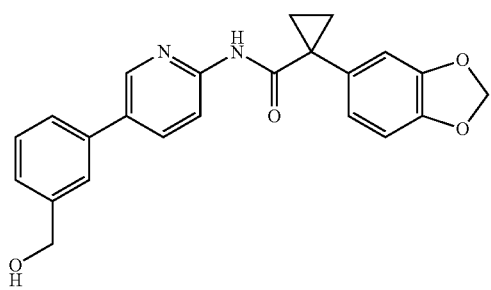 [SMILES: O=C(Nc1ccc(-c2cccc(CO)c2)cn1)C1(c2ccc3c(c2)OCO3)CC1]
98

TABLE 1-continued
Examples of compounds of the present invention
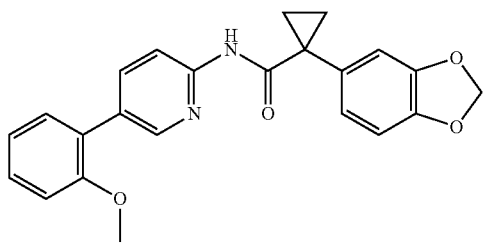 [SMILES: COc1ccccc1-c1ccc(NC(=O)C2(c3ccc4c(c3)OCO4)CC2)nc1]
99
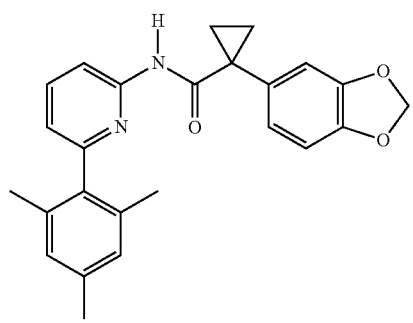 [SMILES: Cc1cc(C)c(-c2cccc(NC(=O)C3(c4ccc5c(c4)OCO5)CC3)n2)c(C)c1]
100
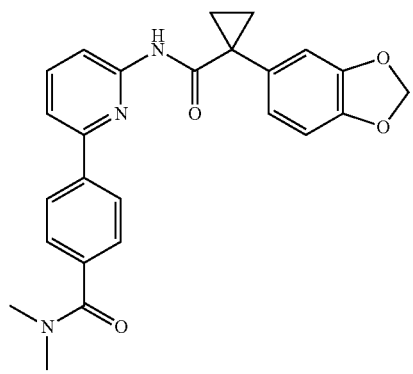 [SMILES: CN(C)C(=O)c1ccc(-c2cccc(NC(=O)C3(c4ccc5c(c4)OCO5)CC3)n2)cc1]
101
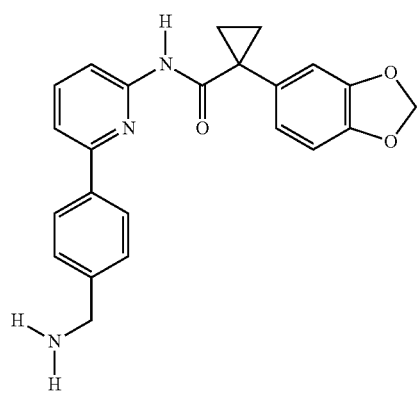 [SMILES: NCc1ccc(-c2cccc(NC(=O)C3(c4ccc5c(c4)OCO5)CC3)n2)cc1]
102

TABLE 1-continued
Examples of compounds of the present invention
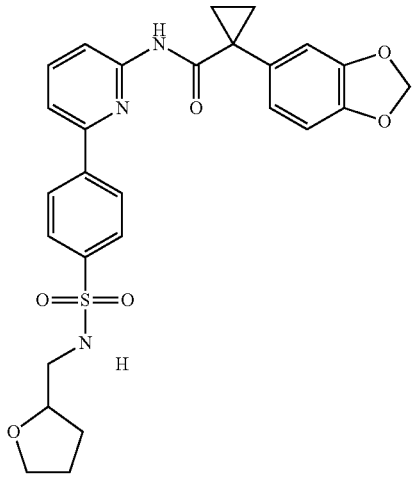 103
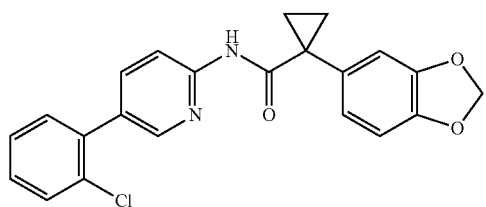 [SMILES: O=C(Nc1ccc(-c2ccccc2Cl)cn1)C1(c2ccc3c(c2)OCO3)CC1] 104
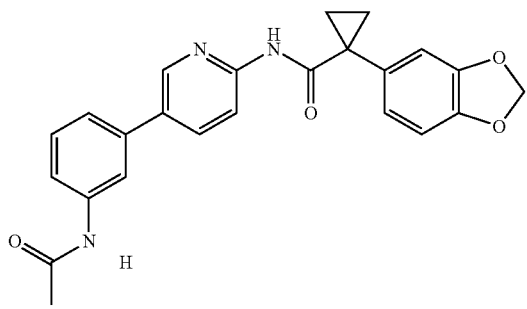 105
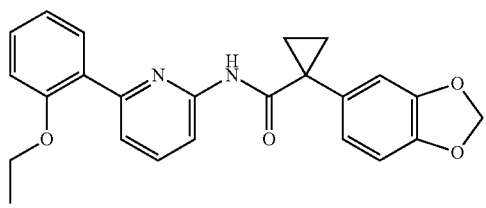 [SMILES: CCOc1ccccc1-c1cccc(NC(=O)C2(c3ccc4c(c3)OCO4)CC2)n1] 106
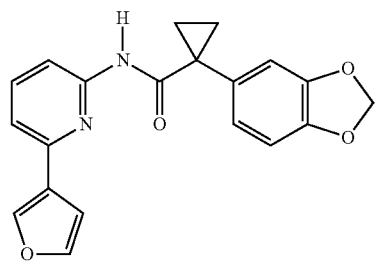 [SMILES: O=C(Nc1cccc(-c2ccoc2)n1)C1(c2ccc3c(c2)OCO3)CC1] 107

115
TABLE 1-continued
Examples of compounds of the present invention
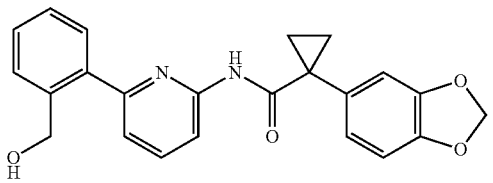 [SMILES: O=C(Nc1cccc(-c2ccccc2CO)n1)C1(c2ccc3c(c2)OCO3)CC1]
108
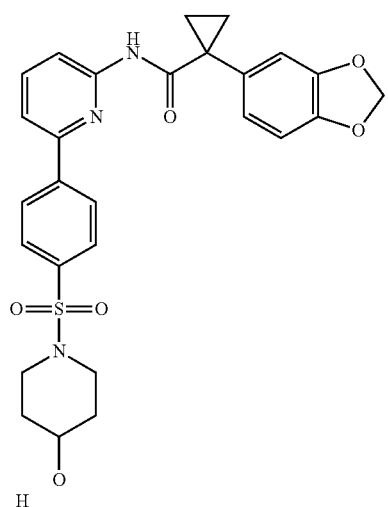
109
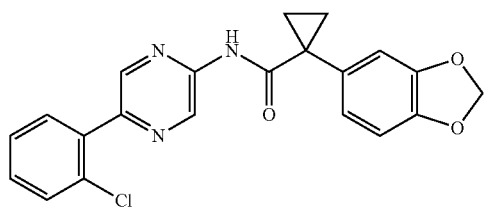 [SMILES: O=C(Nc1cnc(-c2ccccc2Cl)cn1)C1(c2ccc3c(c2)OCO3)CC1]
110
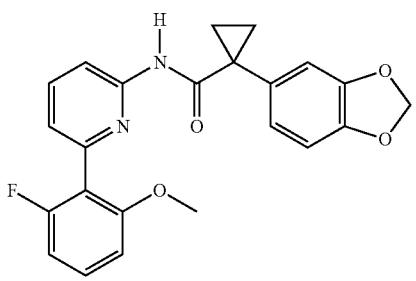 [SMILES: COc1cccc(F)c1-c1cccc(NC(=O)C2(c3ccc4c(c3)OCO4)CC2)n1]
111
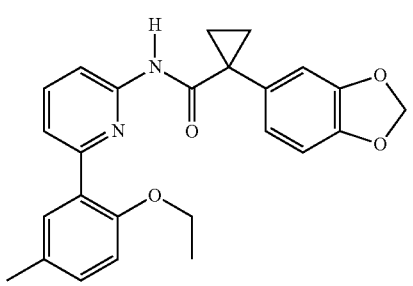 [SMILES: CCOc1ccc(C)cc1-c1cccc(NC(=O)C2(c3ccc4c(c3)OCO4)CC2)n1]
112

TABLE 1-continued
Examples of compounds of the present invention
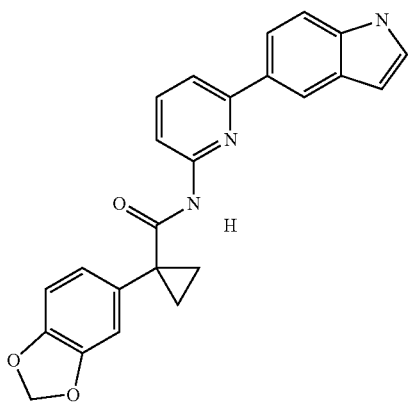 113
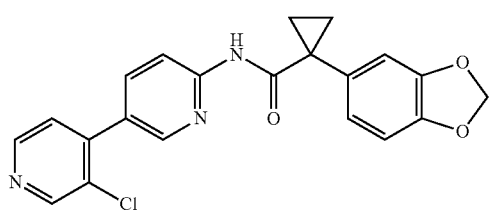 [SMILES: O=C(Nc1ccc(-c2ccncc2Cl)cn1)C1(c2ccc3c(c2)OCO3)CC1] 114
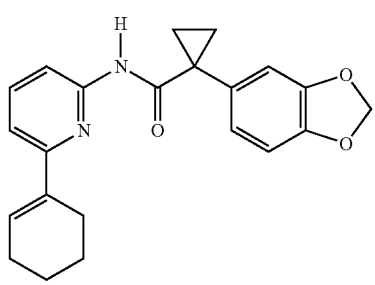 [SMILES: O=C(Nc1cccc(C2=CCCCC2)n1)C1(c2ccc3c(c2)OCO3)CC1] 115
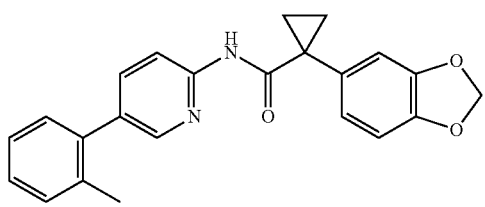 [SMILES: Cc1ccccc1-c1ccc(NC(=O)C2(c3ccc4c(c3)OCO4)CC2)nc1] 116
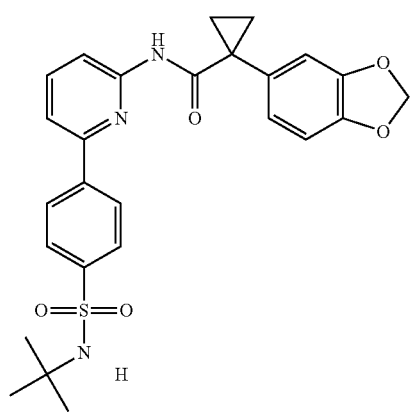 117

TABLE 1-continued
Examples of compounds of the present invention
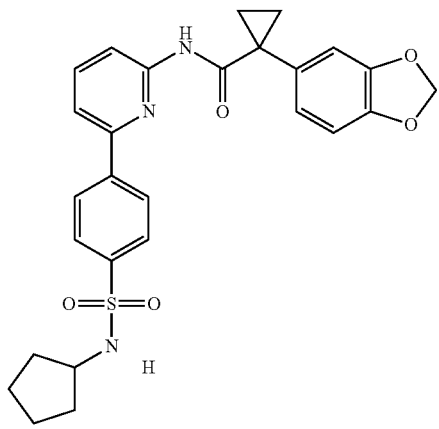
118
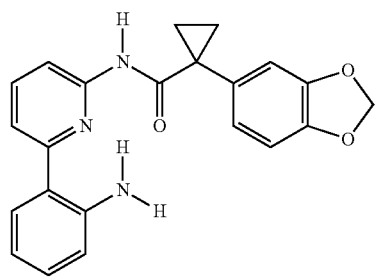 [SMILES: Nc1ccccc1-c1cccc(NC(=O)C2(c3ccc4c(c3)OCO4)CC2)n1]
119
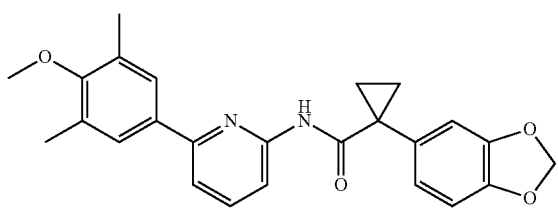 [SMILES: COc1c(C)cc(-c2cccc(NC(=O)C3(c4ccc5c(c4)OCO5)CC3)n2)cc1C]
120
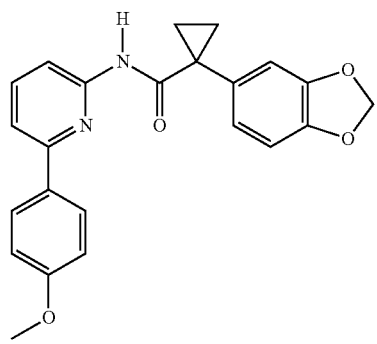
121
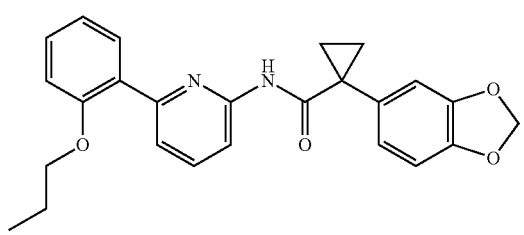 [SMILES: CCCOc1ccccc1-c1cccc(NC(=O)C2(c3ccc4c(c3)OCO4)CC2)n1]
122

TABLE 1-continued
Examples of compounds of the present invention
| | |
|---|---|
| 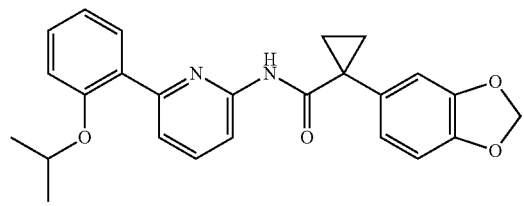 [SMILES: CC(C)Oc1ccccc1-c1cccc(NC(=O)C2(c3ccc4c(c3)OCO4)CC2)n1] | 123 |
| 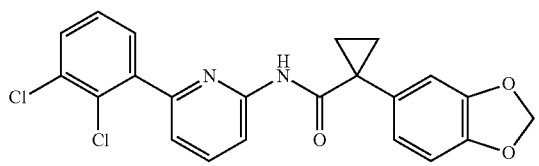 [SMILES: O=C(Nc1cccc(-c2cccc(Cl)c2Cl)n1)C1(c2ccc3c(c2)OCO3)CC1] | 124 |
| 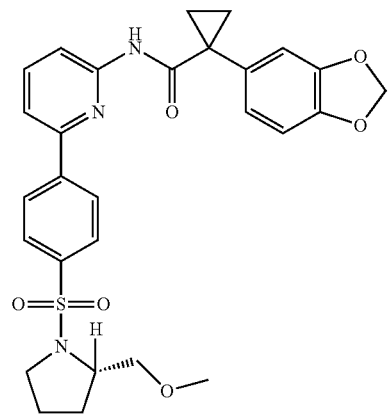 [SMILES: COC[C@@H]1CCCN1S(=O)(=O)c1ccc(-c2cccc(NC(=O)C3(c4ccc5c(c4)OCO5)CC3)n2)cc1] | 125 |
| 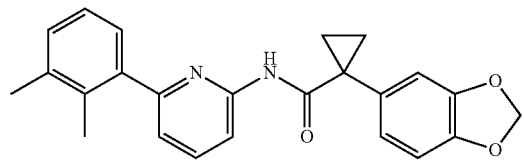 [SMILES: Cc1cccc(-c2cccc(NC(=O)C3(c4ccc5c(c4)OCO5)CC3)n2)c1C] | 126 |
| 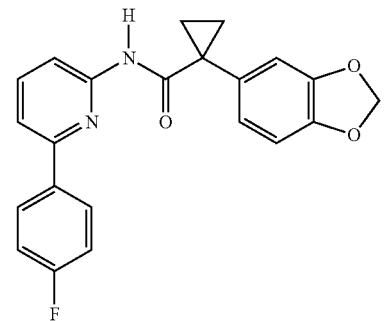 [SMILES: O=C(Nc1cccc(-c2ccc(F)cc2)n1)C1(c2ccc3c(c2)OCO3)CC1] | 127 |
| 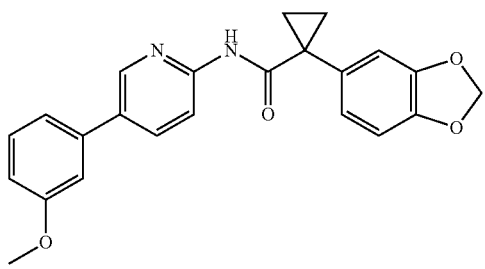 [SMILES: COc1cccc(-c2ccc(NC(=O)C3(c4ccc5c(c4)OCO5)CC3)nc2)c1] | 128 |

TABLE 1-continued
Examples of compounds of the present invention
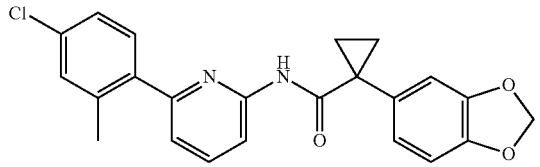 [SMILES: Cc1cc(Cl)ccc1-c1cccc(NC(=O)C2(c3ccc4c(c3)OCO4)CC2)n1]
129
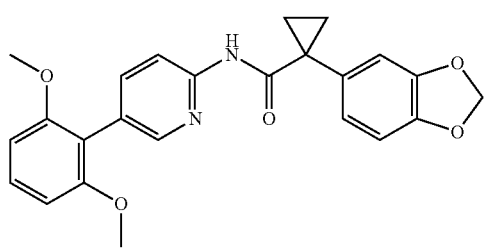 [SMILES: COc1cccc(OC)c1-c1ccc(NC(=O)C2(c3ccc4c(c3)OCO4)CC2)nc1]
130
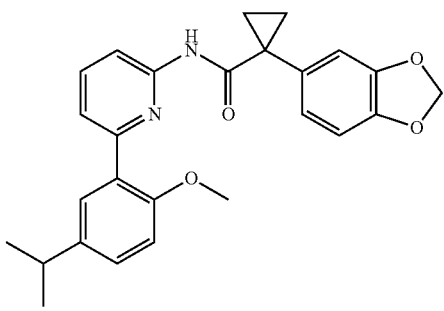 [SMILES: COc1ccc(C(C)C)cc1-c1cccc(NC(=O)C2(c3ccc4c(c3)OCO4)CC2)n1]
131
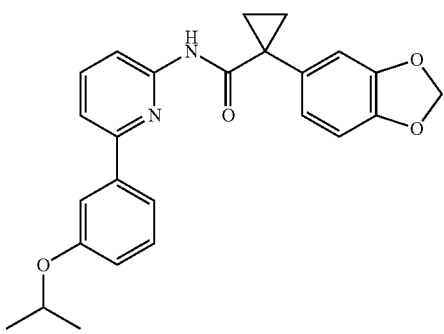 [SMILES: CC(C)Oc1cccc(-c2cccc(NC(=O)C3(c4ccc5c(c4)OCO5)CC3)n2)c1]
132
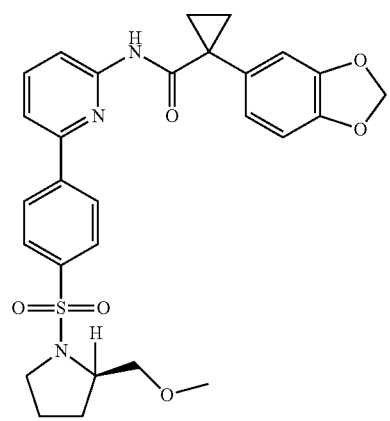 [SMILES: COC[C@H]1CCCN1S(=O)(=O)c1ccc(-c2cccc(NC(=O)C3(c4ccc5c(c4)OCO5)CC3)n2)cc1]
133

125 126
TABLE 1-continued
Examples of compounds of the present invention
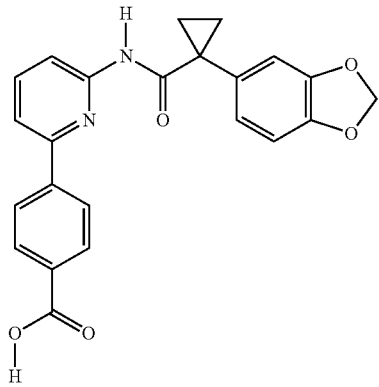 [SMILES: O=C(O)c1ccc(-c2cccc(NC(=O)C3(c4ccc5c(c4)OCO5)CC3)n2)cc1] 134
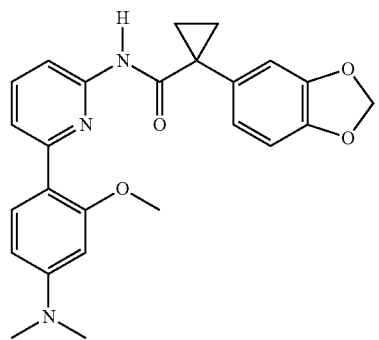 [SMILES: COc1cc(N(C)C)ccc1-c1cccc(NC(=O)C2(c3ccc4c(c3)OCO4)CC2)n1] 135
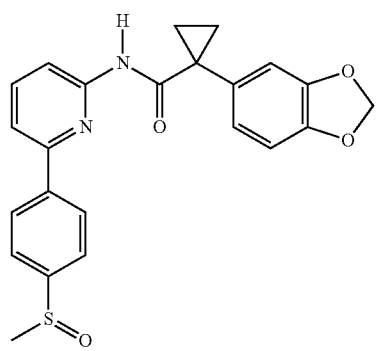 [SMILES: CS(=O)c1ccc(-c2cccc(NC(=O)C3(c4ccc5c(c4)OCO5)CC3)n2)cc1] 136
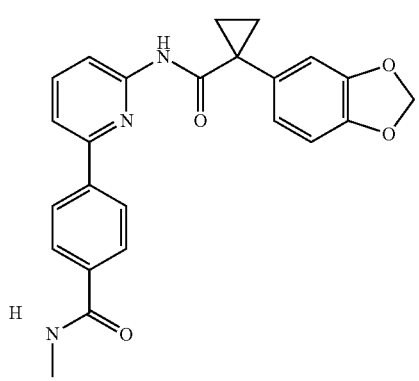 137

TABLE 1-continued
Examples of compounds of the present invention
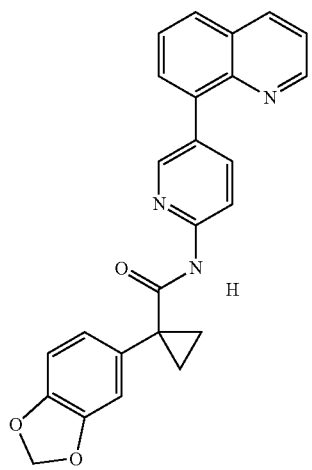
138
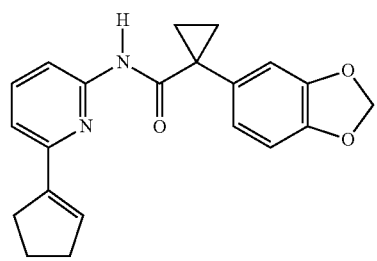 [SMILES: O=C(Nc1cccc(C2=CCCC2)n1)C1(c2ccc3c(c2)OCO3)CC1]
139
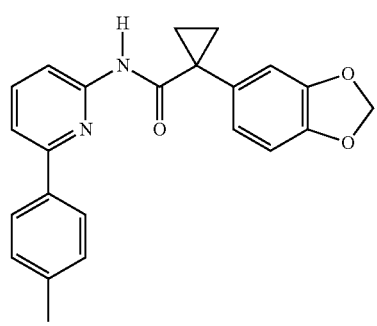 [SMILES: Cc1ccc(-c2cccc(NC(=O)C3(c4ccc5c(c4)OCO5)CC3)n2)cc1]
140
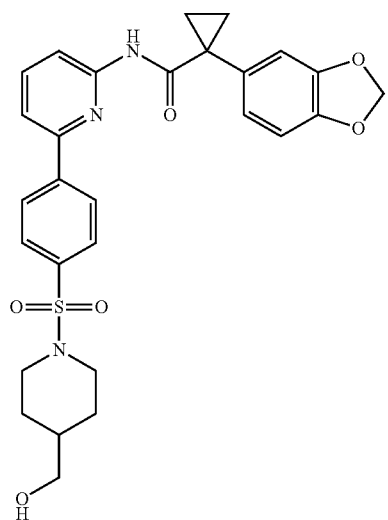 [SMILES: O=C(Nc1cccc(-c2ccc(S(=O)(=O)N3CCC(CO)CC3)cc2)n1)C1(c2ccc3c(c2)OCO3)CC1]
141

TABLE 1-continued
Examples of compounds of the present invention
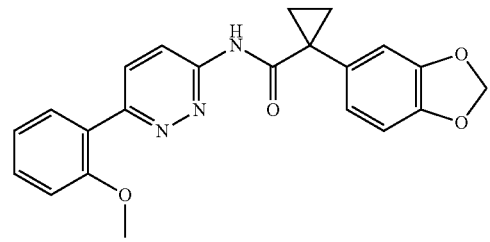 [SMILES: COc1ccccc1-c1ccc(NC(=O)C2(c3ccc4c(c3)OCO4)CC2)nn1]
142
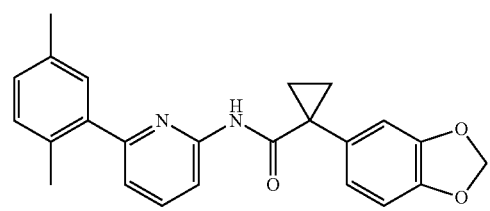 [SMILES: Cc1ccc(C)c(-c2cccc(NC(=O)C3(c4ccc5c(c4)OCO5)CC3)n2)c1]
143
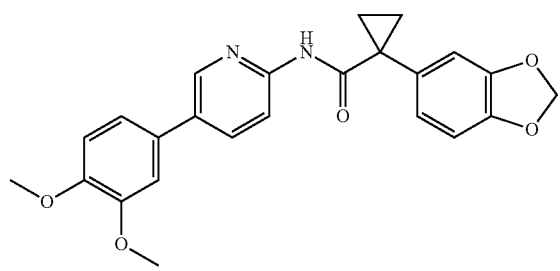 [SMILES: COc1ccc(-c2ccc(NC(=O)C3(c4ccc5c(c4)OCO5)CC3)nc2)cc1OC]
144
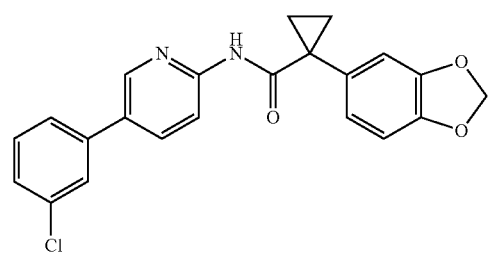 [SMILES: O=C(Nc1ccc(-c2cccc(Cl)c2)cn1)C1(c2ccc3c(c2)OCO3)CC1]
145
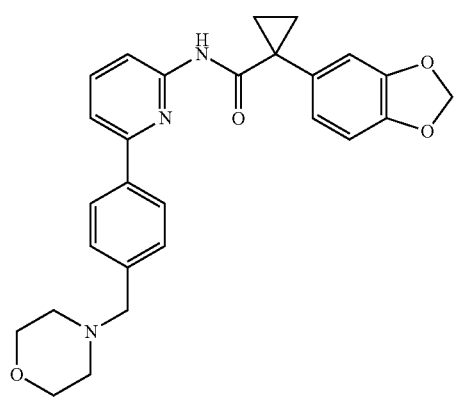 [SMILES: O=C(Nc1cccc(-c2ccc(CN3CCOCC3)cc2)n1)C1(c2ccc3c(c2)OCO3)CC1]
146

TABLE 1-continued
Examples of compounds of the present invention
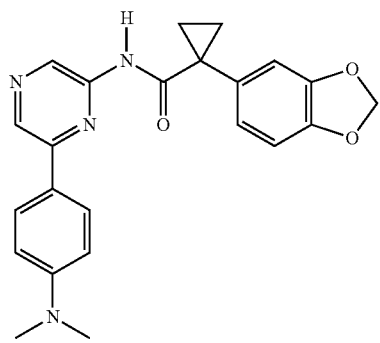 [SMILES: CN(C)c1ccc(-c2cncc(NC(=O)C3(c4ccc5c(c4)OCO5)CC3)n2)cc1] 147
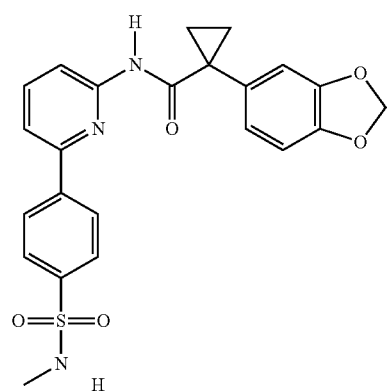 148
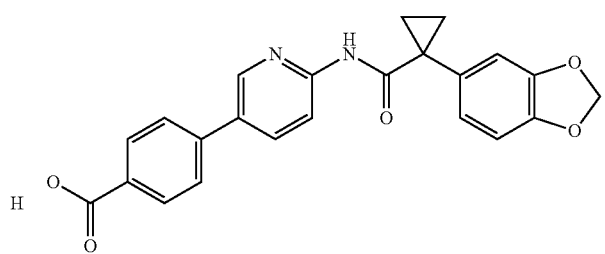 149
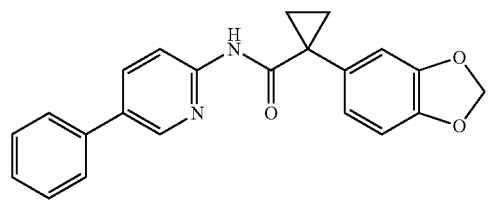 [SMILES: O=C(Nc1ccc(-c2ccccc2)cn1)C1(c2ccc3c(c2)OCO3)CC1] 150
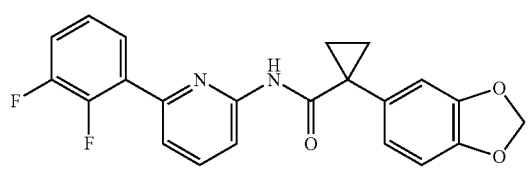 [SMILES: O=C(Nc1cccc(-c2cccc(F)c2F)n1)C1(c2ccc3c(c2)OCO3)CC1] 151
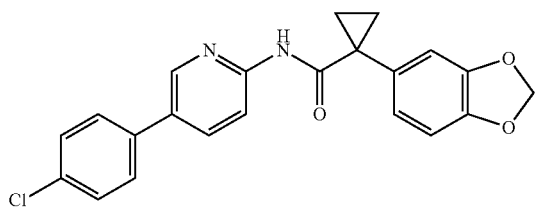 [SMILES: O=C(Nc1ccc(-c2ccc(Cl)cc2)cn1)C1(c2ccc3c(c2)OCO3)CC1] 152

133
TABLE 1-continued
Examples of compounds of the present invention
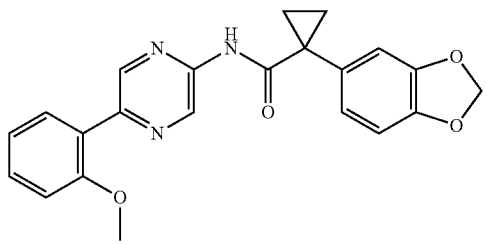 [SMILES: COc1ccccc1-c1cnc(NC(=O)C2(c3ccc4c(c3)OCO4)CC2)cn1]
153
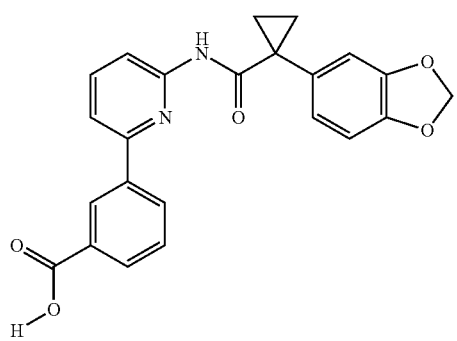 [SMILES: O=C(O)c1cccc(-c2cccc(NC(=O)C3(c4ccc5c(c4)OCO5)CC3)n2)c1]
154
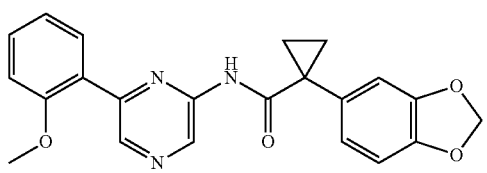 [SMILES: COc1ccccc1-c1cncc(NC(=O)C2(c3ccc4c(c3)OCO4)CC2)n1]
155
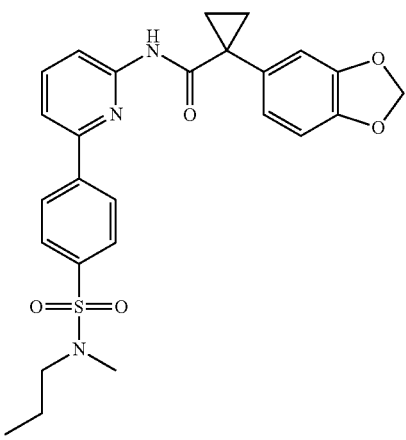 [SMILES: CCCN(C)S(=O)(=O)c1ccc(-c2cccc(NC(=O)C3(c4ccc5c(c4)OCO5)CC3)n2)cc1]
156
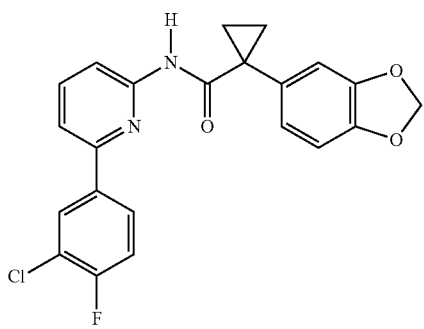 [SMILES: O=C(Nc1cccc(-c2ccc(F)c(Cl)c2)n1)C1(c2ccc3c(c2)OCO3)CC1]
157

TABLE 1-continued
Examples of compounds of the present invention
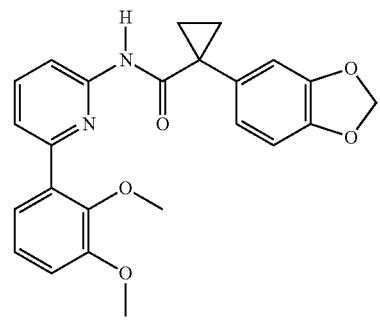 [SMILES: COc1cccc(-c2cccc(NC(=O)C3(c4ccc5c(c4)OCO5)CC3)n2)c1OC]
158
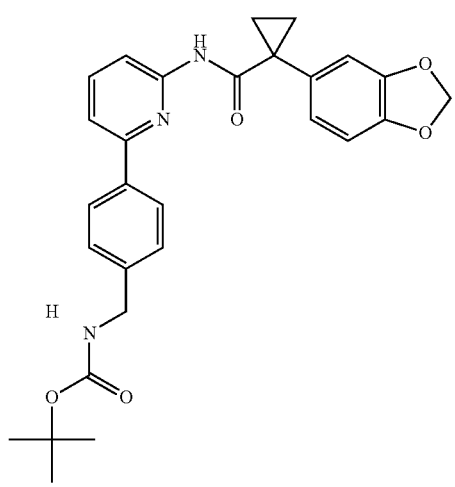
159
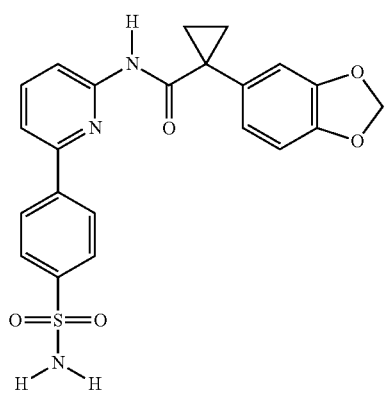 [SMILES: NS(=O)(=O)c1ccc(-c2cccc(NC(=O)C3(c4ccc5c(c4)OCO5)CC3)n2)cc1]
160
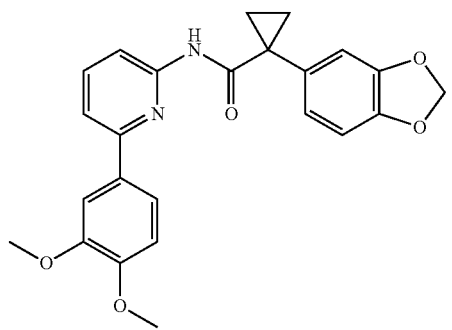 [SMILES: COc1ccc(-c2cccc(NC(=O)C3(c4ccc5c(c4)OCO5)CC3)n2)cc1OC]
161

TABLE 1-continued
Examples of compounds of the present invention
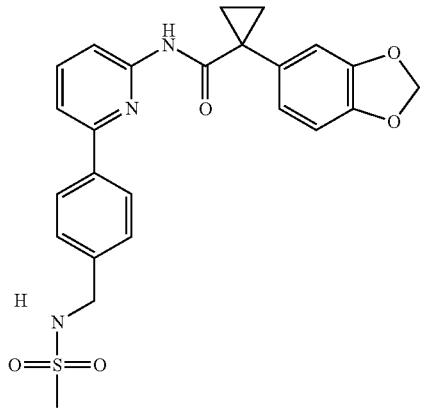
162
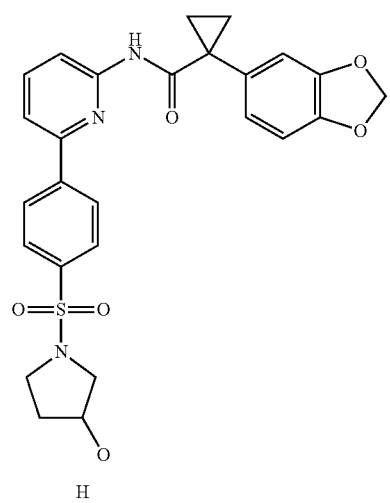
163
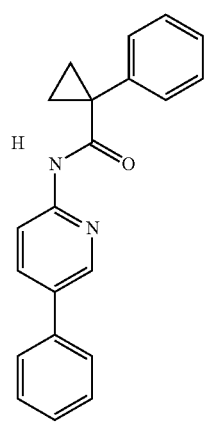
164

TABLE 1-continued
Examples of compounds of the present invention
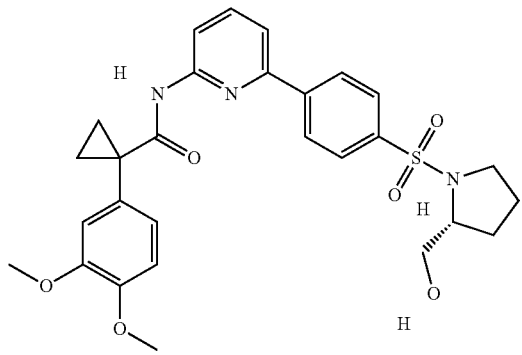
165
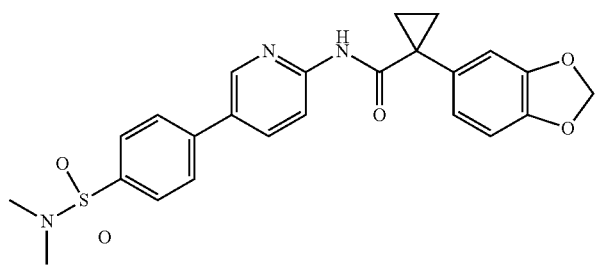
166
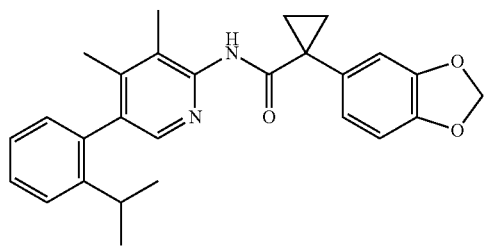 [SMILES: Cc1c(-c2ccccc2C(C)C)cnc(NC(=O)C2(c3ccc4c(c3)OCO4)CC2)c1C]
167
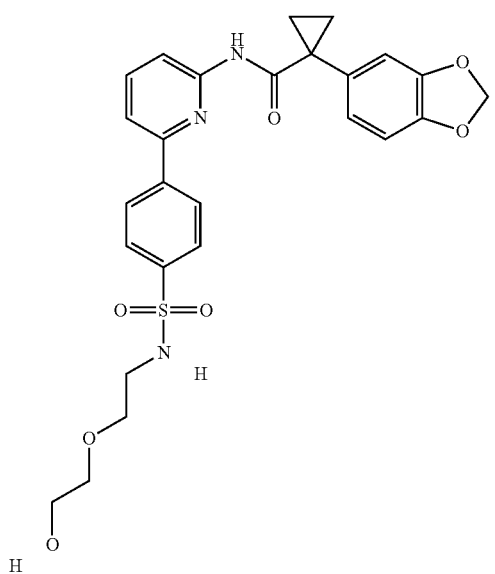
168

TABLE 1-continued
Examples of compounds of the present invention
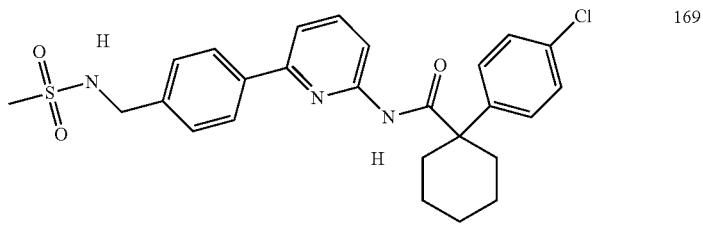
169
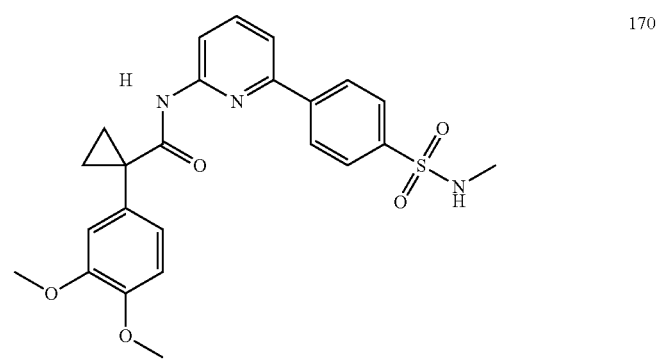
170
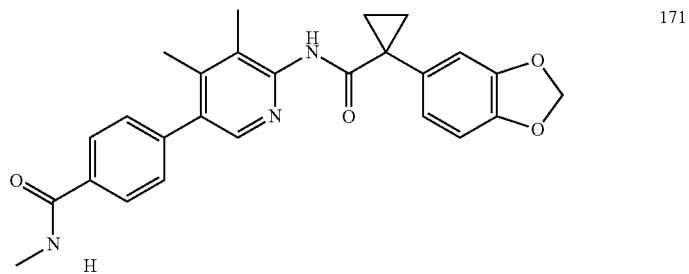
171
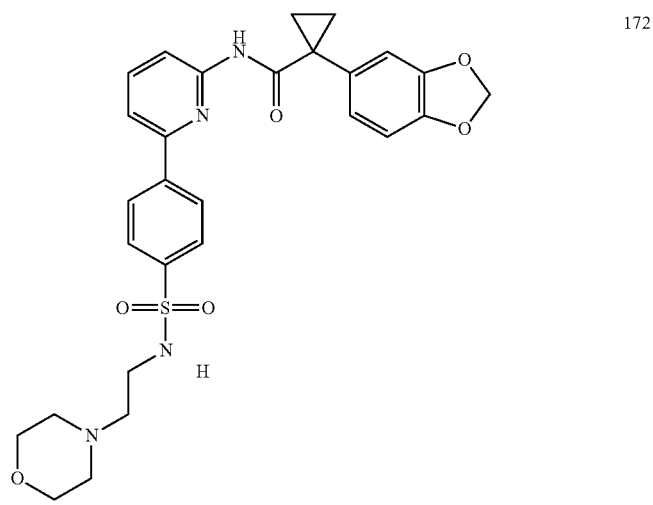
172

TABLE 1-continued
Examples of compounds of the present invention
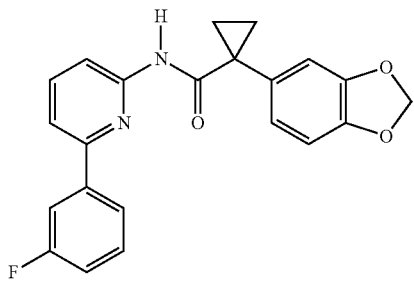 [SMILES: O=C(Nc1cccc(-c2cccc(F)c2)n1)C1(c2ccc3c(c2)OCO3)CC1]
173
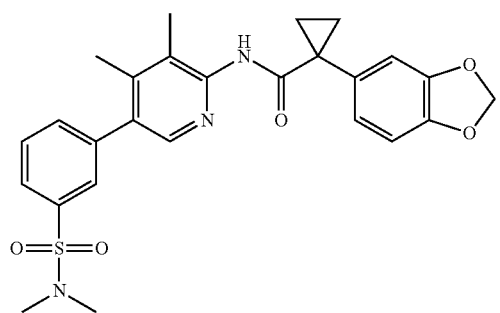 [SMILES: Cc1c(-c2cccc(S(=O)(=O)N(C)C)c2)cnc(NC(=O)C2(c3ccc4c(c3)OCO4)CC2)c1C]
174
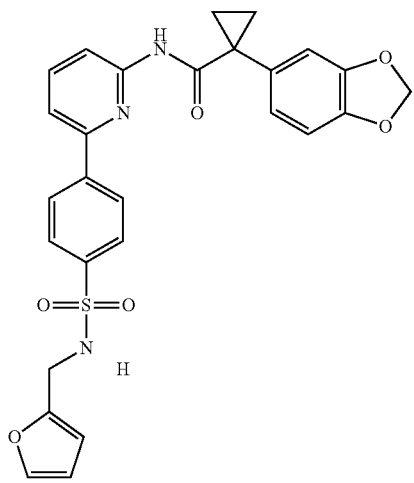
175
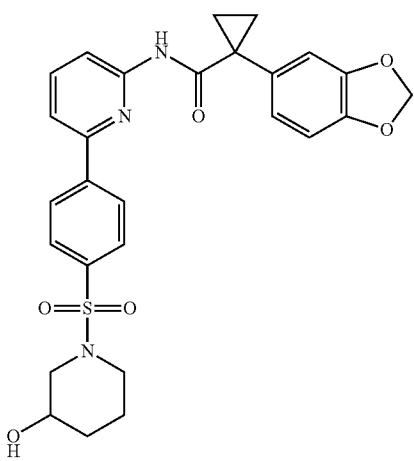 [SMILES: O=C(Nc1cccc(-c2ccc(S(=O)(=O)N3CCCC(O)C3)cc2)n1)C1(c2ccc3c(c2)OCO3)CC1]
176

TABLE 1-continued
Examples of compounds of the present invention
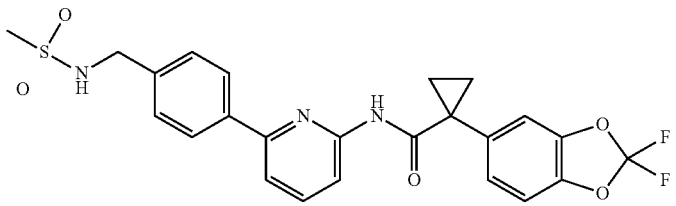
177
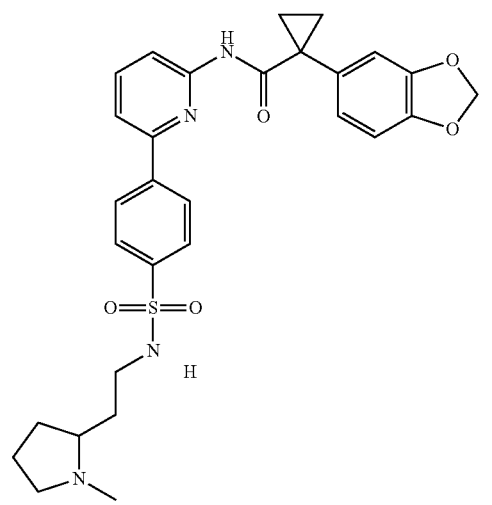
178
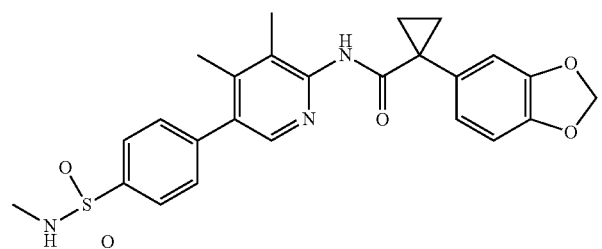
179
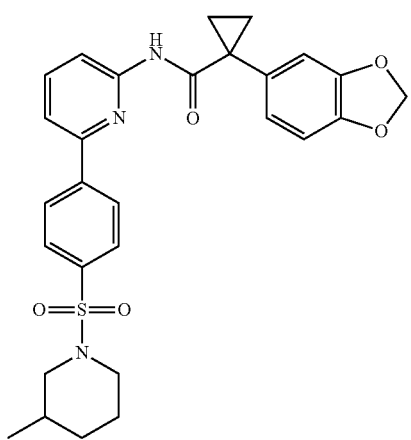 [SMILES: CC1CCCN(S(=O)(=O)c2ccc(-c3cccc(NC(=O)C4(c5ccc6c(c5)OCO6)CC4)n3)cc2)C1]
180

TABLE 1-continued
Examples of compounds of the present invention
| | |
|---|---|
| 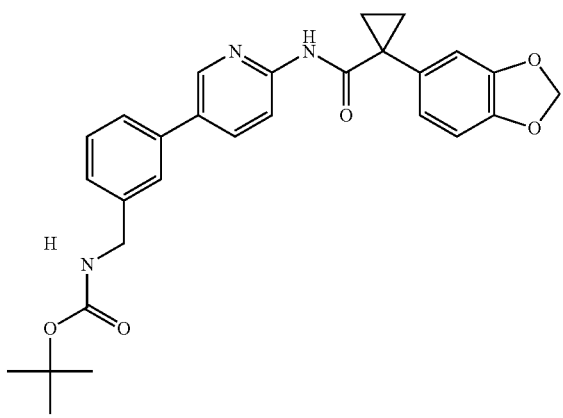 | 181 |
| 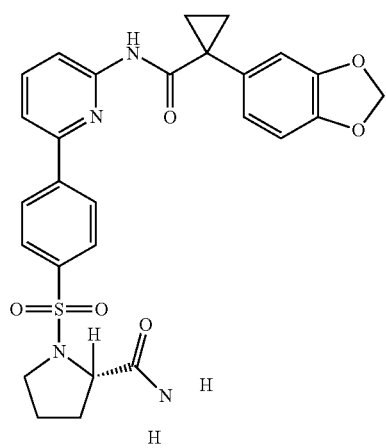 | 182 |
| 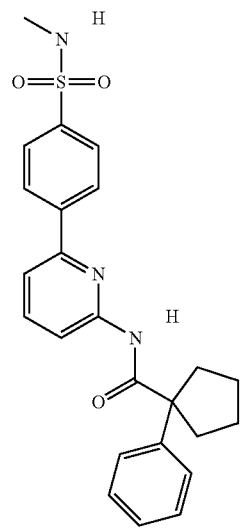 | 183 |

TABLE 1-continued
Examples of compounds of the present invention
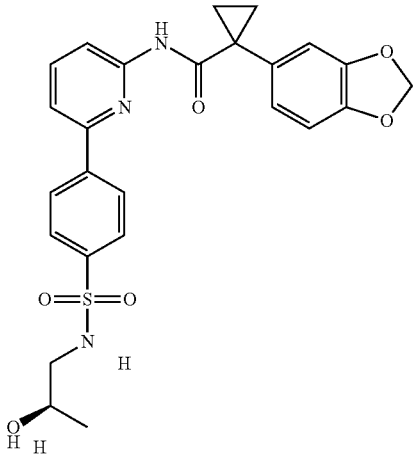
184
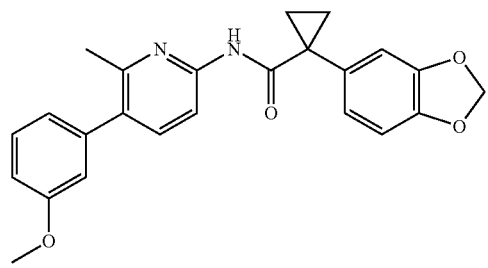
185
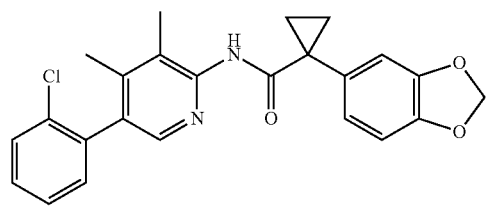 [SMILES: Cc1c(-c2ccccc2Cl)cnc(NC(=O)C2(c3ccc4c(c3)OCO4)CC2)c1C]
186
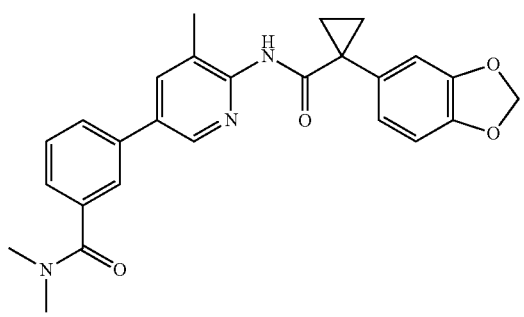 [SMILES: Cc1cc(-c2cccc(C(=O)N(C)C)c2)cnc1NC(=O)C1(c2ccc3c(c2)OCO3)CC1]
187
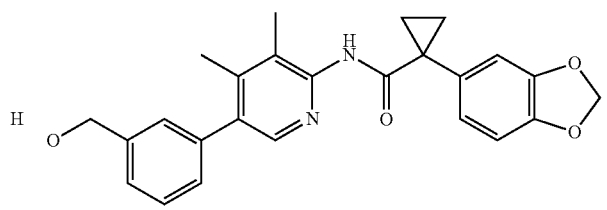
188

TABLE 1-continued
Examples of compounds of the present invention
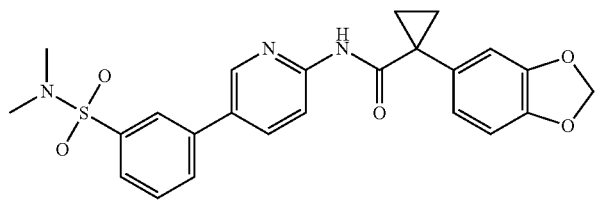 [SMILES: CN(C)S(O)(O)c1cccc(-c2ccc(NC(=O)C3(c4ccc5c(c4)OCO5)CC3)nc2)c1]
189
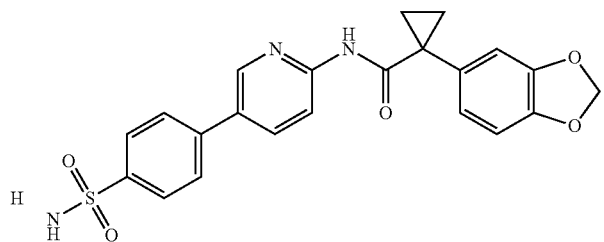
190
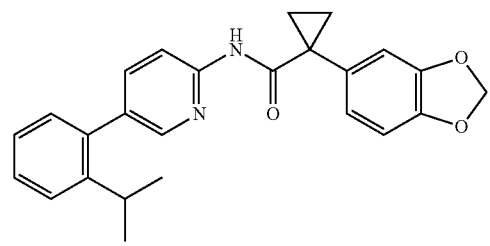 [SMILES: CC(C)c1ccccc1-c1ccc(NC(=O)C2(c3ccc4c(c3)OCO4)CC2)nc1]
191
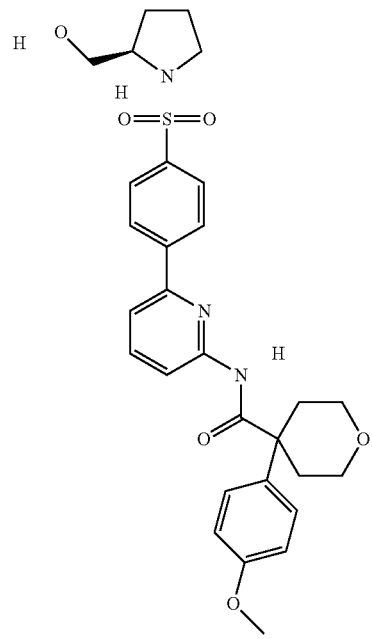
192
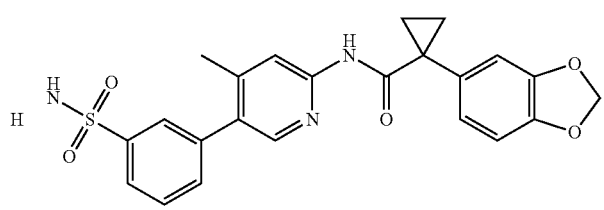
193

TABLE 1-continued
Examples of compounds of the present invention
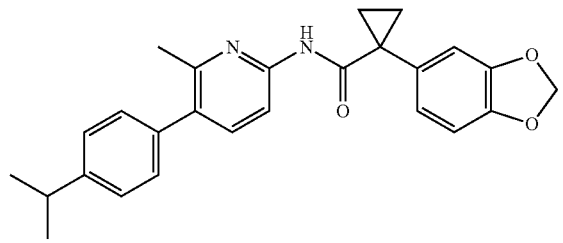 [SMILES: Cc1nc(NC(=O)C2(c3ccc4c(c3)OCO4)CC2)ccc1-c1ccc(C(C)C)cc1]
194
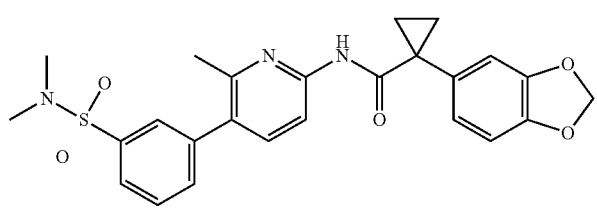
195
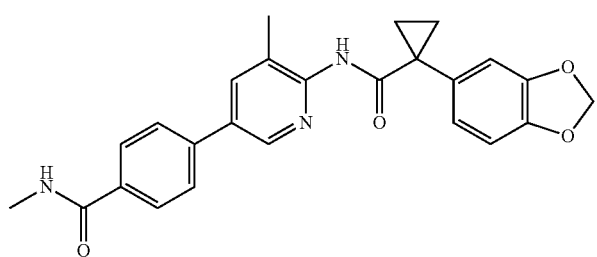 [SMILES: CNC(=O)c1ccc(-c2cnc(NC(=O)C3(c4ccc5c(c4)OCO5)CC3)c(C)c2)cc1]
196
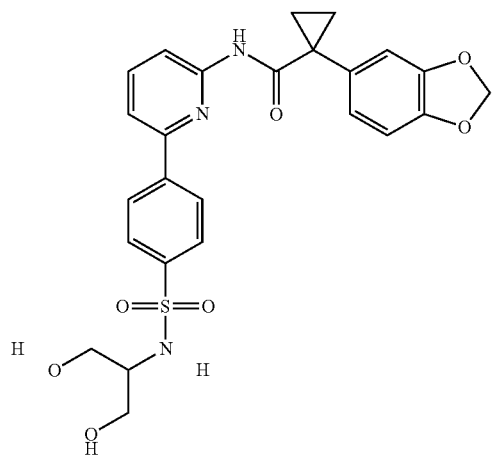
197
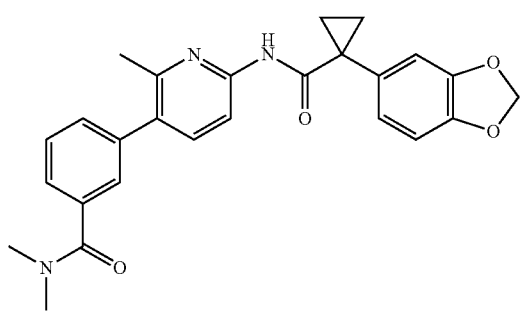
198

TABLE 1-continued
Examples of compounds of the present invention
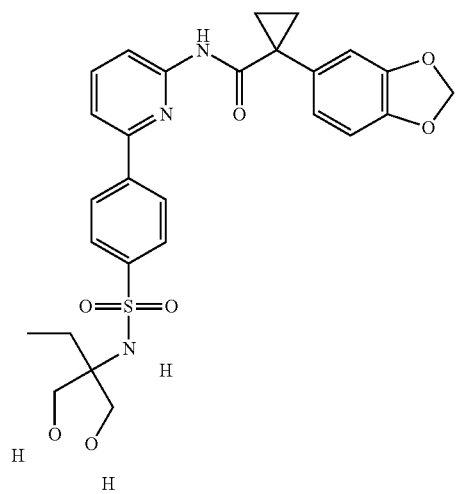
199
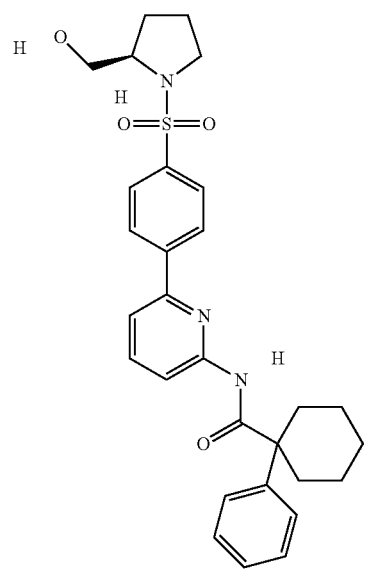
200
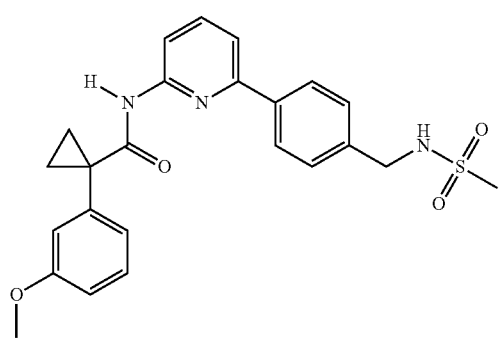 [SMILES: COc1cccc(C2(C(=O)Nc3cccc(-c4ccc(CNS(C)(=O)=O)cc4)n3)CC2)c1]
201

TABLE 1-continued
Examples of compounds of the present invention
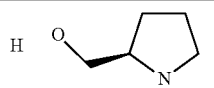
202
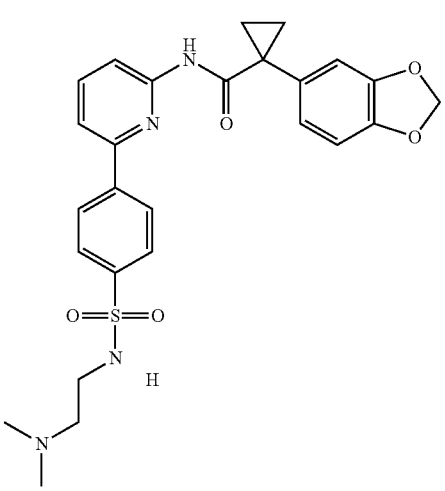
203
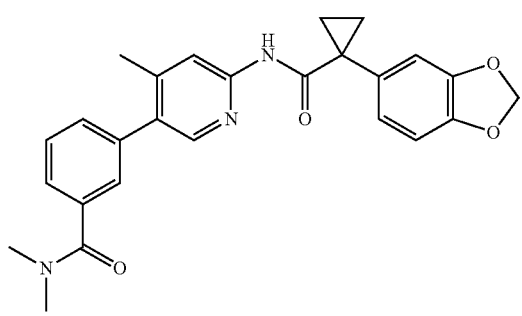 [SMILES: Cc1cc(NC(=O)C2(c3ccc4c(c3)OCO4)CC2)ncc1-c1cccc(C(=O)N(C)C)c1]
204

TABLE 1-continued
Examples of compounds of the present invention
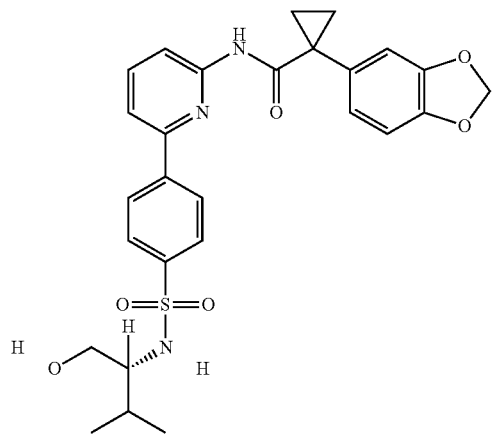
205
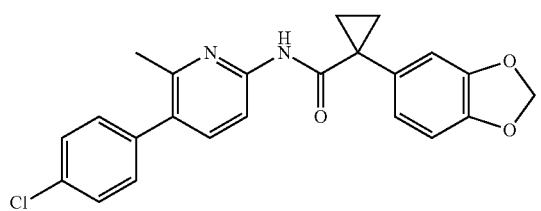 [SMILES: Cc1nc(NC(=O)C2(c3ccc4c(c3)OCO4)CC2)ccc1-c1ccc(Cl)cc1]
206
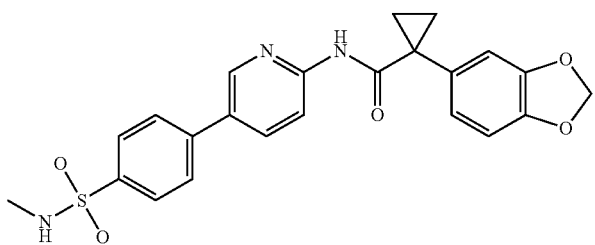 [SMILES: CNS(O)(O)c1ccc(-c2ccc(NC(=O)C3(c4ccc5c(c4)OCO5)CC3)nc2)cc1]
207
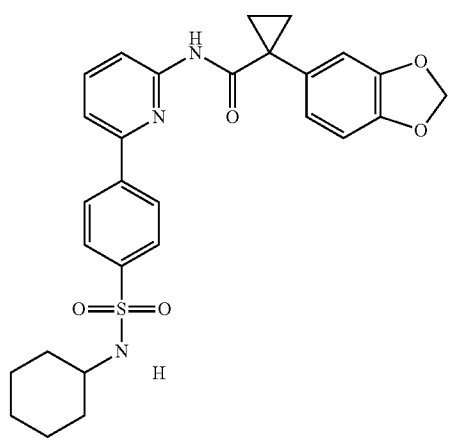
208

TABLE 1-continued
Examples of compounds of the present invention
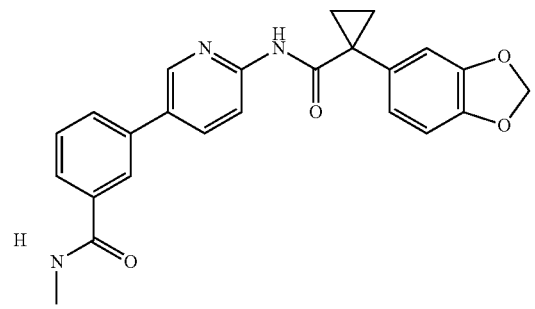
209
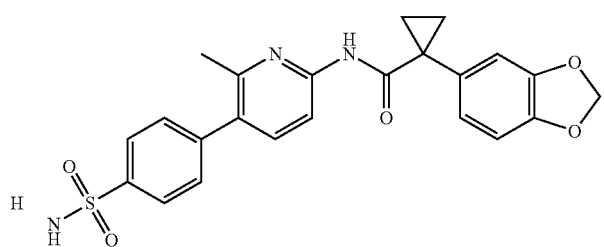
210
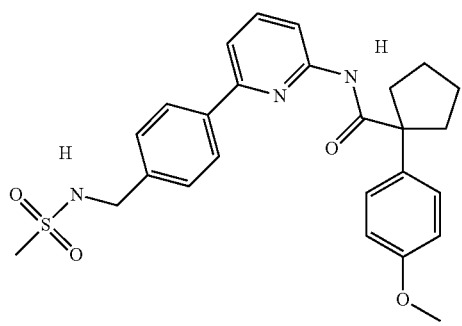
211
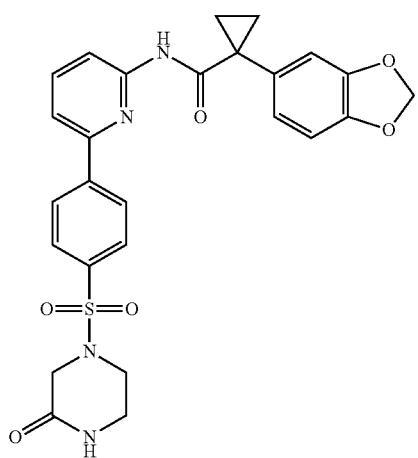 [SMILES: O=C1CN(S(=O)(=O)c2ccc(-c3cccc(NC(=O)C4(c5ccc6c(c5)OCO6)CC4)n3)cc2)CCN1]
212
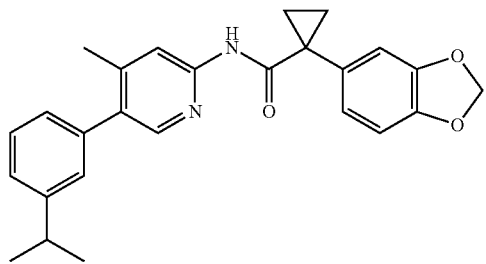 [SMILES: Cc1cc(NC(=O)C2(c3ccc4c(c3)OCO4)CC2)ncc1-c1cccc(C(C)C)c1]
213

TABLE 1-continued
Examples of compounds of the present invention
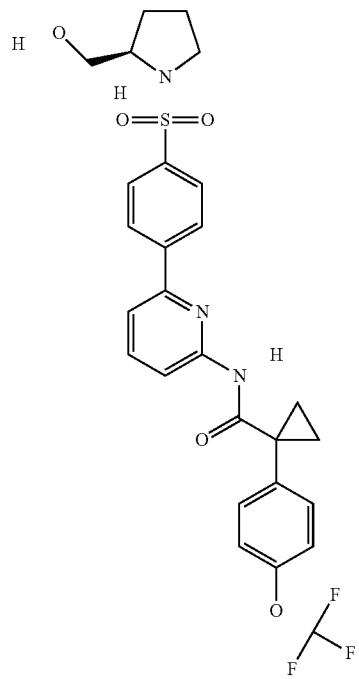
214
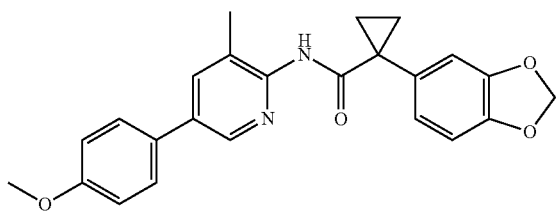 [SMILES: COc1ccc(-c2cnc(NC(=O)C3(c4ccc5c(c4)OCO5)CC3)c(C)c2)cc1]
215
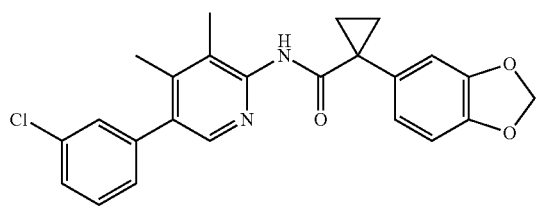 [SMILES: Cc1c(-c2cccc(Cl)c2)cnc(NC(=O)C2(c3ccc4c(c3)OCO4)CC2)c1C]
216
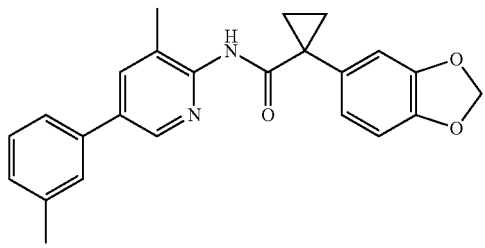 [SMILES: Cc1cccc(-c2cnc(NC(=O)C3(c4ccc5c(c4)OCO5)CC3)c(C)c2)c1]
217
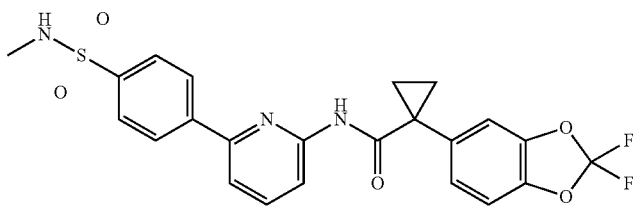
218

TABLE 1-continued
Examples of compounds of the present invention
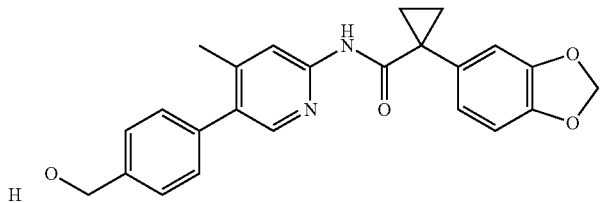
219
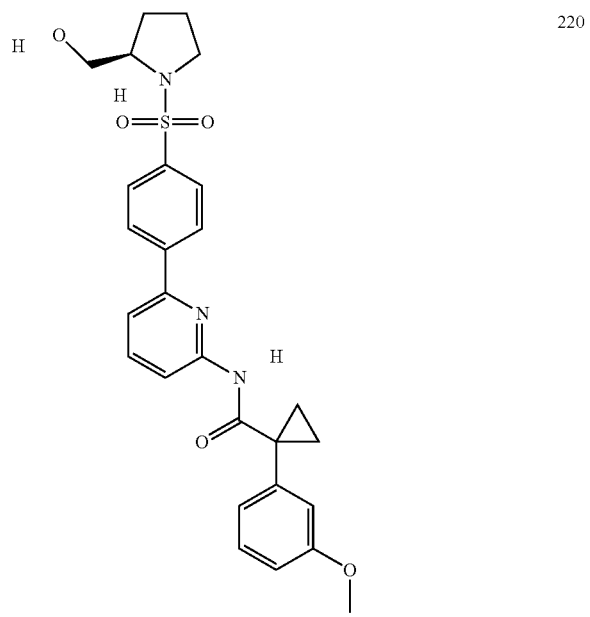
220
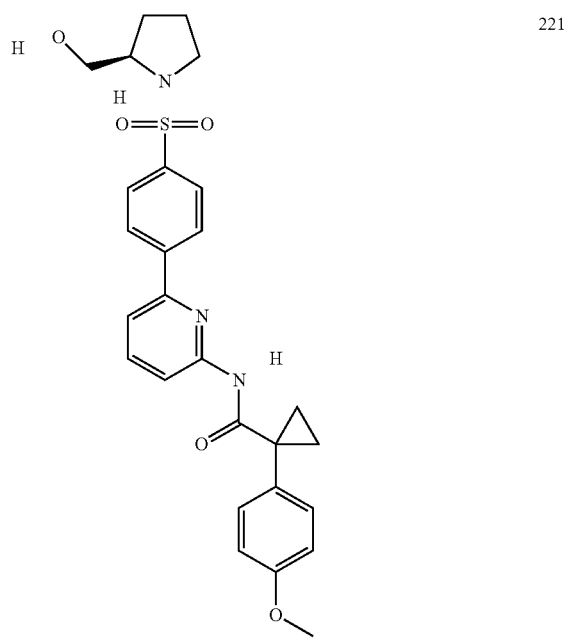
221

TABLE 1-continued
Examples of compounds of the present invention
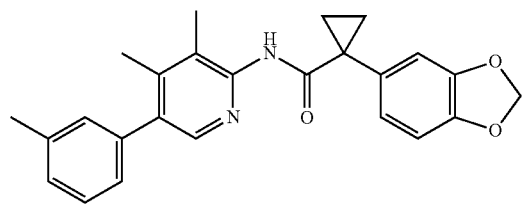 [SMILES: Cc1cccc(-c2cnc(NC(=O)C3(c4ccc5c(c4)OCO5)CC3)c(C)c2C)c1]
222
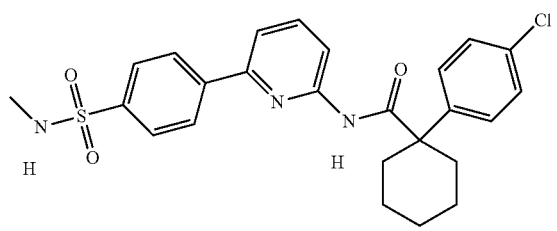
223
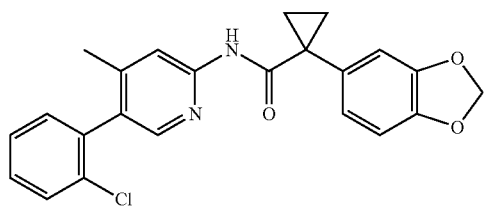 [SMILES: Cc1cc(NC(=O)C2(c3ccc4c(c3)OCO4)CC2)ncc1-c1ccccc1Cl]
224
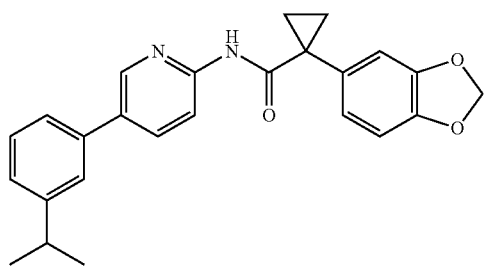 [SMILES: CC(C)c1cccc(-c2ccc(NC(=O)C3(c4ccc5c(c4)OCO5)CC3)nc2)c1]
225
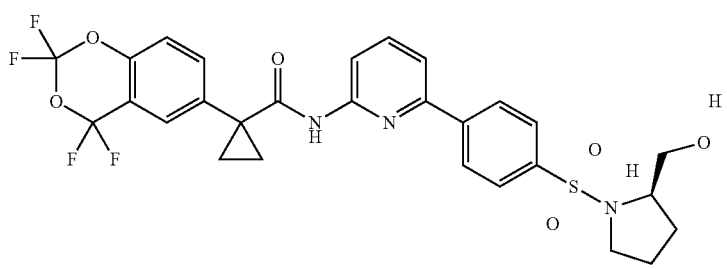
226
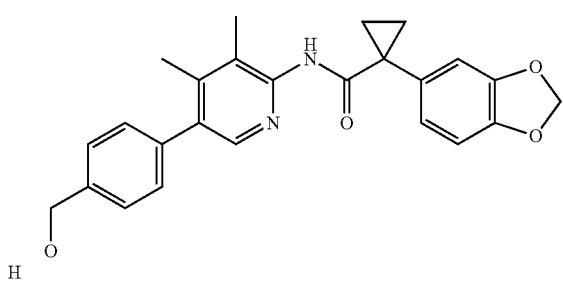
227

TABLE 1-continued
Examples of compounds of the present invention
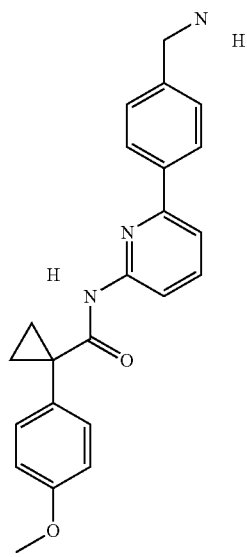
228
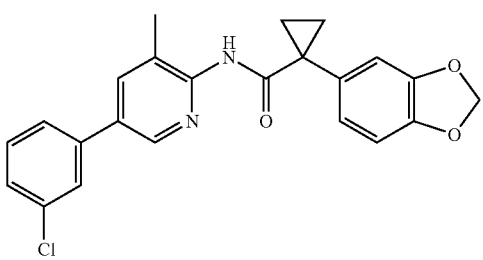 [SMILES: Cc1cc(-c2cccc(Cl)c2)cnc1NC(=O)C1(c2ccc3c(c2)OCO3)CC1]
229
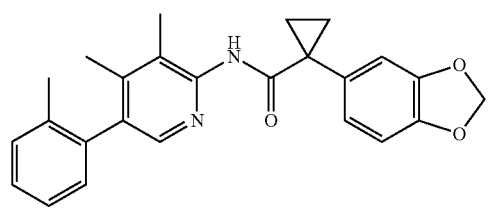 [SMILES: Cc1ccccc1-c1cnc(NC(=O)C2(c3ccc4c(c3)OCO4)CC2)c(C)c1C]
230
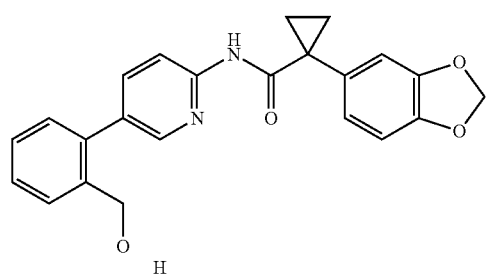
231

TABLE 1-continued
Examples of compounds of the present invention
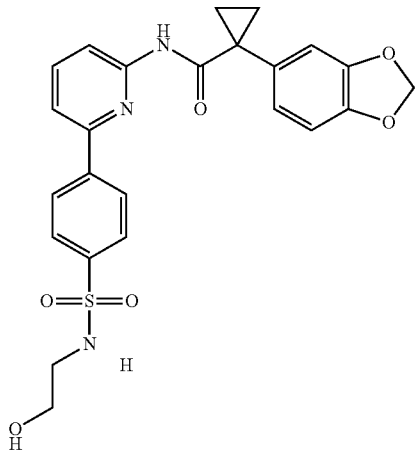
232
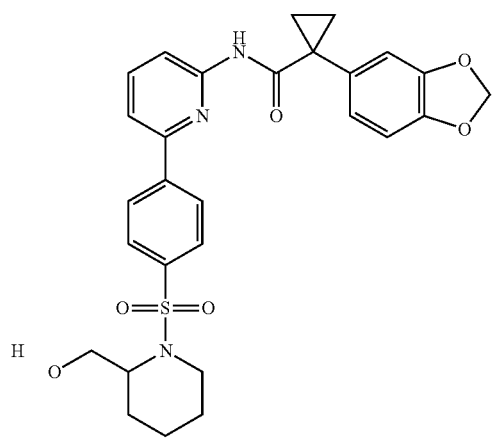
233
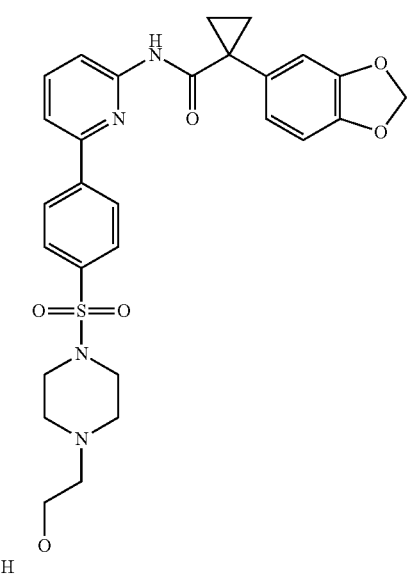
234

TABLE 1-continued
Examples of compounds of the present invention
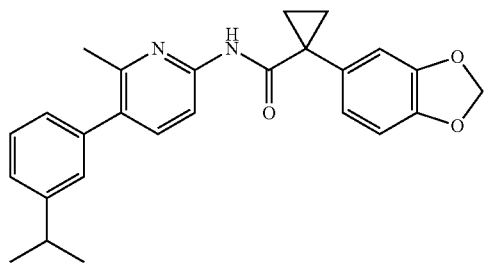 [SMILES: Cc1nc(NC(=O)C2(c3ccc4c(c3)OCO4)CC2)ccc1-c1cccc(C(C)C)c1]
235
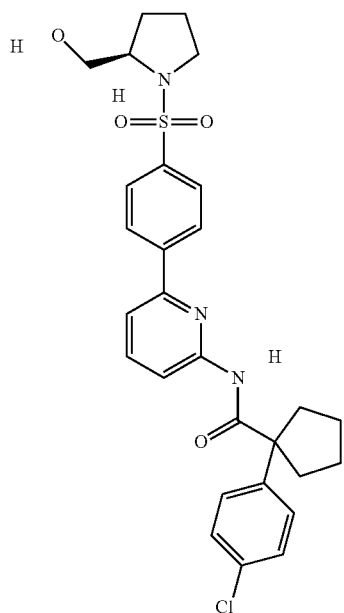
236
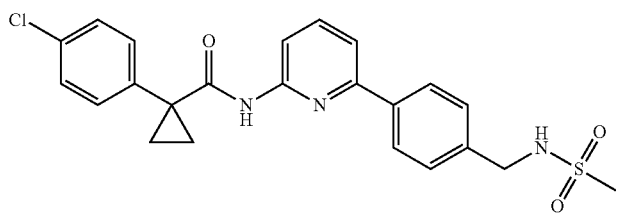 [SMILES: CS(=O)(=O)NCc1ccc(-c2cccc(NC(=O)C3(c4ccc(Cl)cc4)CC3)n2)cc1]
237
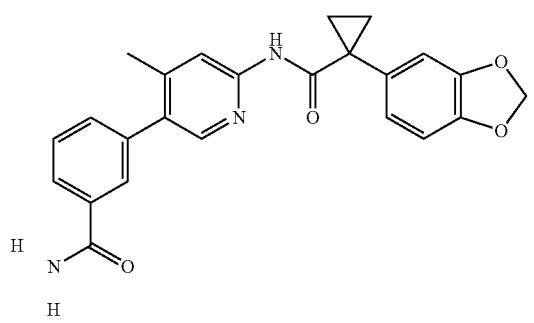
238

175 176
TABLE 1-continued
Examples of compounds of the present invention
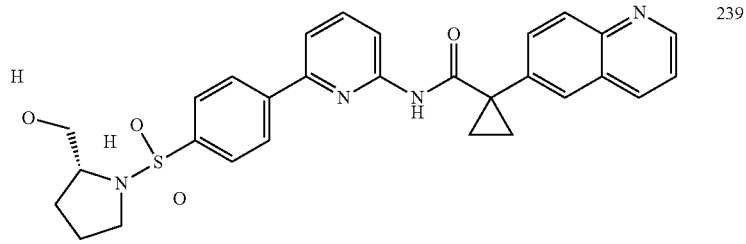
239
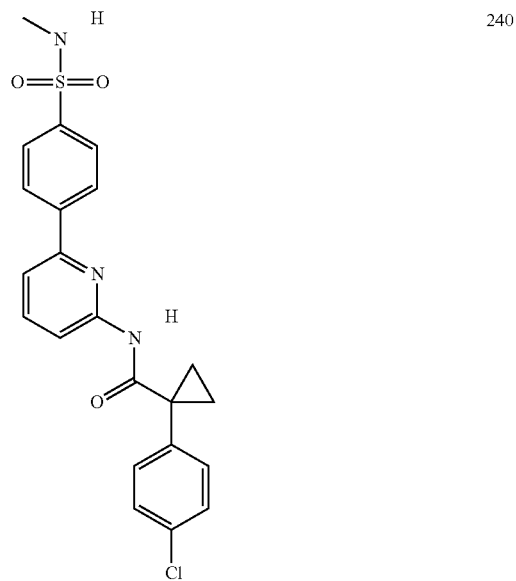
240
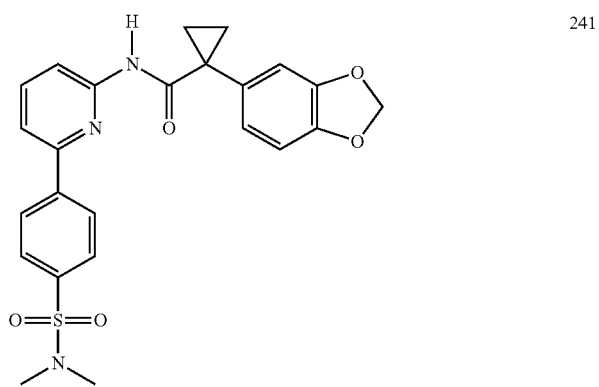
241

TABLE 1-continued
Examples of compounds of the present invention
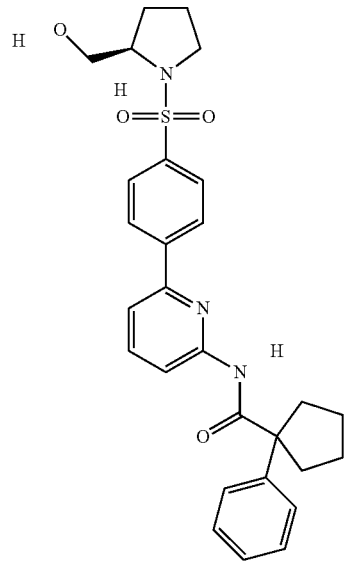
242
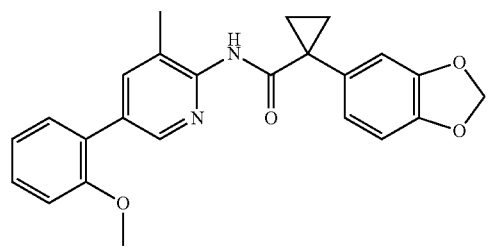 [SMILES: COc1ccccc1-c1cnc(NC(=O)C2(c3ccc4c(c3)OCO4)CC2)c(C)c1]
243
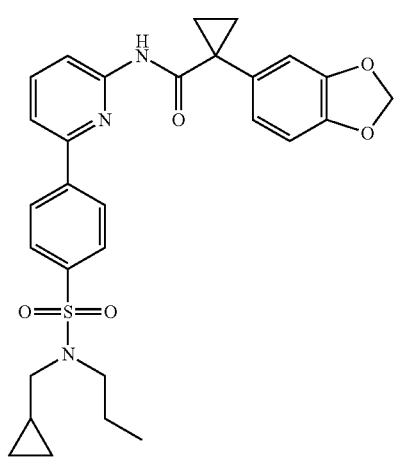 [SMILES: CCCN(CC1CC1)S(=O)(=O)c1ccc(-c2cccc(NC(=O)C3(c4ccc5c(c4)OCO5)CC3)n2)cc1]
244

TABLE 1-continued
Examples of compounds of the present invention
| | |
|---|---|
| 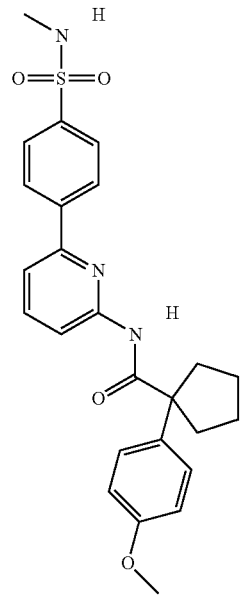 | 245 |
| 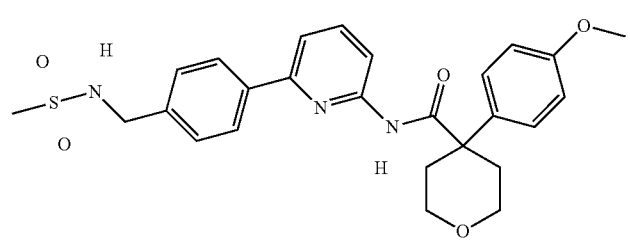 | 246 |
| 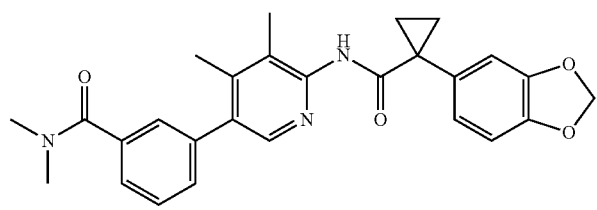 [SMILES: Cc1c(-c2cccc(C(=O)N(C)C)c2)cnc(NC(=O)C2(c3ccc4c(c3)OCO4)CC2)c1C] | 247 |
| 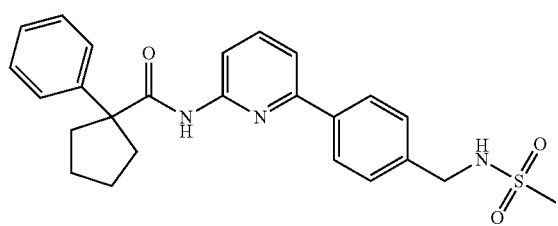 [SMILES: CS(=O)(=O)NCc1ccc(-c2cccc(NC(=O)C3(c4ccccc4)CCCC3)n2)cc1] | 248 |

TABLE 1-continued
Examples of compounds of the present invention
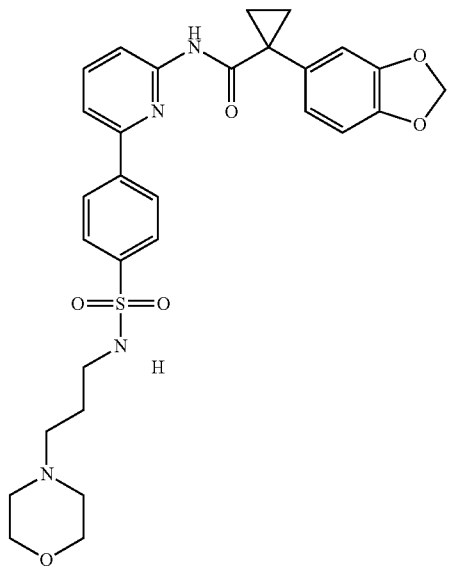
249
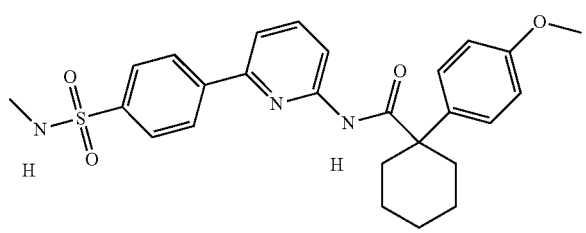
250
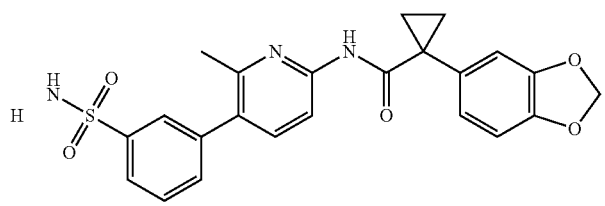
251
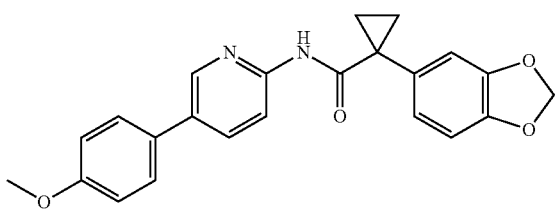 [SMILES: COc1ccc(-c2ccc(NC(=O)C3(c4ccc5c(c4)OCO5)CC3)nc2)cc1]
252
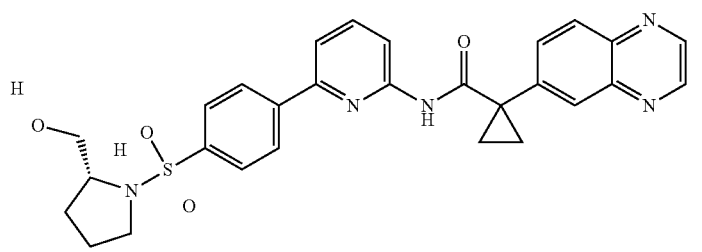
253

US 8,741,933 B2
183
TABLE 1-continued
Examples of compounds of the present invention
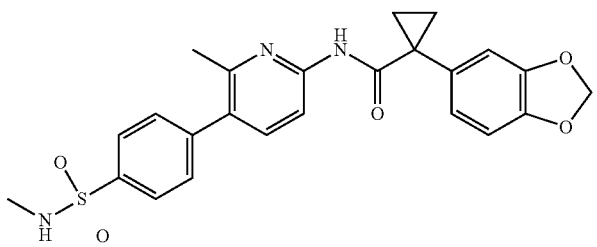
254
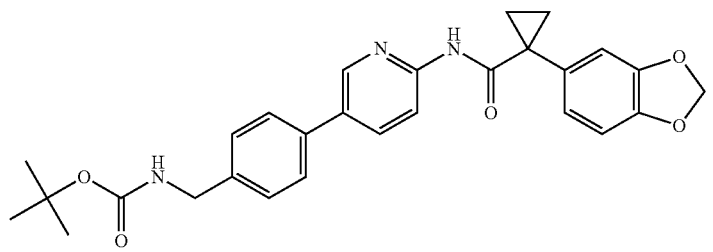 [SMILES: CC(C)(C)OC(=O)NCc1ccc(-c2ccc(NC(=O)C3(c4ccc5c(c4)OCO5)CC3)nc2)cc1]
255
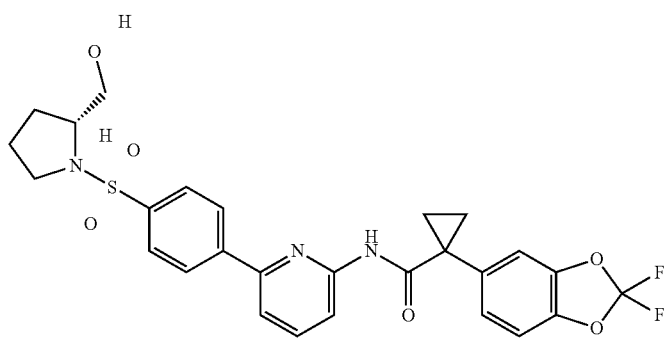
256
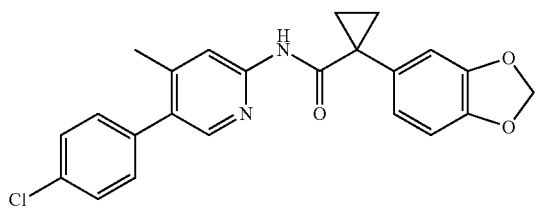 [SMILES: Cc1cc(NC(=O)C2(c3ccc4c(c3)OCO4)CC2)ncc1-c1ccc(Cl)cc1]
257
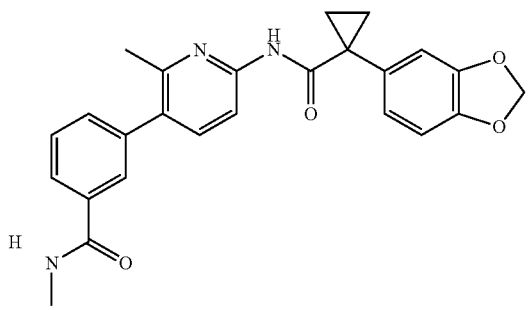
258

TABLE 1-continued
Examples of compounds of the present invention
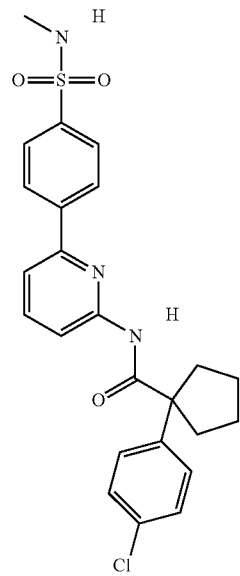
259
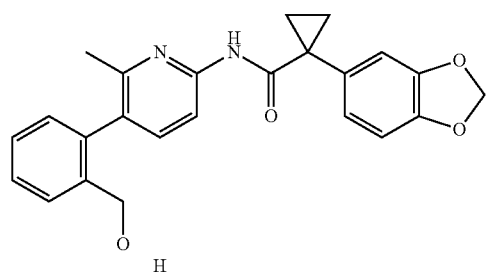
260
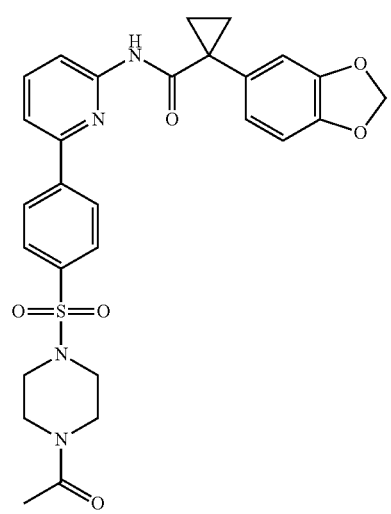 [SMILES: CC(=O)N1CCN(S(=O)(=O)c2ccc(-c3cccc(NC(=O)C4(c5ccc6c(c5)OCO6)CC4)n3)cc2)CC1]
261

TABLE 1-continued
Examples of compounds of the present invention
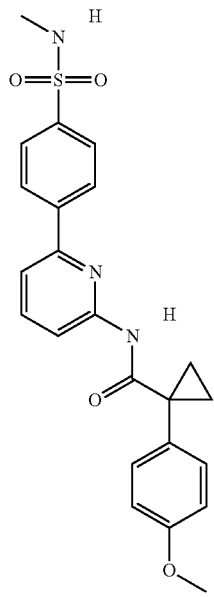
262
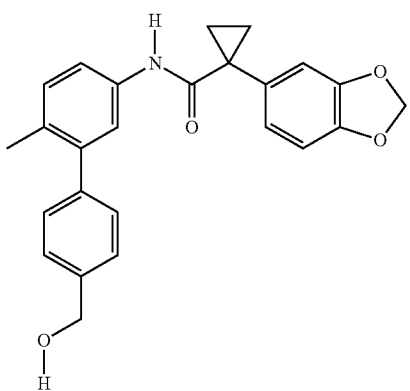 [SMILES: Cc1ccc(NC(=O)C2(c3ccc4c(c3)OCO4)CC2)cc1-c1ccc(CO)cc1]
263
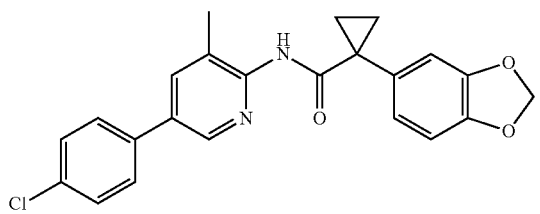 [SMILES: Cc1cc(-c2ccc(Cl)cc2)cnc1NC(=O)C1(c2ccc3c(c2)OCO3)CC1]
264
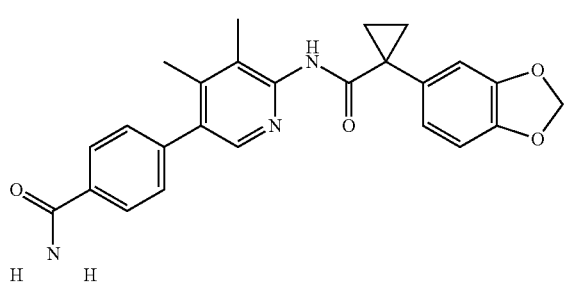
265

TABLE 1-continued
Examples of compounds of the present invention
266
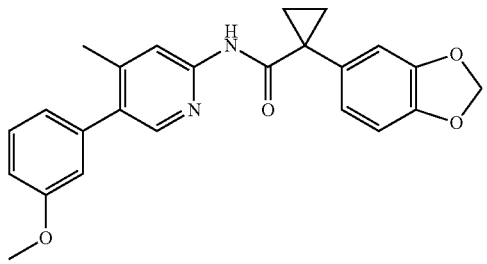 [SMILES: COc1cccc(-c2cnc(NC(=O)C3(c4ccc5c(c4)OCO5)CC3)cc2C)c1]
267
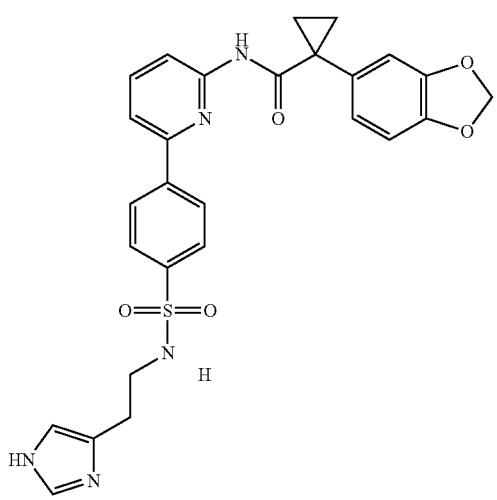
268
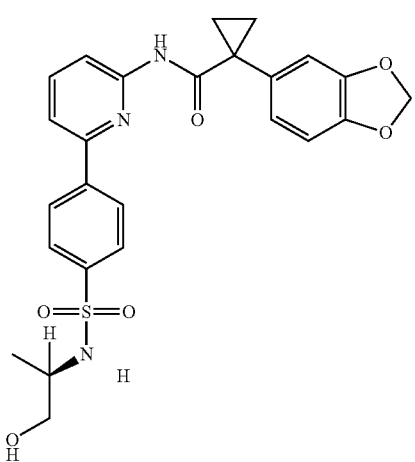
269
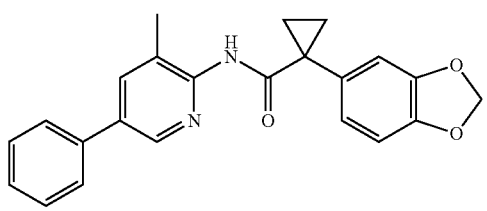 [SMILES: Cc1cc(-c2ccccc2)cnc1NC(=O)C1(c2ccc3c(c2)OCO3)CC1]

TABLE 1-continued
Examples of compounds of the present invention
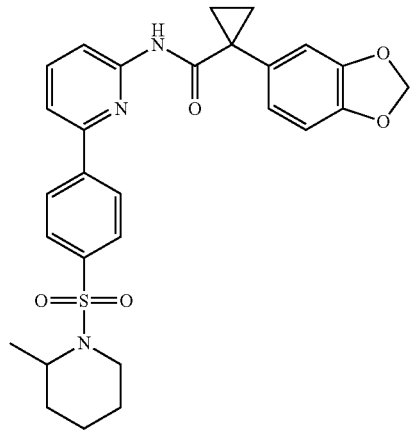 [SMILES: CC1CCCCN1S(=O)(=O)c1ccc(-c2cccc(NC(=O)C3(c4ccc5c(c4)OCO5)CC3)n2)cc1]
270
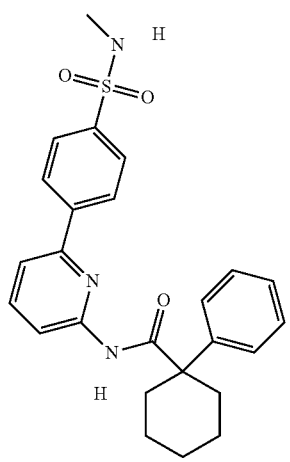
271
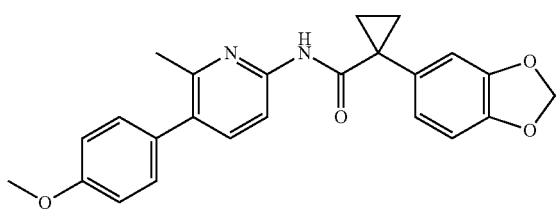 [SMILES: COc1ccc(-c2ccc(NC(=O)C3(c4ccc5c(c4)OCO5)CC3)nc2C)cc1]
272
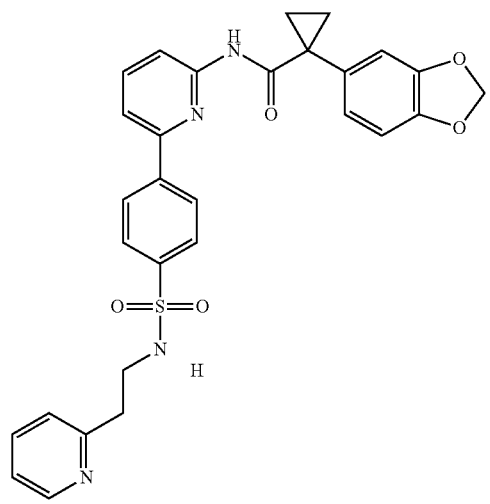
273

TABLE 1-continued
Examples of compounds of the present invention
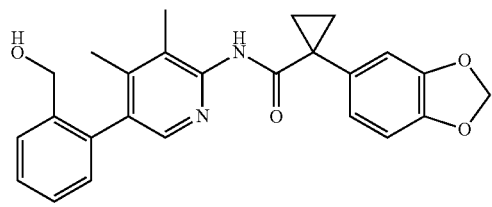 [SMILES: Cc1c(-c2ccccc2CO)cnc(NC(=O)C2(c3ccc4c(c3)OCO4)CC2)c1C]
274
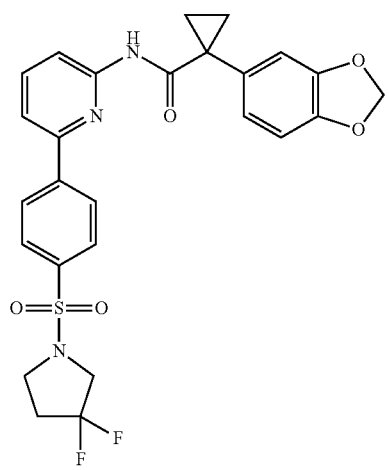 [SMILES: O=C(Nc1cccc(-c2ccc(S(=O)(=O)N3CCC(F)(F)C3)cc2)n1)C1(c2ccc3c(c2)OCO3)CC1]
275
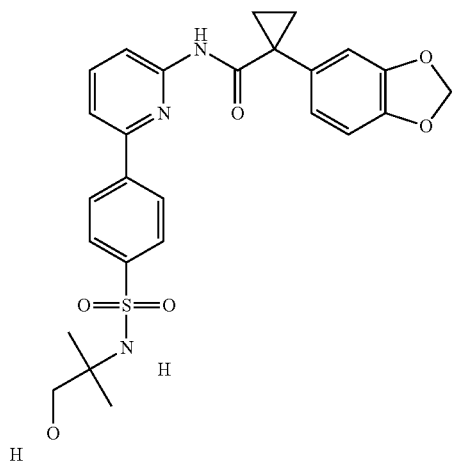
276
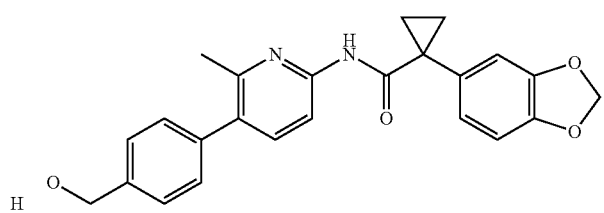
277
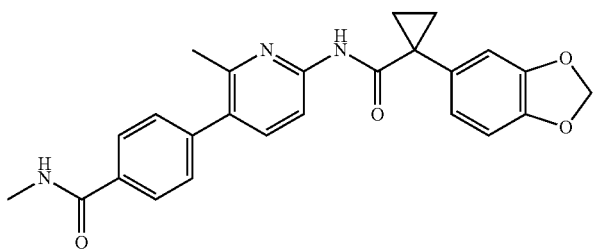 [SMILES: CNC(=O)c1ccc(-c2ccc(NC(=O)C3(c4ccc5c(c4)OCO5)CC3)nc2C)cc1]
278

195 196
TABLE 1-continued
Examples of compounds of the present invention
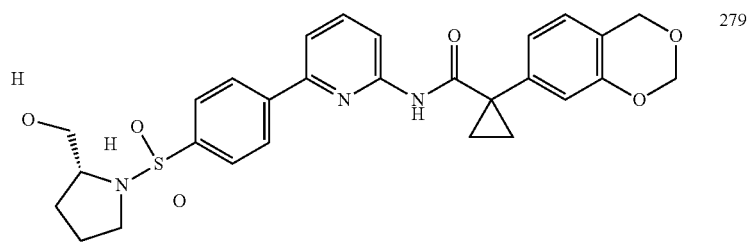
279
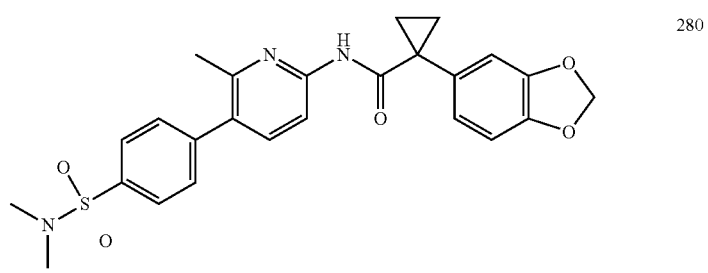
280
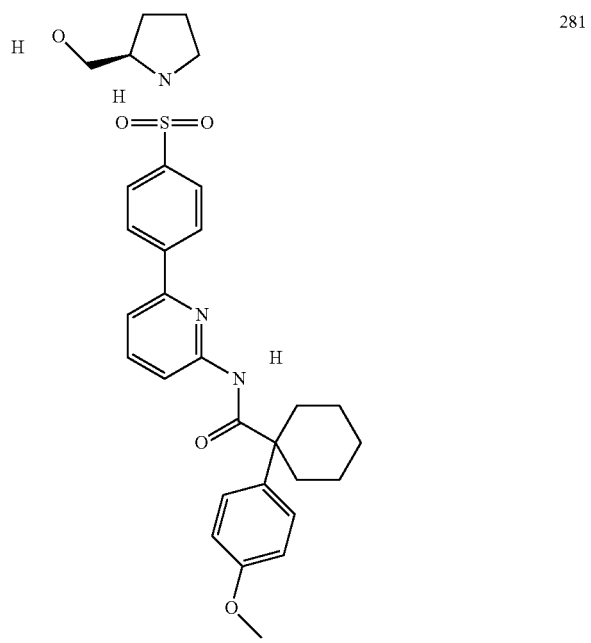
281
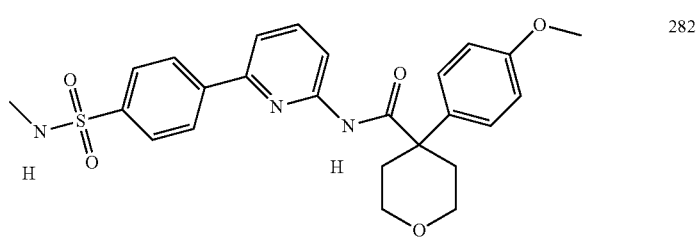
282

TABLE 1-continued
Examples of compounds of the present invention
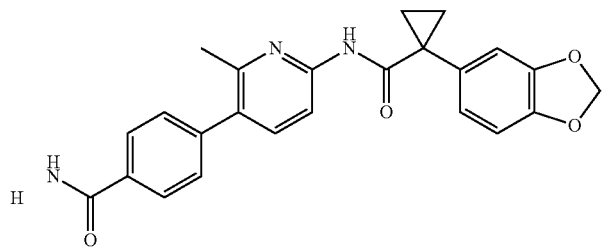
283
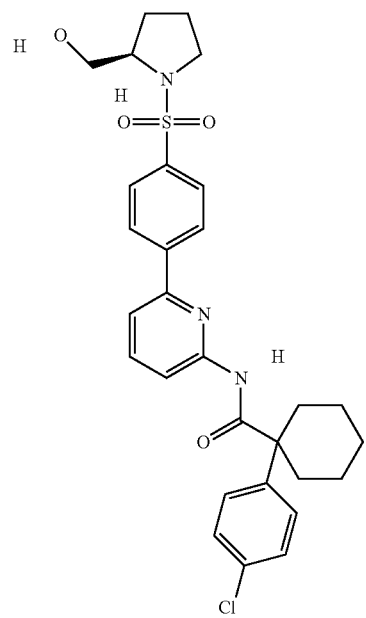
284
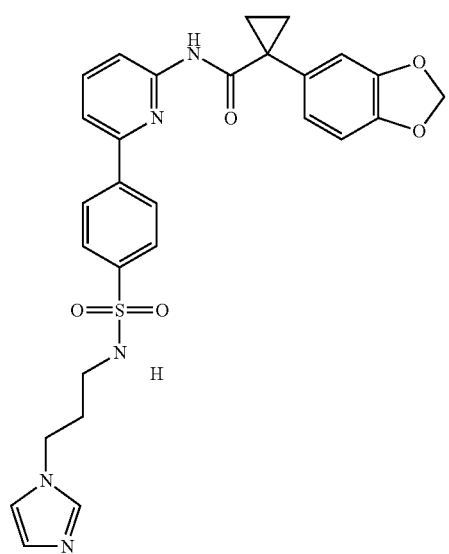
285

TABLE 1-continued
Examples of compounds of the present invention
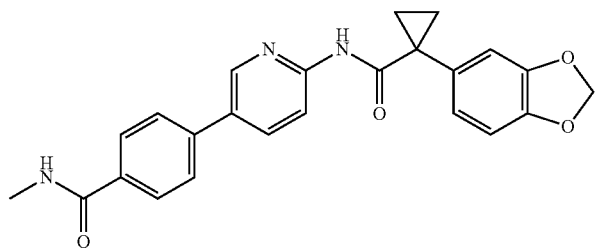 [SMILES: CNC(=O)c1ccc(-c2ccc(NC(=O)C3(c4ccc5c(c4)OCO5)CC3)nc2)cc1]
286
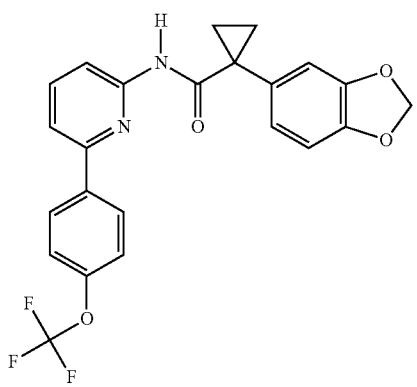 [SMILES: O=C(Nc1cccc(-c2ccc(OC(F)(F)F)cc2)n1)C1(c2ccc3c(c2)OCO3)CC1]
287
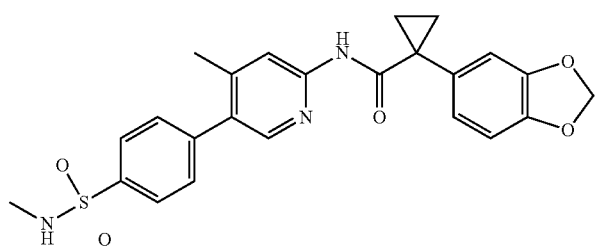
288
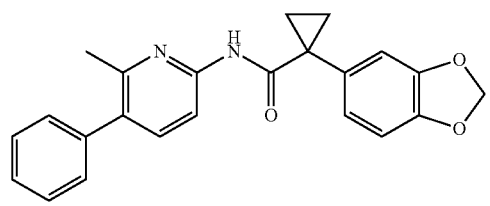 [SMILES: Cc1nc(NC(=O)C2(c3ccc4c(c3)OCO4)CC2)ccc1-c1ccccc1]
289
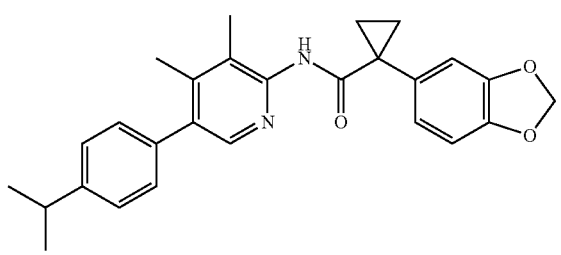 [SMILES: Cc1c(-c2ccc(C(C)C)cc2)cnc(NC(=O)C2(c3ccc4c(c3)OCO4)CC2)c1C]
290

TABLE 1-continued
Examples of compounds of the present invention
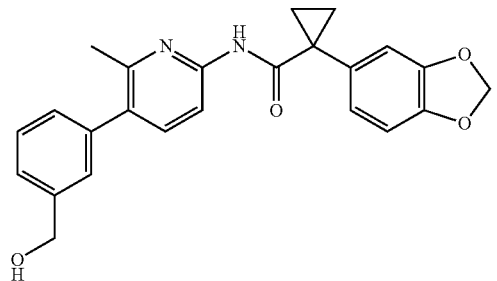 [SMILES: Cc1nc(NC(=O)C2(c3ccc4c(c3)OCO4)CC2)ccc1-c1cccc(CO)c1]
291
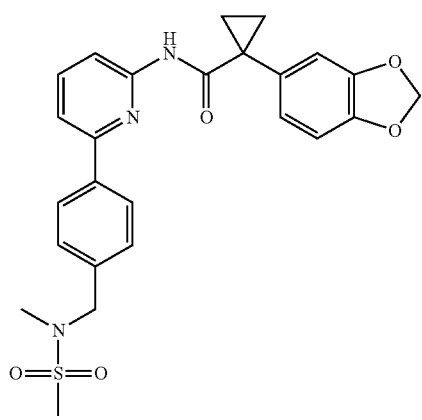 [SMILES: CN(Cc1ccc(-c2cccc(NC(=O)C3(c4ccc5c(c4)OCO5)CC3)n2)cc1)S(C)(=O)=O]
292
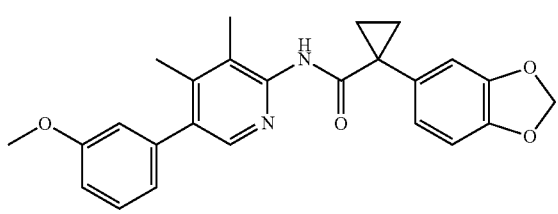 [SMILES: COc1cccc(-c2cnc(NC(=O)C3(c4ccc5c(c4)OCO5)CC3)c(C)c2C)c1]
293
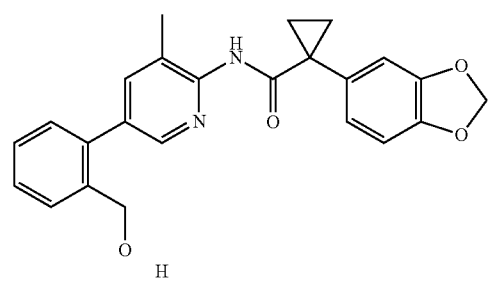
294
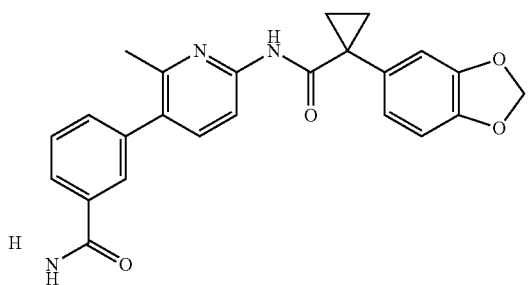
295

US 8,741,933 B2
203
TABLE 1-continued
Examples of compounds of the present invention
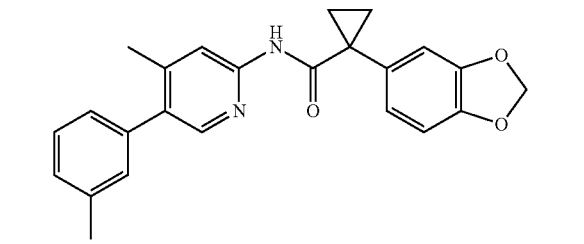 [SMILES: Cc1cccc(-c2cnc(NC(=O)C3(c4ccc5c(c4)OCO5)CC3)cc2C)c1] 296
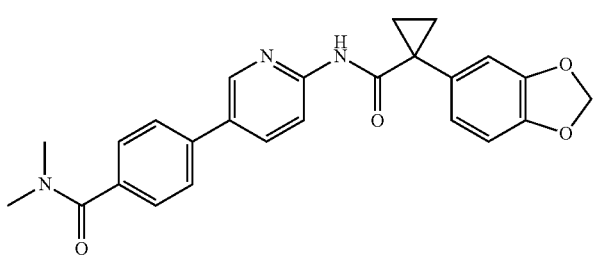 [SMILES: CN(C)C(=O)c1ccc(-c2ccc(NC(=O)C3(c4ccc5c(c4)OCO5)CC3)nc2)cc1] 297
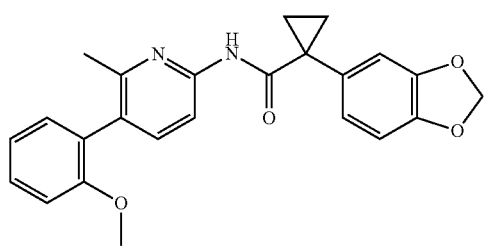 298
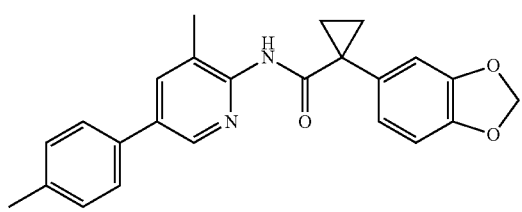 [SMILES: Cc1ccc(-c2cnc(NC(=O)C3(c4ccc5c(c4)OCO5)CC3)c(C)c2)cc1] 299
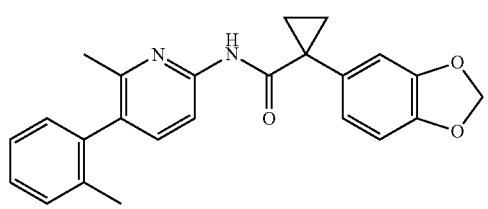 [SMILES: Cc1ccccc1-c1ccc(NC(=O)C2(c3ccc4c(c3)OCO4)CC2)nc1C] 300
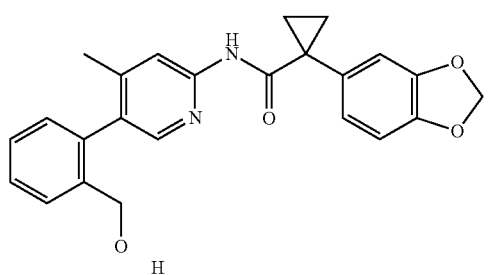 301

TABLE 1-continued
Examples of compounds of the present invention
302
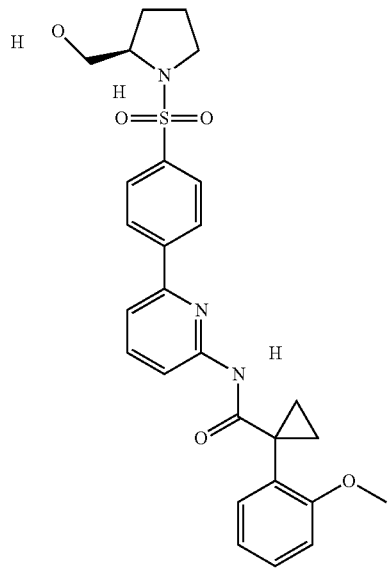
303
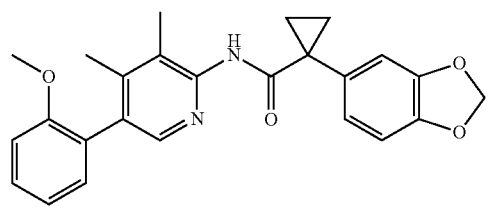 [SMILES: COc1ccccc1-c1cnc(NC(=O)C2(c3ccc4c(c3)OCO4)CC2)c(C)c1C]
304
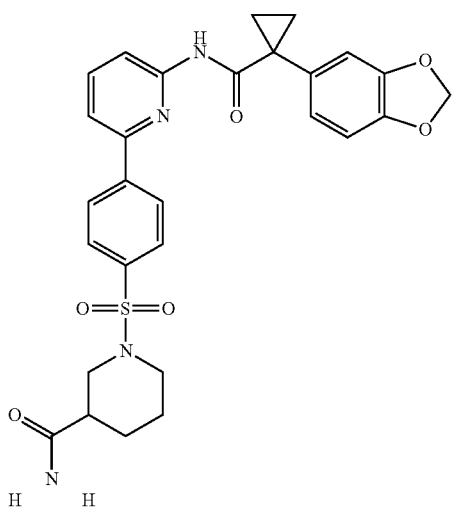
305
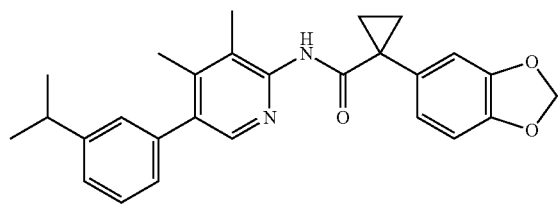 [SMILES: Cc1c(-c2cccc(C(C)C)c2)cnc(NC(=O)C2(c3ccc4c(c3)OCO4)CC2)c1C]

TABLE 1-continued
Examples of compounds of the present invention
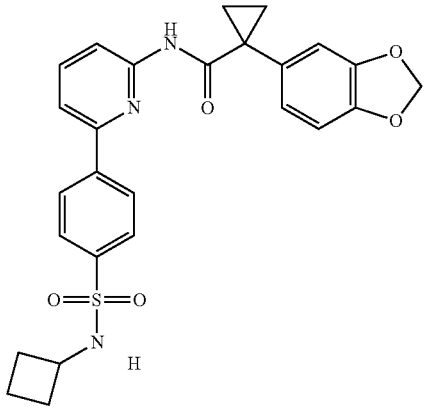
306
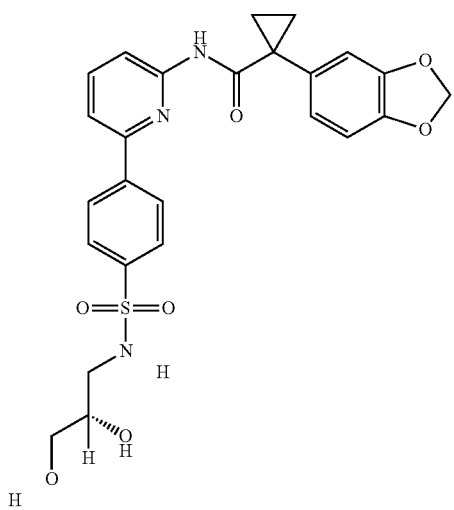
307
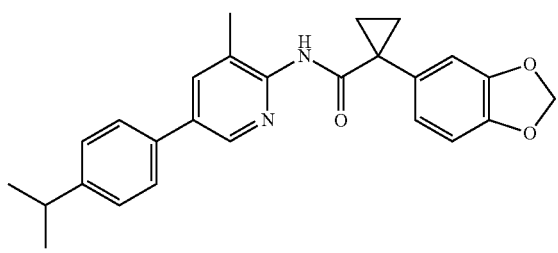 [SMILES: Cc1cc(-c2ccc(C(C)C)cc2)cnc1NC(=O)C1(c2ccc3c(c2)OCO3)CC1]
308
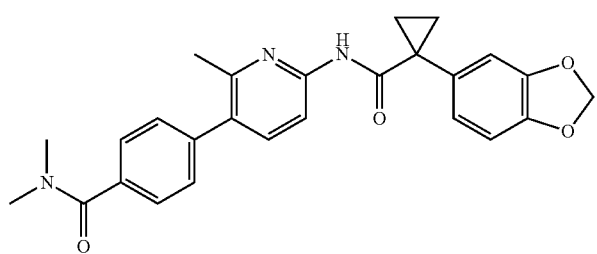
309

TABLE 1-continued
Examples of compounds of the present invention
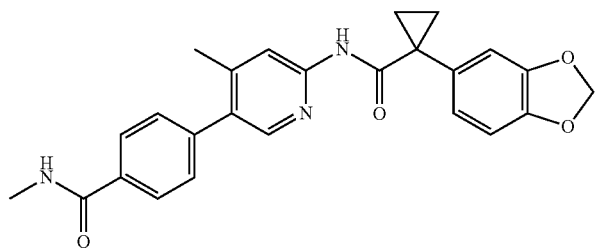 [SMILES: CNC(=O)c1ccc(-c2cnc(NC(=O)C3(c4ccc5c(c4)OCO5)CC3)cc2C)cc1]
310
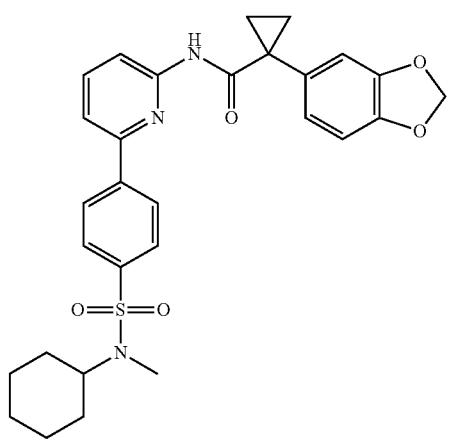 [SMILES: CN(C1CCCCC1)S(=O)(=O)c1ccc(-c2cccc(NC(=O)C3(c4ccc5c(c4)OCO5)CC3)n2)cc1]
311
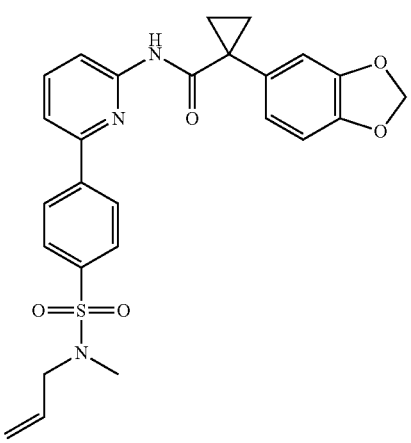 [SMILES: C=CCN(C)S(=O)(=O)c1ccc(-c2cccc(NC(=O)C3(c4ccc5c(c4)OCO5)CC3)n2)cc1]
312
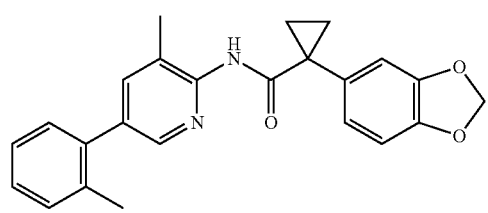 [SMILES: Cc1ccccc1-c1cnc(NC(=O)C2(c3ccc4c(c3)OCO4)CC2)c(C)c1]
313

TABLE 1-continued
Examples of compounds of the present invention
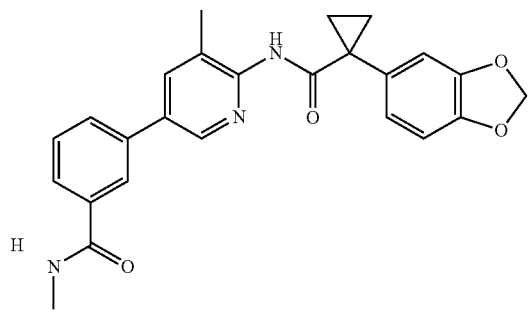
314
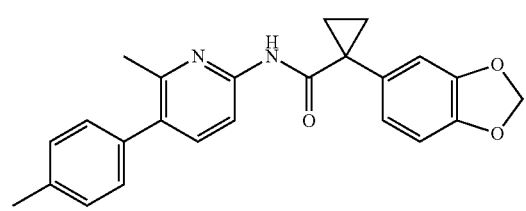 [SMILES: Cc1ccc(-c2ccc(NC(=O)C3(c4ccc5c(c4)OCO5)CC3)nc2C)cc1]
315
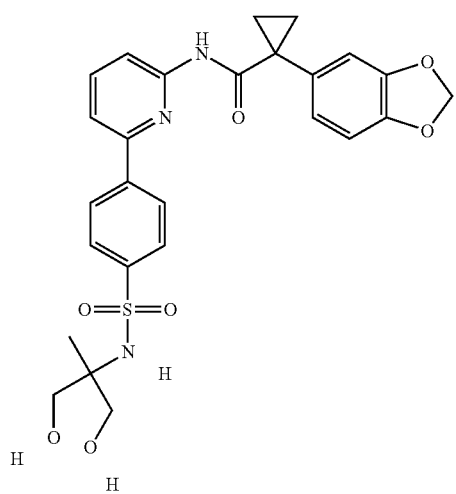
316
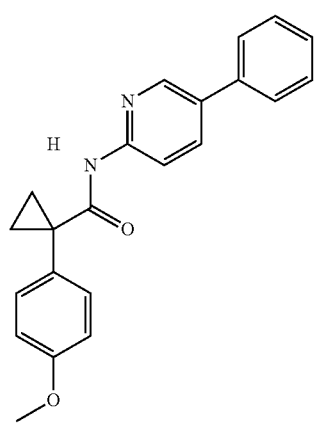
317

TABLE 1-continued
Examples of compounds of the present invention
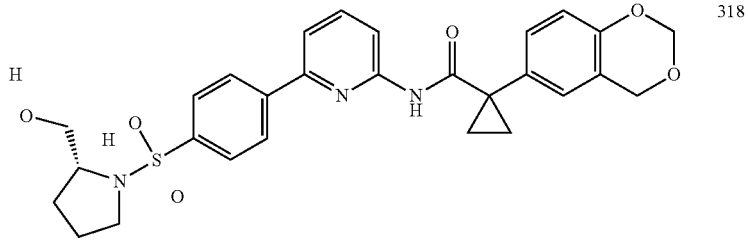
318
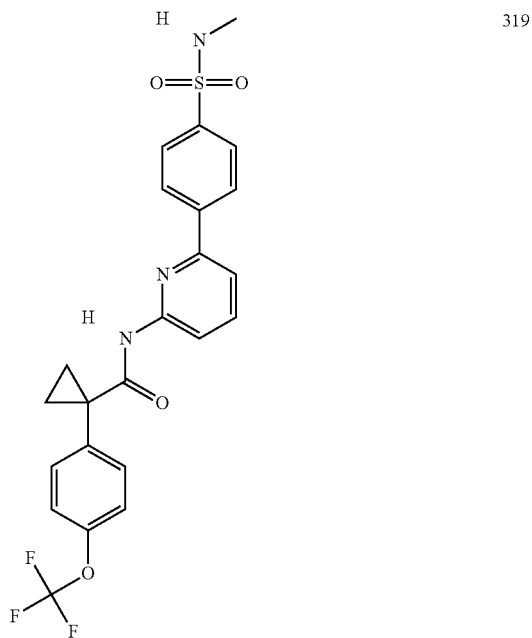
319
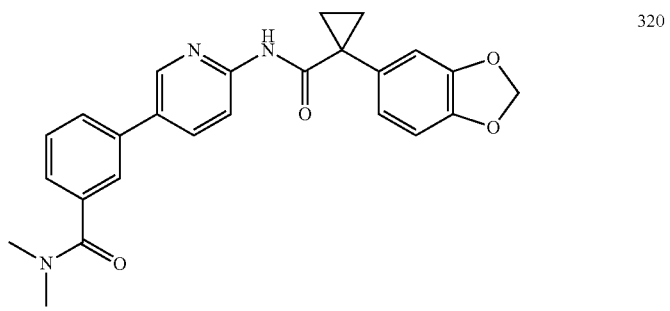
320
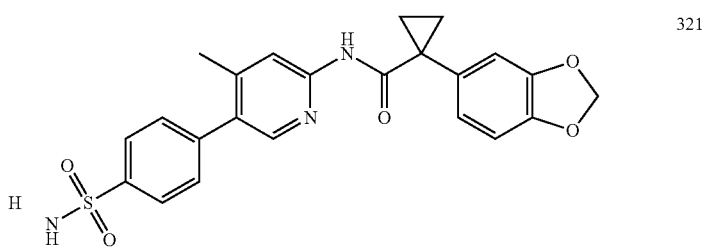
321

TABLE 1-continued
Examples of compounds of the present invention
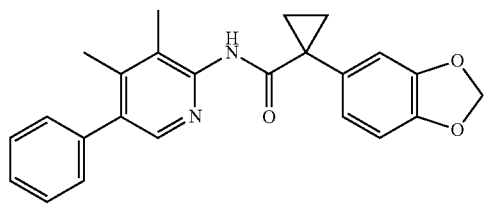 [SMILES: Cc1c(-c2ccccc2)cnc(NC(=O)C2(c3ccc4c(c3)OCO4)CC2)c1C]
322
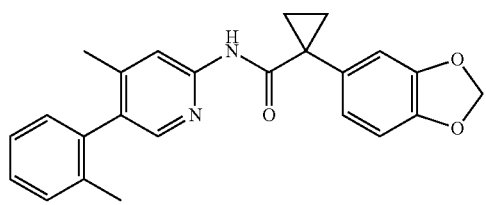 [SMILES: Cc1ccccc1-c1cnc(NC(=O)C2(c3ccc4c(c3)OCO4)CC2)cc1C]
323
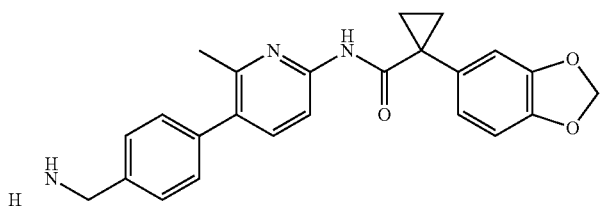
324
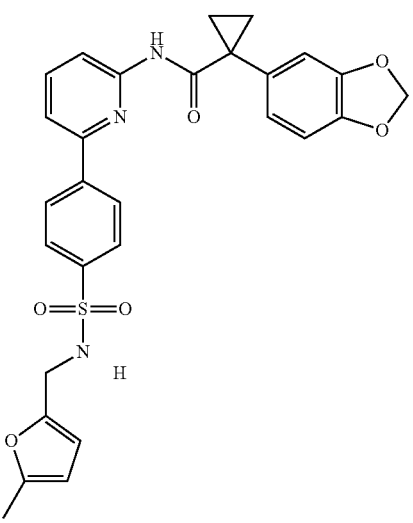
325
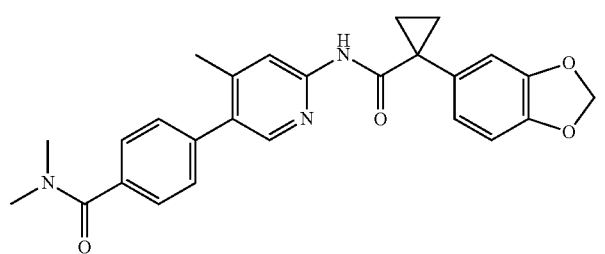 [SMILES: Cc1cc(NC(=O)C2(c3ccc4c(c3)OCO4)CC2)ncc1-c1ccc(C(=O)N(C)C)cc1]
326

TABLE 1-continued
Examples of compounds of the present invention
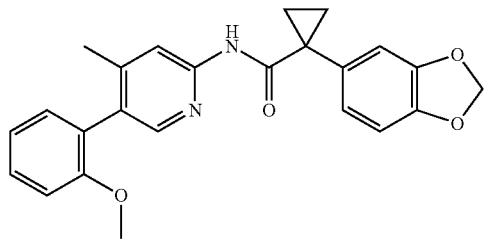 [SMILES: COc1ccccc1-c1cnc(NC(=O)C2(c3ccc4c(c3)OCO4)CC2)cc1C]
327
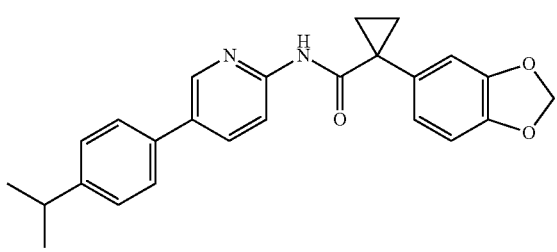 [SMILES: CC(C)c1ccc(-c2ccc(NC(=O)C3(c4ccc5c(c4)OCO5)CC3)nc2)cc1]
328
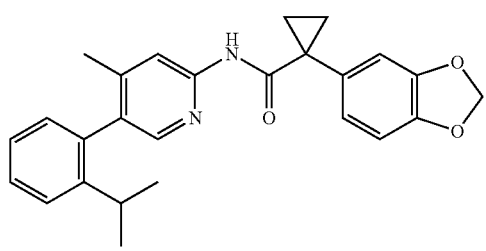 [SMILES: Cc1cc(NC(=O)C2(c3ccc4c(c3)OCO4)CC2)ncc1-c1ccccc1C(C)C]
329
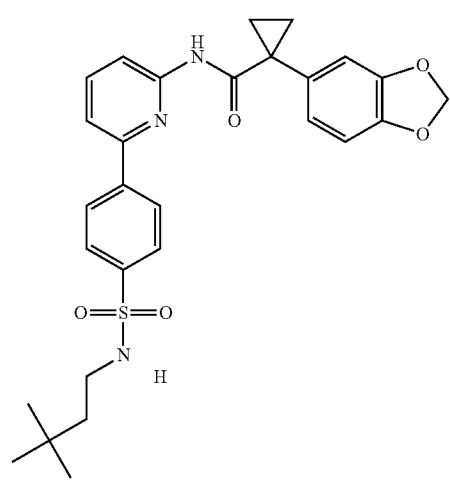
330
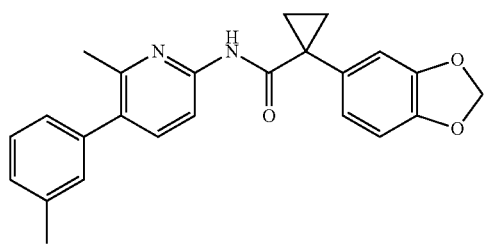 [SMILES: Cc1cccc(-c2ccc(NC(=O)C3(c4ccc5c(c4)OCO5)CC3)nc2C)c1]
331

TABLE 1-continued
Examples of compounds of the present invention
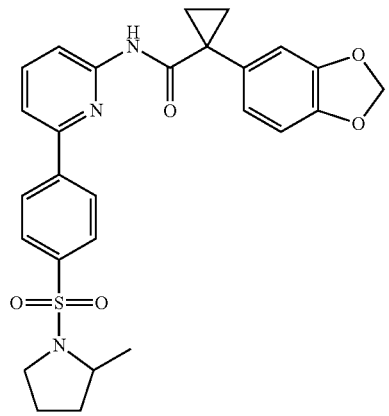 [SMILES: CC1CCCN1S(=O)(=O)c1ccc(-c2cccc(NC(=O)C3(c4ccc5c(c4)OCO5)CC3)n2)cc1] 332
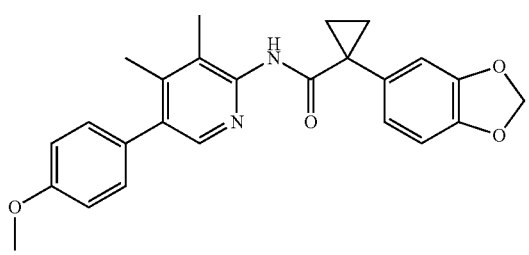 [SMILES: COc1ccc(-c2cnc(NC(=O)C3(c4ccc5c(c4)OCO5)CC3)c(C)c2C)cc1] 333
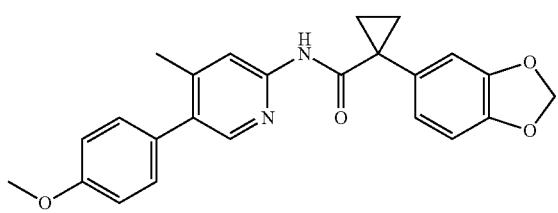 [SMILES: COc1ccc(-c2cnc(NC(=O)C3(c4ccc5c(c4)OCO5)CC3)cc2C)cc1] 334
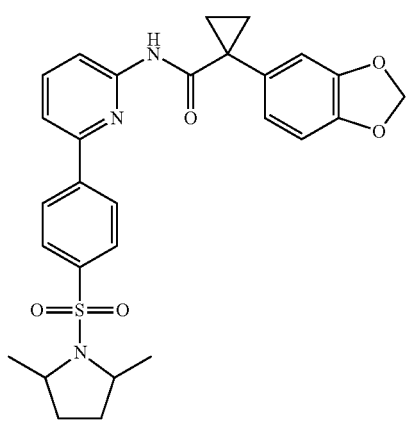 [SMILES: CC1CCC(C)N1S(=O)(=O)c1ccc(-c2cccc(NC(=O)C3(c4ccc5c(c4)OCO5)CC3)n2)cc1] 335

TABLE 1-continued
Examples of compounds of the present invention
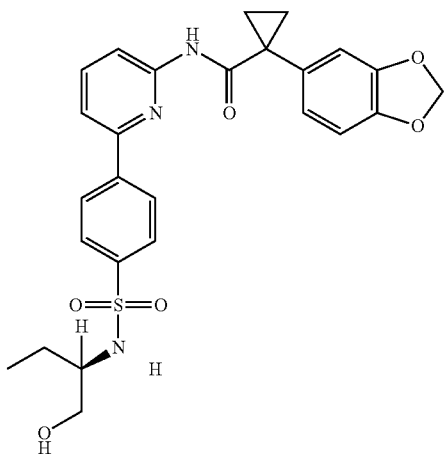
336
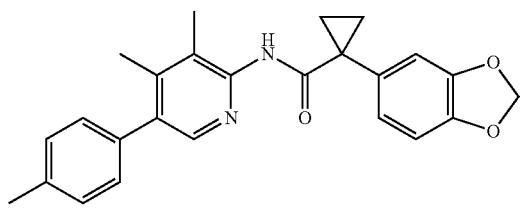 [SMILES: Cc1ccc(-c2cnc(NC(=O)C3(c4ccc5c(c4)OCO5)CC3)c(C)c2C)cc1]
337
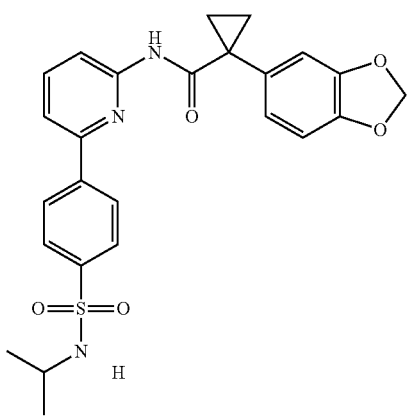
338
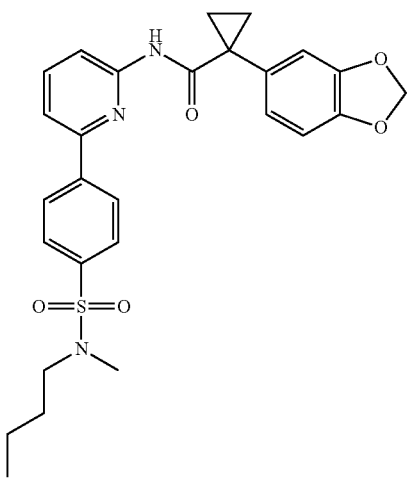 [SMILES: CCCCN(C)S(=O)(=O)c1ccc(-c2cccc(NC(=O)C3(c4ccc5c(c4)OCO5)CC3)n2)cc1]
339

TABLE 1-continued
Examples of compounds of the present invention
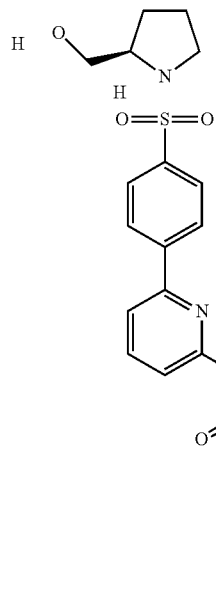
340
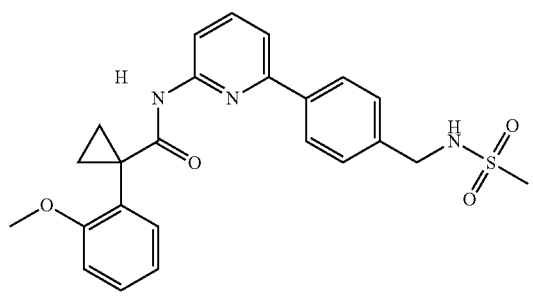
341
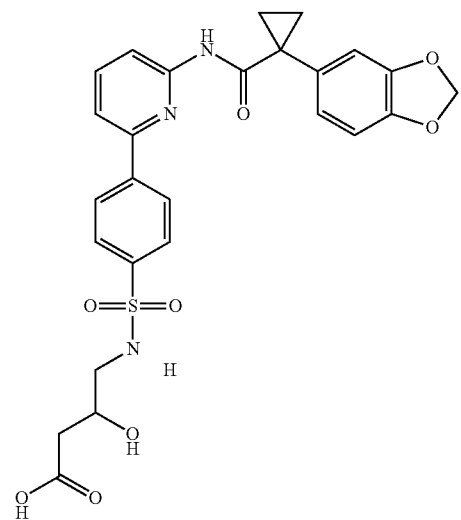
342

TABLE 1-continued
Examples of compounds of the present invention
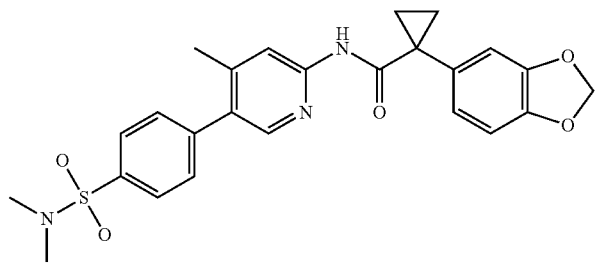 [SMILES: Cc1cc(NC(=O)C2(c3ccc4c(c3)OCO4)CC2)ncc1-c1ccc(S(O)(O)N(C)C)cc1]
343
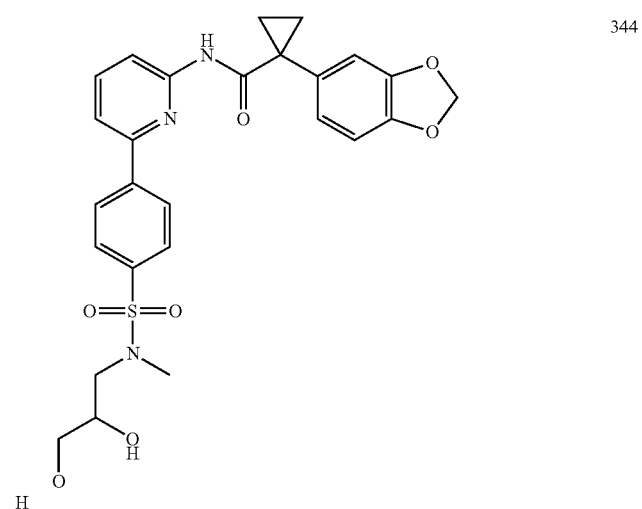
344
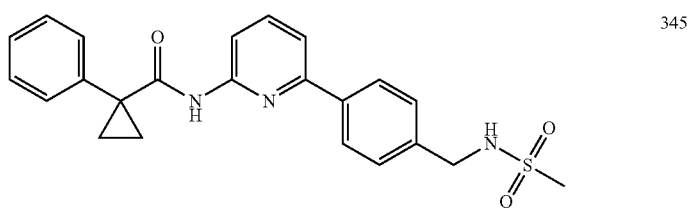
345
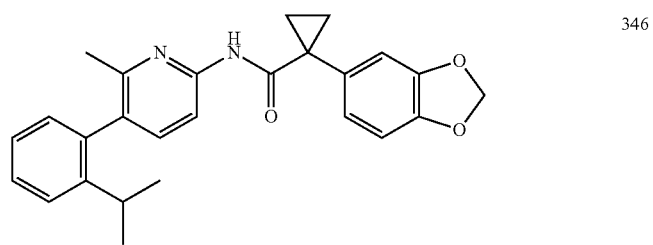
346

TABLE 1-continued
Examples of compounds of the present invention
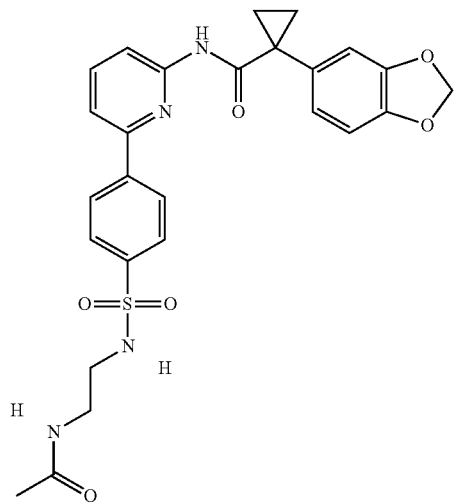 347
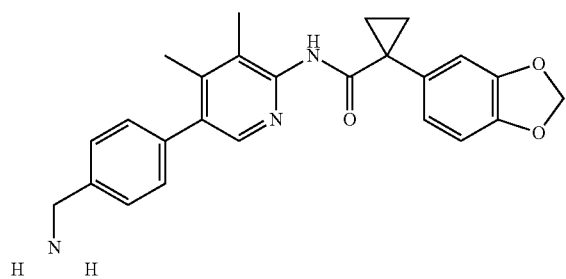 348
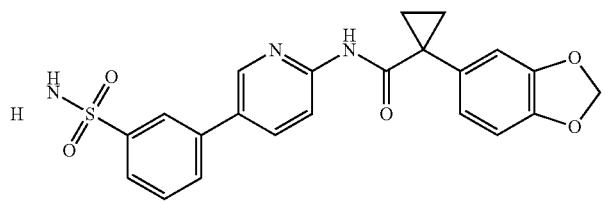 349
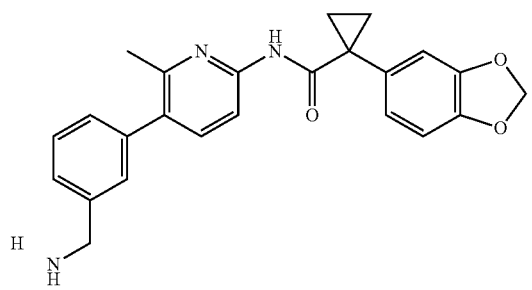 350
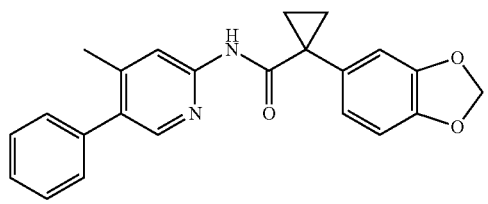 [SMILES: Cc1cc(NC(=O)C2(c3ccc4c(c3)OCO4)CC2)ncc1-c1ccccc1] 351

TABLE 1-continued
Examples of compounds of the present invention
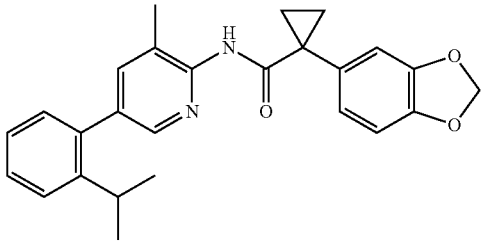 [SMILES: Cc1cc(-c2ccccc2C(C)C)cnc1NC(=O)C1(c2ccc3c(c2)OCO3)CC1] 352
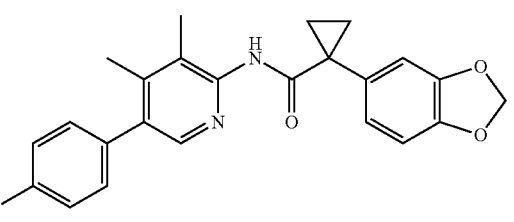 353
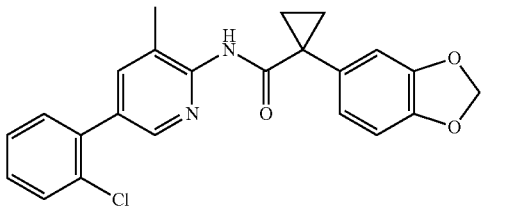 [SMILES: Cc1cc(-c2ccccc2Cl)cnc1NC(=O)C1(c2ccc3c(c2)OCO3)CC1] 354
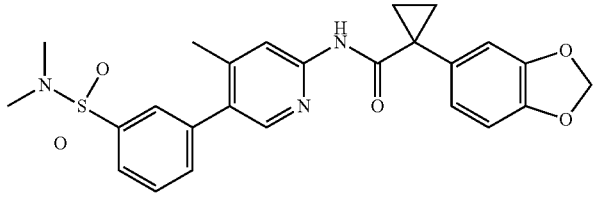 355
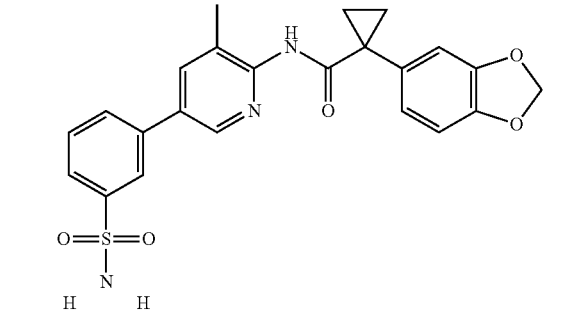 356
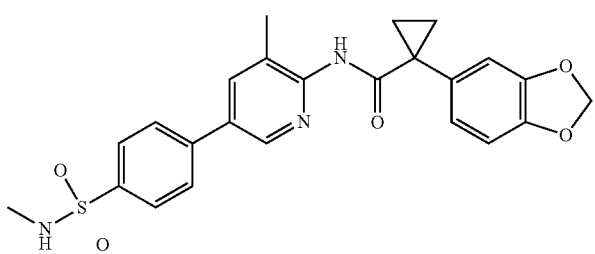 357

TABLE 1-continued
Examples of compounds of the present invention
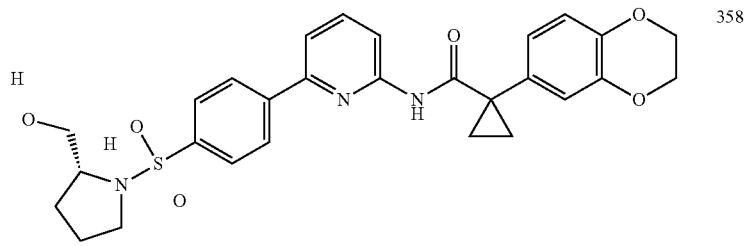
358
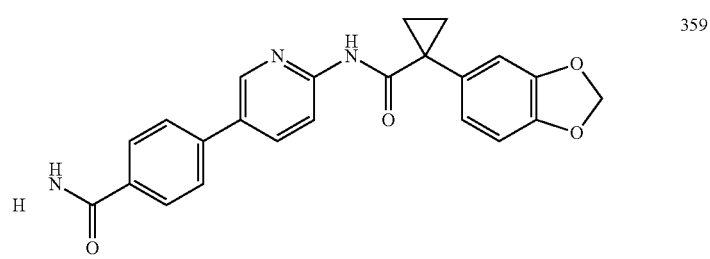
359
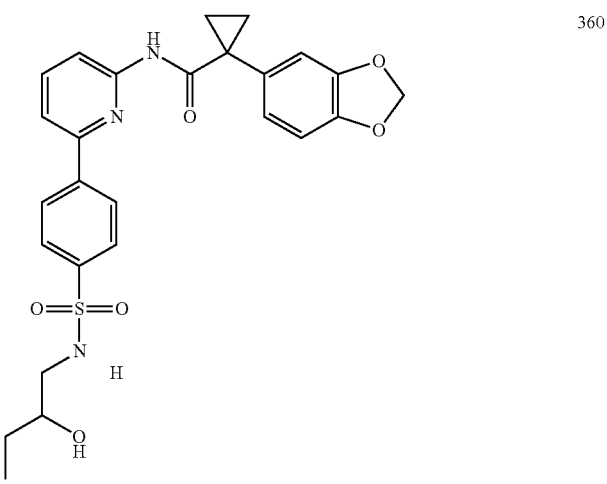
360
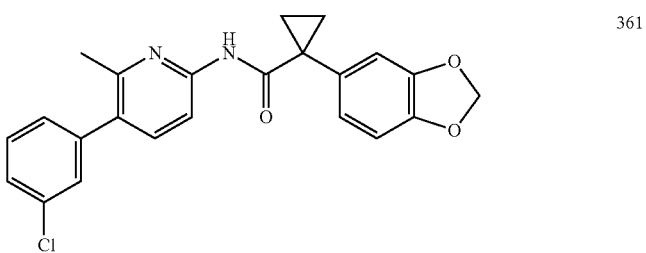
361
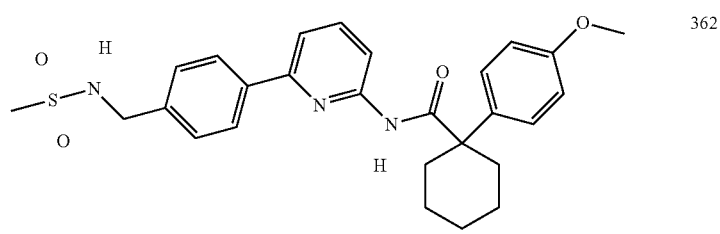
362

TABLE 1-continued
Examples of compounds of the present invention
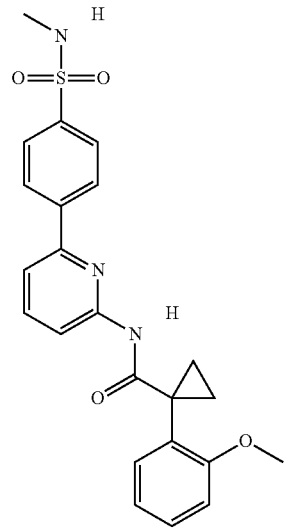
363
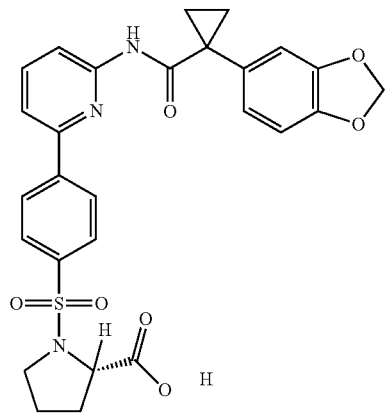
364
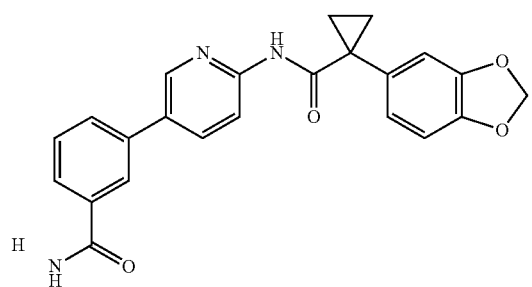
365

TABLE 1-continued
Examples of compounds of the present invention
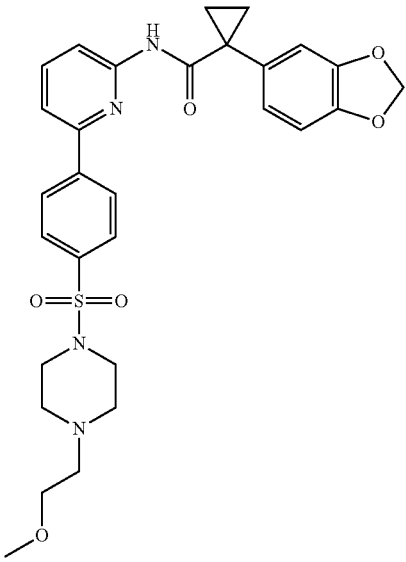 [SMILES: COCCN1CCN(S(=O)(=O)c2ccc(-c3cccc(NC(=O)C4(c5ccc6c(c5)OCO6)CC4)n3)cc2)CC1]
366
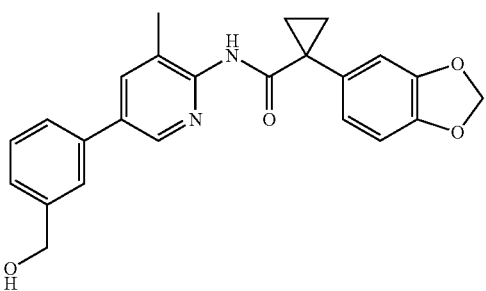 [SMILES: Cc1cc(-c2cccc(CO)c2)cnc1NC(=O)C1(c2ccc3c(c2)OCO3)CC1]
367
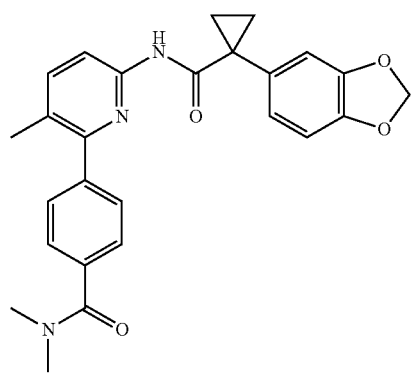 [SMILES: Cc1ccc(NC(=O)C2(c3ccc4c(c3)OCO4)CC2)nc1-c1ccc(C(=O)N(C)C)cc1]
368

TABLE 1-continued
Examples of compounds of the present invention
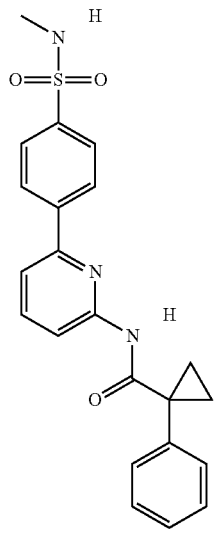
369
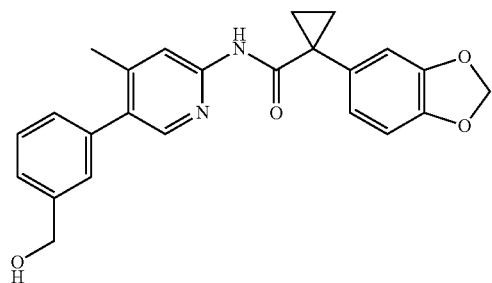 [SMILES: Cc1cc(NC(=O)C2(c3ccc4c(c3)OCO4)CC2)ncc1-c1cccc(CO)c1]
370
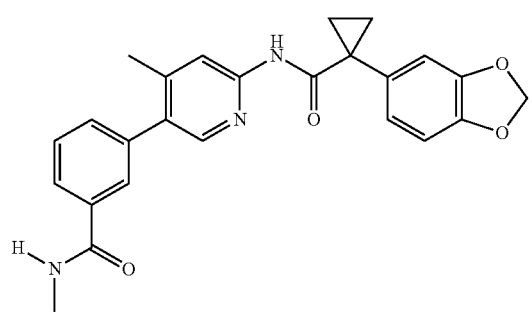 [SMILES: CNC(=O)c1cccc(-c2cnc(NC(=O)C3(c4ccc5c(c4)OCO5)CC3)cc2C)c1]
371

239
TABLE 1-continued
Examples of compounds of the present invention
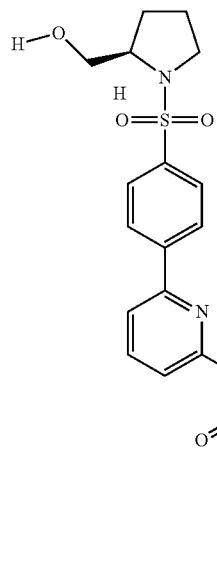
372
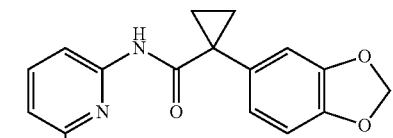
373
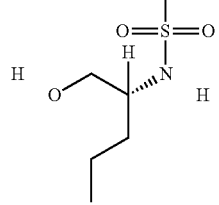
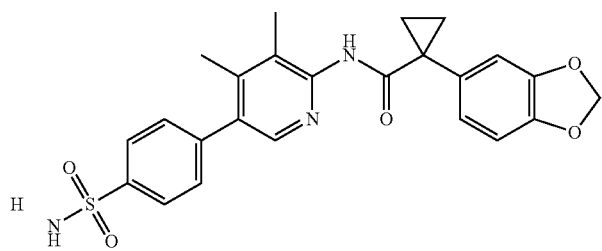
374
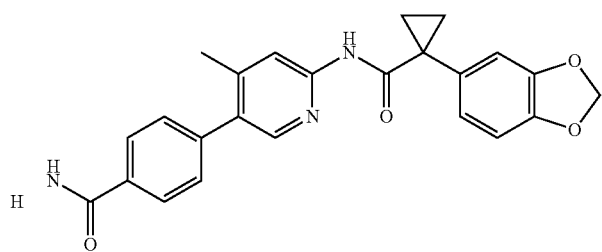
375

TABLE 1-continued
Examples of compounds of the present invention
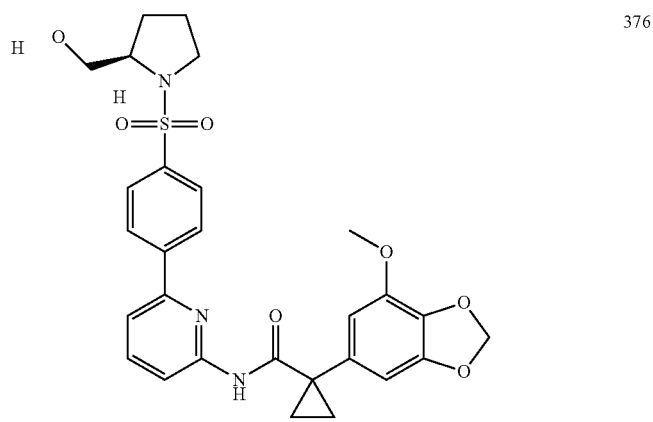
376
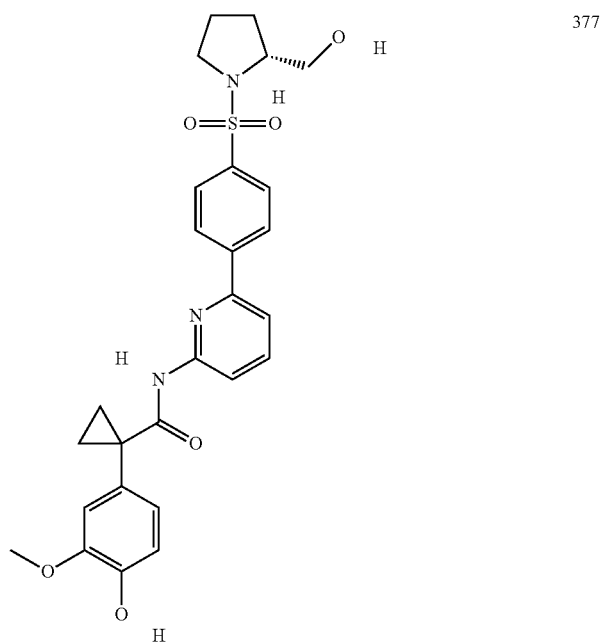
377
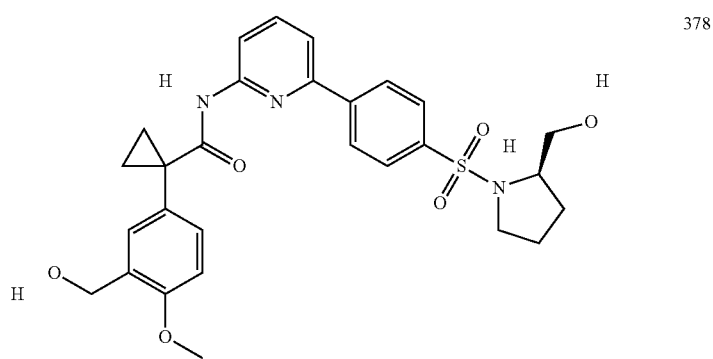
378

TABLE 1-continued
Examples of compounds of the present invention
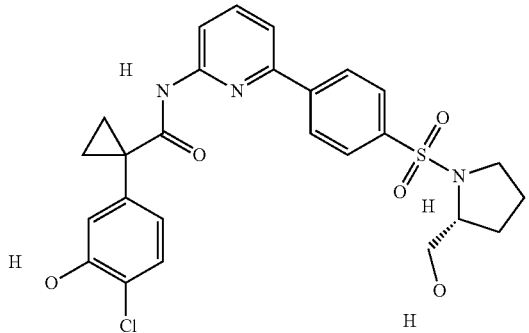
379
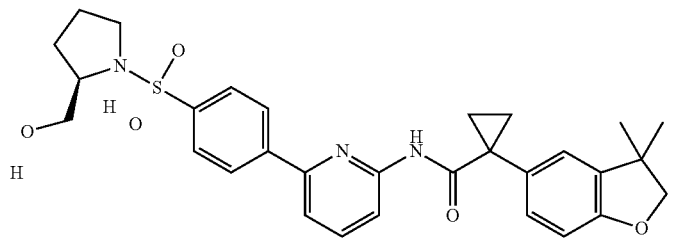
380
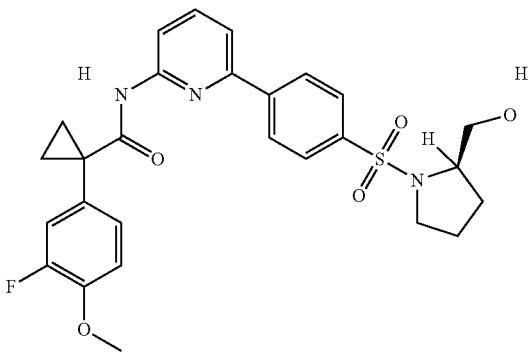
381
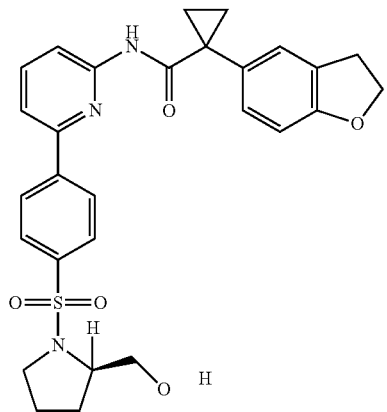
382

TABLE 1-continued
Examples of compounds of the present invention
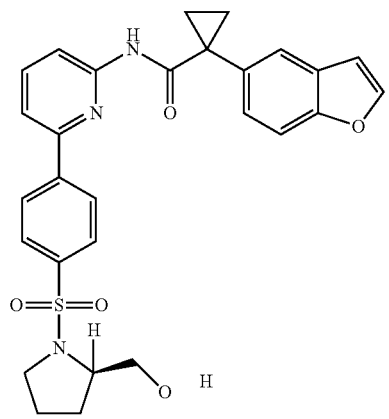
383
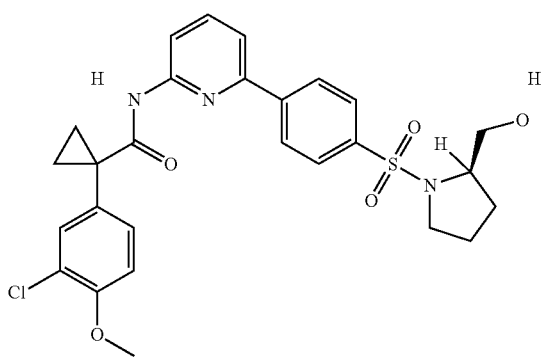
384
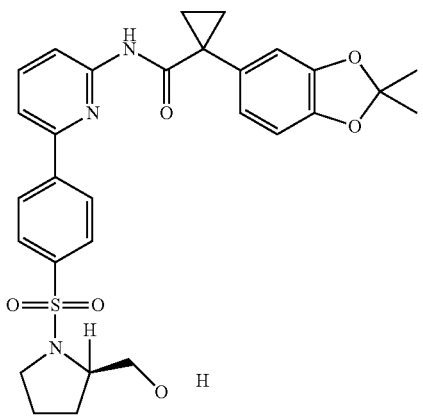
385
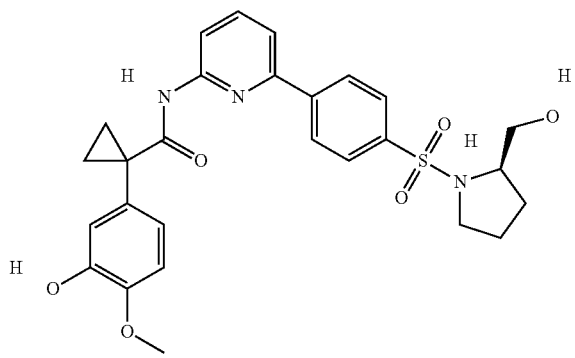
386

TABLE 1-continued
Examples of compounds of the present invention
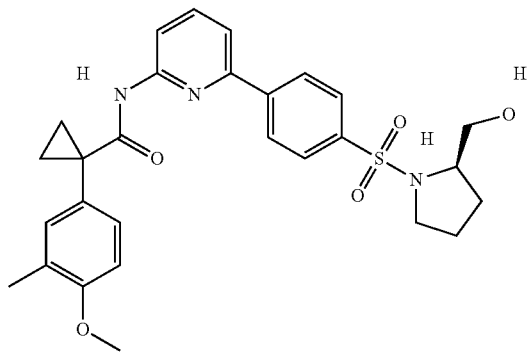
387
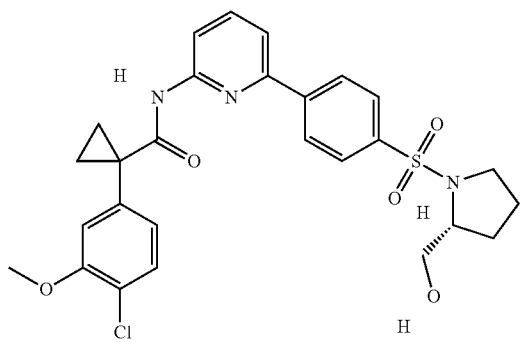
388
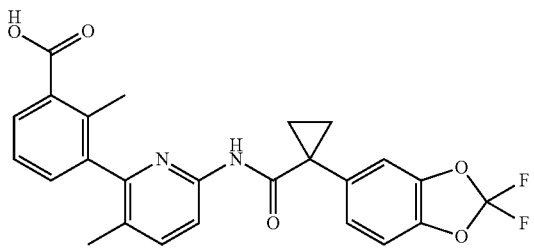 [SMILES: Cc1ccc(NC(=O)C2(c3ccc4c(c3)OC(F)(F)O4)CC2)nc1-c1cccc(C(=O)O)c1C]
389
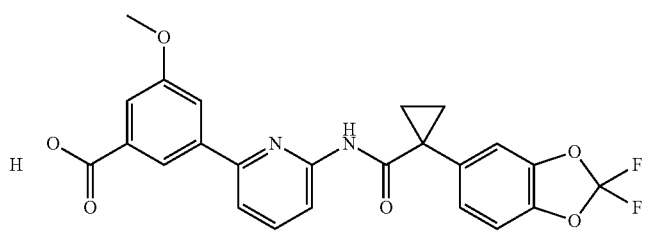
390
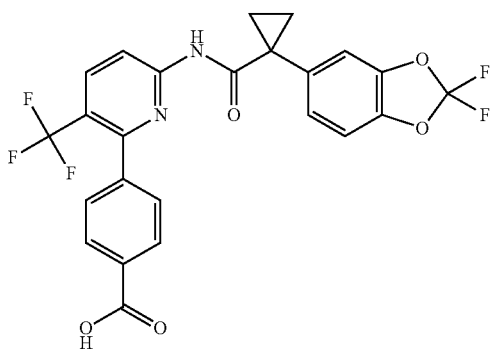 [SMILES: O=C(O)c1ccc(-c2nc(NC(=O)C3(c4ccc5c(c4)OC(F)(F)O5)CC3)ccc2C(F)(F)F)cc1]
391

TABLE 1-continued
Examples of compounds of the present invention
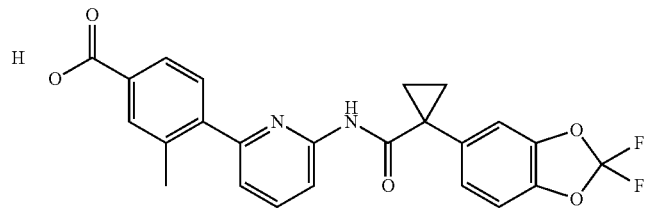
392
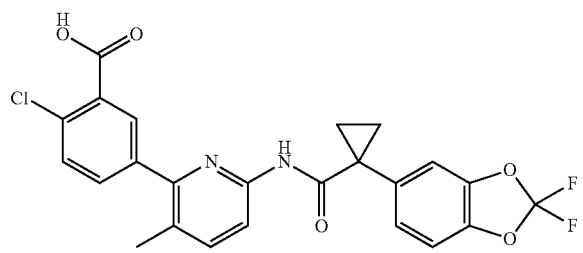 [SMILES: Cc1ccc(NC(=O)C2(c3ccc4c(c3)OC(F)(F)O4)CC2)nc1-c1ccc(Cl)c(C(=O)O)c1]
393
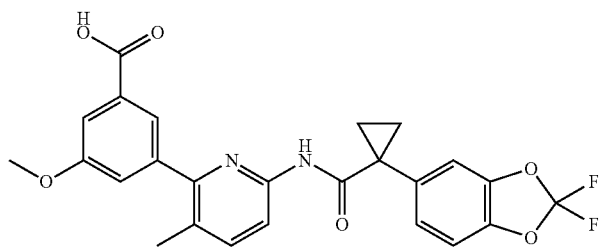 [SMILES: COc1cc(C(=O)O)cc(-c2nc(NC(=O)C3(c4ccc5c(c4)OC(F)(F)O5)CC3)ccc2C)c1]
394
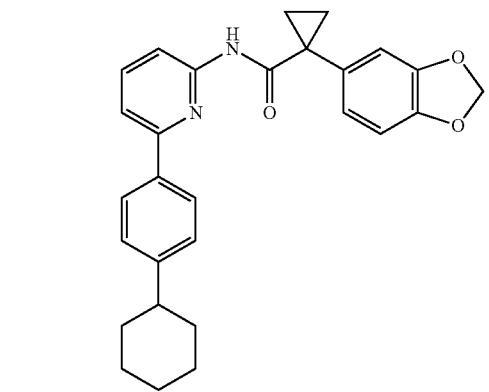 [SMILES: O=C(Nc1cccc(-c2ccc(C3CCCCC3)cc2)n1)C1(c2ccc3c(c2)OCO3)CC1]
395
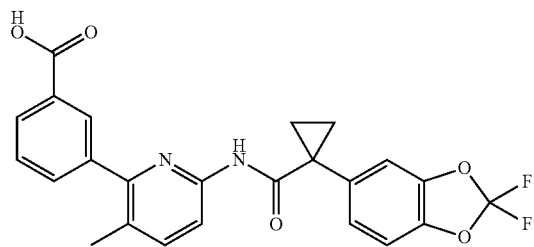 [SMILES: Cc1ccc(NC(=O)C2(c3ccc4c(c3)OC(F)(F)O4)CC2)nc1-c1cccc(C(=O)O)c1]
396
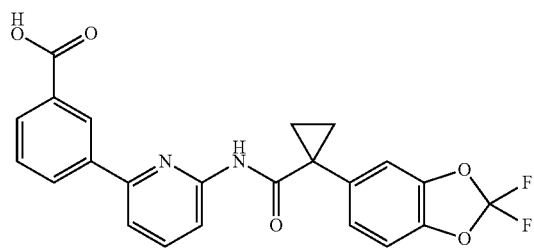 [SMILES: O=C(O)c1cccc(-c2cccc(NC(=O)C3(c4ccc5c(c4)OC(F)(F)O5)CC3)n2)c1]
397

US 8,741,933 B2
251
TABLE 1-continued
Examples of compounds of the present invention
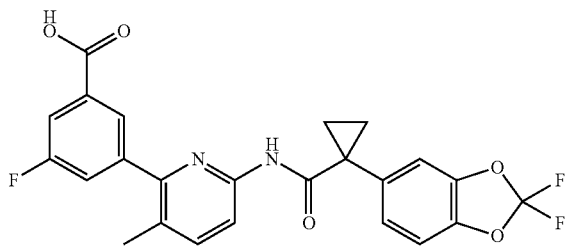 [SMILES: Cc1ccc(NC(=O)C2(c3ccc4c(c3)OC(F)(F)O4)CC2)nc1-c1cc(F)cc(C(=O)O)c1] 398
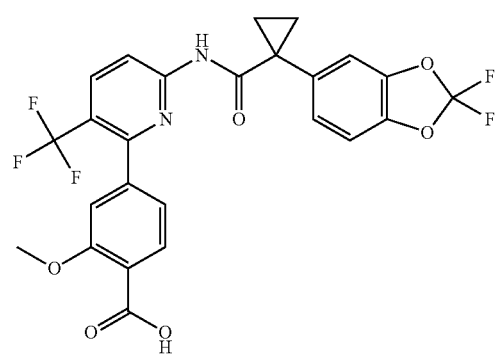 [SMILES: COc1cc(-c2nc(NC(=O)C3(c4ccc5c(c4)OC(F)(F)O5)CC3)ccc2C(F)(F)F)ccc1C(=O)O] 399
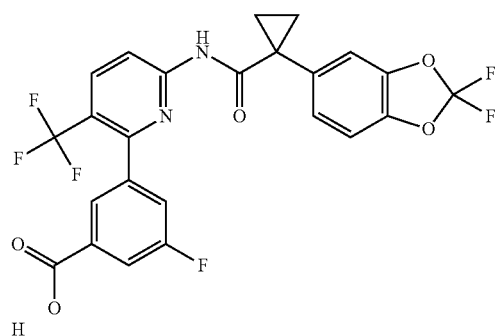 400
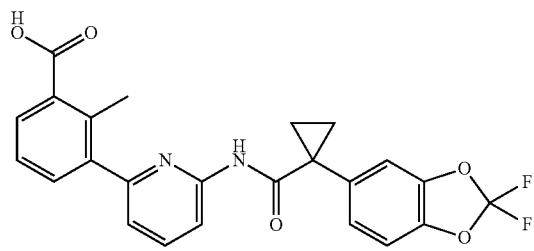 [SMILES: Cc1c(C(=O)O)cccc1-c1cccc(NC(=O)C2(c3ccc4c(c3)OC(F)(F)O4)CC2)n1] 401
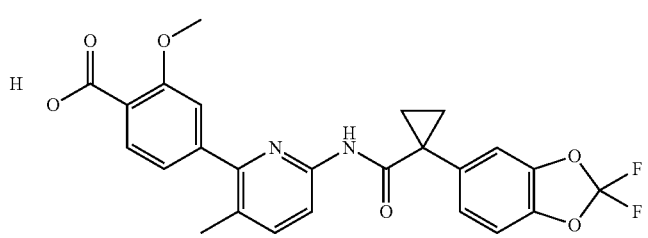 402

TABLE 1-continued
Examples of compounds of the present invention
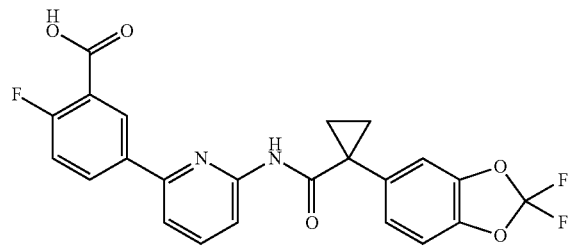 [SMILES: O=C(O)c1cc(-c2cccc(NC(=O)C3(c4ccc5c(c4)OC(F)(F)O5)CC3)n2)ccc1F]
403
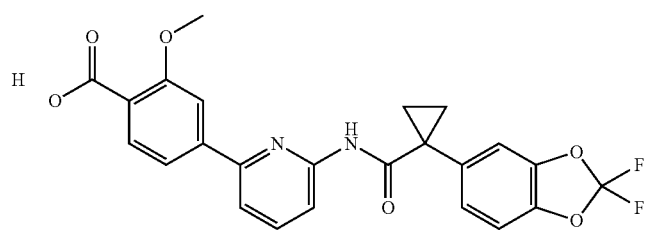
404
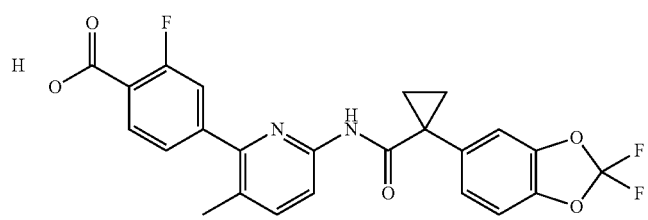
405
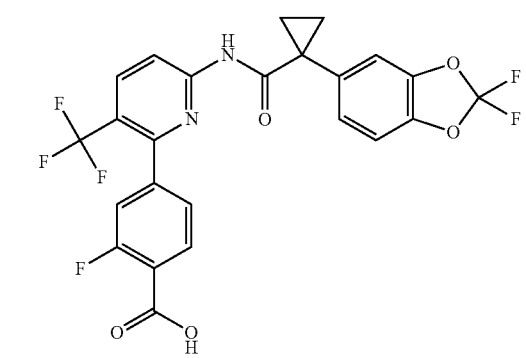 [SMILES: O=C(O)c1ccc(-c2nc(NC(=O)C3(c4ccc5c(c4)OC(F)(F)O5)CC3)ccc2C(F)(F)F)cc1F]
406
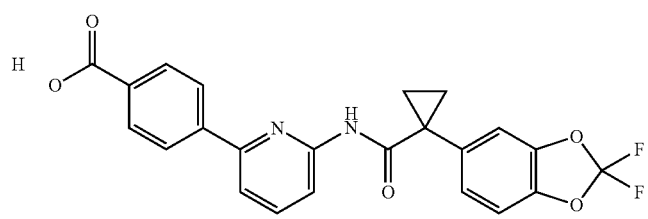
407
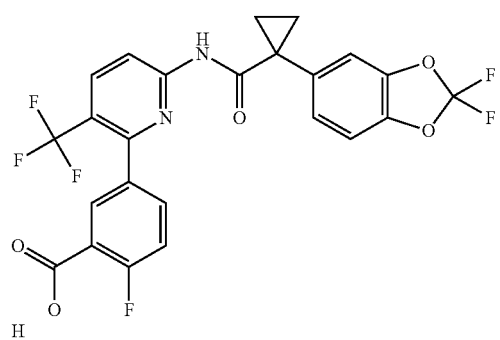
408

TABLE 1-continued
Examples of compounds of the present invention
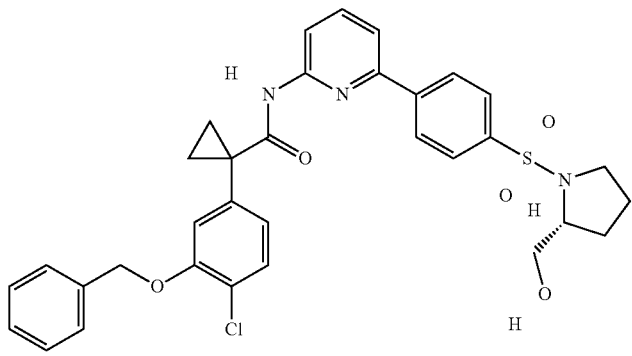
409
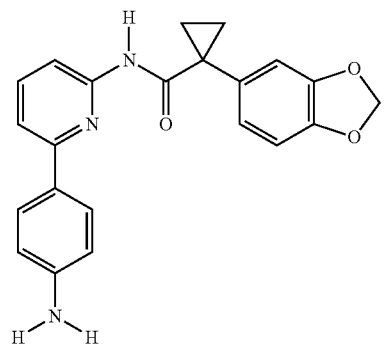 [SMILES: Nc1ccc(-c2cccc(NC(=O)C3(c4ccc5c(c4)OCO5)CC3)n2)cc1]
410
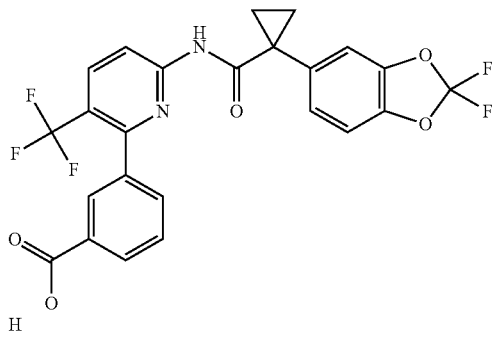
411
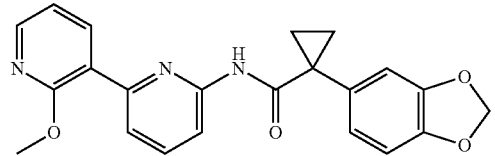 [SMILES: COc1ncccc1-c1cccc(NC(=O)C2(c3ccc4c(c3)OCO4)CC2)n1]
412
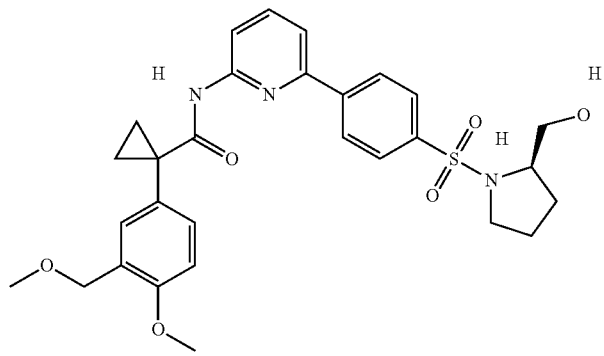
413

TABLE 1-continued
Examples of compounds of the present invention
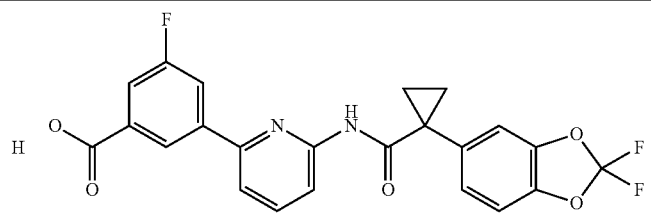
414
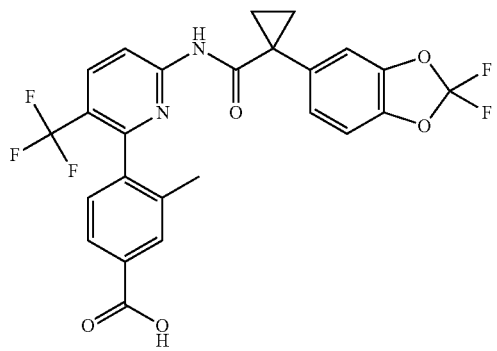 [SMILES: Cc1cc(C(=O)O)ccc1-c1nc(NC(=O)C2(c3ccc4c(c3)OC(F)(F)O4)CC2)ccc1C(F)(F)F]
415
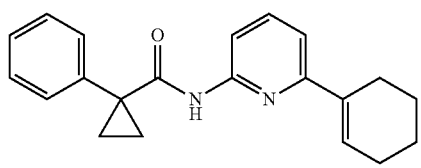 [SMILES: O=C(Nc1cccc(C2=CCCCC2)n1)C1(c2ccccc2)CC1]
416
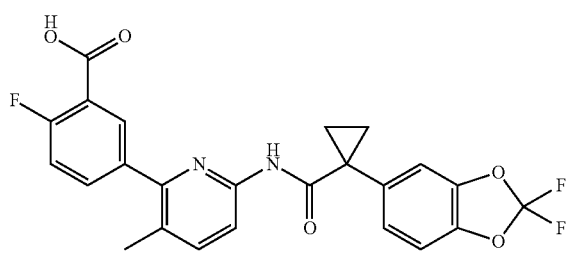 [SMILES: Cc1ccc(NC(=O)C2(c3ccc4c(c3)OC(F)(F)O4)CC2)nc1-c1ccc(F)c(C(=O)O)c1]
417
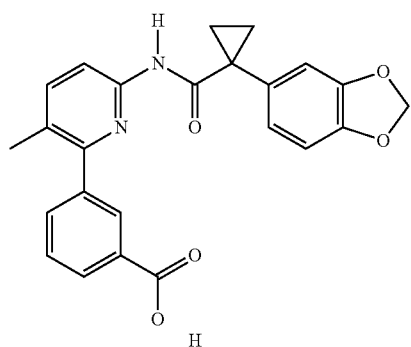
418
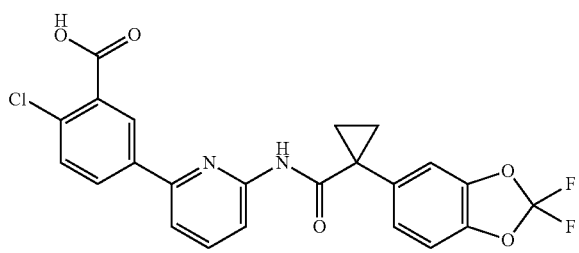 [SMILES: O=C(O)c1cc(-c2cccc(NC(=O)C3(c4ccc5c(c4)OC(F)(F)O5)CC3)n2)ccc1Cl]
419

TABLE 1-continued

Examples of compounds of the present invention

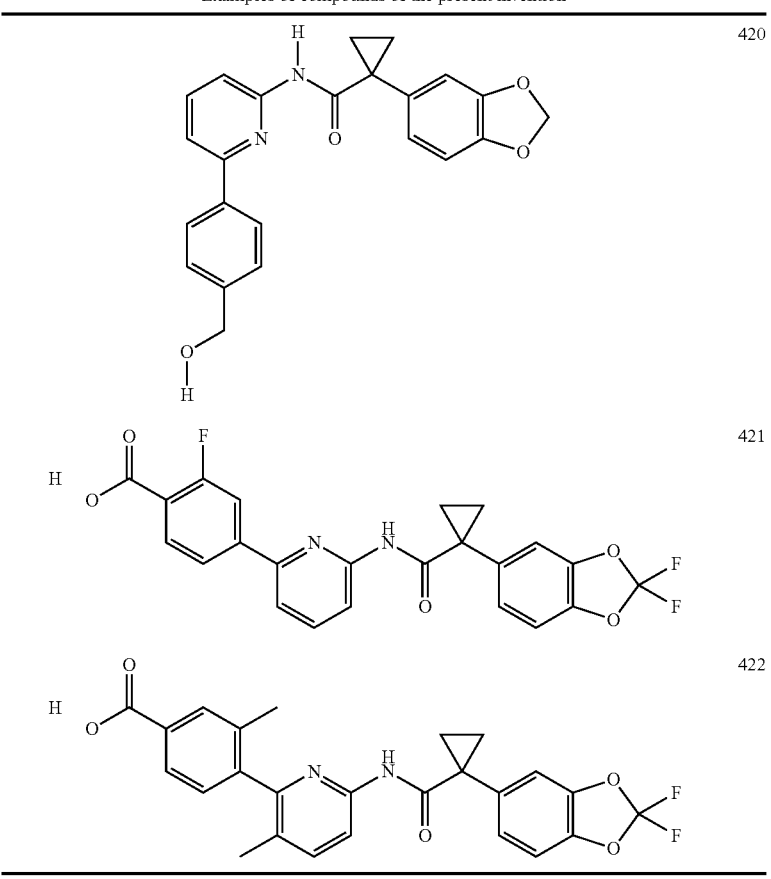

420

421

422

Synthetic Schemes

Compounds of the invention may be prepared by known methods or as illustrated in the examples. In one instance wherein $R_1$ is aryl or heteroaryl, the compounds of the invention may be prepared as illustrated in Scheme I.

Scheme I

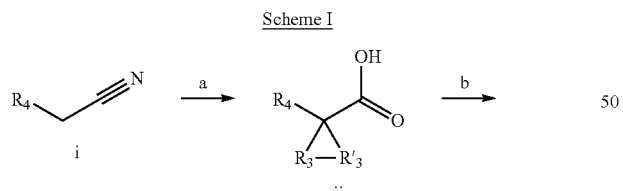

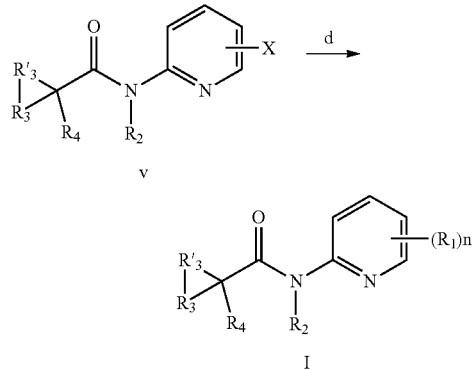

a) 50% NaOH, X—$R_3$—$R'_3$—Y, BTEAC; X, Y = leaving group;
b) $SOCl_2$, DMF;
c) pyridine;
d) $R_1$—$B(OR)_2$, $Pd(dppf)Cl_2$, $K_2CO_3$, DMF, $H_2O$

Scheme II

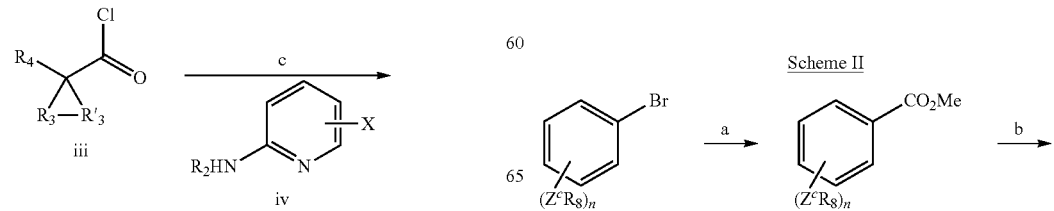

261

-continued

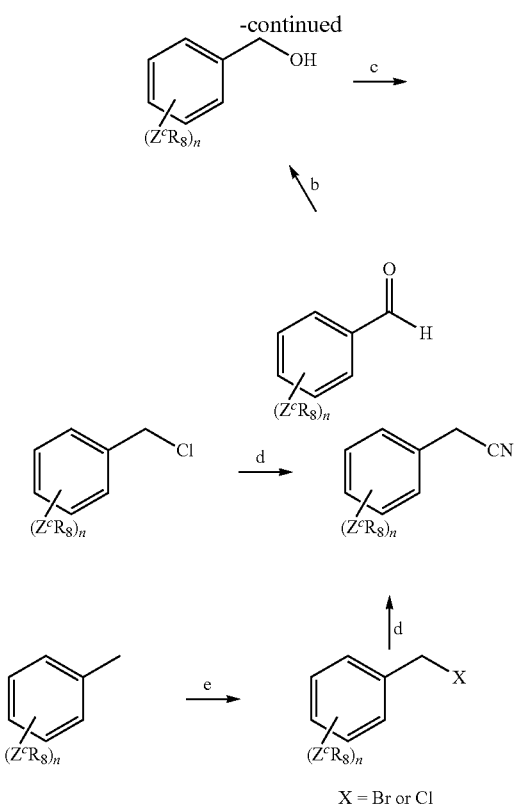

X = Br or Cl
a) Pd(PPh₃)₄, CO, MeOH; b) LiAlH₄, THF; c) SOCl₂; d) NaCN;
e) NBS or NCS, AIBN, CN₄ (X = Br or Cl)

Scheme III

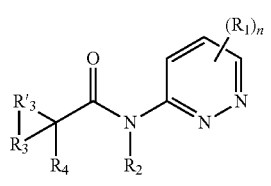

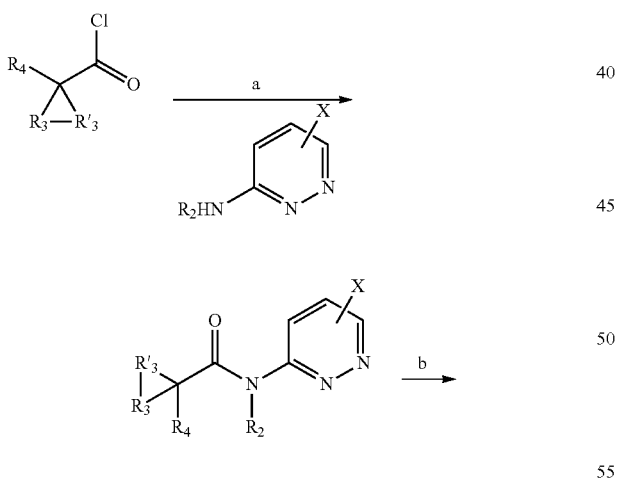

a) pyridine, DCM; b) R₁—B(OR)₂, Pd(dppf)Cl₂, K₂CO₃, DMF, H₂O

262

Scheme IV

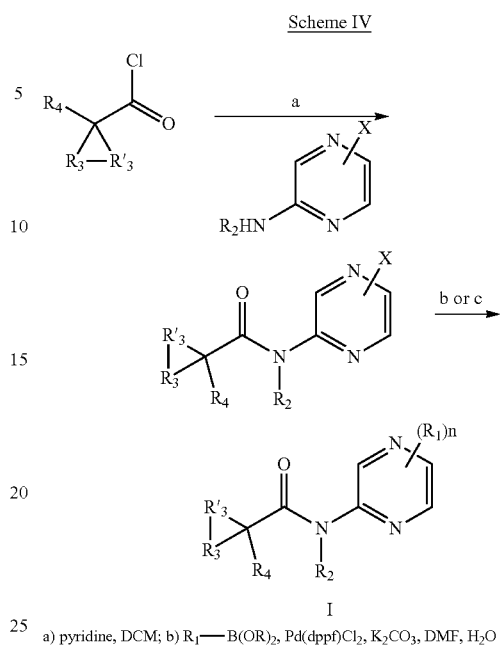

a) pyridine, DCM; b) R₁—B(OR)₂, Pd(dppf)Cl₂, K₂CO₃, DMF, H₂O

Referring to Scheme I, a nitrile of formula i is alkylated (step a) with a dihalo-aliphatic in the presence of a base such as, for example, 50% sodium hydroxide and, optionally, a phase transfer reagent such as, for example, benzyltriethylammonium chloride (BTEAC), to produce the corresponding alkylated nitrile (not shown) which on hydrolysis produces the acid ii. Compounds of formula II are converted to the acid chloride iii with a suitable reagent such as, for example, thionyl chloride/DMF. Reaction of the acid chloride iii with an aminopyridine, wherein X is a halo, of formula iv (step c) produces the amide of formula v. Reaction of the amide v with an optionally substituted boronic acid derivative (step d) in the presence of a catalyst such as, for example, palladium acetate or dichloro-[1,1-bis(diphenylphosphino)ferrocene]palladium(II) (Pd(dppf)Cl₂), provides compounds of the invention wherein R₁ is aryl, heteroaryl, or cycloalkenyl. The boronic acid derivatives vi are commercially available or may be prepared by known methods such as reaction of an aryl bromide with a diborane ester in the presence of a coupling reagent such as, for example, palladium acetate as described in the examples.

In another instance where one R₁ is aryl and another R₁ is an aliphatic, alkoxy, cycloaliphatic, or heterocycloaliphatic, compounds of the invention can be prepared as described in steps a, b, and c of Scheme I using an appropriately substituted aminopyridine such as

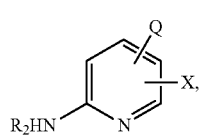

where X is halo and Q is $C_{1-6}$ aliphatic, aryl, heteroaryl, or 3 to 10 membered cycloaliphatic or heterocycloaliphatic as a substitute for the aminopyridine of formula iv.

Formulations, Administrations, and Uses

Pharmaceutically Acceptable Compositions

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, disclose various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by ABC transporter activity. In certain embodiments, the present invention provides a method of treating a condition, disease, or disorder implicated by a deficiency of ABC transporter activity, the method comprising administering a composition comprising a compound of formulae (I, II, III, IV, V-A, V-B, I', I'-A, and I'-B) to a subject, preferably a mammal, in need thereof.

In certain preferred embodiments, the present invention provides a method of treating Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease, Straussler-Scheinker disease, secretory diarrhea, polycystic kidney disease, chronic obstructive pulmonary disease (COPD), dry eye disease, and Sjögren's Syndrome, comprising the step of administering to said mammal an effective amount of a composition comprising a compound of formulae (I, II, III, IV, V-A, V-B, I', I'-A, and I'-B), or a preferred embodiment thereof as set forth above.

According to an alternative preferred embodiment, the present invention provides a method of treating cystic fibrosis comprising the step of administering to said mammal a composition comprising the step of administering to said mammal an effective amount of a composition comprising a compound of formulae (I, II, III, IV, V-A, V-B, I', I'-A, and I'-B), or a preferred embodiment thereof as set forth above.

According to the invention an "effective amount" of the compound or pharmaceutically acceptable composition is that amount effective for treating or lessening the severity of one or more of Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker disease, secretory diarrhea, polycystic kidney disease, chronic obstructive pulmonary disease (COPD), dry eye disease, and Sjögren's Syndrome.

The compounds and compositions, according to the method of the present invention, may be administered using any amount and any route of administration effective for treating or lessening the severity of one or more of Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker disease, secretory diarrhea, polycystic kidney disease, chronic obstructive pulmonary disease (COPD), dry eye disease, and Sjögren's Syndrome.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs.

In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as modulators of ABC transporters. Thus, without wishing to be bound by any particular theory, the compounds and compositions are particularly useful for treating or lessening the severity of a disease, condition, or disorder where hyperactivity or inactivity of ABC transporters is implicated in the disease, condition, or disorder. When hyperactivity or inactivity of an ABC transporter is implicated in a particular disease, condition, or disorder, the disease, condition, or disorder may also be referred to as an "ABC transporter-mediated disease, condition or disorder". Accordingly, in another aspect, the present invention provides a method for treating or lessening the severity of a disease, condition, or disorder where hyperactivity or inactivity of an ABC transporter is implicated in the disease state.

The activity of a compound utilized in this invention as a modulator of an ABC transporter may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating ABC transporter activity in a biological sample or a patient (e.g., in vitro or in vivo), which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of ABC transporter activity in a biological sample is useful for a variety of purposes that are known to one of skill in the art. Examples of such purposes include, but are not limited to, the study of ABC transporters in biological and pathological phenomena; and the comparative evaluation of new modulators of ABC transporters.

In yet another embodiment, a method of modulating activity of an anion channel in vitro or in vivo, is provided comprising the step of contacting said channel with a compound of formulae (I, II, III, IV, V-A, V-B, I', I'-A, and I'-B). In preferred embodiments, the anion channel is a chloride channel or a bicarbonate channel. In other preferred embodiments, the anion channel is a chloride channel.

According to an alternative embodiment, the present invention provides a method of increasing the number of functional ABC transporters in a membrane of a cell, comprising the step of contacting said cell with a compound of formula (I, II, III, IV, V-A, V-B, I', I'-A, and I'-B). The term "functional ABC transporter" as used herein means an ABC transporter that is capable of transport activity. In preferred embodiments, said functional ABC transporter is CFTR.

According to another preferred embodiment, the activity of the ABC transporter is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of a ABC transporter or a fragment thereof in a biological sample in vitro or in vivo comprising (i) a composition comprising a compound of formula (I, II, III, IV, V-A, V-B, I', I'-A, and I'-B) or any of the above embodiments; and (ii) instructions for a.) contacting the composition with the biological sample and b.) measuring activity of said ABC transporter or a fragment thereof. In one embodiment, the kit further comprises instructions for a.) contacting an additional composition with the biological sample; b.) measuring the activity of said ABC transporter or a fragment thereof in the presence of said additional compound, and c.) comparing the activity of the ABC transporter in the presence of the additional compound with the density of the ABC transporter in the presence of a composition of formula (I, II, III, IV, V-A, V-B, I', I'-A, and I'-B). In preferred embodiments, the kit is used to measure the density of CFTR.

Preparations and Examples

General Procedure I: Carboxylic Acid Building Block

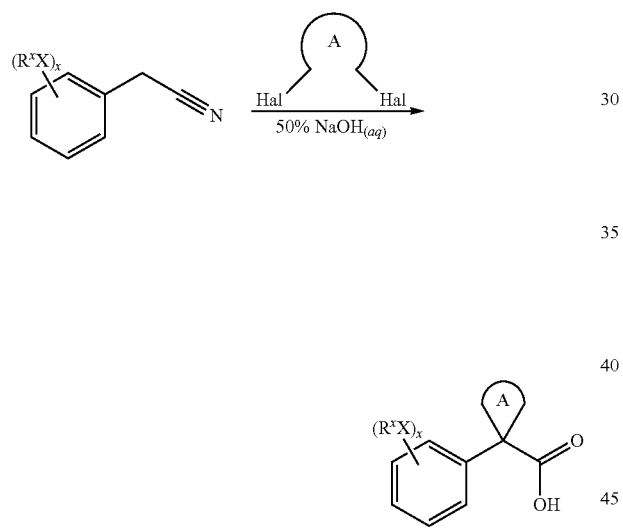

Hal = Cl, Br, I

Benzyltriethylammonium chloride (0.025 equivalents) and the appropriate dihalo compound (2.5 equivalents) were added to a substituted phenyl acetonitrile. The mixture was heated at 70° C. and then 50% sodium hydroxide (10 equivalents) was slowly added to the mixture. The reaction was stirred at 70° C. for 12-24 hours to ensure complete formation of the cycloalkyl moiety and then heated at 130° C. for 24-48 hours to ensure complete conversion from the nitrile to the carboxylic acid. The dark brown/black reaction mixture was diluted with water and extracted with ethyl acetate and then dichloromethane three times each to remove side products. The basic aqueous solution was acidified with concentrated hydrochloric acid to pH less than one and the precipitate which began to form at pH 4 was filtered and washed with 1 M hydrochloric acid two times. The solid material was dissolved in dichloromethane and extracted two times with 1 M hydrochloric acid and one time with a saturated aqueous solution of sodium chloride. The organic solution was dried over sodium sulfate and evaporated to dryness to give the cycloalkylcarboxylic acid.

A. 1-Benzo[1,3]dioxol-5-yl-cyclopropanecarboxylic acid

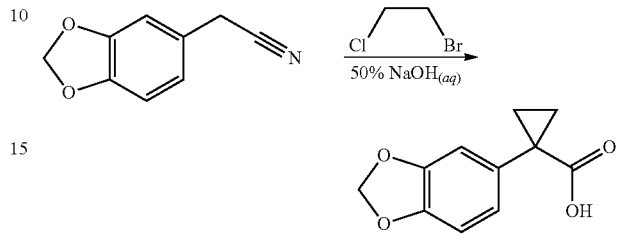

A mixture of benzo[1,3]dioxole-5-acetonitrile (5.10 g, 31.7 mmol), 1-bromo-2-chloro-ethane (9.00 mL, 109 mmol), and benzyltriethylammonium chloride (0.181 g, 0.795 mmol) was heated at 70° C. and then 50% (wt./wt.) aqueous sodium hydroxide (26 mL) was slowly added to the mixture. The reaction was stirred at 70° C. for 18 hours and then heated at 130° C. for 24 hours. The dark brown reaction mixture was diluted with water (400 mL) and extracted once with an equal volume of ethyl acetate and once with an equal volume of dichloromethane. The basic aqueous solution was acidified with concentrated hydrochloric acid to pH less than one and the precipitate filtered and washed with 1 M hydrochloric acid. The solid material was dissolved in dichloromethane (400 mL) and extracted twice with equal volumes of 1 M hydrochloric acid and once with a saturated aqueous solution of sodium chloride. The organic solution was dried over sodium sulfate and evaporated to dryness to give a white to slightly off-white solid (5.23 g, 80%) ESI-MS m/z calc. 206.1. found 207.1 (M+1)$^+$. Retention time of 2.37 minutes. $^1$H NMR (400 MHz, DMSO-d$_6$) δ 1.07-1.11 (m, 2H), 1.38-1.42 (m, 2H), 5.98 (s, 2H), 6.79 (m, 2H), 6.88 (m, 1H), 12.26 (s, 1H).

General Procedure II: Carboxylic Acid Building Block

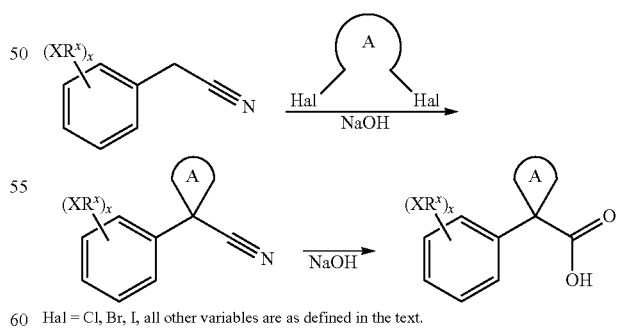

Hal = Cl, Br, I, all other variables are as defined in the text.

Sodium hydroxide (50% aqueous solution, 7.4 equivalents) was slowly added to a mixture of the appropriate phenyl acetonitrile, benzyltriethylammonium chloride (1.1 equivalents), and the appropriate dihalo compound (2.3 equivalents) at 70° C. The mixture was stirred overnight at 70° C. and the reaction mixture was diluted with water (30 mL) and extracted with ethyl acetate. The combined organic layers were dried over sodium sulfate and evaporated to dryness to give the crude cyclopropanecarbonitrile, which was used directly in the next step.

The crude cyclopropanecarbonitrile was heated at reflux in 10% aqueous sodium hydroxide (7.4 equivalents) for 2.5 hours. The cooled reaction mixture was washed with ether (100 mL) and the aqueous phase was acidified to pH 2 with 2M hydrochloric acid. The precipitated solid was filtered to give the cyclopropanecarboxylic acid as a white solid.

General Procedure III: Carboxylic Acid Building Block

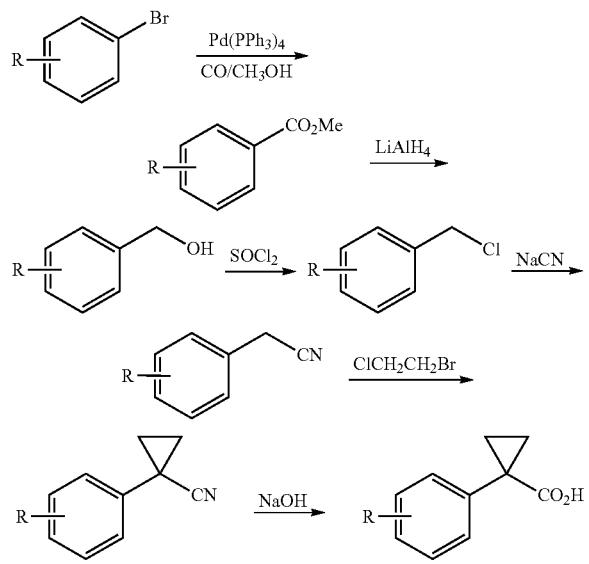

B. 1-(2,2-Difluoro-benzol-1,31-dioxol-5-yl)-cyclopropanecarboxylic acid

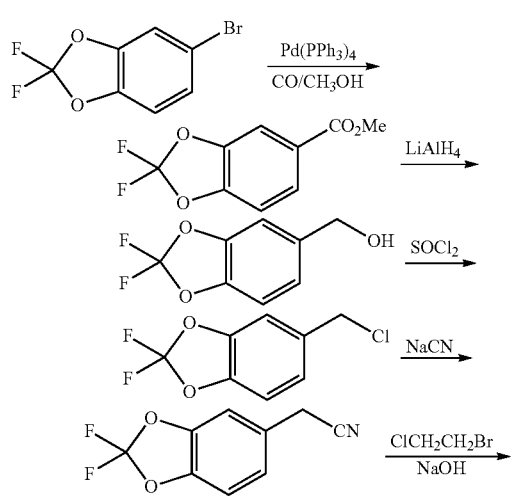

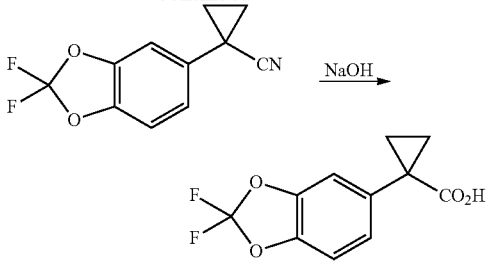

Step a: 2,2-Difluoro-benzo[1,3]dioxole-5-carboxylic acid methyl ester

A solution of 5-bromo-2,2-difluoro-benzo[1,3]dioxole (11.8 g, 50.0 mmol) and tetrakis(triphenylphosphine)palladium (0) [Pd(PPh$_3$)$_4$, 5.78 g, 5.00 mmol] in methanol (20 mL) containing acetonitrile (30 mL) and triethylamine (10 mL) was stirred under a carbon monoxide atmosphere (55 PSI) at 75° C. (oil bath temperature) for 15 hours. The cooled reaction mixture was filtered and the filtrate was evaporated to dryness. The residue was purified by silica gel column chromatography to give crude 2,2-difluoro-benzo[1,3]dioxole-5-carboxylic acid methyl ester (11.5 g), which was used directly in the next step.

Step b: (2,2-Difluoro-benzo[1,3]dioxol-5-yl)-methanol

Crude 2,2-difluoro-benzo[1,3]dioxole-5-carboxylic acid methyl ester (11.5 g) dissolved in 20 mL of anhydrous tetrahydrofuran (THF) was slowly added to a suspension of lithium aluminum hydride (4.10 g, 106 mmol) in anhydrous THF (100 mL) at 0° C. The mixture was then warmed to room temperature. After being stirred at room temperature for 1 hour, the reaction mixture was cooled to 0° C. and treated with water (4.1 g), followed by sodium hydroxide (10% aqueous solution, 4.1 mL). The resulting slurry was filtered and washed with THF. The combined filtrate was evaporated to dryness and the residue was purified by silica gel column chromatography to give (2,2-difluoro-benzo[1,3]dioxol-5-yl)-methanol (7.2 g, 38 mmol, 76% over two steps) as a colorless oil.

Step c: 5-Chloromethyl-2,2-difluoro-benzo[1,3]dioxole

Thionyl chloride (45 g, 38 mmol) was slowly added to a solution of (2,2-difluoro-benzo[1,3]dioxol-5-yl)-methanol (7.2 g, 38 mmol) in dichloromethane (200 mL) at 0° C. The resulting mixture was stirred overnight at room temperature and then evaporated to dryness. The residue was partitioned between an aqueous solution of saturated sodium bicarbonate (100 mL) and dichloromethane (100 mL). The separated aqueous layer was extracted with dichloromethane (150 mL) and the organic layer was dried over sodium sulfate, filtered, and evaporated to dryness to give crude 5-chloromethyl-2,2-difluoro-benzo[1,3]dioxole (4.4 g) which was used directly in the next step.

Step d: (2,2-Difluoro-benzo[1,3]dioxol-5-yl)-acetonitrile

A mixture of crude 5-chloromethyl-2,2-difluoro-benzo[1,3]dioxole (4.4 g) and sodium cyanide (1.36 g, 27.8 mmol) in dimethylsulfoxide (50 mL) was stirred at room temperature overnight. The reaction mixture was poured into ice and extracted with ethyl acetate (300 mL). The organic layer was dried over sodium sulfate and evaporated to dryness to give crude (2,2-difluoro-benzo[1,3]dioxol-5-yl)-acetonitrile (3.3 g) which was used directly in the next step.

Step e: 1-(2,2-Difluoro-benzo[1,3]dioxol-5-yl)-cyclopropanecarbonitrile

Sodium hydroxide (50% aqueous solution, 10 mL) was slowly added to a mixture of crude (2,2-difluoro-benzo[1,3]dioxol-5-yl)-acetonitrile, benzyltriethylammonium chloride (3.00 g, 15.3 mmol), and 1-bromo-2-chloroethane (4.9 g, 38 mmol) at 70° C. The mixture was stirred overnight at 70° C. before the reaction mixture was diluted with water (30 mL) and extracted with ethyl acetate. The combined organic layers were dried over sodium sulfate and evaporated to dryness to give crude 1-(2,2-difluoro-benzo[1,3]dioxol-5-yl)-cyclopropanecarbonitrile, which was used directly in the next step.

Step f: 1-(2,2-Difluoro-benzo[1,3]dioxol-5-yl)-cyclopropanecarboxylic acid 1-(2,2-Difluoro-benzo[1,3]dioxol-5-yl)-cyclopropanecarbonitrile (crude from the last step) was refluxed in 10% aqueous sodium hydroxide (50 mL) for 2.5 hours. The cooled reaction mixture was washed with ether (100 mL) and the aqueous phase was acidified to pH 2 with 2M hydrochloric acid. The precipitated solid was filtered to give 1-(2,2-difluoro-benzo[1,3]dioxol-5-yl)-cyclopropanecarboxylic acid as a white solid (0.15 g, 1.6% over four steps). ESI-MS m/z calc. 242.2. found 243.3 (M+1)$^+$; $^1$H NMR (CDCl$_3$) δ 7.14-7.04 (m, 2H), 6.98-6.96 (m, 1H), 1.74-1.64 (m, 2H), 1.26-1.08 (m, 2H).

C. 2-(4-Chloro-3-methoxyphenyl)acetonitrile

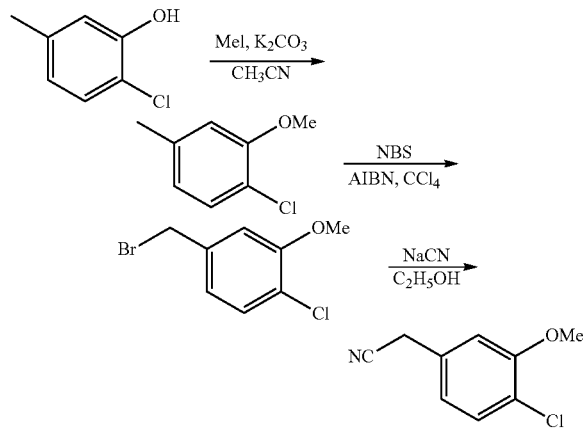

Step a: 1-Chloro-2-methoxy-4-methyl-benzene

To a solution of 2-chloro-5-methyl-phenol (93 g, 0.65 mol) in CH$_3$CN (700 mL) was added CH$_3$I (111 g, 0.78 mol) and K$_2$CO$_3$ (180 g, 1.3 mol). The mixture was stirred at 25° C. overnight. The solid was filtered off and the filtrate was evaporated under vacuum to give 1-chloro-2-methoxy-4-methyl-benzene (90 g, 89%). $^1$H NMR (300 MHz, CDCl$_3$) δ 7.22 (d, J=7.8 Hz, 1H), 6.74-6.69 (m, 2H), 3.88 (s, 3H), 2.33 (s, 3H).

Step b: 4-Bromomethyl-1-chloro-2-methoxy-benzene

To a solution of 1-chloro-2-methoxy-4-methyl-benzene (50 g, 0.32 mol) in CCl$_4$ (350 mL) was added NBS (57.2 g, 0.32 mol) and AIBN (10 g, 60 mmol). The mixture was heated at reflux for 3 hours. The solvent was evaporated under vacuum and the residue was purified by column chromatography on silica gel (Petroleum Ether/EtOAc=20:1) to give 4-bromomethyl-1-chloro-2-methoxy-benzene (69 g, 92%). $^1$H NMR (400 MHz, CDCl$_3$) δ 7.33-7.31 (m, 1H), 6.95-6.91 (m, 2H), 4.46 (s, 2H), 3.92 (s, 3H).

Step c: 2-(4-Chloro-3-methoxyphenyl)acetonitrile

To a solution of 4-bromomethyl-1-chloro-2-methoxy-benzene (68.5 g, 0.29 mol) in C$_2$H$_5$OH (90%, 500 mL) was added NaCN (28.5 g, 0.58 mol). The mixture was stirred at 60° C. overnight. Ethanol was evaporated and the residue was dissolved in H$_2$O. The mixture was extracted with ethyl acetate (300 mL×3). The combined organic layers were washed with brine, dried over Na$_2$SO$_4$ and purified by column chromatography on silica gel (Petroleum Ether/EtOAc 30:1) to give 2-(4-chloro-3-methoxyphenyl)acetonitrile (25 g, 48%). $^1$H NMR (400 MHz, CDCl$_3$) δ 7.36 (d, J=8 Hz, 1H), 6.88-6.84 (m, 2H), 3.92 (s, 3H), 3.74 (s, 2H). $^{13}$C NMR (100 MHz, CDCl$_3$) δ 155.4, 130.8, 129.7, 122.4, 120.7, 117.5, 111.5, 56.2, 23.5.

D. (4-Chloro-3-hydroxy-phenyl)-acetonitrile

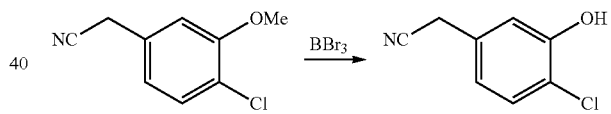

BBr$_3$ (16.6 g, 66 mmol) was slowly added to a solution of 2-(4-chloro-3-methoxyphenyl)acetonitrile (12 g, 66 mmol) in DCM (120 mL) at −78° C. under N$_2$. The reaction temperature was slowly increased to room temperature. The reaction mixture was stirred overnight and then poured into ice-water. The organic layer was separated and the aqueous layer was extracted with DCM (40 mL×3). The combined organic layers were washed with water, brine, dried over Na$_2$SO$_4$, and concentrated under vacuum to give (4-chloro-3-hydroxyphenyl)-acetonitrile (9.3 g, 85%). $^1$H NMR (300 MHz, CDCl$_3$) δ 7.34 (d, J=8.4 Hz, 1H), 7.02 (d, J=2.1 Hz, 1H), 6.87 (dd, J=2.1, 8.4 Hz, 1H), 5.15 (brs, 1H), 3.72 (s, 2H).

E. 1-(3-(Hydroxymethyl)-4-methoxyphenyl)cyclopropanecarboxylic acid

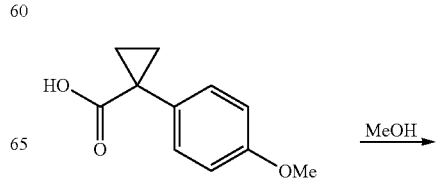

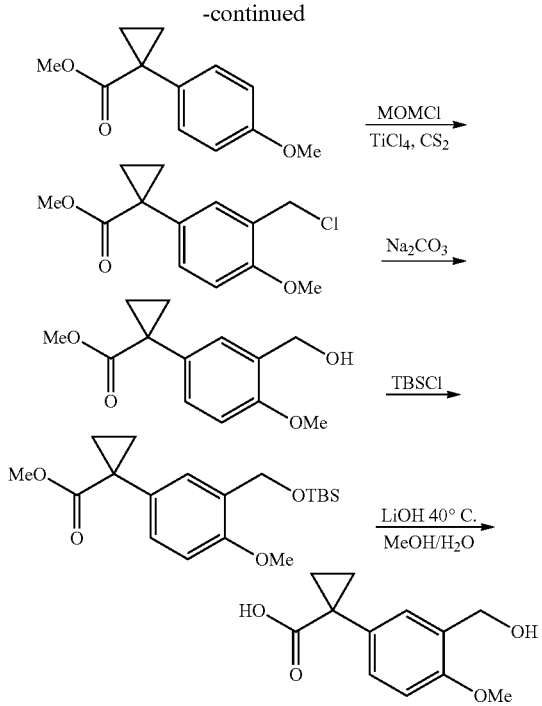

Step a:
1-(4-Methoxy-phenyl)-cyclopropanecarboxylic acid methyl ester

To a solution of 1-(4-methoxy-phenyl)-cyclopropanecarboxylic acid (50.0 g, 0.26 mol) in MeOH (500 mL) was added toluene-4-sulfonic acid monohydrate (2.5 g, 13 mmol) at room temperature. The reaction mixture was heated at reflux for 20 hours. MeOH was removed by evaporation under vacuum and EtOAc (200 mL) was added. The organic layer was washed with sat. aq. NaHCO$_3$ (100 mL) and brine, dried over anhydrous Na$_2$SO$_4$ and evaporated under vacuum to give 1-(4-methoxy-phenyl)-cyclopropanecarboxylic acid methyl ester (53.5 g, 99%). $^1$H NMR (CDCl$_3$, 400 MHz) δ 7.25-7.27 (m, 2H), 6.85 (d, J=8.8 Hz, 2H), 3.80 (s, 3H), 3.62 (s, 3H), 1.58 (m, 2H), 1.15 (m, 2H).

Step b: 1-(3-Chloromethyl-4-methoxy-phenyl)-cyclopropanecarboxylic acid methyl ester To a solution of 1-(4-methoxy-phenyl)-cyclopropanecarboxylic acid methyl ester (30.0 g, 146 mmol) and MOMCl (29.1 g, 364 mmol) in CS$_2$ (300 mL) was added TiCl$_4$ (8.30 g, 43.5 mmol) at 5° C. The reaction mixture was heated at 30° C. for 1 day and poured into ice-water. The mixture was extracted with CH$_2$Cl$_2$ (150 mL×3). The combined organic extracts were evaporated under vacuum to give crude 1-(3-chloromethyl-4-methoxy-phenyl)-cyclopropanecarboxylic acid methyl ester (38.0 g), which was used in the next step without further purification.

Step c: 1-(3-Hydroxymethyl-4-methoxy-phenyl)-cyclopropanecarboxylic acid methyl ester To a suspension of crude 1-(3-chloromethyl-4-methoxy-phenyl)-cyclopropanecarboxylic acid methyl ester (20.0 g) in water (350 mL) was added Bu$_4$NBr (4.0 g) and Na$_2$CO$_3$ (90.0 g, 0.85 mol) at room temperature. The reaction mixture was heated at 65° C. overnight. The resulting solution was acidified with aq. HCl (2 mol/L) and extracted with EtOAc (200 mL×3). The organic layer was washed with brine, dried over anhydrous Na$_2$SO$_4$ and evaporated under vacuum to give crude product, which was purified by column (Petroleum Ether/EtOAc 15:1) to give 1-(3-hydroxymethyl-4-methoxyphenyl)-cyclopropanecarboxylic acid methyl ester (8.0 g, 39%). $^1$H NMR (CDCl$_3$, 400 MHz) δ 7.23-7.26 (m, 2H), 6.83 (d, J=8.0 Hz, 1H), 4.67 (s, 2H), 3.86 (s, 3H), 3.62 (s, 3H), 1.58 (q, J=3.6 Hz, 2H), 1.14-1.17 (m, 2H).

Step d: 1-[3-(tert-Butyl-dimethyl-silanyloxymethyl)-4-methoxy-phenyl]cyclopropane-carboxylic acid methyl ester To a solution of 1-(3-hydroxymethyl-4-methoxy-phenyl)-cyclopropanecarboxylic acid methyl ester (8.0 g, 34 mmol) in CH$_2$Cl$_2$ (100 mL) were added imidazole (5.8 g, 85 mmol) and TBSCl (7.6 g, 51 mmol) at room temperature. The mixture was stirred overnight at room temperature. The mixture was washed with brine, dried over anhydrous Na$_2$SO$_4$ and evaporated under vacuum to give crude product, which was purified by column (Petroleum Ether/EtOAc 30:1) to give 1-[3-(tert-butyl-dimethyl-silanyloxymethyl)-4-methoxy-phenyl]-cyclopropanecarboxylic acid methyl ester (6.7 g, 56%). $^1$H NMR (CDCl$_3$, 400 MHz) δ 7.44-7.45 (m, 1H), 7.19 (dd, J=2.0, 8.4 Hz, 1H), 6.76 (d, J=8.4 Hz, 1H), 4.75 (s, 2H), 3.81 (s, 3H), 3.62 (s, 3H), 1.57-1.60 (m, 2H), 1.15-1.18 (m, 2H), 0.96 (s, 9H), 0.11 (s, 6H).

Step e: 1-(3-Hydroxymethyl-4-methoxy-phenyl)-cyclopropanecarboxylic acid

To a solution of 1-[3-(tert-butyl-dimethyl-silanyloxymethyl)-4-methoxy-phenyl]-cyclopropanecarboxylic acid methyl ester (6.2 g, 18 mmol) in MeOH (75 mL) was added a solution of LiOH.H$_2$O (1.50 g, 35.7 mmol) in water (10 mL) at 0° C. The reaction mixture was stirred overnight at 40° C. MeOH was removed by evaporation under vacuum. AcOH (1 mol/L, 40 mL) and EtOAc (200 mL) were added. The organic layer was separated, washed with brine, dried over anhydrous Na$_2$SO$_4$ and evaporated under vacuum to provide 1-(3-hydroxymethyl-4-methoxy-phenyl)-cyclopropanecarboxylic acid (5.3 g).

F. 2-(3-Fluoro-4-methoxyphenyl)acetonitrile

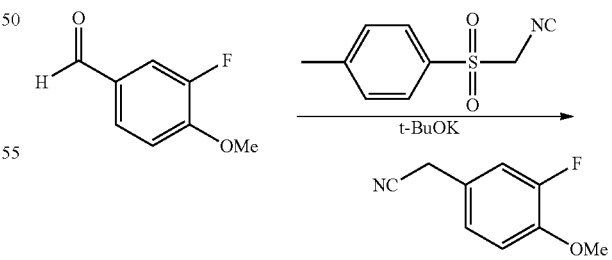

To a suspension of t-BuOK (25.3 g, 0.207 mol) in THF (150 mL) was added a solution of TosMIC (20.3 g, 0.104 mol) in THF (50 mL) at −78° C. The mixture was stirred for 15 minutes, treated with a solution of 3-fluoro-4-methoxy-benzaldehyde (8.00 g, 51.9 mmol) in THF (50 mL) dropwise, and continued to stir for 1.5 hours at −78° C. To the cooled reaction mixture was added methanol (50 mL). The mixture was heated at reflux for 30 minutes. Solvent of the reaction mixture was removed to give a crude product, which was dissolved in water (200 mL). The aqueous phase was extracted with EtOAc (100 mL×3). The combined organic layers were dried and evaporated under reduced pressure to give crude product, which was purified by column chromatography (Petroleum Ether/EtOAc 10:1) to afford 2-(3-fluoro-4-methoxyphenyl)acetonitrile (5.0 g, 58%). $^1$H NMR (400 MHz, CDCl$_3$) δ 7.02-7.05 (m, 2H), 6.94 (t, J=8.4 Hz, 1H), 3.88 (s, 3H), 3.67 (s, 2H). $^{13}$C NMR (100 MHz, CDCl$_3$) δ 152.3, 147.5, 123.7, 122.5, 117.7, 115.8, 113.8, 56.3, 22.6.

G. 2-(3-Chloro-4-methoxyphenyl)acetonitrile

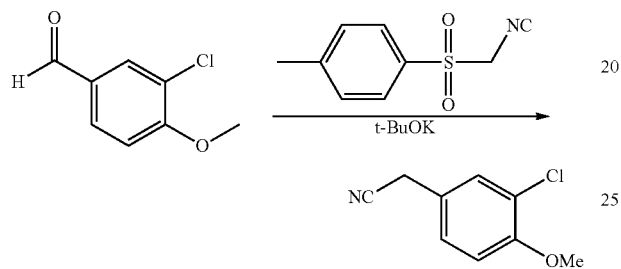

To a suspension of t-BuOK (4.8 g, 40 mmol) in THF (30 mL) was added a solution of TosMIC (3.9 g, 20 mmol) in THF (10 mL) at −78° C. The mixture was stirred for 10 minutes, treated with a solution of 3-chloro-4-methoxy-benzaldehyde (1.65 g, 10 mmol) in THF (10 mL) dropwise, and continued to stir for 1.5 hours at −78° C. To the cooled reaction mixture was added methanol (10 mL). The mixture was heated at reflux for 30 minutes. Solvent of the reaction mixture was removed to give a crude product, which was dissolved in water (20 mL). The aqueous phase was extracted with EtOAc (20 mL×3). The combined organic layers were dried and evaporated under reduced pressure to give crude product, which was purified by column chromatography (Petroleum Ether/EtOAc 10:1) to afford 2-(3-chloro-4-methoxyphenyl) acetonitrile (1.5 g, 83%). $^1$H NMR (400 MHz, CDCl$_3$) δ 7.33 (d, J=2.4 Hz, 1H), 7.20 (dd, J=2.4, 8.4 Hz, 1H), 6.92 (d, J=8.4 Hz, 1H), 3.91 (s, 3H), 3.68 (s, 2H). $^{13}$C NMR (100 MHz, CDCl$_3$) δ 154.8, 129.8, 127.3, 123.0, 122.7, 117.60, 112.4, 56.2, 22.4.

H. 1-(3,3-Dimethyl-2,3-dihydrobenzofuran-5-yl) cyclopropanecarboxylic acid

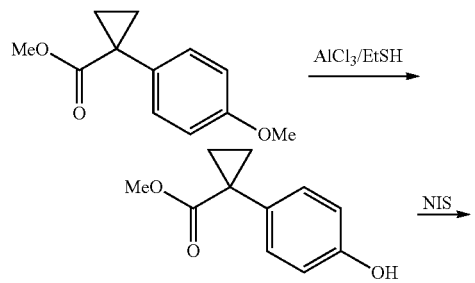

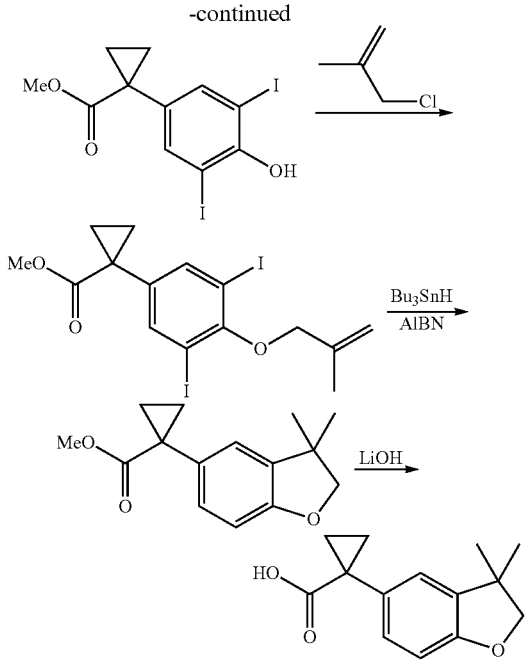

Step a:
1-(4-Hydroxy-phenyl)-cyclopropanecarboxylic acid methyl ester

To a solution of methyl 1-(4-methoxyphenyl)cyclopropanecarboxylate (10.0 g, 48.5 mmol) in DCM (80 mL) was added EtSH (16 mL) under ice-water bath. The mixture was stirred at 0° C. for 20 min before AlCl$_3$ (19.5 g, 0.15 mmol) was added slowly at 0° C. The mixture was stirred at 0° C. for 30 min. The reaction mixture was poured into ice-water, the organic layer was separated, and the aqueous phase was extracted with DCM (50 mL×3). The combined organic layers were washed with H$_2$O, brine, dried over Na$_2$SO$_4$ and evaporated under vacuum to give 1-(4-hydroxy-phenyl)-cyclopropanecarboxylic acid methyl ester (8.9 g, 95%). $^1$H NMR (400 MHz, CDCl$_3$) δ 7.20-7.17 (m, 2H), 6.75-6.72 (m, 2H), 5.56 (s, 1H), 3.63 (s, 3H), 1.60-1.57 (m, 2H), 1.17-1.15 (m, 2H).

Step b: 1-(4-Hydroxy-3,5-diiodo-phenyl)-cyclopropanecarboxylic acid methyl ester To a solution of 1-(4-hydroxy-phenyl)-cyclopropanecarboxylic acid methyl ester (8.9 g, 46 mmol) in CH$_3$CN (80 mL) was added NIS (15.6 g, 69 mmol). The mixture was stirred at room temperature for 1 hour. The reaction mixture was concentrated and the residue was purified by column chromatography on silica gel (Petroleum Ether/EtOAc 10:1) to give 1-(4-hydroxy-3,5-diiodo-phenyl)-cyclopropanecarboxylic acid methyl ester (3.5 g, 18%). $^1$H NMR (400 MHz, CDCl$_3$) δ 7.65 (s, 2H), 5.71 (s, 1H), 3.63 (s, 3H), 1.59-1.56 (m, 2H), 1.15-1.12 (m, 2H).

Step c: 1-[3,5-Diiodo-4-(2-methyl-allyloxy)-phenyl]-cyclopropanecarboxylic acid methyl ester A mixture of 1-(4-hydroxy-3,5-diiodo-phenyl)-cyclopropanecarboxylic acid methyl ester (3.2 g, 7.2 mmol), 3-chloro-2-methyl-propene (1.0 g, 11 mmol), K$_2$CO$_3$ (1.2 g, 8.6 mmol), NaI (0.1 g, 0.7 mmol) in acetone (20 mL) was stirred at 20° C. overnight. The solid was filtered off and the filtrate was concentrated under vacuum to give 1-[3,5-d]iodo-4-(2-methyl-allyloxy)-phenyl]-cyclopropane-carboxylic acid methyl ester (3.5 g, 97%). $^1$H NMR (300 MHz, CDCl$_3$) δ 7.75 (s, 2H), 5.26 (s, 1H), 5.06 (s, 1H), 4.38 (s, 2H), 3.65 (s, 3H), 1.98 (s, 3H), 1.62-1.58 (m, 2H), 1.18-1.15 (m, 2H).

Step d: 1-(3,3-Dimethyl-2,3-dihydro-benzofuran-5-yl)-cyclopropanecarboxylic acid methyl ester To a solution of 1-[3,5-d]iodo-4-(2-methyl-allyloxy)-phenyl]-cyclopropane-carboxylic acid methyl ester (3.5 g, 7.0 mmol) in toluene (15 mL) was added Bu$_3$SnH (2.4 g, 8.4 mmol) and AIBN (0.1 g, 0.7 mmol). The mixture was heated at reflux overnight. The reaction mixture was concentrated under vacuum and the residue was purified by column chromatography on silica gel (Petroleum Ether/EtOAc 20:1) to give 1-(3,3-dimethyl-2,3-dihydro-benzofuran-5-yl)-cyclopropanecarboxylic acid methyl ester (1.05 g, 62%). $^1$H NMR (400 MHz, CDCl$_3$) δ 7.10-7.07 (m, 2H), 6.71 (d, J=8 Hz, 1H), 4.23 (s, 2H), 3.62 (s, 3H), 1.58-1.54 (m, 2H), 1.34 (s, 6H), 1.17-1.12 (m, 2H).

Step e: 1-(3,3-Dimethyl-2,3-dihydrobenzofuran-5-yl)cyclopropanecarboxylic acid To a solution of 1-(3,3-dimethyl-2,3-dihydro-benzofuran-5-yl)-cyclopropanecarboxylic acid methyl ester (1 g, 4 mmol) in MeOH (10 mL) was added LiOH (0.40 g, 9.5 mmol). The mixture was stirred at 40° C. overnight. HCl (10%) was added slowly to adjust the pH to 5. The resulting mixture was extracted with ethyl acetate (10 mL×3). The extracts were washed with brine and dried over Na$_2$SO$_4$. The solvent was removed under vacuum and the crude product was purified by preparative HPLC to give 1-(3,3-dimethyl-2,3-dihydrobenzofuran-5-yl)cyclopropanecarboxylic acid (0.37 g, 41%). $^1$H NMR (400 MHz, CDCl$_3$) δ 7.11-7.07 (m, 2H), 6.71 (d, J=8 Hz, 1H), 4.23 (s, 2H), 1.66-1.63 (m, 2H), 1.32 (s, 6H), 1.26-1.23 (m, 2H).

I. 2-(7-Methoxybenzo[d][1,3]-dioxol-5-yl)acetonitrile

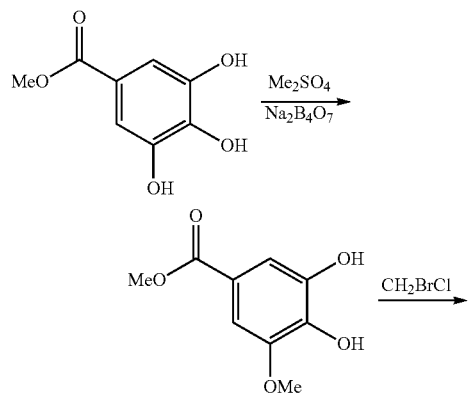

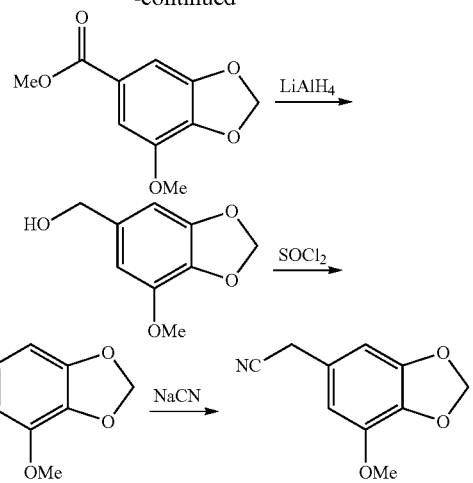

Step a: 3,4-Dihydroxy-5-methoxybenzoate

To a solution of 3,4,5-trihydroxy-benzoic acid methyl ester (50 g, 0.27 mol) and Na$_2$B$_4$O$_7$ (50 g) in water (1000 mL) was added Me$_2$SO$_4$ (120 mL) and aqueous NaOH solution (25%, 200 mL) successively at room temperature. The mixture was stirred at room temperature for 6 h before it was cooled to 0° C. The mixture was acidified to pH ~2 by adding conc. H$_2$SO$_4$ and then filtered. The filtrate was extracted with EtOAc (500 mL×3). The combined organic layers were dried over anhydrous Na$_2$SO$_4$ and evaporated under reduced pressure to give methyl 3,4-dihydroxy-5-methoxybenzoate (15.3 g 47%), which was used in the next step without further purification.

Step b: Methyl 7-methoxybenzo[d][1,3]dioxole-5-carboxylate

To a solution of methyl 3,4-dihydroxy-5-methoxybenzoate (15.3 g, 0.078 mol) in acetone (500 mL) was added CH$_2$BrCl (34.4 g, 0.27 mol) and K$_2$CO$_3$ (75 g, 0.54 mol) at 80° C. The resulting mixture was heated at reflux for 4 h. The mixture was cooled to room temperature and solid K$_2$CO$_3$ was filtered off. The filtrate was concentrated under reduced pressure, and the residue was dissolved in EtOAc (100 mL). The organic layer was washed with water, dried over anhydrous Na$_2$SO$_4$, and evaporated under reduced pressure to give the crude product, which was purified by column chromatography on silica gel (Petroleum Ether/Ethyl Acetate=10:1) to afford methyl 7-methoxybenzo[d][1,3]dioxole-5-carboxylate (12.6 g, 80%). $^1$H NMR (400 MHz, CDCl$_3$) δ 7.32 (s, 1H), 7.21 (s, 1H), 6.05 (s, 2H), 3.93 (s, 3H), 3.88 (s, 3H).

Step c: (7-Methoxybenzo[d][1,3]dioxol-5-yl)methanol

To a solution of methyl 7-methoxybenzo[d][1,3]dioxole-5-carboxylate (13.9 g, 0.040 mol) in THF (100 mL) was added LiAlH$_4$ (3.1 g, 0.080 mol) in portions at room temperature. The mixture was stirred for 3 h at room temperature. The reaction mixture was cooled to 0° C. and treated with water (3.1 g) and NaOH (10%, 3.1 mL) successively. The slurry was filtered off and washed with THF. The combined filtrates were evaporated under reduced pressure to give (7-methoxy-benzo[d][1,3]dioxol-5-yl)methanol (7.2 g, 52%). $^1$H NMR (400 MHz, CDCl$_3$) δ 6.55 (s, 1H), 6.54 (s, 1H), 5.96 (s, 2H), 4.57 (s, 2H), 3.90 (s, 3H).

Step d: 6-(Chloromethyl)-4-methoxybenzo[d][1,3]dioxole

To a solution of SOCl₂ (150 mL) was added (7-methoxybenzo[d][1,3]dioxol-5-yl)methanol (9.0 g, 54 mmol) in portions at 0° C. The mixture was stirred for 0.5 h. The excess SOCl₂ was evaporated under reduced pressure to give the crude product, which was basified with sat. aq. NaHCO₃ to pH ~7. The aqueous phase was extracted with EtOAc (100 mL×3). The combined organic layers were dried over anhydrous Na₂SO₄ and evaporated to give 6-(chloromethyl)-4-methoxybenzo[d][1,3]dioxole (10.2 g 94%), which was used in the next step without further purification. $^1$H NMR (400 MHz, CDCl₃) δ 6.58 (s, 1H), 6.57 (s, 1H), 5.98 (s, 2H), 4.51 (s, 2H), 3.90 (s, 3H).

Step e: 2-(7-Methoxybenzo[d][1,3]dioxol-5-yl)acetonitrile

To a solution of 6-(chloromethyl)-4-methoxybenzo[d][1,3]dioxole (10.2 g, 40 mmol) in DMSO (100 mL) was added NaCN (2.43 g, 50 mmol) at room temperature. The mixture was stirred for 3 h and poured into water (500 mL). The aqueous phase was extracted with EtOAc (100 mL×3). The combined organic layers were dried over anhydrous Na₂SO₄ and evaporated to give the crude product, which was washed with ether to afford 2-(7-methoxybenzo[d][1,3]dioxol-5-yl)acetonitrile (4.6 g, 45%). $^1$H NMR (400 MHz, CDCl₃) δ 6.49 (s, 2H), 5.98 (s, 2H), 3.91 (s, 3H), 3.65 (s, 2H). $^{13}$C NMR (400 MHz, CDCl₃) δ 148.9, 143.4, 134.6, 123.4, 117.3, 107.2, 101.8, 101.3, 56.3, 23.1.

J. 1-(Benzofuran-5-yl)cyclopropanecarboxylic acid

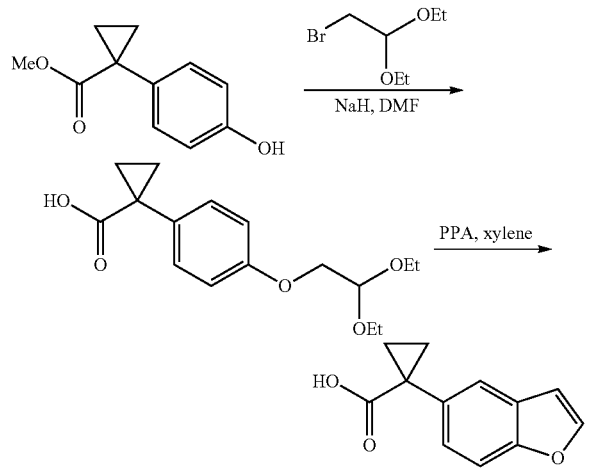

Step a: 1-[4-(2,2-Diethoxy-ethoxy)-phenyl]-cyclopropanecarboxylic acid

To a stirred solution of 1-(4-hydroxy-phenyl)-cyclopropanecarboxylic acid methyl ester (15.0 g, 84.3 mmol) in DMF (50 mL) was added sodium hydride (6.7 g, 170 mmol, 60% in mineral oil) at 0° C. After hydrogen evolution ceased, 2-bromo-1,1-diethoxy-ethane (16.5 g, 84.3 mmol) was added dropwise to the reaction mixture. The reaction was stirred at 160° C. for 15 hours. The reaction mixture was poured onto ice (100 g) and extracted with CH₂Cl₂. The combined organics were dried over Na₂SO₄. The solvent was evaporated under vacuum to give crude 1-[4-(2,2-diethoxy-ethoxy)-phenyl]-cyclopropanecarboxylic acid (10 g), which was used directly in the next step without purification.

Step b: 1-Benzofuran-5-yl-cyclopropanecarboxylic acid

To a suspension of crude 1-[4-(2,2-diethoxy-ethoxy)-phenyl]-cyclopropanecarboxylic acid (20 g, ~65 mmol) in xylene (100 mL) was added PPA (22.2 g, 64.9 mmol) at room temperature. The mixture was heated at reflux (140° C.) for 1 hour before it was cooled to room temperature and decanted from the PPA. The solvent was evaporated under vacuum to obtain the crude product, which was purified by preparative HPLC to provide 1-(benzofuran-5-yl)cyclopropanecarboxylic acid (1.5 g, 5%). $^1$H NMR (400 MHz, DMSO-d₆) δ 12.25 (br s, 1H), 7.95 (d, J=2.8 Hz, 1H), 7.56 (d, J=2.0 Hz, 1H), 7.47 (d, J=11.6 Hz, 1H), 7.25 (dd, J=2.4, 11.2 Hz, 1H), 6.89 (d, J=1.6 Hz, 1H), 1.47-1.44 (m, 2H), 1.17-1.14 (m, 2H).

K. 1-(2,3-Dihydrobenzofuran-5-yl)cyclopropanecarboxylic acid

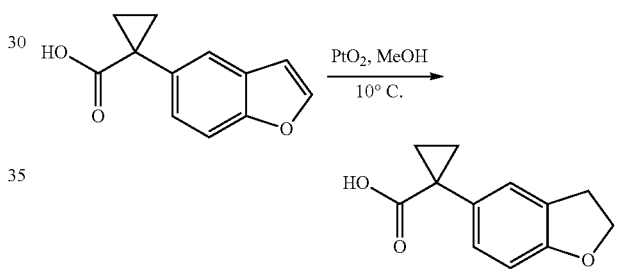

To a solution of 1-(benzofuran-5-yl)cyclopropanecarboxylic acid (700 mg, 3.47 mmol) in MeOH (10 mL) was added PtO₂ (140 mg, 20%) at room temperature. The stirred reaction mixture was hydrogenated under hydrogen (1 atm) at 10° C. for 3 days. The reaction mixture was filtered. The solvent was evaporated under vacuum to afford the crude product, which was purified by preparative HPLC to give 1-(2,3-dihydrobenzofuran-5-yl)cyclopropanecarboxylic acid (330 mg, 47%). $^1$H NMR (400 MHz, CDCl₃) δ 7.20 (s, 1H), 7.10 (d, J=10.8 Hz, 1H), 6.73 (d, J=11.2 Hz, 1H), 4.57 (t, J=11.6 Hz, 2H), 3.20 (t, J=11.6 Hz, 2H), 1.67-1.63 (m, 2H), 1.25-1.21 (m, 2H).

L. 2-(2,2-Dimethylbenzo[d][1,3]-dioxol-5-yl)acetonitrile

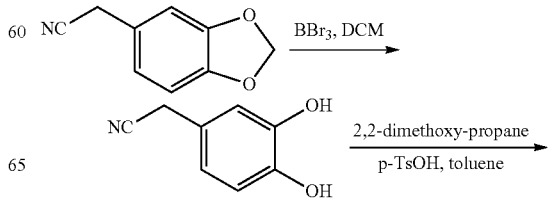

-continued

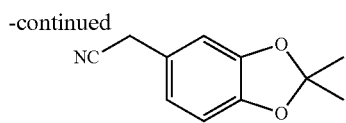

Step a: (3,4-Dihydroxy-phenyl)-acetonitrile

To a solution of benzo[1,3]dioxol-5-yl-acetonitrile (0.50 g, 3.1 mmol) in CH$_2$Cl$_2$ (15 mL) was added dropwise BBr$_3$ (0.78 g, 3.1 mmol) at −78° C. under N$_2$. The mixture was slowly warmed to room temperature and stirred overnight. H$_2$O (10 mL) was added to quench the reaction and the CH$_2$Cl$_2$ layer was separated. The aqueous phase was extracted with CH$_2$Cl$_2$ (2×7 mL). The combined organics were washed with brine, dried over Na$_2$SO$_4$ and purified by column chromatography on silica gel (Petroleum Ether/EtOAc 5:1) to give (3,4-dihydroxy-phenyl)-acetonitrile (0.25 g, 54%) as a white solid. $^1$H NMR (DMSO-d$_6$, 400 MHz) δ 9.07 (s, 1H), 8.95 (s, 1H), 6.68-6.70 (m, 2H), 6.55 (dd, J=8.0, 2.0 Hz, 1H), 3.32 (s, 2H).

Step b: 2-(2,2-Dimethylbenzo[d][1,3]dioxol-5-yl)acetonitrile

To a solution of (3,4-dihydroxy-phenyl)-acetonitrile (0.2 g, 1.3 mmol) in toluene (4 mL) was added 2,2-dimethoxy-propane (0.28 g, 2.6 mmol) and TsOH (0.010 g, 0.065 mmol). The mixture was heated at reflux overnight. The reaction mixture was evaporated to remove the solvent and the residue was dissolved in ethyl acetate. The organic layer was washed with NaHCO$_3$ solution, H$_2$O, brine, and dried over Na$_2$SO$_4$. The solvent was evaporated under reduced pressure to give a residue, which was purified by column chromatography on silica gel (Petroleum Ether/EtOAc 10:1) to give 2-(2,2-dimethylbenzo[d][1,3]dioxol-5-yl)acetonitrile (40 mg, 20%). $^1$H NMR (CDCl$_3$, 400 MHz) δ 6.68-6.71 (m, 3H), 3.64 (s, 2H), 1.67 (s, 6H).

M. 2-(3-(Benzyloxy)-4-chlorophenyl)acetonitrile

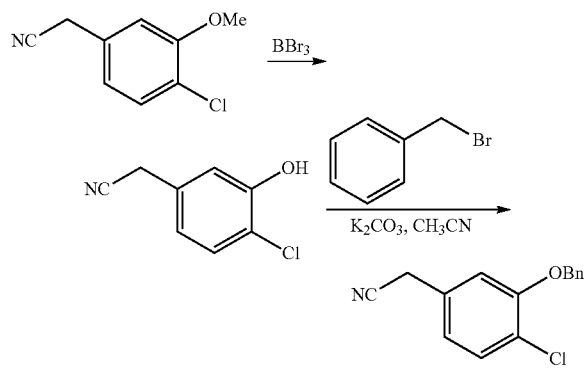

Step a: (4-Chloro-3-hydroxy-phenyl)acetonitrile

BBr$_3$ (16.6 g, 66 mmol) was slowly added to a solution of 2-(4-chloro-3-methoxyphenyl)acetonitrile (12 g, 66 mmol) in DCM (120 mL) at −78° C. under N$_2$. The reaction temperature was slowly increased to room temperature. The reaction mixture was stirred overnight and then poured into ice and water. The organic layer was separated, and the aqueous layer was extracted with DCM (40 mL×3). The combined organic layers were washed with water, brine, dried over Na$_2$SO$_4$, and concentrated under vacuum to give (4-chloro-3-hydroxy-phenyl)-acetonitrile (9.3 g, 85%). $^1$H NMR (300 MHz, CDCl$_3$) δ 7.34 (d, J=8.4 Hz, 1H), 7.02 (d, J=2.1 Hz, 1H), 6.87 (dd, J=2.1, 8.4 Hz, 1H), 5.15 (brs, 1H), 3.72 (s, 2H).

Step b: 2-(3-(Benzyloxy)-4-chlorophenyl)acetonitrile

To a solution of (4-chloro-3-hydroxy-phenyl)acetonitrile (6.2 g, 37 mmol) in CH$_3$CN (80 mL) was added K$_2$CO$_3$ (10.2 g, 74 mmol) and BnBr (7.6 g, 44 mmol). The mixture was stirred at room temperature overnight. The solids were filtered off and the filtrate was evaporated under vacuum. The residue was purified by column chromatography on silica gel (Petroleum Ether/Ethyl Acetate 50:1) to give 2-(3-(benzyloxy)-4-chlorophenyl)acetonitrile (5.6 g, 60%). $^1$H NMR (400 MHz, CDCl$_3$) δ 7.48-7.32 (m, 6H), 6.94 (d, J=2 Hz, 2H), 6.86 (dd, J=2.0, 8.4 Hz, 1H), 5.18 (s, 2H), 3.71 (s, 2H).

N. 2-(Quinoxalin-6-yl)acetonitrile

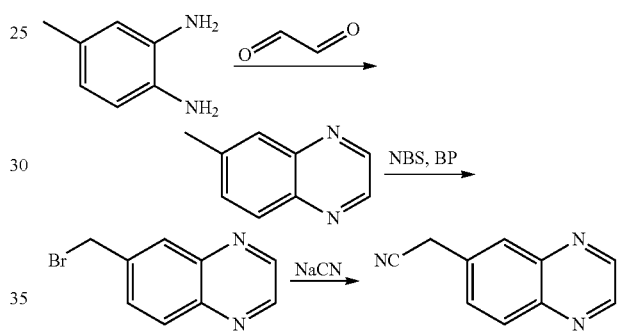

Step a: 6-Methylquinoxaline

To a solution of 4-methylbenzene-1,2-diamine (50.0 g, 0.41 mol) in isopropanol (300 mL) was added a solution of glyoxal (40% in water, 65.3 g, 0.45 mol) at room temperature. The reaction mixture was heated at 80° C. for 2 hours and evaporated under vacuum to give 6-methylquinoxaline (55 g, 93%), which was used directly in the next step. $^1$H NMR (300 MHz, CDCl$_3$) δ 8.77 (dd, J=1.5, 7.2 Hz, 2H), 7.99 (d, J=8.7 Hz, 1H), 7.87 (s, 1H), 7.60 (dd, J=1.5, 8.4 Hz, 1H), 2.59 (s, 3H).

Step b: 6-Bromomethylquinoxaline

To a solution of 6-methylquinoxaline (10.0 g, 69.4 mmol) in CCl$_4$ (80 mL) was added NBS (13.5 g, 76.3 mmol) and benzoyl peroxide (BP, 1.7 g, 6.9 mmol) at room temperature. The mixture was heated at reflux for 2 hours. After cooling, the mixture was evaporated under vacuum to give a yellow solid, which was extracted with Petroleum Ether (50 mL×5). The extracts were concentrated under vacuum. The organics were combined and concentrated to give crude 6-bromomethylquinoxaline (12.0 g), which was used directly in the next step. $^1$H NMR (300 MHz, CDCl$_3$) δ 8.85-8.87 (m, 2H), 8.10-8.13 (m, 2H), 7.82 (dd, J=2.1, 8.7 Hz, 1H), 4.70 (s, 2H).

Step c: 2-(Quinoxalin-6-yl)acetonitrile

To a solution of crude 6-bromomethylquinoxaline (36.0 g) in 95% ethanol (200 mL) was added NaCN (30.9 g, 0.63 mol)

at room temperature. The mixture was heated at 50° C. for 3 hours and then concentrated under vacuum. Water (100 mL) and ethyl acetate (100 mL) were added. The organic layer was separated and the aqueous layer was extracted with ethyl acetate. The combined organics were washed with brine, dried over $Na_2SO_4$ and concentrated under vacuum. The residue was purified by silica gel column (Petroleum Ether/EtOAc 10:1) to give 2-(quinoxalin-6-yl)acetonitrile (7.9 g, 23% over two steps). $^1$H NMR (300 MHz, $CDCl_3$) δ 8.88-8.90 (m, 2H), 8.12-8.18 (m, 2H), 7.74 (dd, J=2.1, 8.7 Hz, 1H), 4.02 (s, 2H). MS (ESI) m/z $(M+H)^+$170.0.

O. 2-(Quinolin-6-yl)acetonitrile

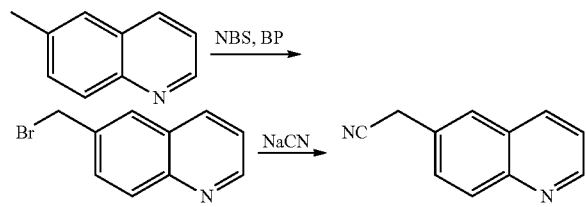

Step a: 6-Bromomethylquinoline

To a solution of 6-methylquinoline (2.15 g, 15.0 mmol) in $CCl_4$ (30 mL) was added NBS (2.92 g, 16.5 mmol) and benzoyl peroxide (BP, 0.36 g, 1.5 mmol) at room temperature. The mixture was heated at reflux for 2 hours. After cooling, the mixture was evaporated under vacuum to give a yellow solid, which was extracted with Petroleum Ether (30 mL×5). The extracts were concentrated under vacuum to give crude 6-bromomethylquinoline (1.8 g), which was used directly in the next step.

Step b: 2-(Quinolin-6-yl)acetonitrile

To a solution of crude 6-bromomethylquinoline (1.8 g) in 95% ethanol (30 mL) was added NaCN (2.0 g, 40.8 mmol) at room temperature. The mixture was heated at 50° C. for 3 hours and then concentrated under vacuum. Water (50 mL) and ethyl acetate (50 mL) were added. The organic layer was separated and the aqueous layer was extracted with ethyl acetate. The combined organics were washed with brine, dried over $Na_2SO_4$ and concentrated under vacuum. The combined crude product was purified by column (Petroleum Ether/EtOAc 5:1) to give 2-(quinolin-6-yl)acetonitrile (0.25 g, 8% over two steps). $^1$H NMR (300 MHz, $CDCl_3$) δ 8.95 (dd, J=1.5, 4.2 Hz, 1H), 8.12-8.19 (m, 2H), 7.85 (s, 1H), 7.62 (dd, J=2.1, 8.7 Hz, 1H), 7.46 (q, J=4.2 Hz, 1H), 3.96 (s, 2H). MS (ESI) m/e $(M+H)^+$169.0.

P. 2-(2,3-Dihydrobenzo[b][1,4]dioxin-6-yl)acetonitrile

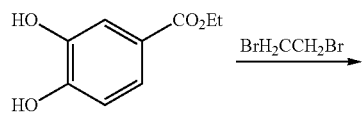

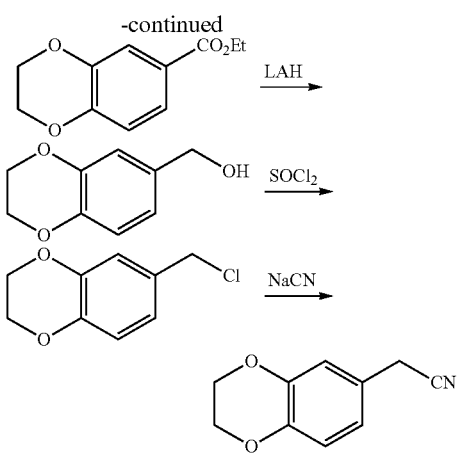

Step a: 2,3-Dihydro-benzo[1,4]dioxine-6-carboxylic acid ethyl ester

To a suspension of $Cs_2CO_3$ (270 g, 1.49 mol) in DMF (1000 mL) were added 3,4-dihydroxybenzoic acid ethyl ester (54.6 g, 0.3 mol) and 1,2-dibromoethane (54.3 g, 0.29 mol) at room temperature. The resulting mixture was stirred at 80° C. overnight and then poured into ice-water. The mixture was extracted with EtOAc (200 mL×3). The combined organic layers were washed with water (200 mL×3) and brine (100 mL), dried over $Na_2SO_4$ and concentrated to dryness. The residue was purified by column (Petroleum Ether/Ethyl Acetate 50:1) on silica gel to obtain 2,3-dihydro-benzo[1,4]dioxine-6-carboxylic acid ethyl ester (18 g, 29%). $^1$H NMR (300 MHz, $CDCl_3$) δ 7.53 (dd, J=1.8, 7.2 Hz, 2H), 6.84-6.87 (m, 1H), 4.22-4.34 (m, 6H), 1.35 (t, J=7.2 Hz, 3H).

Step b: (2,3-Dihydro-benzo[1,4]dioxin-6-yl)-methanol

To a suspension of LAH (2.8 g, 74 mmol) in THF (20 mL) was added dropwise a solution of 2,3-dihydro-benzo[1,4]dioxine-6-carboxylic acid ethyl ester (15 g, 72 mmol) in THF (10 mL) at 0° C. under $N_2$. The mixture was stirred at room temperature for 1 h and then quenched carefully with addition of water (2.8 mL) and NaOH (10%, 28 mL) with cooling. The precipitated solid was filtered off and the filtrate was evaporated to dryness to obtain (2,3-dihydro-benzo[1,4]dioxin-6-yl)-methanol (10.6 g). $^1$H NMR (300 MHz, DMSO-$d_6$) δ 6.73-6.78 (m, 3H), 5.02 (t, J=5.7 Hz, 1H), 4.34 (d, J=6.0 Hz, 2H), 4.17-4.20 (m, 4H).

Step c: 6-Chloromethyl-2,3-dihydro-benzo[1,4]dioxine

A mixture of (2,3-dihydro-benzo[1,4]dioxin-6-yl)methanol (10.6 g) in $SOCl_2$ (10 mL) was stirred at room temperature for 10 min and then poured into ice-water. The organic layer was separated and the aqueous phase was extracted with dichloromethane (50 mL×3). The combined organic layers were washed with $NaHCO_3$ (sat solution), water and brine, dried over $Na_2SO_4$ and concentrated to dryness to obtain 6-chloromethyl-2,3-dihydro-benzo[1,4]dioxine (12 g, 88% over two steps), which was used directly in next step.

Step d: 2-(2,3-Dihydrobenzo[b][1,4]dioxin-6-yl)acetonitrile

A mixture of 6-chloromethyl-2,3-dihydro-benzo[1,4]dioxine (12.5 g, 67.7 mmol) and NaCN (4.30 g, 87.8 mmol) in DMSO (50 mL) was stirred at rt for 1 h. The mixture was poured into water (150 mL) and then extracted with dichloromethane (50 mL×4). The combined organic layers were washed with water (50 mL×2) and brine (50 mL), dried over $Na_2SO_4$ and concentrated to dryness. The residue was purified by column (Petroleum Ether/Ethyl Acetate 50:1) on silica gel to obtain 2-(2,3-dihydrobenzo[b][1,4]dioxin-6-yl)acetonitrile as a yellow oil (10.2 g, 86%). $^1$H-NMR (300 MHz, $CDCl_3$) δ 6.78-6.86 (m, 3H), 4.25 (s, 4H), 3.63 (s, 2H).

Q. 2-(2,2,4,4-Tetrafluoro-4H-benzo[d][1,3]dioxin-6-yl)acetonitrile

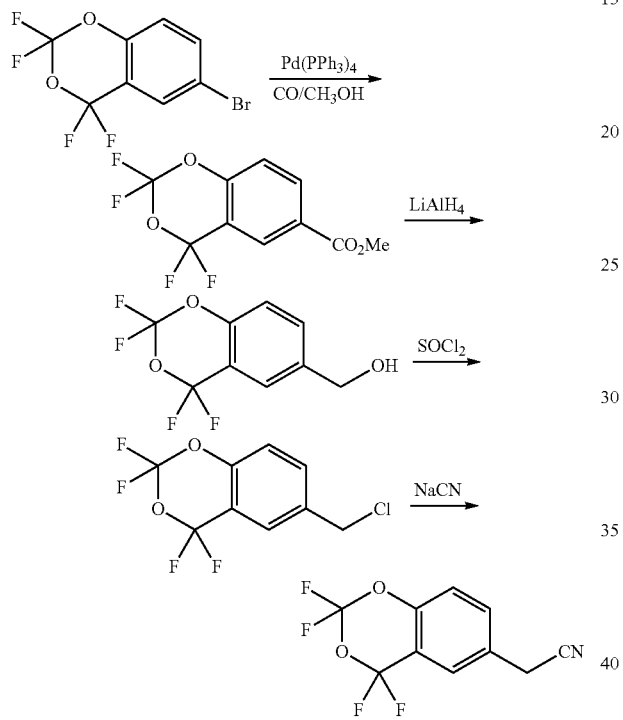

Step a: 2,2,4,4-Tetrafluoro-4H-benzo[1,3]dioxine-6-carboxylic acid methyl ester A suspension of 6-bromo-2,2,4,4-tetrafluoro-4H-benzo[1,3]dioxine (4.75 g, 16.6 mmol) and $Pd(PPh_3)_4$ (950 mg, 8.23 mmol) in MeOH (20 mL), MeCN (30 mL) and $Et_3N$ (10 mL) was stirred under carbon monoxide atmosphere (55 psi) at 75° C. (oil bath temperature) overnight. The cooled reaction mixture was filtered and the filtrate was concentrated. The residue was purified by silica gel column (Petroleum Ether) to give 2,2,4,4-tetrafluoro-4H-benzo[1,3]dioxine-6-carboxylic acid methyl ester (3.75 g, 85%). $^1$H NMR ($CDCl_3$, 300 MHz) δ 8.34 (s, 1H), 8.26 (dd, J=2.1, 8.7 Hz, 1H), 7.22 (d, J=8.7 Hz, 1H), 3.96 (s, 3H).

Step b: (2,2,4,4-Tetrafluoro-4H-benzo[1,3]dioxin-6-yl)methanol

To a suspension of LAH (2.14 g, 56.4 mmol) in dry THF (200 mL) was added dropwise a solution of 2,2,4,4-tetrafluoro-4H-benzo[1,3]dioxine-6-carboxylic acid methyl ester (7.50 g, 28.2 mmol) in dry THF (50 mL) at 0° C. After being stirred at 0° C. for 1 h, the reaction mixture was treated with water (2.14 g) and 10% NaOH (2.14 mL). The slurry was filtered and washed with THF. The combined filtrates were evaporated to dryness to give the crude (2,2,4,4-tetrafluoro-4H-benzo[1,3]dioxin-6-yl)-methanol (6.5 g), which was used directly in the next step. $^1$H NMR ($CDCl_3$, 300 MHz) δ 7.64 (s, 1H), 7.57-7.60 (m, 1H), 7.58 (d, J=8.7 Hz, 1H), 4.75 (s, 2H).

Step c: 6-Chloromethyl-2,2,4,4-tetrafluoro-4H-benzo[1,3]dioxine

A mixture of (2,2,4,4-tetrafluoro-4H-benzo[1,3]dioxin-6-yl)-methanol (6.5 g) in thionyl chloride (75 mL) was heated at reflux overnight. The resulting mixture was concentrated under vacuum. The residue was basified with aqueous saturated $NaHCO_3$. The aqueous layer was extracted with dichloromethane (50 mL×3). The combined organic layers were dried over $Na_2SO_4$, filtrated, and concentrated under reduced pressure to give 6-chloromethyl-2,2,4,4-tetrafluoro-4H-benzo[1,3]dioxine (6.2 g), which was used directly in the next step. $^1$H NMR ($CDCl_3$, 300 MHz) δ 7.65 (s, 1H), 7.61 (dd, J=2.1, 8.7 Hz, 1H), 7.15 (d, J=8.4 Hz, 1H), 4.60 (s, 2H).

Step d: (2,2,4,4-Tetrafluoro-4H-benzo[1,3]dioxin-6-yl)-acetonitrile

A mixture of 6-chloromethyl-2,2,4,4-tetrafluoro-4H-benzo[1,3]dioxine (6.2 g) and NaCN (2.07 g, 42.3 mmol) in DMSO (50 mL) was stirred at room temperature for 2 h. The reaction mixture was poured into ice and extracted with EtOAc (50 mL×3). The combined organic layers were dried over anhydrous $Na_2SO_4$, and evaporated to give a crude product, which was purified by silica gel column (Petroleum Ether/EtOAc 10:1) to give (2,2-difluoro-benzo[1,3]dioxol-5-yl)-acetonitrile (4.5 g, 68% over 3 steps). $^1$H NMR ($CDCl_3$, 300 MHz) δ 7.57-7.60 (m, 2H), 7.20 (d, J=8.7 Hz, 1H), 3.82 (s, 2H).

R. 2-(4H-Benzo[d][1,3]dioxin-7-yl)acetonitrile

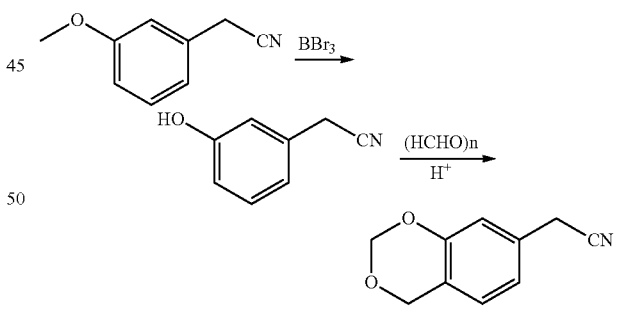

Step a: (3-Hydroxyphenyl)acetonitrile

To a solution of (3-methoxyphenyl)acetonitrile (150 g, 1.03 mol) in $CH_2Cl_2$ (1000 mL) was added $BBr_3$ (774 g, 3.09 mol) dropwise at −70° C. The mixture was stirred and warmed to room temperature slowly. Water (300 mL) was added at 0° C. The resulting mixture was extracted with $CH_2Cl_2$. The combined organic layers were dried over anhydrous $Na_2SO_4$, filtered, and evaporated under vacuum. The crude residue was purified by column (Petroleum Ether/EtOAc 10:1) to give (3-hydroxyphenyl)acetonitrile (75.0 g, 55%). ¹H NMR (CDCl₃, 300 MHz) δ 7.18-7.24 (m, 1H), 6.79-6.84 (m, 3H), 3.69 (s, 2H).

Step b: 2-(4H-Benzo[d][1,3]dioxin-7-yl)acetonitrile

To a solution of (3-hydroxyphenyl)acetonitrile (75.0 g, 0.56 mol) in toluene (750 mL) was added paraformaldehyde (84.0 g, 2.80 mol) and toluene-4-sulfonic acid monohydrate (10.7 g, 56.0 mmol) at room temperature. The reaction mixture was heated at reflux for 40 minutes. Toluene was removed by evaporation. Water (150 mL) and ethyl acetate (150 mL) were added. The organic layer was separated and the aqueous layer was extracted with ethyl acetate. The combined organics were washed with brine, dried over anhydrous Na₂SO₄ and evaporated under vacuum. The residue was separated by preparative HPLC to give 2-(4H-benzo[d][1,3]dioxin-7-yl)acetonitrile (4.7 g, 5%). ¹H NMR (300 MHz, CDCl₃) δ 6.85-6.98 (m, 3H), 5.25 (d, J=3.0 Hz, 2H), 4.89 (s, 2H), 3.69 (s, 2H).

S. 2-(4H-Benzo[d][1,3]dioxin-6-yl)acetonitrile

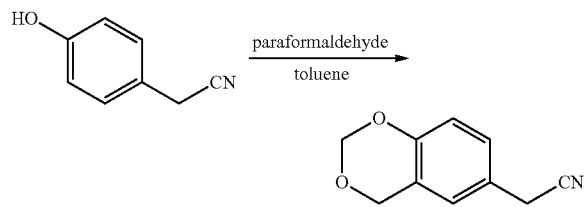

To a solution of (4-hydroxyphenyl)acetonitrile (17.3 g, 0.13 mol) in toluene (350 mL) were added paraformaldehyde (39.0 g, 0.43 mmol) and toluene-4-sulfonic acid monohydrate (2.5 g, 13 mmol) at room temperature. The reaction mixture was heated at reflux for 1 hour. Toluene was removed by evaporation. Water (150 mL) and ethyl acetate (150 mL) were added. The organic layer was separated and the aqueous layer was extracted with ethyl acetate. The combined organics were washed with brine, dried over Na₂SO₄ and evaporated under vacuum. The residue was separated by preparative HPLC to give 2-(4H-benzo[d][1,3]dioxin-6-yl)acetonitrile (7.35 g, 32%). ¹H NMR (400 MHz, CDCl₃) δ 7.07-7.11 (m, 1H), 6.95-6.95 (m, 1H), 6.88 (d, J=11.6 Hz, 1H), 5.24 (s, 2H), 4.89 (s, 2H), 3.67 (s, 2H).

T. 2-(3-(Benzyloxy)-4-methoxyphenyl)acetonitrile

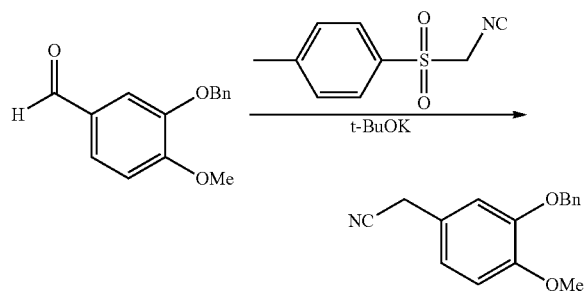

To a suspension of t-BuOK (20.15 g, 0.165 mol) in THF (250 mL) was added a solution of TosMIC (16.1 g, 82.6 mmol) in THF (100 mL) at −78° C. The mixture was stirred for 15 minutes, treated with a solution of 3-benzyloxy-4-methoxy-benzaldehyde (10.0 g, 51.9 mmol) in THF (50 mL) dropwise, and continued to stir for 1.5 hours at −78° C. To the cooled reaction mixture was added methanol (50 mL). The mixture was heated at reflux for 30 minutes. Solvent of the reaction mixture was removed to give a crude product, which was dissolved in water (300 mL). The aqueous phase was extracted with EtOAc (100 mL×3). The combined organic layers were dried and evaporated under reduced pressure to give crude product, which was purified by column chromatography (Petroleum Ether/EtOAc 10:1) to afford 2-(3-(Benzyloxy)-4-methoxyphenyl)acetonitril (5.0 g, 48%). ¹H NMR (300 MHz, CDCl₃) δ 7.48-7.33 (m, 5H), 6.89-6.86 (m, 3H), 5.17 (s, 2H), 3.90 (s, 3H), 3.66 (s, 2H). ¹³C NMR (75 MHz, CDCl₃) δ 149.6, 148.6, 136.8, 128.8, 128.8, 128.2, 127.5, 127.5, 122.1, 120.9, 118.2, 113.8, 112.2, 71.2, 56.2, 23.3.

The following Table 2 contains a list of carboxylic acid building blocks that were commercially available, or prepared by one of the methods described above:

TABLE 2

| Carboxylic acid building blocks. | |
| --- | --- |
| Compound | Name |
| A-1 | 1-benzo[1,3]dioxol-5-ylcyclopropane-1-carboxylic acid |
| A-2 | 1-(2,2-difluorobenzo[1,3]dioxol-5-yl)cyclopropane-1-carboxylic acid |
| A-3 | 1-(3,4-dimethoxyphenyl)cyclopropane-1-carboxylic acid |
| A-4 | 1-(3-methoxyphenyl)cyclopropane-1-carboxylic acid |
| A-5 | 1-(2-methoxyphenyl)cyclopropane-1-carboxylic acid |
| A-6 | 1-[4-(trifluoromethoxy)phenyl]cyclopropane-1-carboxylic acid |
| A-8 | tetrahydro-4-(4-methoxyphenyl)-2H-pyran-4-carboxylic acid |
| A-9 | 1-phenylcyclopropane-1-carboxylic acid |
| A-10 | 1-(4-methoxyphenyl)cyclopropane-1-carboxylic acid |
| A-11 | 1-(4-chlorophenyl)cyclopropane-1-carboxylic acid |
| A-13 | 1-phenylcyclopentanecarboxylic acid |
| A-14 | 1-phenylcyclohexanecarboxylic acid |
| A-15 | 1-(4-methoxyphenyl)cyclopentanecarboxylic acid |
| A-16 | 1-(4-methoxyphenyl)cyclohexanecarboxylic acid |
| A-17 | 1-(4-chlorophenyl)cyclohexanecarboxylic acid |
| A-18 | 1-(2,3-dihydrobenzo[b][1,4]dioxin-6-yl)cyclopropanecarboxylic acid |
| A-19 | 1-(4H-benzo[d][1,3]dioxin-7-yl)cyclopropanecarboxylic acid |
| A-20 | 1-(2,2,4,4-tetrafluoro-4H-benzo[d][1,3]dioxin-6-yl)cyclopropanecarboxylic acid |
| A-21 | 1-(4H-benzo[d][1,3]dioxin-6-yl)cyclopropanecarboxylic acid |
| A-22 | 1-(quinoxalin-6-yl)cyclopropanecarboxylic acid |
| A-23 | 1-(quinolin-6-yl)cyclopropanecarboxylic acid |
| A-24 | 1-(4-chlorophenyl)cyclopentanecarboxylic acid |
| A-25 | 1-(benzofuran-5-yl)cyclopropanecarboxylic acid |
| A-26 | 1-(4-chloro-3-methoxyphenyl)cyclopropanecarboxylic acid |
| A-27 | 1-(3-(hydroxymethyl)-4-methoxyphenyl)cyclopropanecarboxylic acid |
| A-28 | 1-(2,3-dihydrobenzofuran-5-yl)cyclopropanecarboxylic acid |
| A-29 | 1-(3-fluoro-4-methoxyphenyl)cyclopropanecarboxylic acid |
| A-30 | 1-(3-chloro-4-methoxyphenyl)cyclopropanecarboxylic acid |
| A-31 | 1-(3-hydroxy-4-methoxyphenyl)cyclopropanecarboxylic acid |
| A-32 | 1-(4-hydroxy-3-methoxyphenyl)cyclopropanecarboxylic acid |
| A-33 | 1-(2,2-dimethylbenzo[d][1,3]dioxol-5-yl)cyclopropanecarboxylic acid |
| A-34 | 1-(3,3-dimethyl-2,3-dihydrobenzofuran-5-yl)cyclopropanecarboxylic acid |
| A-35 | 1-(7-methoxybenzo[d][1,3]dioxol-5-yl)cyclopropanecarboxylic acid |
| A-36 | 1-(4-chloro-3-hydroxyphenyl)cyclopropanecarboxylic acid |
| A-37 | 1-(4-methoxy-3-methylphenyl)cyclopropanecarboxylic acid |
| A-38 | 1-(3-(benzyloxy)-4-chlorophenyl)cyclopropanecarboxylic acid |

TABLE 2-continued

Carboxylic acid building blocks.

| Compound | Name |
|---|---|
| A-45 | 1-(4-methoxy-3-(methoxymethyl)phenyl)cyclopropanecarboxylic acid |

U. 6-Chloro-5-methylpyridin-2-amine

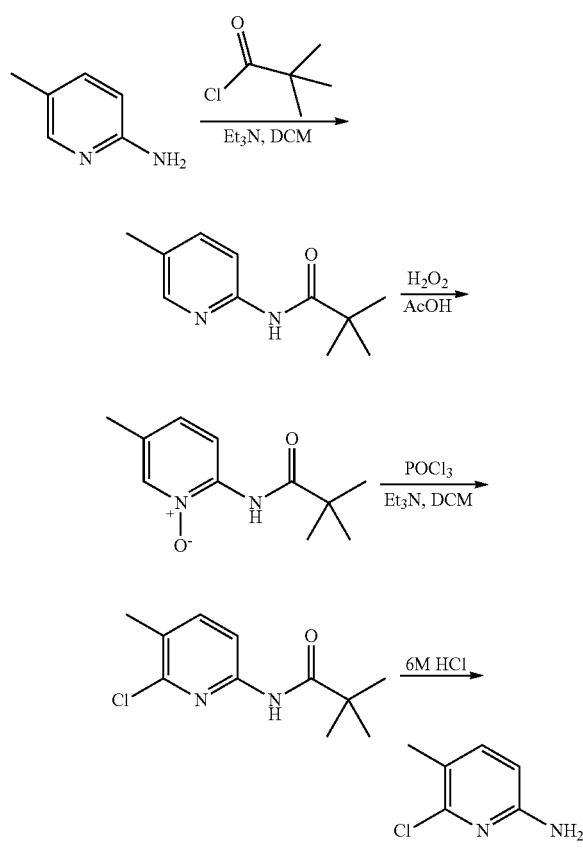

Step a: 2,2-Dimethyl-N-(5-methyl-pyridin-2-yl)-propionamide

To a stirred solution of 5-methylpyridin-2-amine (200 g, 1.85 mol) in anhydrous CH$_2$Cl$_2$ (1000 mL) was added drop-wise a solution of Et$_3$N (513 mL, 3.70 mol) and 2,2-dimethyl-propionyl chloride (274 mL, 2.22 mol) at 0° C. under N$_2$. The ice bath was removed and stirring was continued at room temperature for 2 hours. The reaction was poured into ice (2000 g). The organic layer was separated and the remaining aqueous layer was extracted with CH$_2$Cl$_2$ (3×). The combined organics were dried over Na$_2$SO$_4$ and evaporated to afford 2,2-dimethyl-N-(5-methyl-pyridin-2-yl)-propionamide (350 g), which was used in the next step without further purification. $^1$H NMR (400 MHz, CDCl$_3$) δ 8.12 (d, J=8.4 Hz, 1H), 8.06 (d, J=1.2 Hz, 1H), 7.96 (s, 1H), 7.49 (dd, J=1.6, 8.4 Hz, 1H), 2.27 (s, 1H), 1.30 (s, 9H).

Step b: 2,2-Dimethyl-N-(5-methyl-1-oxy-pyridin-2-yl)-propionamide

To a stirred solution of 2,2-dimethyl-N-(5-methyl-pyridin-2-yl)-propionamide (100 g, 0.52 mol) in AcOH (500 mL) was added drop-wise 30% H$_2$O$_2$ (80 mL, 2.6 mol) at room temperature. The mixture was stirred at 80° C. for 12 hours. The reaction mixture was evaporated under vacuum to obtain 2,2-dimethyl-N-(5-methyl-1-oxy-pyridin-2-yl)-propionamide (80 g, 85% purity). $^1$H NMR (400 MHz, CDCl$_3$) δ 10.26 (br s, 1H), 8.33 (d, J=8.4 Hz, 1H), 8.12 (s, 1H), 7.17 (dd, J=0.8, 8.8 Hz, 1H), 2.28 (s, 1H), 1.34 (s, 9H).

Step c: N-(6-Chloro-5-methyl-pyridin-2-yl)-2,2-dimethyl-propionamide

To a stirred solution of 2,2-dimethyl-N-(5-methyl-1-oxy-pyridin-2-yl)-propionamide (10 g, 48 mmol) in anhydrous CH$_2$Cl$_2$ (50 mL) was added Et$_3$N (60 mL, 240 mmol) at room temperature. After being stirred for 30 min, POCl$_3$ (20 mL) was added drop-wise to the reaction mixture. The reaction was stirred at 50° C. for 15 hours. The reaction mixture was poured into ice (200 g). The organic layer was separated and the remaining aqueous layer was extracted with CH$_2$Cl$_2$ (3×). The combined organics were dried over Na$_2$SO$_4$. The solvent was evaporated under vacuum to obtain the crude product, which was purified by chromatography (Petroleum Ether/EtOAc 100:1) to provide N-(6-chloro-5-methyl-pyridin-2-yl)-2,2-dimethyl-propionamide (0.5 g, 5%). $^1$H NMR (400 MHz, CDCl$_3$) δ 8.09 (d, J=8.0 Hz, 1H), 7.94 (br s, 1H), 7.55 (d, J=8.4 Hz, 1H), 2.33 (s, 1H), 1.30 (s, 9H).

Step d: 6-Chloro-5-methyl-pyridin-2-ylamine

To N-(6-chloro-5-methyl-pyridin-2-yl)-2,2-dimethyl-propionamide (4.00 g, 17.7 mmol) was added 6 N HCl (20 mL) at room temperature. The mixture was stirred at 80° C. for 12 hours. The reaction mixture was basified with drop-wise addition of sat. NaHCO$_3$ to pH 8-9, and then the mixture was extracted with CH$_2$Cl$_2$ (3×). The organic phases were dried over Na$_2$SO$_4$ and evaporated under vacuum to obtain the 6-chloro-5-methyl-pyridin-2-ylamine (900 mg, 36%). $^1$H NMR (400 MHz, CDCl$_3$) δ 7.28 (d, J=8.0 Hz, 1H), 6.35 (d, J=8.0 Hz, 1H), 4.39 (br s, 2H), 2.22 (s, 3H). MS (ESI) m/z: 143 (M+H$^+$).

V. 6-Chloro-5-(trifluoromethyl)pyridin-2-amine

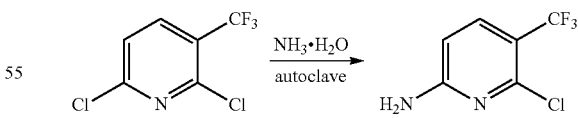

2,6-Dichloro-3-(trifluoromethyl)pyridine (5.00 g, 23.2 mmol) and 28% aqueous ammonia (150 mL) were placed in a 250 mL autoclave. The mixture was heated at 93° C. for 21 h. The reaction was cooled to rt and extracted with EtOAc (100 mL×3). The combined organic extracts were dried over anhydrous Na$_2$SO$_4$ and evaporated under vacuum to give the crude product, which was purified by column chromatography on silica gel (2-20% EtOAc in petroleum ether as eluant) to give 6-chloro-5-(trifluoromethyl)pyridin-2-amine (2.1 g, 46% yield). $^1$H NMR (400 MHz, DMSO-d$_6$) δ 7.69 (d, J=8.4 Hz, 1H), 7.13 (br s, 2H), 6.43 (d, J=8.4 Hz, 1H). MS (ESI) m/z (M+H)$^+$197.2

General Procedure IV: Coupling Reactions

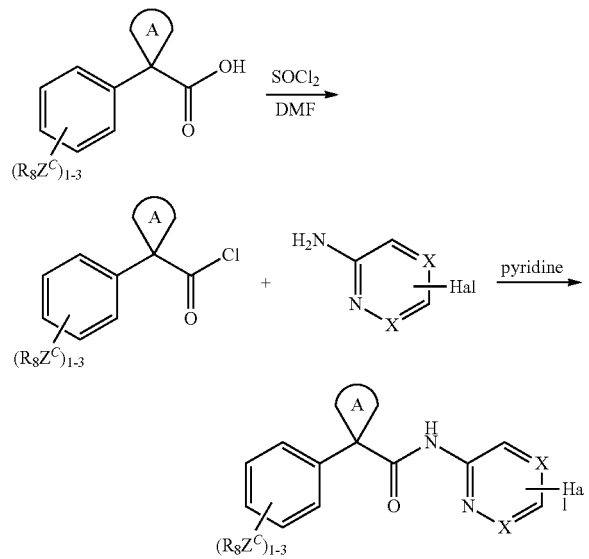

Hal = Cl, Br, I, all other variables. Ring A is the ring formed by R$_3$ and R'$_3$.
X = C or N One equivalent of the appropriate carboxylic acid was placed in an oven-dried flask under nitrogen. Thionyl chloride (3 equivalents) and a catalytic amount of N,N-dimethylformamide was added and the solution was allowed to stir at 60° C. for 30 minutes. The excess thionyl chloride was removed under vacuum and the resulting solid was suspended in a minimum of anhydrous pyridine. This solution was slowly added to a stirred solution of one equivalent the appropriate aminoheterocycle dissolved in a minimum of anhydrous pyridine. The resulting mixture was allowed to stir for 15 hours at 110° C. The mixture was evaporated to dryness, suspended in dichloromethane, and then extracted three times with 1N NaOH. The organic layer was then dried over sodium sulfate, evaporated to dryness, and then purified by column chromatography.

W. 1-(Benzo[d][1,3]dioxol-5-yl)-N-(5-bromopyridin-2-yl)cyclopropane-carboxamide (B-1)

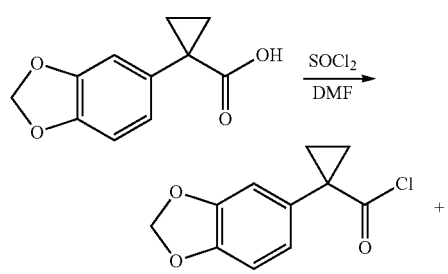

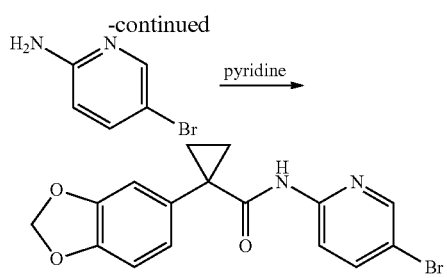

1-Benzo[1,3]dioxol-5-yl-cyclopropanecarboxylic acid (2.38 g, 11.5 mmol) was placed in an oven-dried flask under nitrogen. Thionyl chloride (2.5 mL) and N,N-dimethylformamide (0.3 mL) were added and the solution was allowed to stir for 30 minutes at 60° C. The excess thionyl chloride was removed under vacuum and the resulting solid was suspended in 7 mL of anhydrous pyridine. This solution was then slowly added to a solution of 5-bromo-pyridin-2-ylamine (2.00 g, 11.6 mmol) suspended in 10 mL of anhydrous pyridine. The resulting mixture was allowed to stir for 15 hours at 110° C. The mixture was then evaporated to dryness, suspended in 100 mL of dichloromethane, and washed with three 25 mL portions of 1N NaOH. The organic layer was dried over sodium sulfate, evaporated to near dryness, and then purified by silica gel column chromatography utilizing dichloromethane as the eluent to yield the pure product (3.46 g, 83%) ESI-MS m/z calc. 361.2. found 362.1 (M+1)$^+$; Retention time 3.40 minutes. $^1$H NMR (400 MHz, DMSO-d$_6$) δ 1.06-1.21 (m, 2H), 1.44-1.51 (m, 2H), 6.07 (s, 2H), 6.93-7.02 (m, 2H), 7.10 (d, J=1.6 Hz, 1H), 8.02 (d, J=1.6 Hz, 2H), 8.34 (s, 1H), 8.45 (s, 1H).

X. 1-(Benzo[d][1,3]-dioxol-6-yl)-N-(6-bromopyridin-2-yl)cyclopropane-carboxamide (B-2)

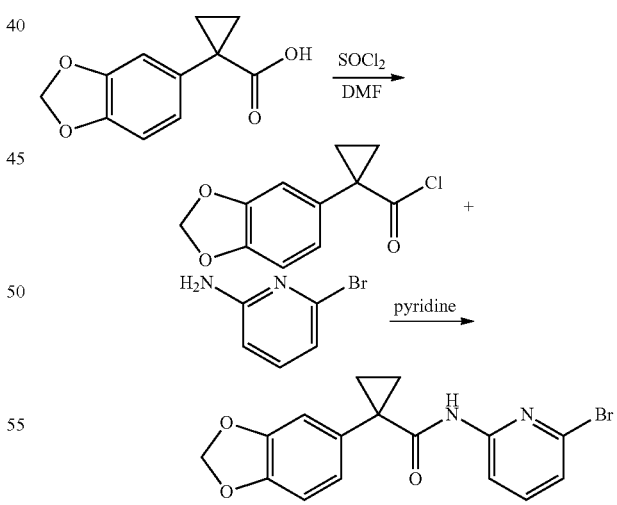

(1-Benzo[1,3]dioxol-5-yl-cyclopropanecarboxylic acid (1.2 g, 5.8 mmol) was placed in an oven-dried flask under nitrogen. Thionyl chloride (2.5 mL) and N,N-dimethylformamide (0.3 mL) were added and the solution was allowed to stir at 60° C. for 30 minutes. The excess thionyl chloride was removed under vacuum and the resulting solid was suspended in 5 mL of anhydrous pyridine. This solution was then slowly added to a solution of 6-bromopyridin-2-amine (1.0 g, 5.8 mmol) suspended in 10 mL of anhydrous pyridine. The resulting mixture was allowed to stir for 15 hours at 110° C. The mixture was then evaporated to dryness, suspended in 50 mL of dichloromethane, and washed with three 20 mL portions of 1N NaOH. The organic layer was dried over sodium sulfate, evaporated to near dryness, and then purified by silica gel column chromatography utilizing dichloromethane containing 2.5% triethylamine as the eluent to yield the pure product. ESI-MS m/z calc. 361.2. found 362.1 (M+1)$^+$; Retention time 3.43 minutes. $^1$H NMR (400 MHz, DMSO-$d_6$) δ 1.10-1.17 (m, 2H), 1.42-1.55 (m, 2H), 6.06 (s, 2H), 6.92-7.02 (m, 2H), 7.09 (d, J=1.6 Hz, 1H), 7.33 (d, J=7.6 Hz, 1H), 7.73 (t, J=8.0 Hz, 1H), 8.04 (d, J=8.2 Hz, 1H), 8.78 (s, 1H).

The compounds in the following Table 3 were prepared in a manner analogous to that described above:

TABLE 3

Exemplary compounds synthesized according to Preparations W and X.

| Compound | Name | Retention Time (min) | (M + 1)$^+$ | $^1$H NMR (400 MHz, DMSO-$d_6$) |
|---|---|---|---|---|
| B-3 | 1-(Benzo[d][1,3]dioxol-5-yl)-N-(5-bromo-6-methylpyridin-2-yl)cyclopropanecarboxamide | 3.58 | 375.3 | $^1$H NMR (400 MHz, DMSO-$d_6$) δ 8.39 (s, 1H), 7.95 (d, J = 8.7 Hz, 1H), 7.83 (d, J = 8.8 Hz, 1H), 7.10 (d, J = 1.6 Hz, 1H), 7.01-6.94 (m, 2H), 6.06 (s, 2H), 2.41 (s, 3H), 1.48-1.46 (m, 2H), 1.14-1.10 (m, 2H) |
| B-4 | 1-(Benzo[d][1,3]dioxol-5-yl)-N-(6-chloro-5-methylpyridin-2-yl)cyclopropanecarboxamide | 2.90 | 331.0 | $^1$H NMR (400 MHz, DMSO-$d_6$) δ 8.64 (s, 1H), 7.94-7.91 (m, 1H), 7.79-7.77 (m, 1H), 7.09 (m, 1H), 7.00-6.88 (m, 2H), 6.06 (s, 2H), 2.25 (s, 3H), 1.47-1.44 (m, 2H), 1.13-1.10 (m, 2H) |
| B-5 | 1-(Benzo[d][1,3]dioxol-5-yl)-N-(5-bromo-4-methylpyridin-2-yl)cyclopropanecarboxamide | 3.85 | 375.1 | $^1$H NMR (400 MHz, DMSO-$d_6$) δ 8.36 (s, 1H), 8.30 (s, 1H), 8.05 (s, 1H), 7.09 (d, J = 1.6 Hz, 1H), 7.01-6.95 (m, 2H), 6.07 (s, 2H), 2.35 (s, 3H), 1.49-1.45 (m, 2H), 1.16-1.13 (m, 2H) |
| B-6 | 1-(Benzo[d][1,3]dioxol-5-yl)-N-(5-bromo-3,4-dimethylpyridin-2-yl)cyclopropanecarboxamide | 3.25 | 389.3 | $^1$H NMR (400 MHz, DMSO-$d_6$) δ 8.82 (s, 1H), 8.35 (s, 1H), 7.01 (m, 1H), 6.96-6.89 (m, 2H), 6.02 (s, 2H), 2.35 (s, 3H), 2.05 (s, 3H), 1.40-1.38 (m, 2H), 1.08-1.05 (m, 2H) |
| B-7 | 1-(Benzo[d][1,3]dioxol-5-yl)-N-(5-bromo-3-methylpyridin-2-yl)cyclopropanecarboxamide | 2.91 | 375.1 | |
| B-8 | 1-(Benzo[d][1,3]dioxol-5-yl)-N-(6-chloropyridazin-3-yl)cyclopropanecarboxamide | 2.88 | 318.3 | $^1$H NMR (400 MHz, DMSO-$d_6$) δ 1.15-1.19 (m, 2H), 1.48-1.52 (m, 2H), 6.05 (s, 2H), 6.93-7.01 (m, 2H), 7.09 (d, J = 1.7 Hz, 1H), 7.88 (d, J = 9.4 Hz, 1H), 8.31 (d, J = 9.4 Hz, 1H), 9.46 (s, 1H) |
| B-9 | 1-(Benzo[d][1,3]dioxol-5-yl)-N-(5-bromopyrazin-2-yl)cyclopropanecarboxamide | 3.20 | 318.3 | $^1$H NMR (400 MHz, DMSO-$d_6$) δ 1.13-1.18 (m, 2H), 1.47-1.51 (m, 2H), 6.04 (s, 2H), 6.90-6.99 (m, 2H), 7.06 (d, J = 1.6 Hz, 1H),, 8.47 (s, 1H), 9.21 (s, 1H), 9.45 (s, 1H) |

TABLE 3-continued

Exemplary compounds synthesized according to Preparations W and X.

| Compound | Name | Retention Time (min) | (M + 1)+ | 1H NMR (400 MHz, DMSO-d6) |
|---|---|---|---|---|
| B-10 | 1-(Benzo[d][1,3]dioxol-5-yl)-N-(6-chloropyrazin-2-yl)cyclopropanecarboxamide | 3.45 | 362.1 | 1H NMR (400 MHz, DMSO-d6) δ 1.12-1.23 (m, 2H), 1.41-1.58 (m, 2H), 6.04 (s, 2H), 6.90-7.00 (m, 2H), 7.07 (d, J = 1.6 Hz, 1H), 8.55 (s, 1H), 8.99-9.21 (m, 2H) |
| B-11 | N-(6-bromopyridin-2-yl)-1-(2,2-difluorobenzo[d][1,3]dioxol-5-yl)cyclopropanecarboxamide | 2.12 | 397.3 | 1H NMR (400 MHz, DMSO-d6) δ 9.46 (s, 1H), 8.01-7.99 (m, 1H), 7.75-7.71 (m, 1H), 7.54 (m, 1H), 7.41-7.39 (m, 1H), 7.36-7.30 (m, 2H), 1.52-1.49 (m, 2H), 1.20-1.17 (m, 2H) |
| B-12 | N-(6-chloro-5-methylpyridin-2-yl)-1-(2,2-difluorobenzo[d][1,3]dioxol-5-yl)cyclopropanecarboxamide | 2.18 | 367.1 | 1H NMR (400 MHz, DMSO-d6) δ 9.30 (s, 1H), 7.89-7.87 (m, 1H), 7.78-7.76 (m, 1H), 7.53 (m, 1H), 7.41-7.39 (m, 1H), 7.33-7.30 (m, 1H), 2.26 (s, 3H), 1.51-1.49 (m, 2H), 1.18-1.16 (m, 2H) |
| B-13 | N-(6-chloro-5-(trifluoromethyl)pyridin-2-yl)-1-(2,2-difluorobenzo[d][1,3]dioxol-5-yl)cyclopropanecarboxamide | 1.98 | 421.1 | 1H NMR (400 MHz, DMSO-d6) δ 10.09 (s, 1H), 8.29 (m, 1H), 8.16 (m, 1H), 7.53 (m, 1H), 7.41-7.38 (m, 1H), 7.34-7.29 (m, 1H), 1.56-1.53 (m, 2H), 1.24-1.22 (m, 2H) |

General Procedure V: Compounds of Formula I

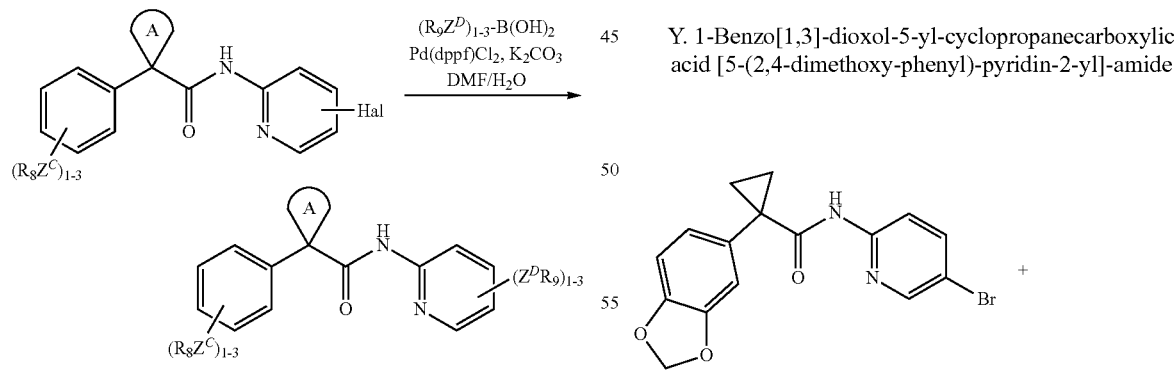

Hal = Cl, Br, I. Ring A is the ring formed by $R_3$ and $R'_3$.

The appropriate aryl halide (1 equivalent) was dissolved in 1 mL of N,N-dimethylformamide (DMF) in a reaction tube. The appropriate boronic acid (1.3 equivalents), 0.1 mL of an aqueous 2 M potassium carbonate solution (2 equivalents), and a catalytic amount of Pd(dppf)Cl$_2$ (0.09 equivalents) were added and the reaction mixture was heated at 80° C. for three hours or at 150° C. for 5 min in the microwave. The resulting material was cooled to room temperature, filtered, and purified by reverse-phase preparative liquid chromatography.

Y. 1-Benzo[1,3]-dioxol-5-yl-cyclopropanecarboxylic acid [5-(2,4-dimethoxy-phenyl)-pyridin-2-yl]-amide

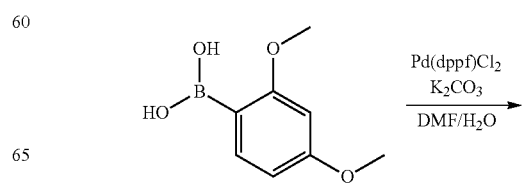

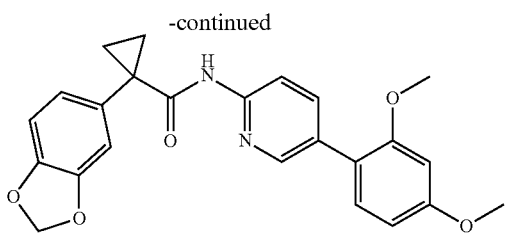

1-Benzo[1,3]dioxol-5-yl-cyclopropanecarboxylic acid (5-bromo-pyridin-2-yl)-amide (36.1 mg, 0.10 mmol) was dissolved in 1 mL of N,N-dimethylformamide in a reaction tube. 2,4-Dimethoxybenzeneboronic acid (24 mg, 0.13 mmol), 0.1 mL of an aqueous 2 M potassium carbonate solution, and a catalytic amount of Pd(dppf)Cl$_2$ (6.6 mg, 0.0090 mmol) were added and the reaction mixture was heated at 80° C. for three hours. The resulting material was cooled to room temperature, filtered, and purified by reverse-phase preparative liquid chromatography to yield the pure product as a trifluoroacetic acid salt. ESI-MS m/z calc. 418.2. found 419.0 (M+1)$^+$. Retention time 3.18 minutes. $^1$H NMR (400 MHz, CD$_3$CN) δ 1.25-1.29 (m, 2H), 1.63-1.67 (m, 2H), 3.83 (s, 3H), 3.86 (s, 3H), 6.04 (s, 2H), 6.64-6.68 (m, 2H), 6.92 (d, J=8.4 Hz, 1H), 7.03-7.06 (m, 2H), 7.30 (d, J=8.3 Hz, 1H), 7.96 (d, J=8.9 Hz, 1H), 8.14 (dd, J=8.9, 2.3 Hz, 1H), 8.38 (d, J=2.2 Hz, 1H), 8.65 (s, 1H).

Z. 1-Benzo[1,3]-dioxol-5-yl-cyclopropanecarboxylic acid[6-(4-dimethylamino-phenyl)-pyridin-2-yl]-amide

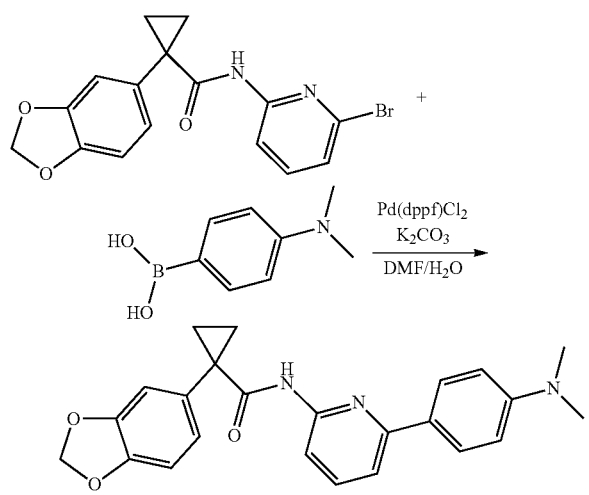

1-Benzo[1,3]dioxol-5-yl-cyclopropanecarboxylic acid (6-bromo-pyridin-2-yl)-amide (36 mg, 0.10 mmol) was dissolved in 1 mL of N,N-dimethylformamide in a reaction tube. 4-(Dimethylamino)phenylboronic acid (21 mg, 0.13 mmol), 0.1 mL of an aqueous 2 M potassium carbonate solution, and (Pd(dppf)Cl$_2$ (6.6 mg, 0.0090 mmol) were added and the reaction mixture was heated at 80° C. for three hours. The resulting material was cooled to room temperature, filtered, and purified by reverse-phase preparative liquid chromatography to yield the pure product as a trifluoroacetic acid salt. ESI-MS m/z calc. 401.2. found 402.5 (M+1)$^+$. Retention time 2.96 minutes. $^1$H NMR (400 MHz, CD$_3$CN) δ 1.23-1.27 (m, 2H), 1.62-1.66 (m, 2H), 3.04 (s, 6H), 6.06 (s, 2H), 6.88-6.90 (m, 2H), 6.93-6.96 (m, 1H), 7.05-7.07 (m, 2H), 7.53-7.56 (m, 1H), 7.77-7.81 (m, 3H), 7.84-7.89 (m, 1H), 8.34 (s, 1H).

The following schemes were utilized to prepare additional boronic esters which were not commercially available:

AA. 1-Methyl-4-[4-(4,4,5,5-tetramethyl-1,3,2-dioxaborolan-2-yl)phenyl]-sulfonylpiperazine

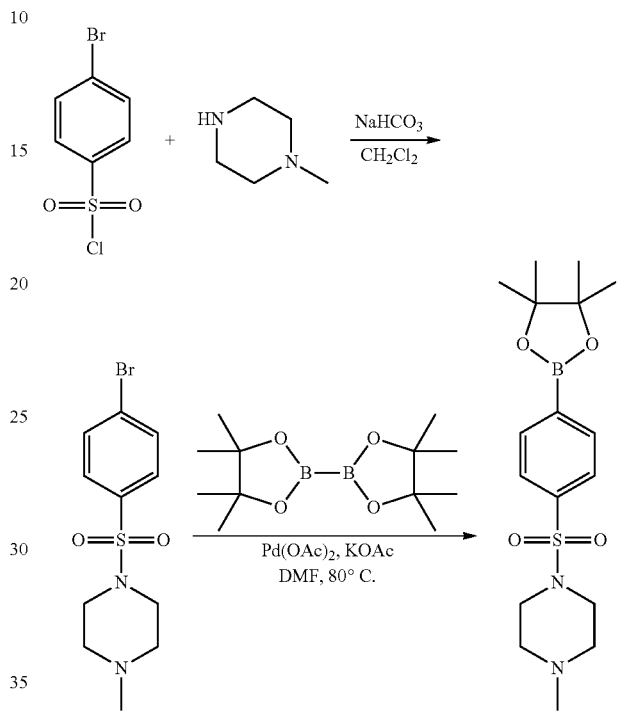

Step a:
1-(4-Bromophenylsulfonyl)-4-methylpiperazine

A solution of 4-bromobenzene-1-sulfonyl chloride (256 mg, 1.00 mmol) in 1 mL of dichloromethane was slowly added to a vial (40 mL) containing 5 mL of a saturated aqueous solution of sodium bicarbonate, dichloromethane (5 mL) and 1-methylpiperazine (100 mg, 1.00 mmol). The reaction was stirred at room temperature overnight. The phases were separated and the organic layer was dried over magnesium sulfate. Evaporation of the solvent under reduced pressure provided the required product, which was used in the next step without further purification. ESI-MS m/z calc. 318.0. found 318.9 (M+1)$^+$. Retention time of 1.30 minutes. $^1$H NMR (300 MHz, CDCl$_3$) δ 7.65 (d, J=8.7 Hz, 2H), 7.58 (d, J=8.7 Hz, 2H), 3.03 (t, J=4.2 Hz, 4H), 2.48 (t, J=4.2 Hz, 4H), 2.26 (s, 3H).

Step b: 1-Methyl-4-[4-(4,4,5,5-tetramethyl-1,3,2-dioxaborolan-2-yl)phenyl]sulfonyl-piperazine A 50 mL round bottom flask was charged with 1-(4-bromophenyl-sulfonyl)-4-methylpiperazine (110 mg, 0.350 mmol), bis-(pinacolato)-diboron (93 mg, 0.37 mmol), palladium acetate (6 mg, 0.02 mmol), and potassium acetate (103 mg, 1.05 mmol) in N,N-dimethylformamide (6 mL). The mixture was degassed by gently bubbling argon through the solution for 30 minutes at room temperature. The mixture was then heated at 80° C. under argon until the reaction was complete (4 hours). The desired product, 1-methyl-4-[4-(4,4,5,5-tetramethyl-1,3,2-dioxaborolan-2-yl)phenyl]-sulfonyl-piperazine, and the bi-aryl product, 4-(4-methylpiperazin-1-ylsulfonyl)-phenyl-phenylsulfonyl-4-methylpiperazine, were obtained in a ratio of 1:2 as indicated by LC/MS analysis. The mixture was used without further purification.

BB. 4,4,5,5-Tetramethyl-2-(4-(2-(methylsulfonyl) ethyl)phenyl)-1,3,2-dioxaborolane

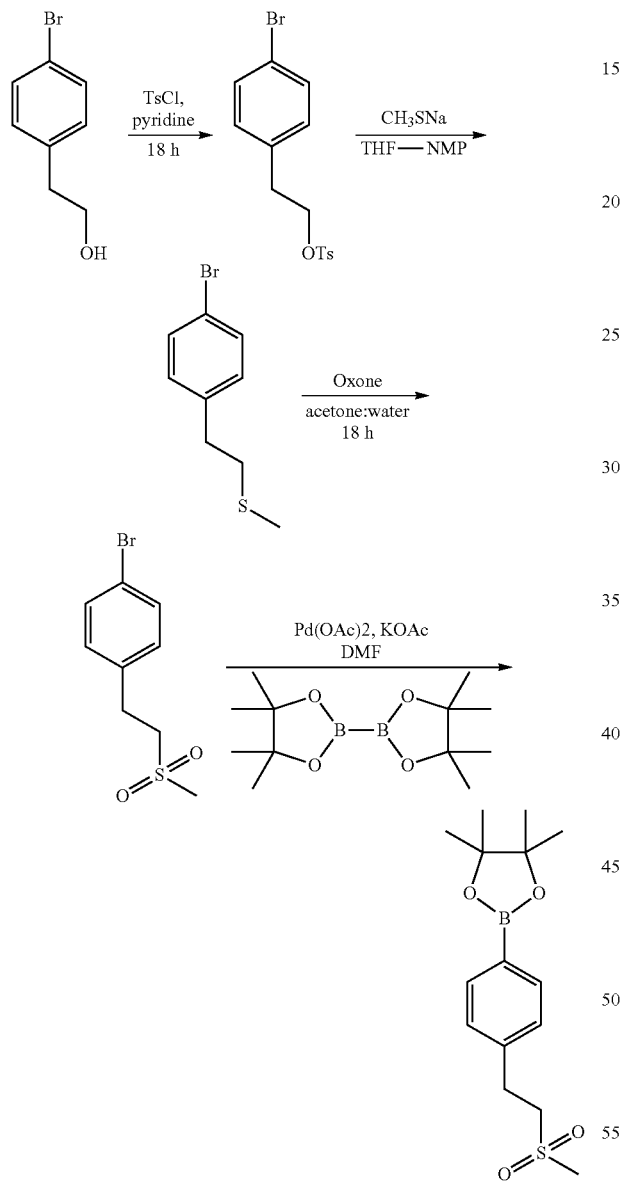

Step a: 4-Bromophenethyl-4-methylbenzenesulfonate

To a 50 mL round-bottom flask was added p-bromophenethyl alcohol (1.0 g, 4.9 mmol), followed by the addition of pyridine (15 mL). To this clear solution was added, under argon, p-toluenesulfonyl chloride (TsCl) (1.4 g, 7.5 mmol) as a solid. The reaction mixture was purged with Argon and stirred at room temperature for 18 hours. The crude mixture was treated with 1N HCl (20 mL) and extracted with ethyl acetate (5×25 mL). The organic fractions were dried over $Na_2SO_4$, filtered, and concentrated to yield 4-bromophenethyl-4-methylbenzenesulfonate (0.60 g, 35%) as a yellowish liquid. $^1$H-NMR (Acetone-$d_6$, 300 MHz) δ 7.64 (d, J=8.4 Hz, 2H), 7.40-7.37 (d, J=8.7 Hz, 4H), 7.09 (d, J=8.5 Hz, 2H), 4.25 (t, J=6.9 Hz, 2H), 2.92 (t, J=6.3 Hz, 2H), 2.45 (s, 3H).

Step b: (4-Bromophenethyl)(methyl)sulfane

To a 20 mL round-bottom flask were added 4-bromophenethyl 4-methylbenzenesulfonate (0.354 g, 0.996 mmol) and $CH_3SNa$ (0.10 g, 1.5 mmol), followed by the addition of THF (1.5 mL) and N-methyl-2-pyrrolidinone (1.0 mL). The mixture was stirred at room temperature for 48 hours, and then treated with a saturated aqueous solution of sodium bicarbonate (10 mL). The mixture was extracted with ethyl acetate (4×10 mL), dried over $Na_2SO_4$, filtered, and concentrated to yield (4-bromophenethyl)(methyl)sulfane (0.30 g crude) as a yellowish oil. $^1$H-NMR (CDCl$_3$, 300 MHz) δ 7.40 (d, J=8.4 Hz, 2H), 7.06 (d, J=8.4 Hz, 2H), 2.89-2.81 (m, 2H), 2.74-2.69 (m, 2H), 2.10 (s, 3H).

Step c: 1-Bromo-4-(2-methylsulfonyl)-ethylbenzene

To a 20 mL round-bottom flask were added (4-bromophenethyl)-(methyl)sulfane (0.311 g, 1.34 mmol) and Oxone (3.1 g, 0.020 mol), followed by the addition of a 1:1 mixture of acetone/water (10 mL). The mixture was vigorously stirred at room temperature for 20 hours, before being concentrated. The aqueous mixture was extracted with ethyl acetate (3×15 mL) and dichloromethane (3×10 mL). The organic fractions were combined, dried with $Na_2SO_4$, filtered, and concentrated to yield a white semisolid. Purification of the crude material by flash chromatography yielded 1-bromo-4-(2-methylsulfonyl)-ethylbenzene (0.283 g, 80%). $^1$H-NMR (DMSO-$d_6$, 300 MHz) δ 7.49 (d, J=8.4 Hz, 2H), 7.25 (d, J=8.7 Hz, 2H), 3.43 (m, 2H), 2.99 (m, 2H), 2.97 (s, 3H).

Step d: 4,4,5,5-Tetramethyl-2-(4-(2-(methylsulfonyl) ethyl)-phenyl)-1,3,2-dioxaborolane 4,4,5,5-Tetramethyl-2-(4-(2-(methylsulfonyl)ethyl)phenyl)-1,3,2-dioxaborolane was prepared in the same manner as described above for 1-methyl-4-[4-(4,4,5,5-tetramethyl-1,3,2-dioxaborolan-2-yl)phenyl]sulfonyl-piperazine, Preparation AA.

CC. tert-Butyl methyl(4-(4,4,5,5-tetramethyl-1,3,2-dioxaborolan-2-yl)benzyl)carbamate

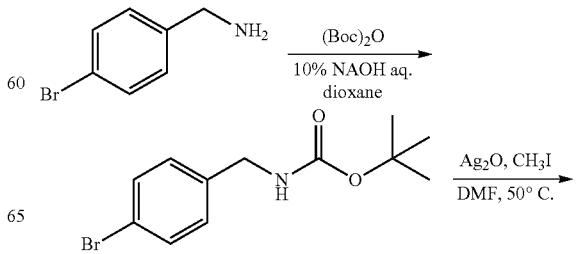

-continued

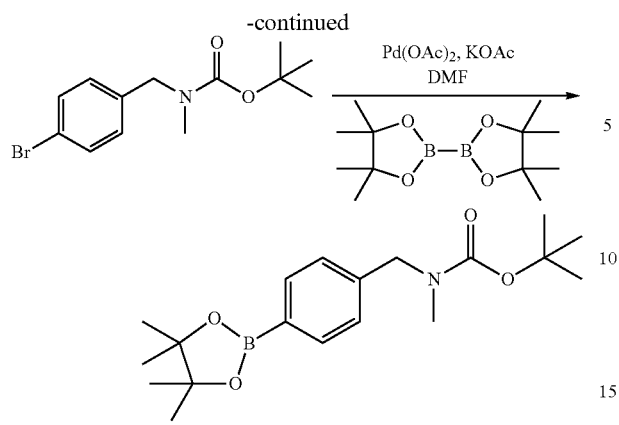

Step a: tert-Butyl-4-bromobenzylcarbamate

Commercially available p-bromobenzylamine hydrochloride (1 g, 4 mmol) was treated with 10% aq. NaOH (5 mL). To the clear solution was added (Boc)$_2$O (1.1 g, 4.9 mmol) dissolved in dioxane (10 mL). The mixture was vigorously stirred at room temperature for 18 hours. The resulting residue was concentrated, suspended in water (20 mL), extracted with ethyl acetate (4×20 mL), dried over Na$_2$SO$_4$, filtered, and concentrated to yield tert-butyl-4-bromobenzylcarbamate (1.23 g, 96%) as a white solid. $^1$H NMR (300 MHz, DMSO-d$_6$) δ 7.48 (d, J=8.4 Hz, 2H), 7.40 (t, J=6 Hz, 1H), 7.17 (d, J=8.4 Hz, 2H), 4.07 (d, J=6.3 Hz, 2H), 1.38 (s, 9H).

Step b: tert-Butyl-4-bromobenzyl(methyl)carbamate

In a 60-mL vial, tert-butyl-4-bromobenzylcarbamate (1.25 g, 4.37 mmol) was dissolved in DMF (12 mL). To this solution was added Ag$_2$O (4.0 g, 17 mmol) followed by the addition of CH$_3$I (0.68 mL, 11 mmol). The mixture was stirred at 50° C. for 18 hours. The reaction mixture was filtered through a bed of celite and the celite was washed with methanol (2×20 mL) and dichloromethane (2×20 mL). The filtrate was concentrated to remove most of the DMF. The residue was treated with water (50 mL) and a white emulsion formed. This mixture was extracted with ethyl acetate (4×25 mL), dried over Na$_2$SO$_4$, and the solvent was evaporated to yield tert-butyl-4-bromobenzyl(methyl)carbamate (1.3 g, 98%) as a yellow oil. $^1$H NMR (300 MHz, DMSO-d$_6$) δ 7.53 (d, J=8.1 Hz, 2H), 7.15 (d, J=8.4 Hz, 2H), 4.32 (s, 2H), 2.74 (s, 3H), 1.38 (s, 9H).

Step c: tert-Butyl 4-(4,4,5,5-tetramethyl-1,3,2-dioxaborolan-2-yl)benzylmethylcarbamate The coupling reaction was achieved in the same manner as described above for 1-methyl-4-[4-(4,4,5,5-tetramethyl-1,3,2-dioxaborolan-2-yl)phenyl]sulfonyl-piperazine, Preparation AA. The Boc protecting group was removed after the coupling reaction by treating the crude reaction mixture with 0.5 mL of 1N HCl in diethyl ether for 18 hours before purification by HPLC.

Additional examples of the invention were prepared following the above procedure with non-substantial changes but using aryl boronic acids given in Table 4.

TABLE 4

Additional exemplary compounds of formula I.

| Compound No. | Amine | Boronic Acid |
|---|---|---|
| 1 | B-2 | [2-(dimethylaminomethyl)phenyl]boronic acid |
| 2 | B-2 | [4-(1-piperidyl)phenyl]boronic acid |
| 3 | B-2 | (3,4-dichlorophenyl)boronic acid |
| 4 | B-2 | (4-morpholinosulfonylphenyl)boronic acid |
| 5 | B-2 | (3-chloro-4-methoxy-phenyl)boronic acid |
| 6 | B-2 | (6-methoxy-3-pyridyl)boronic acid |
| 7 | B-2 | (4-dimethylaminophenyl)boronic acid |
| 8 | B-2 | (4-morpholinophenyl)boronic acid |
| 9 | B-2 | [4-(acetylaminomethyl)phenyl]boronic acid |
| 10 | B-2 | (2-hydroxyphenyl)boronic acid |
| 11 | B-1 | 2-dihydroxyboranylbenzoic acid |
| 12 | B-1 | (6-methoxy-3-pyridyl)boronic acid |
| 14 | B-2 | (2,4-dimethylphenyl)boronic acid |
| 15 | B-2 | [3-(hydroxymethyl)phenyl]boronic acid |
| 16 | B-2 | 3-dihydroxyboranylbenzoic acid |
| 17 | B-2 | (3-ethoxyphenyl)boronic acid |
| 18 | B-2 | (3,4-dimethylphenyl)boronic acid |
| 19 | B-1 | [4-(hydroxymethyl)phenyl]boronic acid |
| 20 | B-1 | 3-pyridylboronic acid |
| 21 | B-2 | (4-ethylphenyl)boronic acid |
| 23 | B-2 | 4,4,5,5-tetramethyl-2-(4-(2-(methylsulfonyl)ethyl)phenyl)-1,3,2-dioxaborolane |
| 24 | B-1 | benzo[1,3]dioxol-5-ylboronic acid |
| 25 | B-2 | (3-chlorophenyl)boronic acid |
| 26 | B-2 | (3-methylsulfonylaminophenyl)boronic acid |
| 27 | B-2 | (3,5-dichlorophenyl)boronic acid |
| 28 | B-2 | (3-methoxyphenyl)boronic acid |
| 29 | B-1 | (3-hydroxyphenyl)boronic acid |
| 31 | B-2 | phenylboronic acid |
| 32 | B-2 | (2,5-difluorophenyl)boronic acid |
| 33 | B-8 | phenylboronic acid |
| 36 | B-2 | (2-methylsulfonylaminophenyl)boronic acid |
| 37 | B-1 | 1H-indol-5-ylboronic acid |
| 38 | B-2 | 2,2,2-trifluoro-N-(4-(4,4,5,5-tetramethyl-1,3,2-dioxaborolan-2-yl)benzyl)acetamide |
| 39 | B-2 | (2-chlorophenyl)boronic acid |
| 40 | B-1 | m-tolylboronic acid |
| 41 | B-2 | (2,4-dimethoxypyrimidin-5-yl)boronic acid |
| 42 | B-2 | (4-methoxycarbonylphenyl)boronic acid |
| 43 | B-2 | tert-butyl 4-(4,4,5,5-tetramethyl-1,3,2-dioxaborolan-2-yl)benzylmethylcarbamate[a] |
| 44 | B-2 | (4-ethoxyphenyl)boronic acid |
| 45 | B-2 | (3-methylsulfonylphenyl)boronic acid |
| 46 | B-2 | (4-fluoro-3-methyl-phenyl)boronic acid |
| 47 | B-2 | (4-cyanophenyl)boronic acid |
| 48 | B-1 | (2,5-dimethoxyphenyl)boronic acid |
| 49 | B-1 | (4-methylsulfonylphenyl)boronic acid |
| 50 | B-1 | cyclopent-1-enylboronic acid |
| 51 | B-2 | o-tolylboronic acid |
| 52 | B-1 | (2,6-dimethylphenyl)boronic acid |
| 53 | B-8 | 2-chlorophenylboronic acid |
| 54 | B-2 | (2,5-dimethoxyphenyl)boronic acid |
| 55 | B-2 | (2-fluoro-3-methoxy-phenyl)boronic acid |
| 56 | B-2 | (2-methoxyphenyl)boronic acid |
| 57 | B-9 | phenylboronic acid |
| 58 | B-2 | (4-isopropoxyphenyl)boronic acid |
| 59 | B-2 | (4-carbamoylphenyl)boronic acid |
| 60 | B-2 | (3,5-dimethylphenyl)boronic acid |
| 61 | B-2 | (4-isobutylphenyl)boronic acid |
| 62 | B-1 | (4-cyanophenyl)boronic acid |
| 63 | B-10 | phenylboronic acid |
| 64 | B-2 | N-ethyl-4-(4,4,5,5-tetramethyl-1,3,2-dioxaborolan-2-yl)-benzenesulfonamide |
| 65 | B-1 | 2,3-dihydrobenzofuran-5-ylboronic acid |
| 66 | B-2 | (4-chlorophenyl)boronic acid |
| 67 | B-2 | (4-chloro-3-methyl-phenyl)boronic acid |
| 68 | B-2 | (2-fluorophenyl)boronic acid |
| 69 | B-2 | benzo[1,3]dioxol-5-ylboronic acid |
| 70 | B-2 | (4-morpholinocarbonylphenyl)boronic acid |
| 71 | B-1 | cyclohex-1-enylboronic acid |
| 72 | B-2 | (3,4,5-trimethoxyphenyl)boronic acid |
| 73 | B-2 | [4-(dimethylaminomethyl)phenyl]boronic acid |
| 74 | B-2 | m-tolylboronic acid |
| 77 | B-2 | (3-cyanophenyl)boronic acid |

TABLE 4-continued

Additional exemplary compounds of formula I.

| Compound No. | Amine | Boronic Acid |
|---|---|---|
| 78 | B-2 | [3-(tert-butoxycarbonylaminomethyl)-phenyl]boronicacid[a] |
| 79 | B-2 | (4-methylsulfonylphenyl)boronic acid |
| 80 | B-1 | p-tolylboronic acid |
| 81 | B-2 | (2,4-dimethoxyphenyl)boronic acid |
| 82 | B-2 | (2-methoxycarbonylphenyl)boronic acid |
| 83 | B-2 | (2,4-difluorophenyl)boronic acid |
| 84 | B-2 | (4-isopropylphenyl)boronic acid |
| 85 | B-2 | [4-(2-dimethylaminoethylcarbamoyl)-phenyl]boronic acid |
| 86 | B-1 | (2,4-dimethoxyphenyl)boronic acid |
| 87 | B-1 | benzofuran-2-ylboronic acid |
| 88 | B-2 | 2,3-dihydrobenzofuran-5-ylboronic acid |
| 89 | B-2 | (3-fluoro-4-methoxy-phenyl)boronic acid |
| 91 | B-1 | (3-cyanophenyl)boronic acid |
| 92 | B-1 | (4-dimethylaminophenyl)boronic acid |
| 93 | B-2 | (2,6-dimethoxyphenyl)boronic acid |
| 94 | B-2 | (2-methoxy-5-methyl-phenyl)boronic acid |
| 95 | B-2 | (3-acetylaminophenyl)boronic acid |
| 96 | B-1 | (2,4-dimethoxypyrimidin-5-yl)boronic acid |
| 97 | B-2 | (5-fluoro-2-methoxy-phenyl)boronic acid |
| 98 | B-1 | [3-(hydroxymethyl)phenyl]boronic acid |
| 99 | B-1 | (2-methoxyphenyl)boronic acid |
| 100 | B-2 | (2,4,6-trimethylphenyl)boronic acid |
| 101 | B-2 | [4-(dimethylcarbamoyl)phenyl]boronic acid |
| 102 | B-2 | [4-(tert-butoxycarbonylaminomethyl)-phenyl]boronic acid[a] |
| 104 | B-1 | (2-chlorophenyl)boronic acid |
| 105 | B-1 | (3-acetylaminophenyl)boronic acid |
| 106 | B-2 | (2-ethoxyphenyl)boronic acid |
| 107 | B-2 | 3-furylboronic acid |
| 108 | B-2 | [2-(hydroxymethyl)phenyl]boronic acid |
| 110 | B-9 | 2-chlorophenylboronic acid |
| 111 | B-2 | (2-fluoro-6-methoxy-phenyl)boronic acid |
| 112 | B-2 | (2-ethoxy-5-methyl-phenyl)boronic acid |
| 113 | B-2 | 1H-indol-5-ylboronic acid |
| 114 | B-1 | (3-chloro-4-pyridyl)boronic acid |
| 115 | B-2 | cyclohex-1-enylboronic acid |
| 116 | B-1 | o-tolylboronic acid |
| 119 | B-2 | (2-aminophenyl)boronic acid |
| 120 | B-2 | (4-methoxy-3,5-dimethyl-phenyl)boronic acid |
| 121 | B-2 | (4-methoxyphenyl)boronic acid |
| 122 | B-2 | (2-propoxyphenyl)boronic acid |
| 123 | B-2 | (2-isopropoxyphenyl)boronic acid |
| 124 | B-2 | (2,3-dichlorophenyl)boronic acid |
| 126 | B-2 | (2,3-dimethylphenyl)boronic acid |
| 127 | B-2 | (4-fluorophenyl)boronic acid |
| 128 | B-1 | (3-methoxyphenyl)boronic acid |
| 129 | B-2 | (4-chloro-2-methyl-phenyl)boronic acid |
| 130 | B-1 | (2,6-dimethoxyphenyl)boronic acid |
| 131 | B-2 | (5-isopropyl-2-methoxy-phenyl)boronic acid |
| 132 | B-2 | (3-isopropoxyphenyl)boronic acid |
| 134 | B-2 | 4-dihydroxyboranylbenzoic acid |
| 135 | B-2 | (4-dimethylamino-2-methoxy-phenyl)boronic acid |
| 136 | B-2 | (4-methylsulfinylphenyl)boronic acid |
| 137 | B-2 | [4-(methylcarbamoyl)phenyl]boronic acid |
| 138 | B-1 | 8-quinolylboronic acid |
| 139 | B-2 | cyclopent-1-enylboronic acid |
| 140 | B-2 | p-tolylboronic acid |
| 142 | B-8 | 2-methoxyphenylboronic acid |
| 143 | B-2 | (2,5-dimethylphenyl)boronic acid |
| 144 | B-1 | (3,4-dimethoxyphenyl)boronic acid |
| 145 | B-1 | (3-chlorophenyl)boronic acid |
| 146 | B-2 | [4-(morpholinomethyl)phenyl]boronic acid |
| 147 | B-10 | 4-(dimethylamino)phenylboronic acid |
| 148 | B-2 | [4-(methylsulfamoyl)phenyl]boronic acid |
| 149 | B-1 | 4-dihydroxyboranylbenzoic acid |
| 150 | B-1 | phenylboronic acid |
| 151 | B-2 | (2,3-difluorophenyl)boronic acid |
| 152 | B-1 | (4-chlorophenyl)boronic acid |
| 153 | B-9 | 2-methoxyphenylboronic acid |
| 154 | B-2 | 3-dihydroxyboranylbenzoic acid |
| 155 | B-10 | 2-methoxyphenylboronic acid |
| 157 | B-2 | (3-chloro-4-fluoro-phenyl)boronic acid |
| 158 | B-2 | (2,3-dimethoxyphenyl)boronic acid |
| 159 | B-2 | [4-(tert-butoxycarbonylaminomethyl)-phenyl]boronic acid |
| 160 | B-2 | (4-sulfamoylphenyl)boronic acid |
| 161 | B-2 | (3,4-dimethoxyphenyl)boronic acid |
| 162 | B-2 | [4-(methylsulfonylamino-methyl)phenyl]boronic acid |
| 166 | B-1 | 4-(N,N-dimethylsulfamoyl)phenylboronic acid |
| 167 | B-6 | 2-isopropylphenylboronic acid |
| 171 | B-6 | 4-(methylcarbamoyl)phenylboronic acid |
| 173 | B-2 | 3-fluorophenylboronic acid |
| 174 | B-6 | 3-(N,N-dimethylsulfamoyl)phenylboronic acid |
| 179 | B-6 | 4-(N-methylsulfamoyl)phenylboronic acid |
| 181 | B-1 | 3-((tert-butoxycarbonylamino)methyl)-phenylboronic acid |
| 185 | B-3 | 3-methoxyphenylboronic acid |
| 186 | B-6 | 2-chlorophenylboronic acid |
| 187 | B-7 | 3-(dimethylcarbamoyl)phenylboronic acid |
| 188 | B-6 | 3-(hydroxymethyl)phenylboronic acid |
| 189 | B-1 | 3-(N,N-dimethylsulfamoyl)phenylboronic acid |
| 190 | B-1 | 4-sulfamoylphenylboronic acid |
| 191 | B-1 | 2-isopropylphenylboronic acid |
| 193 | B-5 | 3-sulfamoylphenylboronic acid |
| 194 | B-3 | 4-isopropylphenylboronic acid |
| 195 | B-3 | 3-(N,N-dimethylsulfamoyl)phenylboronic acid |
| 196 | B-7 | 4-(methylcarbamoyl)phenylboronic acid |
| 198 | B-3 | 3-(dimethylcarbamoyl)phenylboronic acid |
| 204 | B-5 | 3-(dimethylcarbamoyl)phenylboronic acid |
| 206 | B-3 | 4-chlorophenylboronic acid |
| 207 | B-1 | 4-(N-methylsulfamoyl)phenylboronic acid |
| 209 | B-1 | 3-(methylcarbamoyl)phenylboronic acid |
| 210 | B-3 | 4-sulfamoylphenylboronic acid |
| 213 | B-5 | 3-isopropylphenylboronic acid |
| 215 | B-7 | 4-methoxyphenylboronic acid |
| 216 | B-6 | 3-chlorophenylboronic acid |
| 217 | B-7 | m-tolylboronic acid |
| 219 | B-5 | 4-(hydroxymethyl)phenylboronic acid |
| 222 | B-6 | m-tolylboronic acid |
| 224 | B-5 | 2-chlorophenylboronic acid |
| 225 | B-1 | 3-isopropylphenylboronic acid |
| 227 | B-6 | 4-(hydroxymethyl)phenylboronic acid |
| 229 | B-7 | 3-chlorophenylboronic acid |
| 230 | B-6 | o-tolylboronic acid |
| 231 | B-1 | 2-(hydroxymethyl)phenylboronic acid |
| 235 | B-3 | 3-isopropylphenylboronic acid |
| 238 | B-5 | 3-carbamoylphenylboronic acid |
| 241 | B-2 | 4-(N,N-dimethylsulfamoyl)phenylboronic acid |
| 243 | B-7 | 2-methoxyphenylboronic acid |
| 247 | B-6 | 3-(dimethylcarbamoyl)phenylboronic acid |
| 251 | B-3 | 3-sulfamoylphenylboronic acid |
| 252 | B-1 | 4-methoxyphenylboronic acid |
| 254 | B-3 | 4-(N-methylsulfamoyl)phenylboronic acid |
| 255 | B-1 | 4-((tert-butoxycarbonylamino)methyl)-phenylboronic acid |
| 257 | B-5 | 4-chlorophenylboronic acid |
| 258 | B-3 | 3-(methylcarbamoyl)phenylboronic acid |
| 260 | B-3 | 2-(hydroxymethyl)phenylboronic acid |
| 263 | B-4 | 4-(hydroxymethyl)phenylboronic acid |
| 264 | B-7 | 4-chlorophenylboronic acid |
| 265 | B-6 | 4-carbamoylphenylboronic acid |
| 266 | B-5 | 3-methoxyphenylboronic acid |
| 269 | B-7 | phenylboronic acid |
| 272 | B-3 | 4-methoxyphenylboronic acid |
| 274 | B-6 | 2-(hydroxymethyl)phenylboronic acid |
| 277 | B-3 | 4-(hydroxymethyl)phenylboronic acid |
| 278 | B-3 | 3-(methylcarbamoyl)phenylboronic acid |
| 280 | B-3 | 4-(N,N-dimethylsulfamoyl)phenylboronic acid |
| 283 | B-3 | 4-carbamoylphenylboronic acid |
| 286 | B-1 | 4-(methylcarbamoyl)phenylboronic acid |
| 287 | B-2 | 4-(trifluoromethoxy)phenylboronic acid |
| 288 | B-5 | 4-(N-methylsulfamoyl)phenylboronic acid |
| 289 | B-3 | phenylboronic acid |
| 290 | B-6 | 4-isopropylphenylboronic acid |
| 291 | B-3 | 3-(hydroxymethyl)phenylboronic acid |
| 293 | B-6 | 3-methoxyphenylboronic acid |
| 294 | B-7 | 2-(hydroxymethyl)phenylboronic acid |

TABLE 4-continued

Additional exemplary compounds of formula I.

| Compound No. | Amine | Boronic Acid |
|---|---|---|
| 295 | B-3 | 3-carbamoylphenylboronic acid |
| 296 | B-5 | m-tolylboronic acid |
| 297 | B-1 | 4-(dimethylcarbamoyl)phenylboronic acid |
| 298 | B-3 | 2-methoxyphenylboronic acid |
| 299 | B-7 | p-tolylboronic acid |
| 300 | B-3 | o-tolylboronic acid |
| 301 | B-5 | 2-(hydroxymethyl)phenylboronic acid |
| 303 | B-6 | 2-methoxyphenylboronic acid |
| 305 | B-6 | 3-isopropylphenylboronic acid |
| 308 | B-7 | 4-isopropylphenylboronic acid |
| 309 | B-3 | 4-(dimethylcarbamoyl)phenylboronic acid |
| 310 | B-5 | 4-(methylcarbamoyl)phenylboronic acid |
| 313 | B-7 | o-tolylboronic acid |
| 314 | B-7 | 3-(methylcarbamoyl)phenylboronic acid |
| 315 | B-3 | p-tolylboronic acid |
| 320 | B-1 | 3-(dimethylcarbamoyl)phenylboronic acid |
| 321 | B-5 | 4-sulfamoylphenylboronic acid |
| 322 | B-6 | phenylboronic acid |
| 323 | B-5 | o-tolylboronic acid |
| 324 | B-3 | 4-((tert-butoxycarbonylamino)methyl)-phenylboronic acid[a] |
| 326 | B-5 | 4-(dimethylcarbamoyl)phenylboronic acid |
| 327 | B-5 | 2-methoxyphenylboronic acid |
| 328 | B-1 | 4-isopropylphenylboronic acid |
| 329 | B-5 | 2-isopropylphenylboronic acid |
| 331 | B-3 | m-tolylboronic acid |
| 333 | B-6 | 4-methoxyphenylboronic acid |
| 334 | B-5 | 4-methoxyphenylboronic acid |
| 337 | B-6 | p-tolylboronic acid |
| 343 | B-5 | 4-(N,N-dimethylsulfamoyl)phenylboronic acid |
| 346 | B-3 | 2-isopropylphenylboronic acid |
| 348 | B-6 | 4-((tert-butoxycarbonylamino)methyl)phenylboronic acid[a] |
| 349 | B-1 | 3-sulfamoylphenylboronic acid |
| 350 | B-3 | 3-((tert-butoxycarbonylamino)methyl)phenylboronic acid[a] |
| 351 | B-5 | phenylboronic acid |
| 352 | B-7 | 2-isopropylphenylboronic acid |
| 353 | B-6 | 4-chlorophenylboronic acid |
| 354 | B-7 | 2-chlorophenylboronic acid |
| 355 | B-5 | 3-(N,N-dimethylsulfamoyl)phenylboronic acid |
| 356 | B-7 | 3-sulfamoylphenylboronic acid |
| 357 | B-7 | 4-(N-methylsulfamoyl)phenylboronic acid |
| 359 | B-1 | 4-carbamoylphenylboronic acid |
| 361 | B-3 | 3-chlorophenylboronic acid |
| 365 | B-1 | 3-carbamoylphenylboronic acid |
| 367 | B-7 | 3-(hydroxymethyl)phenylboronic acid |
| 368 | B-4 | 4-(dimethylcarbamoyl)phenylboronic acid |
| 370 | B-5 | 3-(hydroxymethyl)phenylboronic acid |
| 371 | B-5 | 3-(methylcarbamoyl)phenylboronic acid |
| 374 | B-6 | 4-sulfamoylphenylboronic acid |
| 375 | B-5 | 4-carbamoylphenylboronic acid |
| 389 | B-12 | 2-methyl-3-(4,4,5,5-tetramethyl-1,3,2-dioxaborolan-2-yl)benzoic acid |
| 390 | B-11 | 3-methoxy-5-(4,4,5,5-tetramethyl-1,3,2-dioxaborolan-2-yl)benzoic acid |
| 391 | B-13 | 4-(4,4,5,5-tetramethyl-1,3,2-dioxaborolan-2-yl)benzoic acid |
| 392 | B-11 | 3-methyl-4-(4,4,5,5-tetramethyl-1,3,2-dioxaborolan-2-yl)benzoic acid |
| 393 | B-12 | 2-chloro-5-(4,4,5,5-tetramethyl-1,3,2-dioxaborolan-2-yl)benzoic acid |
| 394 | B-12 | 3-methoxy-5-(4,4,5,5-tetramethyl-1,3,2-dioxaborolan-2-yl)benzoic acid |
| 395 | B-2 | 4-cyclohexylphenylboronic acid |
| 396 | B-12 | 3-(4,4,5,5-tetramethyl-1,3,2-dioxaborolan-2-yl)benzoic acid |
| 397 | B-11 | 3-(4,4,5,5-tetramethyl-1,3,2-dioxaborolan-2-yl)benzoic acid |
| 398 | B-12 | 3-fluoro-5-(4,4,5,5-tetramethyl-1,3,2-dioxaborolan-2-yl)benzoic acid |
| 399 | B-13 | 2-methoxy-4-(4,4,5,5-tetramethyl-1,3,2-dioxaborolan-2-yl)benzoic acid |
| 400 | B-13 | 3-fluoro-5-(4,4,5,5-tetramethyl-1,3,2-dioxaborolan-2-yl)benzoic acid |
| 401 | B-11 | 2-methyl-3-(4,4,5,5-tetramethyl-1,3,2-dioxaborolan-2-yl)benzoic acid |
| 402 | B-12 | 2-methoxy-4-(4,4,5,5-tetramethyl-1,3,2-dioxaborolan-2-yl)benzoic acid |
| 403 | B-11 | 2-fluoro-5-(4,4,5,5-tetramethyl-1,3,2-dioxaborolan-2-yl)benzoic acid |
| 404 | B-11 | 2-methoxy-4-(4,4,5,5-tetramethyl-1,3,2-dioxaborolan-2-yl)benzoic acid |
| 405 | B-12 | 2-fluoro-4-(4,4,5,5-tetramethyl-1,3,2-dioxaborolan-2-yl)benzoic acid |
| 406 | B-13 | 2-fluoro-4-(4,4,5,5-tetramethyl-1,3,2-dioxaborolan-2-yl)benzoic acid |
| 407 | B-11 | 4-(4,4,5,5-tetramethyl-1,3,2-dioxaborolan-2-yl)benzoic acid |
| 408 | B-13 | 2-fluoro-5-(4,4,5,5-tetramethyl-1,3,2-dioxaborolan-2-yl)benzoic acid |
| 410 | B-2 | 4-(4,4,5,5-tetramethyl-1,3,2-dioxaborolan-2-yl)aniline |
| 411 | B-13 | 3-(4,4,5,5-tetramethyl-1,3,2-dioxaborolan-2-yl)benzoic acid |
| 412 | B-2 | 2-methoxypyridin-3-ylboronic acid |
| 414 | B-11 | 3-fluoro-5-(4,4,5,5-tetramethyl-1,3,2-dioxaborolan-2-yl)benzoic acid |
| 415 | B-13 | 3-methyl-4-(4,4,5,5-tetramethyl-1,3,2-dioxaborolan-2-yl)benzoic acid |
| 417 | B-12 | 2-fluoro-5-(4,4,5,5-tetramethyl-1,3,2-dioxaborolan-2-yl)benzoic acid |
| 418 | B-4 | 3-(4,4,5,5-tetramethyl-1,3,2-dioxaborolan-2-yl)benzoic acid |
| 419 | B-11 | 2-chloro-5-(4,4,5,5-tetramethyl-1,3,2-dioxaborolan-2-yl)benzoic acid |
| 420 | B-2 | 4-(hydroxymethyl)phenylboronic acid |
| 421 | B-11 | 2-fluoro-4-(4,4,5,5-tetramethyl-1,3,2-dioxaborolan-2-yl)benzoic acid |
| 422 | B-12 | 3-methyl-4-(4,4,5,5-tetramethyl-1,3,2-dioxaborolan-2-yl)benzoic acid |

[a] The Boc protecting group was removed after the coupling reaction by treating the crude reaction mixture with 0.5 mL of 1N HCl in diethyl ether for 18 hours before purification by HPLC.

Further examples of the invention may be prepared by modification of intermediates as illustrated above.

Compound Derivatization after Coupling:

DD. 1-(Benzo[d][1,3]-dioxol-5-yl)-N-(6 (4 (2 methylpyrrolidin-1-ylsulfonyl)phenyl)pyridin-2-yl)cyclopropanecarboxamide

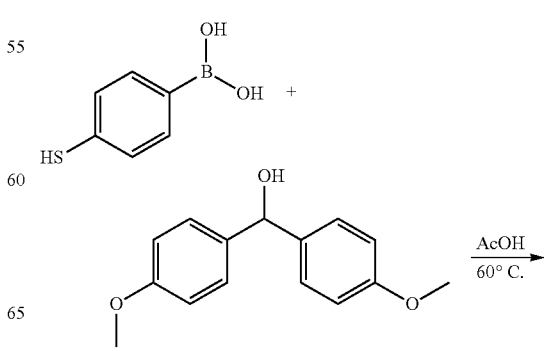

311
-continued

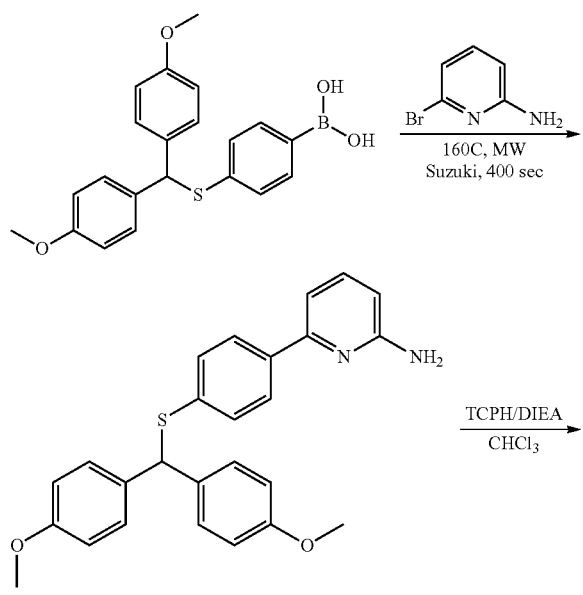

312
-continued

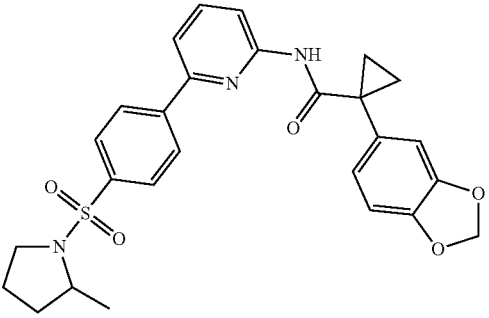

Step a: 4-(4,4'-Dimethoxybenzhydryl)-thiophenyl boronic acid 4,4'-Dimethoxybenzhydrol (2.7 g, 11 mmol) and 4-mercaptophenylboronic acid (1.54 g, 10 mmol) were dissolved in 20 mL AcOH and heated at 60° C. for 1 h. Solvent was evaporated and the residue was dried under high vacuum. This material was used without further purification.

Step b: 6-(4-(Bis(4-methoxyphenyl)methylthio)phenyl)pyridin-2-amine 4-(4,4'-Dimethoxybenzhydryl)-thiophenyl boronic acid (10 mmol) and 2-amino-6-bromopyridine (1.73 g, 10 mmol) were dissolved in MeCN (40 mL) followed by addition of Pd(PPh$_3$)$_4$ (~50 mg) and aq. K$_2$CO$_3$ (1M, 22 mL). The reaction mixture was heated portion wise in a microwave oven (160° C., 400 sec). The products were distributed between ethyl acetate and water. The organic layer was washed with water, brine and dried over MgSO$_4$. Evaporation of the volatiles yielded an oil that was used without purification in the next step. ESI-MS m/z calc. 428.0. found 429.1 (M+1).

Step c: 1-(Benzo[d][1,3]dioxol-5-yl)-N-(6-(4-(bis(4-methoxyphenyl)methylthio)phenyl)-pyridin-2-yl)cyclopropanecarboxamide 6-[(4,4'-Dimethoxybenzhydryl)-4-thiophenyl]pyridin-2-ylamine (~10 mmol) and 1-benzo[1,3]dioxol-5-yl-cyclopropanecarboxylic acid (2.28 g, 11 mmol) were dissolved in chloroform (25 mL) followed by the addition of TCPH (4.1 g, 12 mmol) and DIEA (5 mL, 30 mmol). The reaction mixture was heated at 65° C. for 48 h before the volatiles were removed under reduced pressure. The residue was transferred to a separatory funnel and distributed between water (200 mL) and ethyl acetate (150 mL). The organic layer was washed with 5% NaHCO$_3$ (2×150 mL), water (1×150 mL), brine (1×150 mL) and dried over MgSO$_4$. Evaporation of the solvent yielded crude 1-(benzo[d][1,3]dioxol-5-yl)-N-(6-(4-(bis(4-methoxyphenyl)-methylthio)phenyl)pyridin-2-yl)cyclopropanecarboxamide as a pale oil. ESI-MS m/z calc. 616.0. found 617.0 (M+1) (HPLC purity ~85%, UV254 nm).

Step d: 4-(6-(1-(Benzo[d][1,3]dioxol-5-yl)cyclopropane-carboxamido)pyridin-2-yl)benzenesulfonic acid 1-(Benzo[d][1,3]dioxol-5-yl)-N-(6-(4-(bis(4-methoxyphenyl)methylthio)-phenyl)pyridin-2-yl)cyclopropanecarboxamide (~8.5 mmol) was dissolved in AcOH (75 mL) followed by the addition of 30% H$_2$O$_2$ (10 mL). Additional hydrogen peroxide (10 ml) was added 2 h later. The reaction mixture was stirred at 35-45° C. overnight (~90% conversion, HPLC). The volume of reaction mixture was reduced to a third by evaporation (bath temperature below 40° C.). The reaction mixture was loaded directly onto a prep RP HPLC column (C-18) and purified. Fractions with 4-(6-(1-(benzo[d][1,3]dioxol-5-yl)cyclopropanecarboxamido)pyridin-2-yl)benzenesulfonic acid were collected and evaporated (1.9 g, 43%, cal. based on 4-mercaptophenylboronic acid). ESI-MS m/z calc. 438.0. found 438.9 (M+1).

Step e: 4-(6-(1-(Benzo[d][1,3]dioxol-5-yl)cyclopropane-carboxamido)pyridin-2-yl)benzene-1-sulfonyl chloride 4-(6-(1-(Benzo[d][1,3]dioxol-5-yl)cyclopropanecarboxamido)pyridin-2-yl)benzenesulfonic acid (1.9 g, 4.3 mmol) was dissolved in $POCl_3$ (30 mL) followed by the addition of $SOCl_2$ (3 mL) and DMF (100 μl). The reaction mixture was heated at 70-80° C. for 15 min. The volatiles were evaporated and then re-evaporated with chloroform-toluene. The residual brown oil was diluted with chloroform (22 mL) and used for sulfonylation immediately. ESI-MS m/z calc. 456.0. found 457.1 (M+1).

Step f: 1-(Benzo[d][1,3]dioxol-5-yl)-N-(6-(4-(2-methylpyrrolidin-1-ylsulfonyl)phenyl)pyridin-2-yl)cyclopropanecarboxamide 4-(6-(1-(Benzo[d][1,3]dioxol-5-yl)cyclopropanecarboxamido)pyridin-2-yl)benzene-1-sulfonyl chloride (~35 μmol, 400 μl solution in chloroform) was treated with 2-methylpyrrolidine followed by the addition of DIEA (100 μl). The reaction mixture was kept at room temperature for 1 h, concentrated, then diluted with DMSO (400 μl). The resulting solution was subjected to HPLC purification. Fractions containing the desired material were combined and concentrated in vacuum centrifuge at 40° C. to provide the trifluoroacetic salt of target material (ESI-MS m/z calc. 505.0. found 505.9 (M+1), retention time 4.06 min) $^1$H NMR (250 MHz, DMSO-$d_6$) δ 1.15 (m, 2H), δ 1.22 (d, 3H, J=6.3 Hz), δ 1.41-1.47 (m, 2H), δ 1.51 (m, 2H), δ 1.52-1.59 (m, 2H), δ 3.12 (m, 1H), δ 3.33 (m, 1H), δ 3.64 (m, 1H), δ 6.07 (s, 2H), δ 6.96-7.06 (m, 2H), δ 7.13 (d, 1H, J=1.3 Hz), δ 7.78 (d, 1H, J=8.2 Hz), δ 7.88 (d, 2H, J=8.5 Hz), δ 7.94 (t, 1H, J=8.2 Hz), δ 8.08 (d, 1H, J=8.2 Hz), δ 8.16 (d, 2H, J=8.5 Hz), δ 8.53 (s, 1H).

The compounds in the following table were synthesized as described above using commercially available amines. Additional examples of the invention were prepared following the above procedure with non-substantial changes but using amines given in Table 5.

TABLE 5

Additional exemplary compounds of formula I.

| Compound No. | Amine |
| --- | --- |
| 13 | 1-methylpiperazine |
| 22 | 2,6-dimethylmorpholine |
| 30 | piperidin-3-ylmethanol |
| 34 | 2-(methylamino)ethanol |
| 35 | (R)-pyrrolidin-2-ylmethanol |
| 75 | 2-(pyrrolidin-1-yl)ethanamine |
| 76 | pyrrolidine |
| 90 | piperidine |
| 103 | (tetrahydrofuran-2-yl)methanamine |
| 109 | piperidin-4-ol |
| 117 | 2-methylpropan-2-amine |
| 118 | cyclopentanamine |

TABLE 5-continued

Additional exemplary compounds of formula I.

| Compound No. | Amine |
| --- | --- |
| 125 | (S)-2-(methoxymethyl)pyrrolidine |
| 133 | (R)-2-(methoxymethyl)pyrrolidine |
| 141 | piperidin-4-ylmethanol |
| 156 | N-methylpropanamine |
| 163 | pyrrolidin-3-ol |
| 168 | 2-(2-aminoethoxy)ethanol |
| 172 | 2-morpholinoethanamine |
| 175 | furan-2-ylmethanamine |
| 176 | piperidin-3-ol |
| 178 | 2-(1-methylpyrrolidin-2-yl)ethanamine |
| 180 | 3-methylpiperidine |
| 182 | (S)-pyrrolidine-2-carboxamide |
| 184 | (R)-1-aminopropan-2-ol |
| 197 | 2-aminopropane-1,3-diol |
| 199 | 2-amino-2-ethylpropane-1,3-diol |
| 203 | $N^1,N^1$-dimethylethane-1,2-diamine |
| 205 | (R)-2-amino-3-methylbutan-1-ol |
| 208 | cyclohexanamine |
| 212 | piperazin-2-one |
| 232 | 2-aminoethanol |
| 233 | piperidin-2-ylmethanol |
| 234 | 2-(piperazin-1-yl)ethanol |
| 244 | N-(cyclopropylmethyl)propan-1-amine |
| 249 | 3-morpholinopropan-1-amine |
| 261 | 1-(piperazin-1-yl)ethanone |
| 267 | 2-(1H-imidazol-4-yl)ethanamine |
| 268 | (R)-2-aminopropan-1-ol |
| 270 | 2-methylpiperidine |
| 273 | 2-(pyridin-2-yl)ethanamine |
| 275 | 3,3-difluoropyrrolidine |
| 276 | 2-amino-2-methylpropan-1-ol |
| 285 | 3-(1H-imidazol-1-yl)propan-1-amine |
| 304 | piperidine-3-carboxamide |
| 306 | cyclobutanamine |
| 307 | (S)-3-aminopropane-1,2-diol |
| 311 | N-methylcyclohexanamine |
| 312 | N-methylprop-2-en-1-amine |
| 316 | 2-amino-2-methylpropane-1,3-diol |
| 325 | (5-methylfuran-2-yl)methanamine |
| 330 | 3,3-dimethylbutan-1-amine |
| 332 | 2-methylpyrrolidine |
| 335 | 2,5-dimethylpyrrolidine |
| 336 | (R)-2-aminobutan-1-ol |
| 338 | propan-2-amine |
| 339 | N-methylbutan-1-amine |
| 342 | 4-amino-3-hydroxybutanoic acid |
| 344 | 3-(methylamino)propane-1,2-diol |
| 347 | N-(2-aminoethyl)acetamide |
| 360 | 1-aminobutan-2-ol |
| 364 | (S)-pyrrolidine-2-carboxylic acid |
| 366 | 1-(2-methoxyethyl)piperazine |
| 373 | (R)-2-aminopentan-1-ol |

EE. 1-Benzo[1,3]-dioxol-5-yl-N-[6-[4-[(methyl-methylsulfonyl-amino)methyl]phenyl]-2-pyridyl]-cyclopropane-1-carboxamide (Compound No. 292)

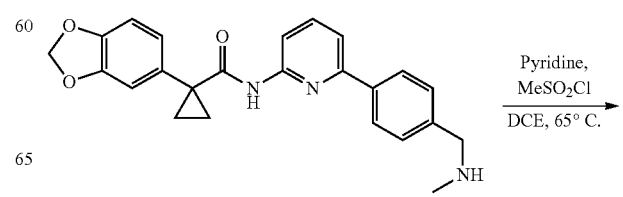

Pyridine, $MeSO_2Cl$
DCE, 65° C.

-continued

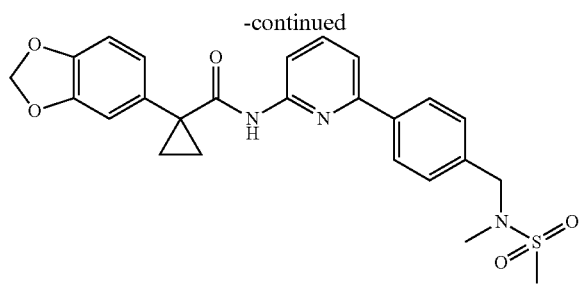

To the starting amine (brown semisolid, 0.100 g, ~0.2 mmol, obtained by treatment of the corresponding t-butyloxycarbonyl derivative by treatment with 1N HCl in ether) was added dichloroethane (DCE) (1.5 mL), followed by the addition of pyridine (0.063 mL, 0.78 mmol) and methansulfonyl chloride (0.03 mL, 0.4 mmol). The mixture was stirred at 65° C. for 3 hours. After this time, LC/MS analysis showed ~50% conversion to the desired product. Two additional equivalents of pyridine and 1.5 equivalents of methansulfonyl chloride were added and the reaction was stirred for 2 hours. The residue was concentrated and purified by HPLC to yield 1-benzo[1,3]dioxol-5-yl-N-[6-[4-[(methyl-methylsulfonyl-amino)methyl]phenyl]-2-pyridyl]-cyclopropane-1-carboxamide (0.020 g, 21% yield) as a white solid. ESI-MS m/z calc. 479.2. found 480.1 (M+1)+.

FF. (R)-1-(3-hydroxy-4-methoxyphenyl)-N-(6-(4-(2-(hydroxymethyl)-pyrrolidin-1-ylsulfonyl)phenyl)pyridin-2-yl)cyclopropanecarboxamide

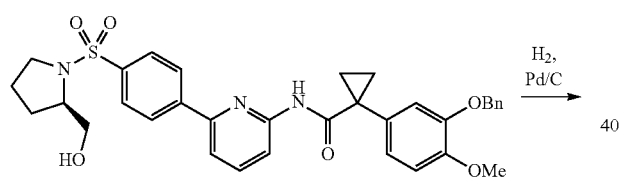

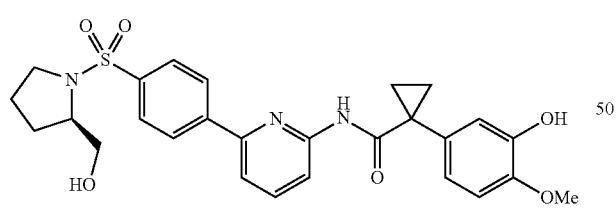

(R)-1-(3-(Benzyloxy)-4-methoxyphenyl)-N-(6-(4-(2-(hydroxymethyl)pyrrolidin-1-ylsulfonyl)phenyl)pyridin-2-yl)cyclopropanecarboxamide (28 mg, 0.046 mmol) was dissolved in ethanol (3 mL). Palladium on charcoal (10%, 20 mg) was added and the reaction was stirred overnight under 1 atm of hydrogen. The catalyst was filtered off and the product was isolated by silica gel chromatography (50-80% EtOAc in hexane) to provide (R)-1-(3-hydroxy-4-methoxyphenyl)-N-(6-(4-(2-(hydroxymethyl)pyrrolidin-1-ylsulfonyl)phenyl)pyridin-2-yl)cyclopropanecarboxamide (8 mg, 34%). ESI-MS m/z calc. 523.4. found 524.3 (M+1)+. Retention time of 3.17 minutes.

2-Amino-5-phenylpyridine (CAS [33421-40-8]) is C-1.

GG. (R)-(1-(4-(6-Aminopyridin-2-yl)phenylsulfonyl)pyrrolidin-2-yl)methanol hydrochloride (C-2)

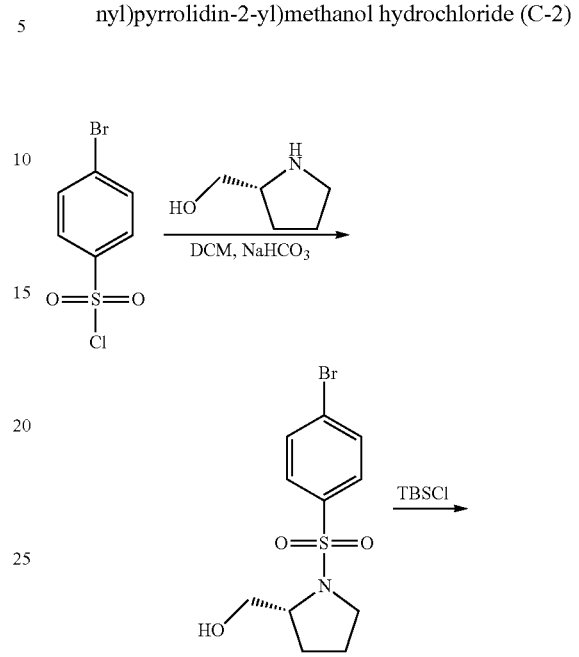

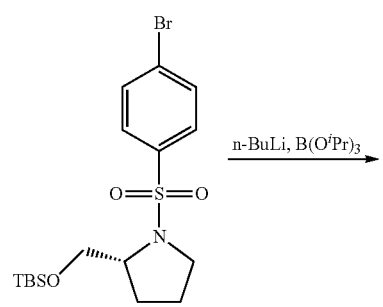

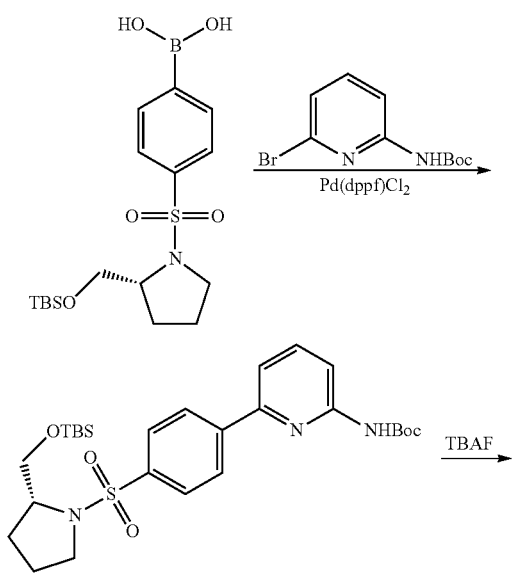

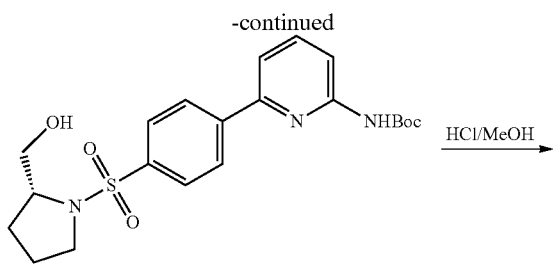

HCl/MeOH

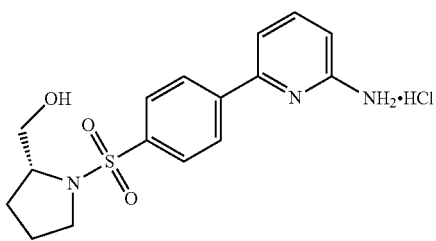

Step a: (R)-(1-(4-Bromophenylsulfonyl)pyrrolidin-2-yl)methanol

To a mixture of sat aq. NaHCO$_3$ (44 g, 0.53 mol), CH$_2$Cl$_2$ (400 mL) and pyrrolidin-2-yl-methanol (53 g, 0.53 mol) was added a solution of 4-bromo-benzenesulfonyl chloride (127 g, 0.50 mol) in CH$_2$Cl$_2$ (100 mL). The reaction was stirred at 20° C. overnight. The organic phase was separated and dried over Na$_2$SO$_4$. Evaporation of the solvent under reduced pressure provided (R)-(1-(4-bromophenylsulfonyl)pyrrolidin-2-yl)methanol (145 g, crude), which was used in the next step without further purification. $^1$H NMR (CDCl$_3$, 300 MHz) δ 7.66-7.73 (m, 4H), 3.59-3.71 (m, 3H), 3.43-3.51 (m, 1H), 3.18-3.26 (m, 1H), 1.680-1.88 (m, 3H), 1.45-1.53 (m, 1H).

Step b: (R)-1-(4-Bromo-benzenesulfonyl)-2-(tert-butyl-dimethyl-silanyloxymethyl)pyrrolidine To a solution of [1-(4-bromo-benzenesulfonyl)-pyrrolidin-2-yl]-methanol (50.0 g, 0.16 mol) and 1H-imidazole (21.3 g, 0.31 mol) in CH$_2$Cl$_2$ (500 mL) was added tert-butylchlorodimethylsilane (35.5 g, 0.24 mol) in portions. After addition, the mixture was stirred for 1 hour at room temperature. The reaction was quenched with water (200 mL) and the separated aqueous layer was extracted with CH$_2$Cl$_2$ (100 mL×3). The combined organic layers were washed with brine, dried over Na$_2$SO$_4$ and evaporated under vacuum to give 1-(4-bromo-benzenesulfonyl)-2-(tert-butyldimethylsilanyloxymethyl)pyrrolidine (68.0 g, 99%). $^1$H NMR (300 MHz, CDCl$_3$) δ 7.63-7.71 (m, 4H), 3.77-3.81 (m, 1H), 3.51-3.63 (m, 2H), 3.37-3.43 (m, 1H), 3.02-3.07 (m, 1H), 1.77-1.91 (m, 2H), 1.49-1.57 (m, 2H), 0.87 (s, 9H), 0.06 (d, J=1.8 Hz, 6H).

Step c: (R)-4-(2-((tert-butyldimethylsilyloxy)methyl)pyrrolidin-1-ylsulfonyl)phenylboronic acid To a solution of 1-(4-bromo-benzenesulfonyl)-2-(tert-butyl-dimethyl-silanyloxymethyl)pyrrolidine (12.9 g, 29.7 mmol) and B(O$^i$Pr)$_3$ (8.4 g, 45 mmol) in dry THF (100 mL) was added dropwise n-BuLi (2.5 M in hexane, 29.7 mL) at −70° C. After addition, the mixture was warmed slowly to −10° C. and treated with HCl (1M, 50 mL). The organic layer was separated and the aqueous layer was extracted with ethyl acetate. The combined organic layers were dried over Na$_2$SO$_4$ and evaporated under vacuum. The organics were combined to give crude (R)-4-(2-((tert-butyldimethylsilyloxy)methyl)pyrrolidin-1-ylsulfonyl)phenylboronic acid (15.0 g), which was used directly in the next step.

Step d: (6-{4-[2-(tert-Butyl-dimethyl-silanyloxymethyl)-pyrrolidine-1-sulfonyl]phenyl}pyridin-2-yl)carbamic acid tert-butyl ester To a solution of (6-bromo-pyridin-2-yl)carbamic acid tert-butyl ester (24.6 g, 90.0 mmol) in DMF (250 mL) were added (R)-4-(2-((tert-butyldimethylsilyloxy)-methyl)pyrrolidin-1-ylsulfonyl)phenylboronic acid (45.0 g), Pd(PPh$_3$)$_4$ (10.4 g, 9.0 mmol), potassium carbonate (18.6 g, 135 mol) and water (200 mL). The resulting mixture was degassed by gently bubbling argon through the solution for 5 minutes at 20° C. The reaction mixture was then heated at 80° C. overnight. DMF was removed under vacuum. To the residue was added EtOAc (300 mL). The mixture was filtered through a pad of silica gel, which was washed with EtOAc (50 mL×3). The combined organic extracts were evaporated under vacuum. The crude residue was purified by column (Petroleum Ether/EtOAc 20:1) to give (6-{4-[2-(tert-butyl-dimethyl-silanyloxymethyl)-pyrrolidine-1-sulfonyl]phenyl}pyridin-2-yl)carbamic acid tert-butyl ester (22.2 g, 45% over 2-steps). $^1$H NMR (300 MHz, CDCl$_3$) δ 8.09 (d, J=8.4 Hz, 2H), 7.88-7.96 (m, 3H), 8.09 (t, J=7.8 Hz, 1H), 7.43-7.46 (m, 1H), 7.38 (s, 1H), 3.83-3.88 (m, 1H), 3.64-3.67 (m, 1H), 3.53-3.59 (m, 1H), 3.41-3.47 (m, 1H), 3.08-3.16 (m, 1H), 1.82-1.91 (m, 2H), 1.67-1.69 (m, 1H), 1.53-1.56 (m, 10H), 0.89 (s, 9H), 0.08 (d, J=2.4 Hz, 6H).

Step e: {6-[4-(2-Hydroxymethyl-pyrrolidine-1-sulfonyl)-phenyl]pyridin-2-ylcarbamic acid tert-butyl ester A solution of crude (6-{4-[2-(tert-butyl-dimethyl-silanyloxymethyl)-pyrrolidine-1-sulfonyl]phenyl}-pyridin-2-yl)carbamic acid tert-butyl ester (22.2 g, 40.5 mmol) and TBAF (21.2 g, 81.0 mmol) in DCM (300 mL) was stirred at room temperature overnight. The mixture was washed with brine (100 mL×3), dried over Na$_2$SO$_4$ and evaporated under vacuum to give {6-[4-(2-hydroxymethyl-pyrrolidine-1-sulfonyl)-phenyl]pyridin-2-yl}carbamic acid tert-butyl ester (15.0 g, 86%), which was used directly in the next step.

Step f: (R)-(1-(4-(6-Aminopyridin-2-yl)phenylsulfonyl)-pyrrolidin-2-yl)methanol hydrochloride (C-2)

A solution of {6-[4-(2-hydroxymethyl-pyrrolidine-1-sulfonyl)-phenyl]pyridin-2-yl}carbamic acid tert-butyl ester (15.0 g, 34.6 mmol) in HCl/MeOH (50 mL, 2M) was heated at reflux for 2 h. After cooling to room temperature, the reaction mixture was evaporated under vacuum and washed with EtOAc to give (R)-(1-(4-(6-aminopyridin-2-yl)phenyl-sulfonyl)pyrrolidin-2-yl)methanol hydrochloride (C-2; 11.0 g, 86%). $^1$H NMR (300 MHz, DMSO-d$_6$) δ 8.18 (d, J=8.7 Hz, 2H), 7.93-7.99 (m, 3H), 7.31 (d, J=7.2 Hz, 1H), 7.03 (d, J=8.7

Hz, 1H), 3.53-3.57 (m, 2H), 3.29-35 (m, 2H), 3.05-3.13 (m, 1H), 1.77-1.78 (m, 2H), 1.40-1.45 (m, 2H). MS (ESI) m/z (M+H)$^+$334.2.

HH. N-(4-(6-Aminopyridin-2-yl)benzyl)methanesulfonamide (C-3)

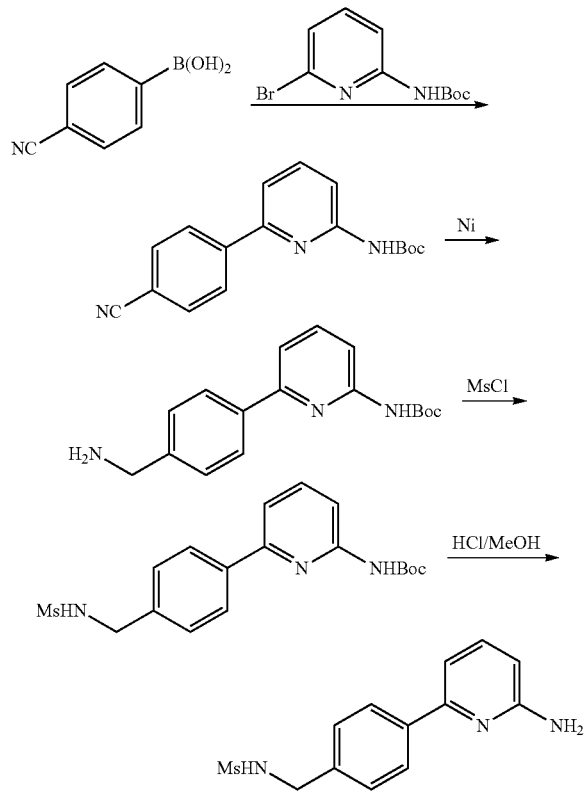

Step a: [6-(4-Cyano-phenyl)-pyridin-2-yl]carbamic acid tert-butyl ester

A mixture of 4-cyanobenzeneboronic acid (7.35 g, 50 mmol), (6-bromo-pyridin-2-yl)carbamic acid tert-butyl ester (13.8 g, 50 mmol), Pd(Ph$_3$P)$_4$ (5.8 g, 0.15 mmol) and K$_2$CO$_3$ (10.4 g, 75 mmol) in DMF/H$_2$O (1:1, 250 mL) was stirred under argon at 80° C. overnight. DMF was evaporated off under reduced pressure and the residue was dissolved in EtOAc (200 mL). The mixture was washed with water and brine, dried over Na$_2$SO$_4$, and concentrated to dryness. The residue was purified by column (Petroleum Ether/EtOAc 50:1) on silica gel to give [6-(4-cyano-phenyl)-pyridin-2-yl] carbamic acid tert-butyl ester (7.0 g, 60%). $^1$H NMR (300 MHz, CDCl$_3$) δ 8.02-8.07 (m, 2H), 7.95 (d, J=8.4 Hz, 1H), 7.71-7.79 (m, 3H), 7.37-7.44 (m, 2H), 1.53 (s, 9H).

Step b: [6-(4-Aminomethyl-phenyl)-pyridin-2-yl]-carbamic acid ten-butyl ester

A suspension of [6-(4-cyano-phenyl)-pyridin-2-yl]carbamic acid tert-butyl ester (7.0 g, 24 mmol), Raney Ni (1.0 g) in EtOH (500 mL) and NH$_3$.H$_2$O (10 mL) was hydrogenated under H$_2$ (50 psi.) at 50° C. for 6 h. The catalyst was filtered off and the filtrate was concentrated to dryness to give [6-(4-aminomethyl-phenyl)-pyridin-2-yl]-carbamic acid ten-butyl ester, which was used directly in next step. $^1$H NMR (300 MHz, CDCl$_3$) δ 7.83-7.92 (m, 3H), 7.70 (t, J=7.8 Hz, 1H), 7.33-7.40 (m, 4H), 3.92 (brs, 2H), 1.53 (s, 9H).

Step c: {6-[4-(Methanesulfonylamino-methyl)-phenyl]-pyridin-2-yl}carbamic acid tert-butyl ester To a solution of [6-(4-aminomethyl-phenyl)-pyridin-2-yl]-carbamic acid tert-butyl ester (5.7 g 19 mmol) and Et$_3$N (2.88 g, 29 mmol) in dichloromethane (50 mL) was added dropwise MsCl (2.7 g, 19 mmol) at 0° C. The reaction mixture was stirred at this temperature for 30 min, and then washed with water and brine, dried over Na$_2$SO$_4$ and concentrated to dryness. The residue was recrystallized with DCM/Petroleum Ether (1:3) to give {6-[4-(methanesulfonylamino-methyl)-phenyl]-pyridin-2-yl}carbamic acid tert-butyl ester (4.0 g, 44% over two steps). $^1$H NMR (300 MHz, CDCl$_3$) δ 7.90-7.97 (m, 3H), 7.75 (t, J=8.4, 8.4 Hz, 1H), 7.54-7.59 (m, 1H), 7.38-7.44 (m, 3H), 4.73 (br, 1H), 4.37 (d, J=6.0 Hz, 2H), 2.90 (s, 3H), 1.54 (s, 9H).

Step d: N-(4-(6-Aminopyridin-2-yl)benzyl)methanesulfonamide (C-3)

A mixture of {6-[4-(methanesulfonylamino-methyl)-phenyl]-pyridin-2-yl}carbamic acid tert-butyl ester (11 g, 29 mmol) in HCl/MeOH (4M, 300 mL) was stirred at room temperature overnight. The mixture was concentrated to dryness. The residue was filtered and washed with ether to give N-(4-(6-aminopyridin-2-yl)benzyl)methane sulfonamide (C-3) (7.6 g, 80%) $^1$H NMR (300 MHz, DMSO-d$_6$) δ 14.05 (br s, 1H), 8.24 (br s, 2H), 7.91-7.98 (m, 3H), 7.70 (t, J=6.0 Hz, 1H), 7.53 (d, J=8.1 Hz, 2H), 7.22 (d, J=6.9 Hz, 1H), 6.96 (d, J=9 Hz, 1H), 4.23 (d, J=5.7 Hz, 2H), 2.89 (s, 3H). MS (ESI) m/z (M+H)$^+$: 278.0, II. 4-(6-Aminopyridin-2-yl)-N-methylbenzenesulfonamide hydrochloride (C-4)

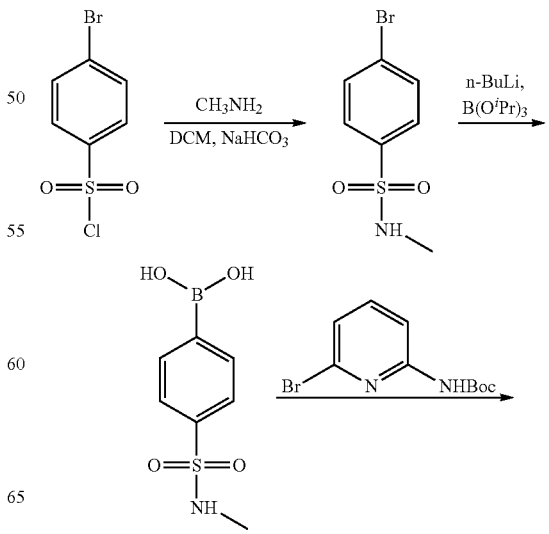

-continued

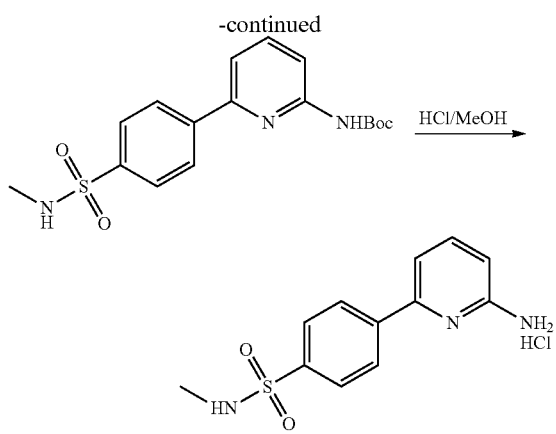

Step a: 4-Bromo-N-methyl-benzenesulfonamide

To a mixture of sat aq. NaHCO$_3$ (42 g, 0.5 mol), CH$_2$Cl$_2$ (400 mL) and methylamine (51.7 g, 0.5 mol, 30% in methanol) was added a solution of 4-bromo-benzenesulfonyl chloride (127 g, 0.5 mol) in CH$_2$Cl$_2$ (100 mL). The reaction was stirred at 20° C. overnight. The organic phase was separated and dried over Na$_2$SO$_4$. Evaporation of the solvent under reduced pressure provided the 4-bromo-N-methyl-benzenesulfonamide (121 g, crude), which was used in the next step without further purification. $^1$H NMR (CDCl$_3$, 300 MHz) δ 7.64-7.74 (m, 4H), 4.62-4.78 (m, 1H), 2.65 (d, J=5.4 Hz, 3H).

Step b: 4-(N-Methylsulfamoyl)phenylboronic acid

To a solution of 4-bromo-N-methyl-benzene sulfonamide (24.9 g, 0.1 mol) and B(O$^i$Pr)$_3$ (28.2 g, 0.15 mol) in THF (200 mL) was added n-BuLi (100 mL, 0.25 mol) at −70° C. The mixture was slowly warmed to 0° C., then 10% HCl solution was added until pH 3-4. The resulting mixture was extracted with EtOAc. The organic layer was dried over Na$_2$SO$_4$, and evaporated under reduced pressure to give 4-(N-methylsulfamoyl)phenylboronic acid (22.5 g, 96%), which was used in the next step without further purification. $^1$H NMR (DMSO-d$_6$, 300 MHz) δ 8.29 (s, 2H), 7.92 (d, J=8.1 Hz, 2H), 7.69 (d, J=8.4 Hz, 2H), 2.36 (d, J=5.1 Hz, 3H).

Step c: tert-Butyl 6-(4-(N-methylsulfamoyl)phenyl) pyridin-2-ylcarbamate

To a solution of 4-(N-methylsulfamoyl)phenylboronic acid (17.2 g, 0.08 mol) and (6-bromo-pyridin-2-yl)carbamic acid tert-butyl ester (21.9 g, 0.08 mol) in DMF (125 mL) and H$_2$O (125 mL) were added Pd(PPh$_3$)$_4$ (9.2 g, 0.008 mol) and K$_2$CO$_3$ (16.6 g, 0.12 mol). The resulting mixture was degassed by gently bubbling argon through the solution for 5 minutes at 20° C. The reaction mixture was then heated at 80° C. for 16 h. The mixture was evaporated under reduced pressure, then poured into H$_2$O, and extracted with EtOAc. The organic phase was dried over Na$_2$SO$_4$, and was evaporated under reduced pressure to give tert-butyl 6-(4-(N-methylsulfamoyl)phenyl)pyridin-2-ylcarbamate (21 g, 58%), which was used in the next step without further purification.

Step d: 4-(6-Aminopyridin-2-yl)-N-methylbenzenesulfonamide hydrochloride

To a solution of tert-butyl 6-(4-(N-methylsulfamoyl)phenyl)pyridin-2-ylcarbamate (8.5 g, 23.4 mmol) in MeOH (10 mL) was added HCl/MeOH (2M, 50 mL) at room temperature. The suspension was stirred at room temperature overnight. The solid product was collected by filtration, washed with MeOH, and dried to give 4-(6-aminopyridin-2-yl)-N-methylbenzenesulfonamide hydrochloride (5.0 g, 71%). $^1$H NMR (300 Hz, DMSO-d$_6$) δ 8.12 (d, J=8.4 Hz, 2H), 7.91-7.96 (m, 3H), 7.58-7.66 (m, 1H), 7.31-7.53 (m, 1H), 7.27 (d, J=6.6, 1H), 6.97 (d, J=9.0, 1H), 2.43 (d, J=4.8 Hz, 3H). MS (ESI) m/z (M+H)$^+$264.0.

The compounds in the following table were synthesized as described above using commercially available or previously described carboxylic acids and amines.

TABLE 6

Additional exemplary compounds of formula I.

| Compound No. | Carboxylic acid | Amine |
| --- | --- | --- |
| 164 | A-9 | C-1 |
| 165 | A-3 | C-2 |
| 169 | A-17 | C-3 |
| 170 | A-3 | C-4 |
| 177 | A-2 | C-3 |
| 183 | A-13 | C-4 |
| 192 | A-8 | C-2 |
| 200 | A-14 | C-2 |
| 201 | A-4 | C-3 |
| 202 | A-15 | C-2 |
| 211 | A-15 | C-3 |
| 214 | A-6 | C-2 |
| 218 | A-2 | C-4 |
| 220 | A-4 | C-2 |
| 221 | A-10 | C-2 |
| 223 | A-17 | C-4 |
| 226 | A-20 | C-2 |
| 228 | A-10 | C-3 |
| 236 | A-24 | C-2 |
| 237 | A-11 | C-3 |
| 239 | A-23 | C-2 |
| 240 | A-11 | C-4 |
| 242 | A-13 | C-2 |
| 245 | A-15 | C-4 |
| 246 | A-8 | C-3 |
| 248 | A-13 | C-3 |
| 250 | A-16 | C-4 |
| 253 | A-22 | C-2 |
| 256 | A-2 | C-2 |
| 259 | A-24 | C-4 |
| 262 | A-10 | C-4 |
| 271 | A-14 | C-4 |
| 279 | A-19 | C-2 |
| 281 | A-16 | C-2 |
| 282 | A-8 | C-4 |
| 284 | A-17 | C-2 |
| 302 | A-5 | C-2 |
| 317 | A-10 | C-1 |
| 318 | A-21 | C-2 |
| 319 | A-6 | C-4 |
| 340 | A-11 | C-2 |
| 341 | A-5 | C-3 |
| 345 | A-9 | C-3 |
| 358 | A-18 | C-2 |
| 362 | A-16 | C-3 |
| 363 | A-5 | C-4 |
| 369 | A-9 | C-4 |
| 372 | A-9 | C-2 |
| 376 | A-35 | C-2 |
| 377 | A-32 | C-2 |
| 378 | A-27 | C-2 |
| 379 | A-36 | C-2 |
| 380 | A-34 | C-2 |
| 381 | A-29 | C-2 |
| 382 | A-28 | C-2 |
| 383 | A-25 | C-2 |
| 384 | A-30 | C-2 |
| 385 | A-33 | C-2 |
| 386 | A-31 | C-2 |
| 387 | A-37 | C-2 |

TABLE 6-continued

Additional exemplary compounds of formula I.

| Compound No. | Carboxylic acid | Amine |
|---|---|---|
| 388 | A-26 | C-2 |
| 409 | A-38 | C-2 |
| 413 | A-45 | C-2 |

Physical data for examples of the invention are given in Table 7.

Additional exemplary compounds 164-388, as shown in Table 1, can also be prepared using appropriate starting materials and methods exemplified for the previously described compounds.

TABLE 7

Physical data for exemplary compounds.

| Compound No. | LCMS [M + H]$^+$ | LCMS RT | NMR |
|---|---|---|---|
| 1 | 416.3 | 2.39 | |
| 2 | 442.5 | 2.7 | |
| 3 | 427.1 | 4.1 | |
| 4 | 508.3 | 3.43 | |
| 5 | 423.3 | 3.72 | |
| 6 | 390.1 | 3.57 | |
| 7 | 402.5 | 2.96 | 1H NMR (400 MHz, CD$_3$CN) δ 1.21-1.29 (m, 2H), 1.62-1.68 (m, 2H), 3.05 (s, 6H), 6.06 (s, 2H), 6.86-6.97 (m, 3H), 7.04-7.08 (m, 2H), 7.53-7.55 (m, 1H), 7.76-7.82 (m, 3H), 7.86 (t, J = 8.0 Hz, 1H), 8.34 (br s, 1H) |
| 8 | 444.5 | 3.09 | |
| 9 | 430.5 | 2.84 | |
| 10 | 375.3 | 3.39 | |
| 11 | 403.5 | 2.83 | |
| 12 | 390 | 3.14 | |
| 14 | 520.2 | 1.38 | |
| 15 | 387.3 | 3.71 | |
| 16 | 389.3 | 2.9 | |
| 17 | 403.5 | 3.33 | |
| 18 | 403.5 | 3.75 | |
| 19 | 387.1 | 3.76 | |
| 20 | 389 | 2.79 | 1H NMR (400 MHz, CD$_3$CN/ DMSO-d$_6$) δ 1.15-1.23 (m, 2H), 1.56-1.61 (m, 2H), 4.60 (s, 2H), 6.05 (s, 2H), 6.94 (d, J = 8.3 Hz, 1H), 7.05-7.09 (m, 2H), 7.44 (d, J = 8.2 Hz, 2H), 7.57-7.62 (m, 2H), 7.92 (s, 1H), 8.00 (dd, J = 2.5, 8.6 Hz, 1H), 8.17 (d, J = 8.6 Hz, 1H), 8.48 (d, J = 1.8 Hz, 1H) |
| 21 | 360 | 2.18 | |
| 22 | 387.3 | 3.77 | |
| 23 | 535.2 | 2.81 | |
| 24 | 464.1 | 2.35 | 1H-NMR (DMSO-d$_6$, 300 MHz) δ 8.40 (s, 1H), 7.96 (d, J = 8.4 Hz, 1H), 7.86 (m, 2H), 7.82 (m, 1H), 7.62 (d, J = 7.8 Hz, 1H), 7.36 (d, J = 7.8 Hz, 1H), 7.11 (d, J = 2.1 Hz, 1H), 7.00 (m, 2H), 6.05 (s, 2H), 3.42 (m, 2H, overlap with water), 3.03 (m, J = 5.4 Hz, 2H), 2.98 (t, 1H), 1.49 (m, 2H), 1.14 (m, 2H). |
| 25 | 403 | 3.29 | 1H NMR (400 MHz, CD$_3$CN/ DMSO-d$_6$) δ 1.14-1.17 (m, 2H), 1.52-1.55 (m, 2H), 6.01 (s, 2H), 6.03 (s, 2H), 6.89-6.96 (m, 2H), 7.01-7.12 (m, 3H), 7.15 (d, J = 1.8 Hz, 1H), 7.93 (dd, J = 8.7, 2.5 Hz, 1H), 8.05-8.11 (m, 2H), 8.39-8.41 (m, 1H) |
| 26 | 393 | 3.88 | |
| 27 | 452.1 | 3.11 | |
| 28 | 427.1 | 4.19 | |
| 29 | 388.9 | 3.58 | |
| 30 | 375.3 | 2.95 | |
| 31 | 535.2 | 2.42 | |
| 32 | 359.1 | 3.48 | |
| 33 | 394.9 | 3.77 | |
| 34 | 360.3 | 2.96 | |

TABLE 7-continued

Physical data for exemplary compounds.

| Compound No. | LCMS [M + H]+ | LCMS RT | NMR |
|---|---|---|---|
| 35 | 495.1 | 2.24 | 1H-NMR (300 MHz, CDCl$_3$) δ 8.22 (d, J = 8.7 Hz, 1H), 7.98 (m, 3H), 7.80 (m, 3H), 7.45 (d, J = 7.5 Hz, 1H), 6.99 (dd, J = 8.1, 1.8 Hz, 2H), 6.95 (d, J = 1.5 Hz, 1H), 6.86 (d, J = 8.1 Hz, 1H), 6.02 (s, 2H), 3.77 (t, J = 5.1 Hz, 2H), 3.17 (m, J = 5.1 Hz, 2H), 2.85 (s, 3H), 1.70 (q, J = 3.6 Hz, 2H), 1.19 (q, J = 3.6 Hz, 2H). |
| 36 | 521.2 | 2.36 | 1H-NMR (300 MHz, DMSO-d$_6$) δ 8.51 (s, 1H), 8.15 (d, J = 9.0 Hz, 2H), 8.06 (d, J = 8.4 Hz, 1H), 7.92 (t, J = 7.8 Hz, 1H), 7.88 (d, J = 8.1 Hz, 2H), 7.76 (d, J = 7.5 Hz, 1H), 7.11 (d, J = 1.2 Hz, 1H), 7.03 (dd, J = 7.8, 1.8 Hz, 1H), 6.97 (d, J = 7.8 Hz, 1H), 6.06 (s, 2H), 3.55 (m, 2H, overlap with water), 3.15 (m, 2H), 3.07 (m, 1H), 1.77 (m, 2H), 1.50 (dd, J = 7.2, 4.5 Hz, 2H), 1.43 (m, 2H), 1.15 (dd, J = 6.9, 3.9 Hz, 2H). |
| 37 | 452.3 | 3.38 | |
| 38 | 398 | 3.02 | |
| 39 | 483.1 | 2.58 | 1H-NMR (DMSO-d$_6$, 300 MHz) δ 10.01 (t, J = 6.0 Hz, 1H), 8.39 (s, 1H), 7.97 (d, J = 7.8 Hz, 1H), 7.89 (d, J = 8.4 Hz, 1H), 7.83 (d, J = 7.8 Hz, 1H), 7.62 (d, J = 6.9 Hz, 1H), 7.33 (d, J = 8.4 Hz, 2H), 7.11 (d, J = 2.1 Hz, 1H), 7.03 (d, J = 1.5 Hz, 1H), 6.99 (dd, 7.8 Hz, 2H), 6.05 (s, 2H), 4.41 (d, J = 6 Hz, 2H), 1.48 (m, 2H), 1.14 (m, 2H). |
| 40 | 393.1 | 3.89 | |
| 41 | 373.1 | 3.57 | |
| 42 | 421.1 | 3.33 | |
| 43 | 417.3 | 3.62 | |
| 44 | 401.2 | 1.26 | |
| 45 | 403.5 | 3.25 | |
| 46 | 437.3 | 3.19 | |
| 47 | 391.1 | 3.82 | |
| 48 | 384.3 | 3.74 | |
| 49 | 419.3 | 3.27 | |
| 50 | 437 | 3.02 | |
| 51 | 349 | 3.33 | |
| 52 | 373.1 | 3.58 | 1H NMR (400 MHz, CD$_3$CN) δ 1.17-1.20 (m, 2H), 1.58-1.61 (m, 2H), 2.24 (s, 3H), 6.01 (s, 2H), 6.90 (d, J = 8.4 Hz, 1H), 7.04-7.06 (m, 2H), 7.16 (dd, J = 7.5, 0.8 Hz, 1H), 7.23-7.33 (m, 4H), 7.79-7.89 (m, 2H), 8.10 (dd, J = 8.3, 0.8 Hz, 1H) |
| 53 | 387 | 3.62 | |
| 54 | 394.1 | 3.06 | |
| 55 | 419.3 | 2.92 | |
| 56 | 407.5 | 3.55 | |
| 57 | 388.9 | 2.91 | |
| 58 | 360.2 | 3.74 | |
| 59 | 417.3 | 3.64 | |
| 60 | 402.5 | 3.07 | |
| 61 | 387.1 | 3.84 | |
| 62 | 415.3 | 4.1 | |
| 63 | 384 | 3.35 | |
| 64 | 360.3 | 3.58 | |
| 65 | 465.1 | 2.47 | 1H-NMR (300 MHz, CDCl$_3$) δ 8.19 (d, J = 8.1 Hz, 1H), 7.97 (d, J = 8.4 Hz, 2H), 7.92 (s, 1H), 7.89 (d, J = 8.4 Hz, 2H), 7.76 (t, J = 7.5 Hz, 1H), 7.44 (d, J = 7.5 Hz, 1H), 6.99 (m, 1H), 6.95 (br s, 1H), 6.86 (d, J = 8.1 Hz, 1H), 6.02 (s, 2H), 4.37 (t, J = 5.7 Hz, 1H), 3.02 (m, 2H), 1.70 (q, J = 3.9 Hz, 2H), 1.17 (q, J = 3.6 Hz, 2H), 1.11 (t, J = 7.2 Hz, 3H). |

TABLE 7-continued

Physical data for exemplary compounds.

| Compound No. | LCMS [M + H]⁺ | LCMS RT | NMR |
|---|---|---|---|
| 66 | 401 | 3.24 | |
| 67 | 393 | 3.88 | |
| 68 | 407.5 | 4.04 | |
| 69 | 377.1 | 3.26 | |
| 70 | 403.5 | 3.69 | |
| 71 | 472.3 | 3.02 | |
| 72 | 363 | 3.38 | |
| 73 | 449.3 | 3.4 | |
| 74 | 416.3 | 2.43 | |
| 75 | 373.1 | 3.69 | |
| 76 | 534.2 | 1.36 | |
| 77 | 491.2 | 2.7 | |
| 78 | 384.3 | 3.72 | |
| 79 | 388.3 | 2.32 | |
| 80 | 437.3 | 3.42 | |
| 81 | 373 | 3.51 | 1H NMR (400 MHz, $CD_3CN$/DMSO-$d_6$) δ 1.07-1.27 (m, 2H), 1.50-1.67 (m, 2H), 2.36 (s, 3H), 6.10 (s, 2H), 6.92 (d, J = 7.9 Hz, 1H), 7.01-7.09 (m, 2H), 7.28 (d, J = 7.9 Hz, 2H), 7.50 (d, J = 8.2 Hz, 2H), 7.93-8.00 (m, 2H), 8.15 (d, J = 9.3 Hz, 1H), 8.44 (d, J = 2.5 Hz, 1H) |
| 82 | 419 | 2.71 | 1H NMR (400 MHz, $CD_3CN$) δ 1.29-1.32 (m, 2H), 1.68-1.71 (m, 2H), 3.90 (s, 3H), 3.99 (s, 3H), 6.04 (s, 2H), 6.70-6.72 (m, 2H), 6.93 (d, J = 8.4 Hz, 1H), 7.03-7.05 (m, 2H), 7.59 (d, J = 8.2 Hz, 1H), 7.73 (t, J = 7.6 Hz, 2H), 8.01 (t, J = 8.1 Hz, 1H), 8.72 (br s, 1H) |
| 83 | 417.3 | 3.41 | |
| 84 | 394.9 | 3.74 | |
| 85 | 401.3 | 3.97 | |
| 86 | 473.5 | 2.69 | |
| 87 | 419.1 | 3.18 | 1H NMR (400 MHz, $CD_3CN$) δ 1.25-1.31 (m, 2H), 1.62-1.69 (m, 2H), 3.84 (s, 3H), 3.86 (s, 3H), 6.04 (s, 2H), 6.62-6.70 (m, 2H), 6.92 (d, J = 8.4 Hz, 1H), 7.00-7.08 (m, 2H), 7.30 (d, J = 8.3 Hz, 1H), 7.96 (d, J = 8.9 Hz, 1H), 8.14 (dd, J = 8.9, 2.3 Hz, 1H), 8.38 (d, J = 2.2 Hz, 1H), 8.65 (br s, 1H) |
| 88 | 399 | 3.83 | |
| 89 | 401.3 | 3.62 | |
| 90 | 407.3 | 3.59 | |
| 91 | 505.2 | 2.88 | |
| 92 | 384 | 3.36 | 1H NMR (400 MHz, $CD_3CN$) δ 1.27-1.30 (m, 2H), 1.65-1.67 (m, 2H), 6.05 (s, 2H), 6.93 (d, J = 8.4 Hz, 1H), 7.04-7.09 (m, 2H), 7.67 (t, J = 7.7 Hz, 1H), 7.79-7.81 (m, 1H), 7.91-7.94 (m, 1H), 8.02-8.08 (m, 2H), 8.23 (dd, J = 8.9, 2.5 Hz, 1H), 8.50 (d, J = 1.9 Hz, 1H), 8.58 (br s, 1H) |
| 93 | 402 | 2.73 | 1H NMR (400 MHz, $CD_3CN$) δ 1.16-1.24 (m, 2H), 1.57-1.62 (m, 2H), 6.05 (s, 2H), 6.95 (d, J = 7.6 Hz, 1H), 7.05-7.09 (m, 2H), 7.71-7.75 (m, 2H), 7.95 (br s, 1H), 8.04-8.10 (m, 3H), 8.22 (d, J = 8.7 Hz, 1H), 8.54 (d, J = 2.5 Hz, 1H) |
| 94 | 419.3 | 2.8 | |
| 95 | 403.3 | 2.98 | |
| 97 | 416.5 | 3.22 | |
| 98 | 421 | 3 | |
| 99 | 407.1 | 3.32 | |
| 100 | 389 | 2.83 | 1H NMR (400 MHz, $CD_3CN$) δ 1.21-1.26 (m, 2H), 1.60-1.65 (m, 2H), 4.65 (s, 2H), 6.03 (s, 2H), 6.89-6.94 (m, 1H), 7.02-7.08 (m, 2H), 7.36-7.62 (m, 3H), 8.12 (s, |

TABLE 7-continued

Physical data for exemplary compounds.

| Compound No. | LCMS [M + H]+ | LCMS RT | NMR |
|---|---|---|---|
| | | | 2H), 8.36 (br s, 1H), 8.45-8.47 (m, 1H) |
| 101 | 388.9 | 3.27 | 1H NMR (400 MHz, CD$_3$CN) δ 1.22-1.24 (m, 2H), 1.61-1.63 (m, 2H), 3.82 (s, 3H), 6.04 (s, 2H), 6.92 (d, J = 8.4 Hz, 1H), 7.04-7.12 (m, 4H), 7.34 (dd, J = 7.6, 1.7 Hz, 1H), 7.38-7.43 (m, 1H), 8.03 (dd, J = 8.7, 2.3 Hz, 1H), 8.10 (dd, J = 8.7, 0.7 Hz, 1H), 8.27 (br s, 1H), 8.37-8.39 (m, 1H) |
| 102 | 401.3 | 3.77 | |
| 103 | 430.5 | 3.04 | |
| 104 | 388.3 | 2.32 | |
| 105 | 521.2 | 2.46 | |
| 106 | 393 | 3.63 | |
| 107 | 416 | 2.84 | 1H NMR (400 MHz, CD$_3$CN/DMSO-d$_6$) δ 1.13-1.22 (m, 2H), 1.53-1.64 (m, 2H), 2.07 (s, 3H), 6.08 (s, 2H), 6.90-6.95 (m, 1H), 7.01-7.09 (m, 2H), 7.28 (d, J = 8.8 Hz, 1H), 7.37 (t, J = 7.9 Hz, 1H), 7.61 (d, J = 8.8 Hz, 1H), 7.84 (d, J = 1.6 Hz, 1H), 7.95 (dd, J = 2.5, 8.7 Hz, 1H), 8.03 (br s, 1H), 8.16 (d, J = 8.7 Hz, 1H), 8.42 (d, J = 2.4 Hz, 1H), 9.64 (s, 1H) |
| 108 | 403.3 | 3.07 | |
| 109 | 349.1 | 3.29 | |
| 110 | 389.2 | 3.15 | |
| 111 | 521.2 | 2.27 | |
| 112 | 394 | 3.82 | |
| 113 | 407.5 | 3.3 | |
| 114 | 417.1 | 3.17 | |
| 115 | 398.1 | 3.22 | |
| 116 | 394 | 3.1 | 1H NMR (400 MHz, CD$_3$CN) δ 1.18-1.26 (m, 2H), 1.59-1.64 (m, 2H), 6.05 (s, 2H), 6.95 (d, J = 8.4 Hz, 1H), 7.06-7.11 (m, 2H), 7.40 (d, J = 4.9 Hz, 1H), 7.92-7.96 (m, 2H), 8.26 (d, J = 9.3 Hz, 1H), 8.36 (d, J = 1.7 Hz, 1H), 8.56 (d, J = 5.0 Hz, 1H), 8.70 (s, 1H) |
| 117 | 363.3 | 3.48 | |
| 118 | 374.3 | 3.54 | |
| 119 | 494.3 | 3.59 | |
| 120 | 505.2 | 2.9 | |
| 121 | 374.3 | 2.55 | |
| 122 | 417.3 | 3.63 | |
| 123 | 389.3 | 3.47 | |
| 124 | 417.1 | 3.29 | |
| 125 | 417.3 | 3.08 | |
| 126 | 427.3 | 3.89 | |
| 127 | 535.2 | 2.76 | |
| 128 | 386.9 | 3.67 | |
| 129 | 377.1 | 3.67 | |
| 130 | 389.1 | 3.4 | 1H NMR (400 MHz, CD$_3$CN) δ 1.22-1.24 (m, 2H), 1.61-1.63 (m, 2H), 3.86 (s, 3H), 6.05 (s, 2H), 6.93 (d, J = 8.4 Hz, 1H), 6.97-7.00 (m, 1H), 7.05-7.08 (m, 2H), 7.16-7.21 (m, 2H), 7.41 (t, J = 8.0 Hz, 1H), 8.07-8.17 (m, 3H), 8.48-8.48 (m, 1H) |
| 131 | 407.3 | 3.49 | |
| 132 | 419 | 3.09 | 1H NMR (400 MHz, CD$_3$CN) δ 1.17-1.25 (m, 2H), 1.57-1.64 (m, 2H), 3.72 (s, 6H), 6.04 (s, 2H), 6.74 (d, J = 8.4 Hz, 2H), 6.93 (d, J = 8.4 Hz, 1H), 7.05-7.08 (m, 2H), 7.35 (t, J = 8.4 Hz, 1H), 7.75 (d, J = 10.5 Hz, 1H), 8.07-8.14 (m, 3H) |
| 133 | 431.3 | 3.27 | |
| 135 | 417.3 | 3.81 | |

TABLE 7-continued

Physical data for exemplary compounds.

| Compound No. | LCMS [M + H]+ | LCMS RT | NMR |
|---|---|---|---|
| 136 | 535.2 | 2.75 | |
| 137 | 403.5 | 3.35 | |
| 138 | 432.5 | 2.76 | H NMR (400 MHz, CD$_3$CN) δ 1.30-1.35 (m, 2H), 1.69-1.74 (m, 2H), 3.09 (s, 6H), 4.05 (s, 3H), 6.04 (s, 2H), 6.38 (d, J = 2.4 Hz, 1H), 6.50 (dd, J = 9.0, 2.4 Hz, 1H), 6.93 (d, J = 8.4 Hz, 1H), 7.03-7.06 (m, 2H), 7.31 (d, J = 7.7 Hz, 1H), 7.71 (d, J = 8.8 Hz, 2H), 7.97 (t, J = 8.3 Hz, 1H) |
| 139 | 421.1 | 2.71 | |
| 140 | 416.5 | 2.92 | |
| 141 | 410 | 2.83 | 1H NMR (400 MHz, CD$_3$CN) δ 1.28-1.37 (m, 2H), 1.66-1.73 (m, 2H), 6.05 (s, 2H), 6.91-6.97 (m, 1H), 7.05-7.09 (m, 2H), 7.69-7.74 (m, 1H), 7.82 (t, J = 7.7 Hz, 1H), 7.93 (d, J = 7.2 Hz, 1H), 8.04 (d, J = 8.8 Hz, 1H), 8.15 (d, J = 8.2 Hz, 1H), 8.37 (d, J = 8.8 Hz, 1H), 8.58-8.65 (m, 2H), 8.82 (br s, 1H), 8.94 (d, J = 6.2 Hz, 1H) |
| 142 | 349.3 | 3.33 | |
| 143 | 373.1 | 3.68 | |
| 144 | 535.2 | 2.33 | |
| 145 | 390.3 | 3.4 | |
| 146 | 386.9 | 3.72 | |
| 147 | 419.1 | 3.13 | 1H NMR (400 MHz, CD$_3$CN) δ 1.23-1.26 (m, 2H), 1.62-1.64 (m, 2H), 3.86 (s, 3H), 3.89 (s, 3H), 6.04 (s, 2H), 6.93 (d, J = 8.4 Hz, 1H), 7.03-7.07 (m, 3H), 7.17-7.19 (m, 2H), 8.06-8.15 (m, 2H), 8.38 (br s, 1H), 8.45-8.46 (m, 1H) |
| 148 | 393.1 | 3.72 | 1H NMR (400 MHz, CD$_3$CN) δ 1.20-1.27 (m, 2H), 1.58-1.67 (m, 2H), 6.05 (s, 2H), 6.94 (d, J = 8.4 Hz, 1H), 7.05-7.09 (m, 2H), 7.41-7.50 (m, 2H), 7.55-7.59 (m, 1H), 7.66-7.69 (m, 1H), 8.07 (d, J = 11.2 Hz, 1H), 8.11 (br s, 1H), 8.16 (d, J = 8.8 Hz, 1H), 8.48 (d, J = 1.9 Hz, 1H) |
| 149 | 458.5 | 2.42 | |
| 150 | 403.5 | 3.04 | |
| 151 | 452.3 | 3.44 | H NMR (400 MHz, MeOD) δ 1.30-1.36 (m, 2H), 1.71-1.77 (m, 2H), 2.58 (s, 3H), 6.04 (s, 2H), 6.93 (dd, J = 0.8, 7.5 Hz, 1H), 7.04-7.08 (m, 2H), 7.86 (dd, J = 0.8, 7.7 Hz, 1H), 8.00-8.02 (m, 2H), 8.08-8.12 (m, 3H), 8.19-8.23 (m, 1H) |
| 152 | 403 | 2.97 | |
| 153 | 359.1 | 3.36 | 1H NMR (400 MHz, CD$_3$CN) δ 1.24-1.26 (m, 2H), 1.62-1.65 (m, 2H), 6.05 (s, 2H), 6.93 (d, J = 8.4 Hz, 1H), 7.05-7.08 (m, 2H), 7.42-7.46 (m, 1H), 7.49-7.53 (m, 2H), 7.63-7.66 (m, 2H), 8.10-8.16 (m, 2H), 8.33 (br s, 1H), 8.48-8.48 (m, 1H) |
| 154 | 395.1 | 3.34 | |
| 155 | 393 | 3.7 | |
| 156 | 390.2 | 3.7 | |
| 157 | 403.5 | 3.33 | |
| 158 | 390.2 | 3.58 | |
| 159 | 493.2 | 2.85 | |
| 160 | 411.3 | 3.94 | |
| 161 | 419.1 | 3.2 | |
| 162 | 488.1 | 3.62 | |
| 163 | 438.1 | 3 | |
| 164 | 314.1 | 3.38 | |
| 165 | 538.5 | 3.28 | |
| 166 | 466.1 | 2.9 | |
| 167 | 429.3 | 2.95 | |

TABLE 7-continued

Physical data for exemplary compounds.

| Compound No. | LCMS [M + H]+ | LCMS RT | NMR |
|---|---|---|---|
| 168 | 526.3 | 3.189189 | |
| 169 | 498.3 | 3.7 | |
| 170 | 468.3 | 3.27 | |
| 171 | 444.5 | 2.24 | |
| 172 | 551.1 | 2.849824 | |
| 173 | 377 | 3.7 | |
| 174 | 493.9 | 2.69 | |
| 175 | 517.9 | 3.423179 | |
| 176 | 522.3 | 3.49262 | |
| 177 | 502.1 | 3.43 | |
| 178 | 549.1 | 2.906129 | |
| 179 | 480.1 | 2.51 | |
| 180 | 520.3 | 4.295395 | |
| 181 | 488.2 | 3.07 | |
| 182 | 535.1 | 3.267469 | |
| 183 | 436.3 | 3.62 | |
| 184 | 496.3 | 3.265482 | |
| 185 | 403.5 | 2.88 | |
| 186 | 420.9 | 2.86 | |
| 187 | 444.3 | 2.39 | |
| 188 | 417.3 | 2.24 | |
| 189 | 466.1 | 2.88 | |
| 190 | 438.1 | 2.39 | |
| 191 | 401.1 | 3.44 | |
| 192 | 552.3 | 3.18 | |
| 193 | 452.3 | 2.55 | |
| 194 | 415 | 4 | |
| 195 | 479.1 | 1.08 | |
| 196 | 430.5 | 2.34 | |
| 197 | 512.3 | 2.961206 | |
| 198 | 444.5 | 2.75 | H NMR (400 MHz, DMSO-$d_6$) δ 1.11-1.19 (m, 2H), 1.46-1.52 (m, 2H), 2.31 (s, 3H), 2.94 (s, 3H), 2.99 (s, 3H), 6.08 (s, 2H), 6.97-7.05 (m, 2H), 7.13 (d, J = 1.6 Hz, 1H), 7.35 (t, J = 1.5 Hz, 1H), 7.41 (t, J = 7.8 Hz, 2H), 7.51 (t, J = 7.6 Hz, 1H), 7.68 (d, J = 8.4 Hz, 1H), 7.97 (d, J = 8.4 Hz, 1H), 8.34 (s, 1H) |
| 199 | 540.3 | 3.18 | |
| 200 | 520.3 | 3.79 | |
| 201 | 452.3 | 3.22 | |
| 202 | 536.5 | 3.63 | |
| 203 | 509.1 | 2.82 | |
| 204 | 444.5 | 2.5 | |
| 205 | 524.3 | 3.48 | |
| 206 | 407.5 | 3.6 | |
| 207 | 452.1 | 2.62 | |
| 208 | 520.3 | 4.06 | |
| 209 | 416.1 | 2.3 | |
| 210 | 452.3 | 2.8 | H NMR (400 MHz, DMSO-$d_6$) δ 1.11-1.19 (m, 2H), 1.47-1.52 (m, 2H), 2.31 (s, 6.08 (s, 2H), 6.96-7.07 (m, 2H), 7.13 (d, J = 1.6 Hz, 1H), 7.43 (s, 1H), 7.57 (d, J = 8.1 Hz, 2H), 7.69 (d, J = 8.5 Hz, 2H), 7.89 (d, J = 8.2 Hz, 2H), 7.99 (d, J = 8.4 Hz, 1H), 8.38 (s, 1H) |
| 211 | 480.3 | 3.33 | |
| 212 | 521.1 | 3.23 | |
| 213 | 415.3 | 3.4 | |
| 214 | 562.3 | 3.71 | |
| 215 | 403.3 | 2.67 | |
| 216 | 421.1 | 2.91 | |
| 217 | 387.1 | 2.89 | |
| 218 | 488.3 | 3.73 | |
| 219 | 403.7 | 2.43 | |
| 220 | 508.5 | 3.46 | |
| 221 | 508.3 | 3.46 | |
| 222 | 401.1 | 2.76 | |
| 223 | 484.5 | 3.95 | |
| 224 | 407.5 | 3.23 | |
| 225 | 401.2 | 3.49 | |
| 226 | 608.3 | 3.58 | |
| 227 | 417.1 | 2.24 | |

TABLE 7-continued

Physical data for exemplary compounds.

| Compound No. | LCMS [M + H]+ | LCMS RT | NMR |
|---|---|---|---|
| 228 | 452.3 | 3.21 | |
| 229 | 407.1 | 3.08 | |
| 230 | 401.3 | 2.68 | |
| 231 | 389.1 | 2.36 | |
| 232 | 481.9 | 3.155919 | |
| 233 | 535.9 | 3.58 | |
| 234 | 551.1 | 2.90 | |
| 235 | 415.3 | 3.71 | H NMR (400 MHz, DMSO-$d_6$) δ 1.12-1.17 (m, 2H), 1.23 (d, J = 6.9 Hz, 6H), 1.47-1.51 (m, 2H), 2.30 (s, 3H), 2.92 (septet, J = 6.9 Hz, 1H), 6.08 (s, 2H), 6.97-7.05 (m, 2H), 7.12-7.17 (m, 2H), 7.20-7.22 (m, 1H), 7.24-7.26 (m, 1H), 7.36 (t, J = 7.6 Hz, 1H), 7.65 (d, J = 8.4 Hz, 1H), 7.95 (d, J = 8.4 Hz, 1H), 8.32 (s, 1H) |
| 236 | 540.3 | 3.85 | |
| 237 | 456.5 | 3.35 | |
| 238 | 416.5 | 2.35 | |
| 239 | 529.3 | 2.29 | |
| 240 | 442.3 | 3.57 | |
| 241 | 466.3 | 3.5 | |
| 242 | 506.3 | 3.67 | |
| 243 | 403.3 | 2.69 | |
| 244 | 534.3 | 3.93 | |
| 245 | 466.3 | 3.6 | |
| 246 | 496.3 | 2.9 | |
| 247 | 458.5 | 2.3 | |
| 248 | 450.3 | 3.01 | |
| 249 | 565.2 | 2.89 | |
| 250 | 480.5 | 3.74 | |
| 251 | 452.1 | 1.07 | |
| 252 | 389.1 | 2.82 | |
| 253 | 530.3 | 2.8 | |
| 254 | 466.1 | 1.06 | |
| 255 | 488.2 | 3.05 | |
| 256 | 558.3 | 3.46 | |
| 257 | 407.5 | 3.27 | |
| 258 | 430.5 | 2.66 | H NMR (400 MHz, DMSO-$d_6$) δ 1.12-1.18 (m, 2H), 1.47-1.54 (m, 2H), 2.30 (s, 3H), 2.79 (d, J = 4.5 Hz, 3H), 6.08 (s, 2H), 6.96-7.07 (m, 2H), 7.13 (d, J = 1.6 Hz, 1H), 7.48-7.57 (m, 2H), 7.70 (d, J = 8.4 Hz, 1H), 7.78 (d, J = 1.5 Hz, 1H), 7.84 (dt, J = 7.3, 1.7 Hz, 1H), 7.98 (d, J = 8.4 Hz, 1H), 8.36 (s, 1H), 8.50-8.51 (m, 1H) |
| 259 | 470.3 | 3.82 | |
| 260 | 403.1 | 2.27 | |
| 261 | 549.1 | 3.39 | |
| 262 | 438.1 | 3.43 | |
| 263 | 403.3 | 2.8 | |
| 264 | 407.1 | 3.04 | |
| 265 | 430.5 | 2.18 | |
| 266 | 403.3 | 2.96 | |
| 267 | 531.9 | 2.81 | |
| 268 | 496.3 | 3.24 | |
| 269 | 373.5 | 2.76 | |
| 270 | 520.3 | 4.21 | |
| 271 | 450.3 | 3.77 | |
| 272 | 403.2 | 1.09 | |
| 273 | 543.1 | 2.89 | |
| 274 | 417.3 | 2.26 | |
| 275 | 527.9 | 3.91 | |
| 276 | 510.3 | 3.37 | |
| 277 | 403.1 | 2.2 | |
| 278 | 430.5 | 2.68 | H NMR (400 MHz, DMSO-$d_6$) δ 1.12-1.19 (m, 2H), 1.47-1.51 (m, 2H), 2.31 (s, 3H), 2.80 (d, J = 4.5 Hz, 3H), 6.08 (s, 2H), 6.97-7.05 (m, 2H), 7.13 (d, J = 1.6 Hz, 1H), 7.45 (d, J = 8.4 Hz, 2H), 7.68 (d, J = 8.4 Hz, 1H), 7.90 (d, J = 8.5 Hz, 2H), |

TABLE 7-continued

Physical data for exemplary compounds.

| Compound No. | LCMS [M + H]⁺ | LCMS RT | NMR |
|---|---|---|---|
| | | | 7.97 (d, J = 8.3 Hz, 1H), 8.35 (s, 1H), 8.50 (q, J = 4.5 Hz, 1H) |
| 279 | 536.5 | 3.19 | |
| 280 | 480.3 | 3.25 | |
| 281 | 550.5 | 3.78 | |
| 282 | 482.5 | 3.15 | |
| 283 | 416.3 | 2.58 | |
| 284 | 554.3 | 3.99 | |
| 285 | 546.3 | 2.87 | |
| 286 | 416.1 | 2.29 | |
| 287 | 443 | 4.02 | |
| 288 | 466.3 | 2.76 | |
| 289 | 373.1 | 2.84 | |
| 290 | 429.3 | 3 | |
| 291 | 403.1 | 2.24 | |
| 292 | 479.2 | 2.49 | |
| 293 | 417.3 | 2.65 | |
| 294 | 403.5 | 2.39 | |
| 295 | 416.3 | 2.61 | H NMR (400 MHz, DMSO-d$_6$) δ 1.14-1.18 (m, 2H), 1.46-1.54 (m, 2H), 2.31 (s, 3H), 6.08 (s, 2H), 6.97-7.05 (m, 2H), 7.13 (d, J = 1.6 Hz, 1H), 7.44 (s, 1H), 7.49-7.56 (m, 2H), 7.72 (d, J = 8.4 Hz, 1H), 7.83-7.85 (m, 1H), 7.87-7.91 (m, 1H), 7.99 (d, J = 8.4 Hz, 1H), 8.05 (s, 1H), 8.39 (s, 1H) |
| 296 | 387.1 | 3.09 | |
| 297 | 430.2 | 2.38 | |
| 298 | 403.2 | 2.72 | |
| 299 | 387.3 | 2.86 | |
| 300 | 387.3 | 3.03 | |
| 301 | 403.5 | 2.44 | |
| 302 | 508.3 | 3.45 | |
| 303 | 417.3 | 2.58 | |
| 304 | 549.1 | 3.35 | |
| 305 | 429.5 | 3.01 | |
| 306 | 492.3 | 3.81 | |
| 307 | 512.3 | 2.97 | |
| 308 | 415.3 | 2.85 | |
| 309 | 444.5 | 2.75 | |
| 310 | 430.5 | 2.41 | |
| 311 | 534.3 | 3.92 | |
| 312 | 492.3 | 3.99 | |
| 313 | 387.3 | 2.84 | |
| 314 | 430.5 | 2.37 | |
| 315 | 387 | 1.12 | |
| 316 | 526.3 | 3.08 | |
| 317 | 344.2 | 3.35 | |
| 318 | 536.5 | 3.17 | |
| 319 | 492.3 | 3.69 | |
| 320 | 430.2 | 2.38 | |
| 321 | 452.3 | 2.55 | |
| 322 | 387.1 | 2.6 | |
| 323 | 387.1 | 3.01 | |
| 324 | 402.5 | 2.14 | |
| 325 | 531.9 | 3.83 | |
| 326 | 444.5 | 2.5 | |
| 327 | 403.3 | 2.83 | |
| 328 | 401.1 | 3.48 | |
| 329 | 415.3 | 3.36 | |
| 330 | 522.3 | 4.14 | |
| 331 | 387.1 | 3.01 | |
| 332 | 505.9 | 4.06 | |
| 333 | 417.1 | 2.58 | |
| 334 | 403.5 | 2.92 | |
| 335 | 520.3 | 4.22 | |
| 336 | 510.3 | 3.36 | |
| 337 | 401.1 | 2.73 | |
| 338 | 479.9 | 3.44 | |
| 339 | 508.3 | 3.83 | |
| 340 | 512.5 | 3.6 | |
| 341 | 452.3 | 3.15 | |
| 342 | 540.3 | 3.07 | |
| 343 | 480.3 | 3 | |

TABLE 7-continued

Physical data for exemplary compounds.

| Compound No. | LCMS [M + H]⁺ | LCMS RT | NMR |
|---|---|---|---|
| 344 | 526.3 | 3.15 | |
| 345 | 422.1 | 3.21 | |
| 346 | 415 | 4.05 | |
| 347 | 523.1 | 3.10 | |
| 348 | 416.3 | 1.87 | |
| 349 | 438.1 | 2.4 | |
| 350 | 402.5 | 2.18 | |
| 351 | 373.1 | 3.08 | |
| 352 | 415.7 | 3.13 | |
| 353 | 420.9 | 2.9 | |
| 354 | 407.3 | 3.03 | |
| 355 | 480.3 | 2.96 | |
| 356 | 452.3 | 2.47 | |
| 357 | 466.3 | 2.63 | |
| 358 | 536.5 | 3.26 | |
| 359 | 402.1 | 2.2 | |
| 360 | 510.3 | 3.42 | |
| 361 | 407 | 3.11 | |
| 362 | 494.5 | 3.45 | |
| 363 | 438.1 | 3.42 | |
| 364 | 535.9 | 3.44 | |
| 365 | 402.1 | 2.21 | |
| 366 | 565.2 | 3.01 | |
| 367 | 403.5 | 2.36 | |
| 368 | 444.5 | 2.97 | |
| 369 | 408.5 | 3.43 | |
| 370 | 403.3 | 2.45 | |
| 371 | 430.5 | 2.43 | |
| 372 | 478.3 | 3.47 | |
| 373 | 524.3 | 3.50 | |
| 374 | 466.3 | 2.35 | |
| 375 | 416.5 | 2.36 | |
| 376 | 552.3 | 3.42 | |
| 377 | 524.5 | 3.17 | |
| 378 | 538.5 | 3.07 | |
| 379 | 528.3 | 3.33 | |
| 380 | 548.3 | 3.75 | |
| 381 | 526.3 | 3.46 | |
| 382 | 520.5 | 3.48 | |
| 383 | 518.1 | 3.55 | |
| 384 | 542.3 | 3.59 | |
| 385 | 550.5 | 3.69 | |
| 386 | 524.3 | 3.15 | |
| 387 | 522.5 | 3.78 | |
| 388 | 542.2 | 3.6 | |
| 389 | 467.3 | 1.93 | |
| 390 | 469.3 | 1.99 | |
| 391 | 507.5 | 2.12 | |
| 392 | 453.5 | 1.99 | |
| 393 | 487.3 | 2.03 | |
| 394 | 483.5 | 1.92 | |
| 395 | 441.3 | 4.33 | |
| 396 | 453.3 | 1.93 | |
| 397 | 439.5 | 1.94 | |
| 398 | 471.3 | 2 | |
| 399 | 537.5 | 2.1 | |
| 400 | 525.3 | 2.19 | |
| 401 | 453.5 | 1.96 | |
| 402 | 483.3 | 1.87 | |
| 403 | 457.5 | 1.99 | |
| 404 | 469.5 | 1.95 | |
| 405 | 471.3 | 1.98 | |
| 406 | 525.3 | 2.15 | |
| 407 | 439.4 | 1.97 | |
| 408 | 525.1 | 2.14 | |
| 409 | 618.7 | 3.99 | |
| 410 | 374.5 | 2.46 | |
| 411 | 507.5 | 2.14 | |
| 412 | 390.1 | 3.09 | |
| 413 | 552.3 | 4.04 | |
| 414 | 457.5 | 2.06 | |
| 415 | 521.5 | 2.14 | |
| 416 | 319 | 3.32 | |
| 417 | 471.3 | 1.96 | |
| 418 | 417.3 | 1.75 | |

TABLE 7-continued

Physical data for exemplary compounds.

| Compound No. | LCMS [M + H]+ | LCMS RT | NMR |
|---|---|---|---|
| 419 | 473.3 | 2.04 | |
| 420 | 389.3 | 2.94 | |
| 421 | 457.5 | 1.99 | |
| 422 | 467.3 | 1.96 | |

Assays

Assays for Detecting and Measuring ΔF508-CFTR Correction Properties of Compounds JJ. Membrane Potential Optical Methods for Assaying ΔF508-CFTR Modulation Properties of Compounds The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

1. Identification of Correction Compounds

To identify small molecules that correct the trafficking defect associated with F508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 µM forskolin and the CFTR potentiator, genistein (20 µM), were added along with Cl⁻-free medium to each well. The addition of Cl⁻-free medium promoted Cl⁻ efflux in response to ΔF508-CFTR activation and the resulting membrane depolarization was optically monitored using the FRET-based voltage-sensor dyes.

2. Identification of Potentiator Compounds

To identify potentiators of ΔF508-CFTR, a double-addition HTS assay format was developed. During the first addition, a Cl⁻-free medium with or without test compound was added to each well. After 22 sec, a second addition of Cl⁻-free medium containing 2-10 µM forskolin was added to activate ΔF508-CFTR. The extracellular Cl⁻ concentration following both additions was 28 mM, which promoted Cl⁻ efflux in response to ΔF508-CFTR activation and the resulting membrane depolarization was optically monitored using the FRET-based voltage-sensor dyes.

3. Solutions

Bath Solution #1: (in mM) NaCl 160, KCl 4.5, CaCl$_2$ 2, MgCl$_2$ 1, HEPES 10, pH 7.4 with NaOH.

| | |
|---|---|
| Chloride-free bath solution: | Chloride salts in Bath Solution #1 are substituted with gluconate salts. |
| CC2-DMPE: | Prepared as a 10 mM stock solution in DMSO and stored at −20° C. |
| DiSBAC$_2$(3): | Prepared as a 10 mM stock in DMSO and stored at −20° C. |

4. Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1× NEAA, β-ME, 1× pen/strep, and 25 mM HEPES in 175 cm$^2$ culture flasks. For all optical assays, the cells were seeded at 30,000/well in 384-well matrigel-coated plates and cultured for 2 hrs at 37° C. before culturing at 27° C. for 24 hrs for the potentiator assay. For the correction assays, the cells are cultured at 27° C. or 37° C. with and without compounds for 16-24 hours Electrophysiological Assays for Assaying ΔF508-CFTR Modulation Properties of Compounds 1. Using Chamber Assay Using chamber experiments were performed on polarized epithelial cells expressing ΔF508-CFTR to further characterize the ΔF508-CFTR modulators identified in the optical assays. FRT$^{\Delta F508\text{-}CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 Ω/cm$^2$ or more. The solutions were maintained at 27° C. and bubbled with air. The electrode offset potential and fluid resistance were corrected using a cell-free insert. Under these conditions, the current reflects the flow of Cl⁻ through ΔF508-CFTR expressed in the apical membrane. The $I_{SC}$ was digitally acquired using an MP100A-CE interface and AcqKnowledge software (v3.2.6; BIOPAC Systems, Santa Barbara, Calif.).

2. Identification of Correction Compounds

Typical protocol utilized a basolateral to apical membrane Cl⁻ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

3. Identification of Potentiator Compounds

Typical protocol utilized a basolateral to apical membrane Cl⁻ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl⁻ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

4. Solutions

Basolateral solution (in mM): NaCl (135), $CaCl_2$ (1.2), $MgCl_2$ (1.2), $K_2HPO_4$ (2.4), $KHP\ O_4$ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

5. Cell Culture

Fisher rat epithelial (FRT) cells expressing ΔF508-CFTR ($FRT^{\Delta F508-CFTR}$) were used for Ussing chamber experiments for the putative ΔF508-CFTR modulators identified from our optical assays. The cells were cultured on Costar Snapwell cell culture inserts and cultured for five days at 37° C. and 5% $CO_2$ in Coon's modified Ham's F-12 medium supplemented with 5% fetal calf serum, 100 U/ml penicillin, and 100 μg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

6. Whole-Cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 μl of saline and was continuously perifused at a rate of 2 ml/min using a gravity-driven perfusion system.

7. Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 μM forskolin and 20 μM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 μM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 μM of correction compounds significantly increased the cAMP- and genistein-dependent current compared to the 37° C. controls.

8. Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $T_{\Delta F508}$ with similar potency and efficacy observed in the optical assays. In all cells examined, the reversal potential before and during potentiator application was around −30 mV, which is the calculated $Ep_{Cl}$ (−28 mV).

9. Solutions

Intracellular solution (in mM): Cs-aspartate (90), CsCl (50), $MgCl_2$ (1), HEPES (10), and 240 μg/ml amphotericin-B (pH adjusted to 7.35 with CsOH).

Extracellular solution (in mM): N-methyl-D-glucamine (NMDG)-Cl (150), MgCl$_2$ (2), CaCl$_2$ (2), HEPES (10) (pH adjusted to 7.35 with HCl).

10. Cell Culture

NIH3T3 mouse fibroblasts stably expressing ΔF508-CFTR are used for whole-cell recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

11. Single-Channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the non-specific phosphatase inhibitor F$^-$ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o = I/i(N)$, where I=mean current, i=single-channel current amplitude, and N=number of active channels in patch.

12. Solutions

Extracellular solution (in mM): NMDG (150), aspartic acid (150), CaCl$_2$ (5), MgCl$_2$ (2), and HEPES (10) (pH adjusted to 7.35 with Tris base).

Intracellular solution (in mM): NMDG-Cl (150), MgCl$_2$ (2), EGTA (5), TES (10), and Tris base (14) (pH adjusted to 7.35 with HCl).

13. Cell Culture

NIH3T3 mouse fibroblasts stably expressing ΔF508-CFTR are used for excised-membrane patch-clamp recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For single channel recordings, 2,500-5,000 cells were seeded on poly-L-lysine-coated glass coverslips and cultured for 24-48 hrs at 27° C. before use.

The exemplified compounds of Table 1 have an activity with a range of about 100 nM and 20 μM as measured using the assays described hereinabove. The exemplified compounds of Table 1 are found to be sufficiently efficacious as measured using the assays described hereinabove.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating cystic fibrosis in a patient, wherein the patient has a defective gene that causes a deletion of phenylalanine at position 508 of the cystic fibrosis transmembrane conductance regulator amino acid sequence, said method comprising the step of administering to the patient an effective amount of the compound

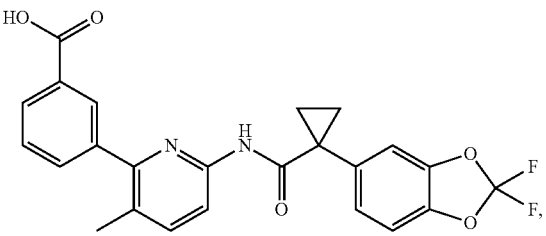 [SMILES: Cc1ccc(NC(=O)C2(c3ccc4c(c3)OC(F)(F)O4)CC2)nc1-c1cccc(C(=O)O)c1]

or a pharmaceutically acceptable salt thereof.

2. The method of claim 1, wherein the patient has two copies of the defective gene.

3. A method of treating cystic fibrosis in a patient, wherein the patient has a defective gene that causes a deletion of phenylalanine at position 508 of the cystic fibrosis transmembrane conductance regulator amino acid sequence, said method comprising the step of administering to said patient an effective amount of a composition comprising:

i) the compound:
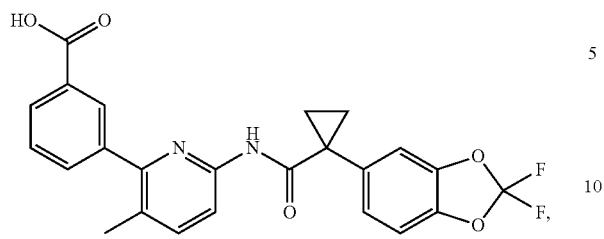
or a pharmaceutically acceptable salt thereof; and
ii) a pharmaceutically acceptable carrier.
4. The method of claim 3, wherein the patient has two copies of the defective gene.
* * * * *